(12) United States Patent
Hammarström et al.

(10) Patent No.: US 8,853,382 B2
(45) Date of Patent: Oct. 7, 2014

(54) EXPRESSION OF ANTIBODY OR A FRAGMENT THEREOF IN LACTOBACILLUS

(75) Inventors: Lennart Hammarström, Huddinge (SE); Harold Marcotte, Huddinge (SE); Miguel Angel Alvarez, Oviedo (ES); Maria Cruz Martin, Oviedo (ES)

(73) Assignee: Hera Pharmaceuticals, Inc., Columbia, MD (US)

( * ) Notice: Subject to any disclaimer, the term of this patent is extended or adjusted under 35 U.S.C. 154(b) by 0 days.

(21) Appl. No.: 13/814,484

(22) PCT Filed: Aug. 4, 2011

(86) PCT No.: PCT/US2011/046670
§ 371 (c)(1),
(2), (4) Date: Aug. 14, 2013

(87) PCT Pub. No.: WO2012/019058
PCT Pub. Date: Feb. 9, 2012

(65) Prior Publication Data
US 2013/0323819 A1 Dec. 5, 2013

(30) Foreign Application Priority Data
Aug. 5, 2010 (GB) .................................. 1013216.5

(51) Int. Cl.
| C07H 21/04 | (2006.01) |
| A61K 39/02 | (2006.01) |
| A61K 48/00 | (2006.01) |
| C12N 15/74 | (2006.01) |
| A61K 35/74 | (2006.01) |
| C07K 16/28 | (2006.01) |
| A61K 35/00 | (2006.01) |
| A61K 39/00 | (2006.01) |

(52) U.S. Cl.
CPC ............ *C12N 15/746* (2013.01); *A61K 35/747* (2013.01); *A61K 2035/115* (2013.01); *A61K 2039/505* (2013.01); *C07K 16/2821* (2013.01); *C07K 16/2845* (2013.01); *C07K 2317/14* (2013.01); *C07K 2317/20* (2013.01); *C07K 2317/569* (2013.01); *C07K 2317/622* (2013.01)
USPC ....... 536/23.53; 536/23.1; 530/300; 530/350; 424/93.2; 424/185.1; 424/234.1

(58) Field of Classification Search
CPC . A61K 35/747; A61K 358/16; A61K 38/164; A61K 38/1774; C07H 21/02; C07H 21/04; C07K 14/335; C12N 15/74
USPC ...................... 530/300, 350; 536/23.1, 23.53; 424/93.2, 185.1, 234.1
See application file for complete search history.

(56) References Cited

U.S. PATENT DOCUMENTS

| 5,747,310 | A | 5/1998 | Sasaki et al. |
| 2002/0164700 | A1 | 11/2002 | Anderson et al. |
| 2003/0022244 | A1 | 1/2003 | Solomon et al. |
| 2005/0220776 | A1 | 10/2005 | Brondstad et al. |
| 2005/0276836 | A1 | 12/2005 | Wilson et al. |
| 2005/0281783 | A1 | 12/2005 | Kinch et al. |
| 2006/0029558 | A1 | 2/2006 | Schlievert et al. |
| 2006/0134101 | A1 | 6/2006 | Larsson et al. |
| 2007/0071742 | A1 | 3/2007 | Fang et al. |
| 2007/0092535 | A1 | 4/2007 | Watts et al. |
| 2009/0123452 | A1 | 5/2009 | Madison |
| 2009/0226418 | A1 | 9/2009 | Frenken et al. |
| 2009/0317404 | A1 | 12/2009 | Markham |
| 2010/0041588 | A1 | 2/2010 | Keay et al. |
| 2010/0047190 | A1 | 2/2010 | Rendl et al. |

FOREIGN PATENT DOCUMENTS

WO 2007/047073 4/2007

OTHER PUBLICATIONS

Alvarez, M.A. ea Al., The Site-Specific Recombination System of the *Lactobacilius* Species Bacteriophage A2 Integrates in Gram-Positive and Gram-Negative Bacteria. Virology 250:185-193, 1998.

Chancey, et al., "*Lactobacilli*-Expressed Single-Chain Variable Fragment (scFv) Specific for Intercellular Adhesion Molecule 1 (ICAM-1) Blocks Cell-Associated HIV-1 Transmission across a Cervical Epithelial Monolayer" J Immunol2006; 176:5627-5636.

Dooley et al., "Selection and characterization of naturally occurring single-domain (IgNAR) antibody fragments from immunized sharks by phage display" Molecular Immunology (2003)40, 25-33.

Kmet, et al,, "Aggrefation-promoting factor in human vaginal *lactobacillus* strains" FEMS Immunol Med Microbiol; vol. 19, pp. 111-114 , 1997.

Kruger, et al. "In situ delivery of passive immunity by *lactobacilli* producing single chain antibodies", Nature biotechnology, 2002, vol. 20, pp. 702-706.

Martin, M.D. et al., "Integrative Expression System for Delivery of Antibody Fragments by *Lactobacilli*" Applied and Environ. Microbiology 77:2174-2179, 2011.

Nuttall et al. "Isolation and characterization of an IgNAR variable domain specific for the human mitochondrial translocase receptor Tom70" Eur. 1. Biochem. (2003) 270. 3543-4554.

Nutall et al. "Selection and affinity maturation of IgNAR variable domains targeting *Plasmodium falciparum* AMA1" Proteins: Structure, Function and Bioinformatics (2004) 55, 187-197.

(Continued)

*Primary Examiner* — Rodney P Swartz
(74) *Attorney, Agent, or Firm* — K&L Gates LLP

(57) ABSTRACT

Described herein are methods and compositions for expressing an antibody or a fragment thereof in a microorganism and use of the microorganism to treat or prevent a pathogenic infection in a mammal.

20 Claims, 22 Drawing Sheets

(56) References Cited

OTHER PUBLICATIONS

Pant, et al, "*Lactobacilli* Expressing Variable Domain of Llama Heavy-Chain Antibody Fragments (Lactobedies) Confer Protection against Rotavirus-Induced Diarrhea" JID 194:1586-8, 2006.

Suran, A.A. et al., Immunoglobulins of the Leopard Shark. I. Isolation and Characterization of 17 S and 7 S Immunoglobulins with Precipitating Activity. J. Immunology, 99: 679-686, 1967.

Ventura et al., "Identification and characterisation of novel surface proteins in, *Lactobacillus johnsonii* and *Lactobacillus gasseri*", Appl Environ Microbiol; vol. 68, pp. 6172-6181 (2002).

Andersen, et al., "In situ gastrointestinal protection against anthrax edema toxin by single-chain antibody fragment producing *lactobacilli*." BMC Biotechnol. Dec. 20, 2011;11:126. doi: 10.1186/1472-6750-11-126.

Pant, et al., "*Lactobacilli* producing bispecific llama-derived anti-rotavirus proteins in vivo for rotavirus-induced diarrhea." Future Microbiol. May 2011;6(5):583-93. doi: 10.2217/fmb.11.32.

| Seq.ID. No. | Sequence | Remarks |
|---|---|---|
| 28 | GTTGGGCCTGAGACCGTCACCAAGACCCCTTCCCTCCACAGGACATGCTGGGCCTGCGCCC<br>CCCACTTCTCGCCCTGGTGGGGCTGCTCTCCCTCGGGTGCGTCCTCTCTCAGGAGTGCACG<br>AAGTTCAAGGTCAGCAGCTGCCGGGAATGCATCGAGTCGGGGCCCGGCTGCACCTGGTGCC<br>AGAAGCTGAACTTCACAGGGCCGGGGGATCCTGACTCCATTCGCTGCGACACCCGGCCACA<br>GCTGCTCATGAGGGGCTGTGCGGCTGACGACATCATGGACCCCACAAGCCTCGCTGAAACC<br>CAGGAAGACCACAATGGGGGCCAGAAGCAGCTGTCCCCACAAAAAGTGACGCTTTACCTGC<br>GACCAGGCCAGGCAGCAGCGTTCAACGTGACCTTCCGGCGGGCCAAGGGCTACCCCATCGA<br>CCTGTACTATCTGATGGACCTCTCCTACTCCATGCTTGATGACCTCAGGAATGTCAAGAAG<br>CTAGGTGGCGACCTGCTCCGGGCCCTCAACGAGATCACCGAGTCCGGCCGCATTGGCTTCG<br>GGTCCTTCGTGGACAAGACCGTGCTGCCGTTCGTGAACACGCACCCTGATAAGCTGCGAAA<br>CCCATGCCCCAACAAGGAGAAAGAGTGCCAGCCCCCGTTTGCCTTCAGGCACGTGCTGAAG<br>CTGACCAACAACTCCAACCAGTTTCAGACCGAGGTCGGGAAGCAGCTGATTTCCGGAAACC<br>TGGATGCACCCGAGGGTGGGCTGGACGCCATGATGCAGGTCGCCGCCTGCCCGGAGGAAAT<br>CGGCTGGCGCAACGTCACGCGGCTGCTGGTGTTTGCCACTGATGACGGCTTCCATTTCGCG<br>GGCGACGGGAAGCTGGGCGCCATCCTGACCCCCAACGACGGCCGCTGTCACCTGGAGGACA<br>ACTTGTACAAGAGGAGCAACGAATTCGACTACCCATCGGTGGGCCAGCTGGCGCACAAGCT<br>GGCTGAAAACAACATCCAGCCCATCTTCGCGGTGACCAGTAGGATGGTGAAGACCTACGAG<br>AAACTCACCGAGATCATCCCCAAGTCAGCCGTGGGGGAGCTGTCTGAGGACTCCAGCAATG<br>TGGTCCATCTCATTAAGAATGCTTACAATAAACTCTCCTCCAGGGTATTCCTGGATCACAA<br>CGCCCTCCCCGACACCCTGAAAGTCACCTACGACTCCTTCTGCAGCAATGGAGTGACGCAC<br>AGGAACCAGCCCAGAGGTGACTGTGATGGCGTGCAGATCAATGTCCCGATCACCTTCCAGG<br>TGAAGGTCACGGCCACAGAGTGCATCCAGGAGCAGTCGTTTGTCATCCGGGCGCTGGGCTT<br>CACGGACATAGTGACCGTGCAGGTCCTTCCCCAGTGTGAGTGCCGGTGCCGGGACCAGAGC<br>AGAGACCGCAGCCTCTGCCATGGCAAGGGCTTCTTGGAGTGCGGCATCTGCAGGTGTGACA<br>CTGGCTACATTGGGAAAAACTGTGAGTGCCAGACACAGGGCCGGAGCAGCCAGGAGCTGGA<br>AGGAAGCTGCCGGAAGGACAACAACTCCATCATCTGCTCAGGGCTGGGGGACTGTGTCTGC<br>GGGCAGTGCCTGTGCCACACCAGCGACGTCCCCGGCAAGCTGATATACGGGCAGTACTGCG<br>AGTGTGACACCATCAACTGTGAGCGCTACAACGGCCAGGTCTGCGGCGGCCCGGGGAGGGG<br>GCTCTGCTTCTGCGGGAAGTGCCGCTGCCACCCGGGCTTTGAGGGCTCAGCGTGCCAGTGC<br>GAGAGGACCACTGAGGGCTGCCTGAACCCGCGGCGTGTTGAGTGTAGTGGTCGTGGCCGGT<br>GCCGCTGCAACGTATGCGAGTGCCATTCAGGCTACCAGCTGCCTCTGTGCCAGGAGTGCCC<br>CGGCTGCCCCTCACCCTGTGGCAAGTACATCTCCTGCGCCGAGTGCCTGAAGTTCGAAAAG<br>GGCCCCTTTGGGAAGAACTGCAGCGCGGCGTGTCCGGGCCTGCAGCTGTCGAACAACCCCG<br>TGAAGGGCAGGACCTGCAAGGAGAGGGACTCAGAGGGCTGCTGGGTGGCCTACACGCTGGA<br>GCAGCAGGACGGGATGGACCGCTACCTCATCTATGTGGATGAGAGCCGAGAGTGTGTGGCA<br>GGCCCCAACATCGCCGCCATCGTCGGGGGCACCGTGGCAGGCATCGTGCTGATCGGCATTC<br>TCCTGCTGGTCATCTGGAAGGCTCTGATCCACCTGAGCGACCTCCGGGAGTACAGGCGCTT<br>TGAGAAGGAGAAGCTCAAGTCCCAGTGGAACAATGATAATCCCCTTTTCAAGAGCGCCACC<br>ACGACGGTCATGAACCCCAAGTTTGCTGAGAGTTAGGAGCACTTGGTGAAGACAAGGCCGT<br>CAGGACCCACCATGTCTGCCCCATCACGCGGCCGAGACATGGCTTGCCACAGCTCTTGAGG<br>ATGTCACCAATTAACCAGAAATCCAGTTATTTTCCACCCTCAAAATGACAGCCATGGCCGG<br>CCCGGTGCTTCTGGGGGCTCGTCGGGGGGACAGCTCCACTCTGACTGGCACAGTCTTTGCA<br>TGGAGACTTGAGGAGGGAGGGCTTGAGGTTGGTGAGGTTAGGTGCGTGTTTCCTGTGCAAG<br>TCAGGACATCAGTCTGATTAAAGGTGGTGCCAATTTATTTACATTTAAACTTGTCAGGGTA<br>TAAAATGACATCCCATTAATTATATTGTTAATCAATCACGTGTATAGAAAAAAAATAAAAC<br>TTCAATACAGGCTGTCCATGGAAAAAAAAAAAAAAAAAAAAAA | hCD18<br>GeneBank:<br>BC005861.2 |
| 29 | MLGLRPPLLALVGLLSLGCVLSQECTKFKVSSCRECIESGPGCTWCQKLNFTGPGDPDSIR<br>CDTRPQLLMRGCAADDIMDPTSLAETQEDHNGGQKQLSPQKVTLYLRPGQAAAFNVTFRRA<br>KGYPIDLYYLMDLSYSMLDDLRNVKKLGGDLLRALNEITESGRIGFGSFVDKTVLPFVNTH<br>PDKLRNPCPNKEKECQPPFAFRHVLKLTNNSNQFQTEVGKQLISGNLDAPEGGLDAMMQVA<br>ACPEEIGWRNVTRLLVFATDDGFHFAGDGKLGAILTPNDGRCHLEDNLYKRSNEFDYPSVG<br>QLAHKLAENNIQPIFAVTSRMVKTYEKLTEIIPKSAVGELSEDSSNVVHLIKNAYNKLSSR<br>VFLDHNALPDTLKVTYDSFCSNGVTHRNQPRGDCDGVQINVPITFQVKVTATECIQEQSFV<br>IRALGFTDIVTVQVLPQCECRCRDQSRDRSLCHGKGFLECGICRCDTGYIGKNCECQTQGR<br>SSQELEGSCRKDNNSIICSGLGDCVCGQCLCHTSDVPGKLIYGQYCECDTINCERYNGQVC<br>GGPGRGLCFCGKCRCHPGFEGSACQCERTTEGCLNPRRVECSGRGRCRCNVCECHSGYQLP<br>LCQECPGCPSPCGKYISCAECLKFEKGPFGKNCSAACPGLQLSNNPVKGRTCKERDSEGCW<br>VAYTLEQQDGMDRYLIYVDESRECVAGPNIAAIVGGTVAGIVLIGILLLVIWKALIHLSDL | hCD18<br>GI: 13543407 |

FIGURE 8 cont.

| | | |
|---|---|---|
| | REYRRFEKEKLKSQWNNDNPLFKSATTTVMNPKFAES | |
| 30 | CCTCTTTCACCCTGTCTAGGTTGCCAGCAAATCCCACGGGCCTCCTGACGCTGCCCCTGGG GCCACAGGTCCCTCGAGTGCTGGAAGGATGAAGGATTCCTGCATCACTGTGATGGCCATGG CGCTGCTGTCTGGGTTCTTTTTCTTCGCGCCGGCCTCGAGCTACAACCTGGACGTGCGGGG CGCGCGGAGCTTCTCCCCACCGCGCGCCGGGAGGCACTTTGGATACCGCGTCCTGCAGGTC GGAAACGGGGTCATCGTGGGAGCTCCAGGGGAGGGGAACAGCACAGGAAGCCTCTATCAGT GCCAGTCGGGCACAGGACACTGCCTGCCAGTCACCCTGAGAGGTTCCAACTATACCTCCAA GTACTTGGGAATGACCTTGGCAACAGACCCCACAGATGGAAGCATTTTGGCCTGTGACCCT GGGCTGTCTCGAACGTGTGACCAGAACACCTATCTGAGTGGCCTGTGTTACCTCTTCCGCC AGAATCTGCAGGGTCCCATGCTGCAGGGGCGCCCTGGTTTTCAGGAATGTATCAAGGGCAA CGTAGACCTGGTATTTCTGTTTGATGGTTCGATGAGCTTGCAGCCAGATGAATTTCAGAAA ATTCTGGACTTCATGAAGGATGTGATGAAGAAACTCAGCAACACTTCGTACCAGTTTGCTG CTGTTCAGTTTTCCACAAGCTACAAAACAGAATTTGATTTCTCAGATTATGTTAAACGGAA GGACCCTGATGCTCTGCTGAAGCATGTAAAGCACATGTTGCTGTTGACCAATACCTTTGGT GCCATCAATTATGTCGCGACAGAGGTGTTCCGGGAGGAGCTGGGGGCCCGGCCAGATGCCA CCAAAGTGCTTATCATCATCACGGATGGGGAGGCCACTGACAGTGGCAACATCGATGCGGC CAAAGACATCATCCGCTACATCATCGGGATTGGAAAGCATTTTCAGACCAAGGAGAGTCAG GAGACCCTCCACAAATTTGCATCAAAACCCGCGAGCGAGTTTGTGAAAATTCTGGACACAT TTGAGAAGCTGAAAGATCTATTCACTGAGCTGCAGAAGAAGATCTATGTCATTGAGGGCAC AAGCAAACAGGACCTGACTTCCTTCAACATGGAGCTGTCCTCCAGCGGCATCAGTGCTGAC CTCAGCAGGGGCCATGCAGTCGTGGGGGCAGTAGGAGCCAAGGACTGGGCTGGGGGCTTTC TTGACCTGAAGGCAGACCTGCAGGATGACACATTTATTGGGAATGAACCATTGACACCAGA AGTGAGAGCAGGCTATTTGGGTTACACCGTGACCTGGCTGCCCTCCCGGCAAAAGACTTCG TTGCTGGCCTCGGGAGCCCCTCGATACCAGCACATGGGCCGAGTGCTGCTGTTCCAAGAGC CACAGGGCGGAGGACACTGGAGCCAGGTCCAGACAATCCATGGGACCCAGATTGGCTCTTA TTTCGGTGGGGAGCTGTGTGGCGTCGACGTGGACCAAGATGGGGAGACAGAGCTGCTGCTG ATTGGTGCCCCACTGTTCTATGGGGAGCAGAGAGGAGGCCGGGTGTTTATCTACCAGAGAA GACAGTTGGGGTTTGAAGAAGTCTCAGAGCTGCAGGGGGACCCCGGCTACCCACTCGGGCG GTTTGGAGAAGCCATCACTGCTCTGACAGACATCAACGGCGATGGGCTGGTAGACGTGGCT GTGGGGGCCCCTCTGGAGGAGCAGGGGGCTGTGTACATCTTCAATGGGAGGCACGGGGGGC TTAGTCCCCAGCCAAGTCAGCGGATAGAAGGGACCCAAGTGCTCTCAGGAATTCAGTGGTT TGGACGCTCCATCCATGGGGTGAAGGACCTTGAAGGGGATGGCTTGGCAGATGTGGCTGTG GGGGCTGAGAGCCAGATGATCGTGCTGAGCTCCCGGCCCGTGGTGGATATGGTCACCCTGA TGTCCTTCTCTCCAGCTGAGATCCCAGTGCATGAAGTGGAGTGCTCCTATTCAACCAGTAA CAAGATGAAAGAAGGAGTTAATATCACAATCTGTTTCCAGATCAAGTCTCTCATCCCCCAG TTCCAAGGCCGCCTGGTTGCCAATCTCACTTACACTCTGCAGCTGGATGGCCACCGGACCA GAAGACGGGGGTTGTTCCCAGGAGGGAGACATGAACTCAGAAGGAATATAGCTGTCACCAC CAGCATGTCATGCACTGACTTCTCATTTCATTTCCCGGTATGTGTTCAAGACCTCATCTCC CCCATCAATGTTTCCCTGAATTTCTCTCTTTGGGAGGAGGAAGGGACACCGAGGGACCAAA GGGCGCAGGGCAAGGACATACCGCCCATCCTGAGACCCTCCCTGCACTCGGAAACCTGGGA GATCCCTTTTGAGAAGAACTGTGGGGAGGACAAGAAGTGTGAGGCAAACTTGAGAGTGTCC TTCTCTCCTGCAAGATCCAGAGCCCTGCGTCTAACTGCTTTTGCCAGCCTCTCTGTGGAGC TGAGCCTGAGTAACTTGGAAGAAGATGCTTACTGGGTCCAGCTGGACCTGCACTTCCCCCC GGGACTCTCCTTCCGCAAGGTGGAGATGCTGAAGCCCCATAGCCAGATACCTGTGAGCTGC GAGGAGCTTCCTGAAGAGTCCAGGCTTCTGTCCAGGGCATTATCTTGCAATGTGAGCTCTC CCATCTTCAAAGCAGGCCACTCGGTTGCTCTGCAGATGATGTTTAATACACTGGTAAACAG CTCCTGGGGGGACTCGGTTGAATTGCACGCCAATGTGACCTGTAACAATGAGGACTCAGAC CTCCTGGAGGACAACTCAGCCACTACCATCATCCCCATCCTGTACCCCATCAACATCCTCA TCCAGGACCAAGAAGACTCCACACTCTATGTCAGTTTCACCCCCAAAGGCCCCAAGATCCA CCAAGTCAAGCACATGTACCAGGTGAGGATCCAGCCTTCCATCCACGACCACAACATACCC ACCCTGGAGGCTGTGGTTGGGGTGCCACAGCCTCCCAGCGAGGGGCCCATCACACACCAGT GGAGCGTGCAGATGGAGCCTCCCGTGCCCTGCCACTATGAGGATCTGGAGAGGCTCCCGGA TGCAGCTGAGCCTTGTCTCCCCGGAGCCCTGTTCCGCTGCCCTGTTGTCTTCAGGCAGGAG ATCCTCGTCCAAGTGATCGGGACTCTGGAGCTGGTGGGAGAGATCGAGGCCTCTTCCATGT TCAGCCTCTGCAGCTCCCTCTCCATCTCCTTCAACAGCAGCAAGCATTTCCACCTCTATGG CAGCAACGCCTCCCTGGCCCAGGTTGTCATGAAGGTTGACGTGGTGTATGAGAAGCAGATG CTCTACCTCTACGTGCTGAGCGGCATCGGGGGCTGCTGCTGCTGCTCATTTTCATAG TGCTGTACAAGGTTGGTTTCTTCAAACGGAACCTGAAGGAGAAGATGGAGGCTGGCAGAGG TGTCCCGAATGGAATCCCTGCAGAAGACTCTGAGCGACTGGCCATCTGGGCAAGAGGCTGGG GATCCCGGCTGCCTGAAGCCCCTCCATGAGAAGGACTCTGAGAGTGGTGGTGGCAAGGACT GAGTCCAGGCCTGTGAGGTGCAGAGTGCCCAGAACTGGACTCAGGATGCCCAGGGCCACTC TGCCTCTGCCTGCATTCTGCCGTGTGCCCTCGGGCGAGTCACTGCCTCTCCCTGGCCCTCA | hCD11a GenBank: DQ131904.1 |

FIGURE 8 cont.

| | | |
|---|---|---|
| | GTTTCCCTATCTCGAACATGGAACTCATTCCTGCCTGTCTCCTTTGCAGGCTCATAGGGAA<br>GACCTGCTGAGGGACCAGCCAAGAGGGCTGCAAAAGTGAGGGCTTGTCATTACCAGACGGT<br>TCACCAGCCTCTCTTGGTTTCCTTCCTTGGAAGAGAATGTCTGATCTAAATGTGGAGAAAC<br>TGTAGTCTCAGGACCTAGGGATGTTCTGGCCCTCACCCCTGCCCTGGGATGTCCACAGATG<br>CCTCCACCCCCAGAACCTGTCCTTGCACACTCCCCTGCACTGGAGTCCAGTCTCTTCTGC<br>TGGCAGAAAGCAAATGTGACCTGTGTCACTACGTGACTGTGGCACACGCCTTGTTCTTGGC<br>CAAAGACCCAAATTCCTTGGCATGCCTTCCAGCACCCTGCAAAATGAGACCCTCGTGGCCTT<br>CCCCAGCCTCTTCTAGAGCCGTGATGCCTCCCTGTTGAAGCTCTGGTGACACCAGCCTTTC<br>TCCCAGGCCAGGCTCCTTCCTGTCTTCCTGCATTCACCCAGACAGCTCCCTCTGCCTGAAC<br>CTTCCATCTCGCCACCCCTCCTTCCTTGACCAGCAGATCCCAGCTCACGTCACACTTGGTT<br>GGGTCCTCACATCTTTCACACTTCCACCAGCCTGCACTACTCCCTCAAAGCACACGTCATG<br>TTTCTTCATCCGGCAGCCTGGATGTTTTTTCCCTGTTTAATGATTGACGTACTTAGCAGCT<br>ATCTCTCAGTGAACTGTGAGGGTAAAGGCTATACTTGTCTTGTTCACCTTGGGATGATGCC<br>TCATGATATGTCAGGGCGTGGGACATCTAGTAGGTGCTTGACATAATTTCACTGAATTAAT<br>GACAGAGCCAGTGGGAAGATACAGAAAAAGAGGGGCTGGGCTGGGCGCGGTGGTTCACGCC<br>TGTAATCCCAGCACTTTGGGAGGCCAAGGAGGGTGGATCACCTGAGGTCAGGAGTTAGAGG<br>CCAGCCTGGCGAAACCCCATCTCTACTAAAAATACAAAATCCAGGCGTGGTGGCACACACC<br>TGTAGTCCCAGCTACTCAGGAGGTTGAGGTAGGAGAATTGCTTGAACCTGGGAGGTGGAGG<br>TTGCAGTGAGCCAAGATTGCGCCATTGCACTCCAGCCTGGGCAACACAGCGAGACTCCGTC<br>TCAAGGAAAAAATAAAAATAAAAAGCGGGCACGGGCCCGTG | |
| 31 | MKDSCITVMAMALLSGFFFFAPASSYNLDVRGARSFSPPRAGRHFGYRVLQVGNGVIVGAP<br>GEGNSTGSLYQCQSGTGHCLPVTLRGSNYTSKYLGMTLATDPTDGSILACDPGLSRTCDQN<br>TYLSGLCYLFRQNLQGPMLQGRPGFQECIKGNVDLVFLFDGSMSLQPDEFQKILDFMKDVM<br>KKLSNTSYQFAAVQFSTSYKTEFDFSDYVKRKDPDALLKHVKHMLLLTNTFGAINYVATEV<br>FREELGARPDATKVLIIITDGEATDSGNIDAAKDIIRYIIGIGKHFQTKESQETLHKFASK<br>PASEFVKILDTFEKLKDLFTELQKKIYVIEGTSKQDLTSFNMELSSSGISADLSRGHAVVG<br>AVGAKDWAGGFLDLKADLQDDTFIGNEPLTPEVRAGYLGYTVTWLPSRQKTSLLASGAPRY<br>QHMGRVLLFQEPQGGGHWSQVQTIHGTQIGSYFGGELCGVDVDQDGETELLLIGAPLFYGE<br>QRGGRVFIYQRRQLGFEEVSELQGDPGYPLGRFGEAITALTDINGDGLVDVAVGAPLEEQG<br>AVYIFNGRHGGLSPQPSQRIEGTQVLSGIQWFGRSIHGVKDLEGDGLADVAVGAESQMIVL<br>SSRPVVDMVTLMSFSPAEIPVHEVECSYSTSNKMKEGVNITICFQIKSLIPQFQGRLVANL<br>TYTLQLDGHRTRRRGLFPGGRHELRRNIAVTTSMSCTDFSFHFPVCVQDLISPINVSLNFS<br>LWEEEGTPRDQRAQGKDIPPILRPSLHSETWEIPFEKNCGEDKKCEANLRVSFSPARSRAL<br>RLTAFASLSVELSLSNLEEDAYWVQLDLHFPPGLSFRKVEMLKPHSQIPVSCEELPEESRL<br>LSRALSCNVSSPIFKAGHSVALQMMFNTLVNSSWGDSVELHANVTCNNEDSDLLEDNSATT<br>IIPILYPINILIQDQEDSTLYVSFTPKGPKIHQVKHMYQVRIQPSIHDHNIPTLEAVVGVP<br>QPPSEGPITHQWSVQMEPPVPCHYEDLERLPDAAEPCLPGALFRCPVVFRQEILVQVIGTL<br>ELVGEIEASSMFSLCSSLSISFNSSKHFHLYGSNASLAQVVMKVDVVYEKQMLYLYVLSGI<br>GGLLLLLLIFIVLYKVGFFKRNLKEKMEAGRGVPNGIPAEDSEQLASGQEAGDPGCLKPLH<br>EKDSESGGGKD | hCD11a<br>GI: 71648768 |
| 32 | GAATTCCGTGGTTCCTCAGTGGTGCCTGCAACCCCTGGTTCACCTCCTTCCAGGTTCTGGC<br>TCCTTCCAGCCATGGCTCTCAGAGTCCTTCTGTTAACAGCCTTGACCTTATGTCATGGGTT<br>CAACTTGGACACTGAAAACGCAATGACCTTCCAAGAGAACGCAAGGGCTTCGGGCAGAGC<br>GTGGTCCAGCTTCAGGGATCCAGGGTGGTTGGAGCCCCCCAGGAGATAGTGGCTGCCA<br>ACCAAAGGGGCAGCCTCTACCAGTGCGACTACAGCACAGGCTCATGCGAGCCCATCCGCCT<br>GCAGGTCCCCGTGGAGGCCGTGAACATGTCCCTGGGCCTGTCCCTGGCAGCCACCACCAGC<br>CCCCCTCAGCTGCTGGCCTGTGGTCCCACCGTGCACCAGACTTGCAGTGAGAACACGTATG<br>TGAAAGGGCTCTGCTTCCTGTTTGGATCCAACCTACGGCAGCAGCCCAGAAGTTCCCAGA<br>GGCCCTCCGAGGGTGTCCTCAAGAGGATAGTGACATTGCCTTCTTGATTGATGGCTCTGGT<br>AGCATCATCCCACATGACTTTCGGCGGATGAAGGAGTTTGTCTCAACTGTGATGGAGCAAT<br>TAAAAAAGTCCAAAACCTTGTTCTCTTTGATGCAGTACTCTGAAGAATTCCGGATTCACTTT<br>TACCTTCAAAGAGTTCCAGAACAACCCTAACCCAAGATCACTGGTGAAGCCAATAACGCAG<br>CTGCTTGGCGGACACACACGGCCACGGGCATCCGCAAAGTGGTACGAGAGCTGTTTAACA<br>TCACCAACGGAGCCCGAAAGAATGCCTTTAAGATCCTAGTTGTCATCACGGATGGAGAAAA<br>GTTTGGCGATCCCTTGGGATATGAGGATGTCATCCCTGAGGCAGACAGAGAGGGAGTCATT<br>CGCTACGTCATTGGGTGGGAGATGCCTTCCGCAGTGAGAAATCCCGCCAAGAGCTTAATA<br>CCATCGCATCCAAGCCGCCTCGTGATCACGTGTTCCAGGTGAATAACTTTGAGGCTCTGAA<br>GACCATTCAGAACCAGCTTCGGGAGAAGATCTTTGCGATCGAGGGTACTCAGACAGGAAGT<br>AGCAGCTCCTTTGAGCATGAGATGTCTCAGGAAGGCTTCAGCGCTGCCATCACCTCTAATG<br>GCCCCTTGCTGAGCACTGTGGGGAGCTATGACTGGGCTGGTGGAGTCTTTCTATATACATC<br>AAAGGAGAAAAGCACCTTCATCAACATGACCAGAGTGGATTCAGACATGAATGATGCTTAC | hCD11b<br>GenBank:<br>J03925.1 |

FIGURE 8 cont.

| | | |
|---|---|---|
| | TTGGGTTATGCTGCCGCCATCATCTTACGGAACCGGGTGCAAAGCCTGGTTCTGGGGGCAC<br>CTCGATATCAGCACATCGGCCTGGTAGCGATGTTCAGGCAGAACACTGGCATGTGGGAGTC<br>CAACGCTAATGTCAAGGGCACCCAGATCGGCGCCTACTTCGGGGCCTCCCTCTGCTCCGTG<br>GACGTGGACAGCAACGGCAGCACCGACCTGGTCCTCATCGGGGCCCCCCATTACTACGAGC<br>AGACCCGAGGGGGCCAGGTGTCCGTGTGCCCCTTGCCCAGGGGGCAGAGGGCTCGGTGGCA<br>GTGTGATGCTGTTCTCTACGGGGAGCAGGGCCAACCCTGGGGCCGCTTTGGGGCAGCCCTA<br>ACAGTGCTGGGGGACGTAAATGGGGACAAGCTGACGGACGTGGCCATTGGGGCCCCAGGAG<br>AGGAGGACAACCGGGGTGCTGTTTACCTGTTTCACGGAACCTCAGGATCTGGCATCAGCCC<br>CTCCCATAGCCAGCGGATAGCAGGCTCCAAGCTCTCTCCCAGGCTCCAGTATTTTGGTCAG<br>TCACTGAGTGGGGGCCAGGACCTCACAATGGATGGACTGGTAGACCTGACTGTAGGAGCCC<br>AGGGGCACGTGCTGCTGCTCAGGTCCCAGCCAGTACTGAGAGTCAAGGCAATCATGGAGTT<br>CAATCCCAGGGAAGTGGCAAGGAATGTATTTGAGTGTAATGATCAGGTGGTGAAAGGCAAG<br>GAAGCCGGAGAGGTCAGAGTCTGCCTCCATGTCCAGAAGAGCACACGGGATCGGCTAAGAG<br>AAGGACAGATCCAGAGTGTTGTGACTTATGACCTGGCTCTGGACTCCGGCCGCCCACATTC<br>CCGCGCCGTCTTCAATGAGACAAAGAACAGCACACGCAGACAGACACAGGTCTTGGGGCTG<br>ACCCAGACTTGTGAGACCCTGAAACTACAGTTGCCGAATTGCATCGAGGACCCAGTGAGCC<br>CCATTGTGCTGCGCCTGAACTTCTCTCTGGTGGGAACGCCATTGTCTGCTTTCGGGAACCT<br>CCGGCCAGTGCTGGCGGAGGATGCTCAGAGACTCTTCACAGCCTTGTTTCCCTTTGAGAAG<br>AATTGTGGCAATGACAACATCTGCCAGGATGACCTCAGCATCACCTTCAGTTTCATGAGCC<br>TGGACTGCCTCGTGGTGGGTGGGCCCCGGGAGTTCAACGTGACAGTGACTGTGAGAAATGA<br>TGGTGAGGACTCCTACAGGACACAGGTCACCTTCTTCTTCCCGCTTGACCTGTCCTACCGG<br>AAGGTGTCCACACTCCAGAACCAGCGCTCACAGCGATCCTGGCGCCTGGCCTGTGAGTCTG<br>CCTCCTCCACCGAAGTGTCTGGGGCCTTGAAGAGCACCAGCTGCAGCATAAACCACCCCAT<br>CTTCCCGGAAAACTCAGAGGTCACCTTTAATATCACGTTTGATGTAGACTCTAAGGCTTCC<br>CTTGGAAACAAACTGCTCCTCAAGGCCAATGTGACCAGTGAGAACAACATGCCCAGAACCA<br>ACAAAACCGAATTCCAACTGGAGCTGCCGGTGAAATATGCTGTCTACATGGTGGTCACCAG<br>CCATGGGGTCTCCACTAAATATCTCAACTTCACGGCCTCAGAGAATACCAGTCGGGTCATG<br>CAGCATCAATATCAGGTCAGCAACCTGGGGCAGAGGAGCCTCCCCATCAGCCTGGTGTTCT<br>TGGTGCCCGTCCGGCTGAACCAGACTGTCATATGGGACCGCCCCAGGTCACCTTCTCCGA<br>GAACCTCTCGAGTACGTGCCACACCAAGGAGCGCTTGCCTCTCACTCCGACTTTCTGGCT<br>GAGCTTCGGAAGGCCCCCGTGGTGAACTGCTCCATCGCTGTCTGCCAGAGAATCCAGTGTG<br>ACATCCCGTTCTTTGGCATCCAGGAAGAATTCAATGCTACCCTCAAAGGCAACCTCTCGTT<br>TGACTGGTACATCAAGACCTCGCATAACCACCTCCTGATCGTGAGCACAGCTGAGATCTTG<br>TTTAACGATTCCGTGTTCACCCTGCTGCCGGGACAGGGGCGTTTGTGAGGTCCCAGACGG<br>AGACCAAAGTGGAGCCGTTCGAGGTCCCCAACCCCCTGCCGCTCATCGTGGGCAGCTCTGT<br>CGGGGGACTGCTGCTCCTGGCCCTCATCACCGCCGCGCGTGTACAAGCTCGGCTTCTTCAAG<br>CGGCAATACAAGGACATGATGAGTGAAGGGGGTCCCCGGGGGCCGAACCCCAGTAGCGGC<br>TCCTTCCCGACAGAGCTGCCTCTCGGTGGCCAGCAGGACTCTGCCCAGACCACACGTAGCC<br>CCCAGGCTGCTGGACACGTCGGACAGCGAAGTATCCCGACAGGACGGGCTTGGGCTTCCA<br>TTTGTGTGTGTGCAAGTGTGTATGTGCGTGTGTGCGAGTGTGTGCAAGTGTCTGTGTGCAA<br>GTGTGTGCACGTGTGCGTGTGCGTGCATGTGCACTCGCACGCCCATGTGTGAGTGTGTGCA<br>AGTATGTGAGTGTGTCCAGTGTGTGTGCGTGTGTCCATGTGTGTGCAGTGTGTGCATGTGT<br>GCGAGTGTGTGCATGTGTGTGCTCAGGGGCGTGTGGCTCACGTGTGTGACTCAGAGTGTCTC<br>TGGCGTGTGGGTAGGTGACGGCAGCGTAGCCTCTCCGGCAGAAGGGAACTGCCTGGGCTCC<br>CTTGTGCGTGGGTAAGCCGCTGCTGGGTTTTCCTCCGGGAGAGGGGACGGTCAATCCTGTG<br>GGTGAAGAGAGAGGGAAACACAGCAGCATCTCTCCACTGAAAGAAGTGGGACTTCCCGTCG<br>CCTGCGAGCCTGCGGCCTGCTGGAACCTGCGCAGCTTGGATGGATACTCCATGAGAAAAGC<br>CGTGGGTGGAACCAGGAGCCTCCTCCACACCAGCGCTGATGCCCAATAAAGATGCCCACTG<br>AGGAATCATGAAGCTTCCTTTCTGGATTCATTTATTATTTCAATGTGACTTTAATTTTTG<br>GATGGATAAGCCTGTCTATGGTACAAAAATCACAAGGCATTCAAGTGTACAGTGAAAAGTC<br>TCCCTTTCCAGATATTCAAGTCACCTCCTTAAAGGTAGTCAAGATTGTGTTTGAGGTTTC<br>CTTCAGACAGATTCCAGGCGATGTGCAAGTGTATGCACGTGTGCACACACCACACACATAC<br>ACACACACAAGCTTTTTACACAAATGGTAGCATACTTTATATTGGTCTGTATCTTGCTTT<br>TTTTCACCAATATTTCTCAGACATCGGTTCATATTAAGACATAAATTACTTTTTCATTCTT<br>TTATACCGCTGCATAGTATTCCATTGTGTGAGTGTACCATAATGTATTTAACCAGTCTTCT<br>TTTGATATACTATTTTCATCTCTTGTTATTGCATCTGCTGAGTTAATAAATCAAATATATG<br>TCAAAAAAAAAAAAAAAAAAAAAAAAAAAAAAAAAAAAAAA | |
| 33 | MALRVLLLTALTLCHGFNLDTENAMTFQENARGFGQSVVQLQGSRVVVGAPQEIVAANQRG<br>SLYQCDYSTGSCEPIRLQVPVEAVNMSLGLSLAATTSPPQLLACGPTVHQTCSENTYVKGL<br>CFLFGSNLRQQPQKFPEALRGCPQEDSDIAFLIDGSGSIIPHDFRRMKEFVSTVMEQLKKS<br>KTLFSLMQYSEEFRIHFTFKEFQNNPNPRSLVKPITQLLGRTHTATGIRKVVRELFNITNG<br>ARKNAFKILVVITDGEKFGDPLGYEDVIPEADREGVIRYVIGVGDAFRSEKSRQELNTIAS | hCD11b<br>GI: 307148 |

FIGURE 8 cont.

| | | |
|---|---|---|
| | KPPRDHVFQVNNFEALKTIQNQLREKIFAIEGTQTGSSSSFEHEMSQEGFSAAITSNGPLL<br>STVGSYDWAGGVFLYTSKEKSTFINMTRVDSDMNDAYLGYAAAIILRNRVQSLVLGAPRYQ<br>HIGLVAMFRQNTGMWESNANVKGTQIGAYFGASLCSVDVDSNGSTDLVLIGAPHYYEQTRG<br>GQVSVCPLPRGQRARWQCDAVLYGEQGQPWGRFGAALTVLGDVNGDKLTDVAIGAPGEEDN<br>RGAVYLFHGTSGSGISPSHSQRIAGSKLSPRLQYFGQSLSGGQDLTMDGLVDLTVGAQGHV<br>LLLRSQPVLRVKAIMEFNPREVARNVFECNDQVVKGKEAGEVRVCLHVQKSTRDRLREGQI<br>QSVVTYDLALDSGRPHSRAVFNETKNSTRRQTQVLGLTQTCETLKLQLPNCIEDPVSPIVL<br>RLNFSLVGTPLSAFGNLRPVLAEDAQRLFTALFPFEKNCGNDNICQDDLSITFSFMSLDCL<br>VVGGPREFNVTVTVRNDGEDSYRTQVTFFFPLDLSYRKVSTLQNQRSQRSWRLACESASST<br>EVSGALKSTSCSINHPIFPENSEVTFNITFDVDSKASLGNKLLLKANVTSENNMPRTNKTE<br>FQLELPVKYAVYMVVTSHGVSTKYLNFTASENTSRVMQHQYQVSNLGQRSLPISLVFLVPV<br>RLNQTVIWDRPQVTFSENLSSTCHTKERLPSHSDFLAELRKAPVVNCSIAVCQRIQCDIPF<br>FGIQEEFNATLKGNLSFDWYIKTSHNHLLIVSTAEILFNDSVFTLLPGQGAFVRSQTETKV<br>EPFEVPNPLPLIVGSSVGGLLLLALITAALYKLGFFKRQYKDMMSEGGPPGAEPQ | |
| 34 | GAATTCCTGCCACTCTTCCTGCAACGGCCCAGGAGCTCAGAGCTCCACATCTGACCTTCTA<br>GTCATGACCAGGACCAGGGCAGCACTCCTCCTGTTCACAGCCTTAGCAACTTCTCTAGGTT<br>TCAACTTGGACACAGAGGAGCTGACAGCCTTCCGTGTGGACAGCGCTGGGTTTGGAGACAG<br>CGTGGTCCAGTATGCCCAACTCCTCGGGTGGTGGTTGGAGCCCCCCAAAAGATAACAGCTGCC<br>AACCAAACGGGTGGCCTCTACCAGTGTGGCTACAGCACTGGTGCCTGTGAGCCCATCGGCC<br>TGCAGGTGCCCCCGGAGGCCGTGAACATGTCCCTGGGCCTGTCCCTGGCGTCTACCACCAG<br>CCCCTTCCCAGCTGCTGGCCTGCGGCCCCACCGTGCACCACGAGTGCGGGAGGAACATGTAC<br>CTCACCGGACTCTGCTTCCTCCTGGGCCCCACCCAGCTCACCCAGAGGCTCCCGGTGTCCA<br>GGCAGGAGTGCCCAAGACAGGAGCAGGACATTGTGTTCCTGATCGATGGCTCAGGCAGCAT<br>CTCCTCCCCGCAACTTTGCCACGATGATGAACTTCGTGAGAGCTGTGATAAGCCAGTTCCAG<br>AGACCCAGCACCCAGTTTTCCCTGATGCAGTTCTCCAACAAATTCCAAACACACTTCACTT<br>TCGAGGAATTCAGGCGCACGTCAAACCCCCTCAGCCTGTTGGCTTCTGTTCACCAGCTGCA<br>AGGGTTTACATACACGGCCACCGCCATCCAAAATGTCGTGCACCGATTGTTCCATGCCTCA<br>TATGGGGCCCGTAGGGATGCCACCAAAATTCTCATTGTCATCACTGATGGGAAGAAAGAAG<br>GCGACAGCCTGGATTATAAGGATGTCATCCCCATGGCTGATGCAGCAGGCATCATCCGCTA<br>TGCAATTGGGGTTGGATTAGCTTTTCAAAACAGAAATTCTTGGAAAGAATTAAATGACATT<br>GCATCGAAGCCCTCCCAGGAACACATATTTAAAGTGGAGGACTTTGATGCTCTGAAAGATA<br>TTCAAAACCAACTGAAGGAGAAGATCTTTGCCATTGAGGGTACGGAGACCACAAGCAGTAG<br>CTCCTTCGAATTGGAGATGGCACAGGAGGGCTTCAGCGCTGTGTTCACACCTGATGGCCCC<br>GTTCTGGGGGCTGTGGGGAGCTTCACCTGGTCTGGAGGTGCCTTCCTGTACCCCCCAAATA<br>TGAGCCTACCTTCATCAACATGTCTCAGGAGAATGTGGACATGAGGGACTCTTACCTGGG<br>TTACTCCACCGAGCTGGCCCTCTGGAAAGGGGTGCAGAGCCTGGTCCTGGGGGCCCCCCGC<br>TACCAGCACACCGGGAAGCTGTCATCTTCACCCAGGTGTCCAGGCAATGGAGGATGAAGG<br>CCGAAGTCACGGGGACTCAGATCGGCTCCTACTTCGGGGCCTCCCTCTGCTCCGTGGACGT<br>AGACACCGACGGCAGCACCGACCTGGTCCTCATCGGGGCCCCCCATTACTACGAGCAGACC<br>CGAGGGGGCCAGGTGTCTGTGTGTCCCTTGCCCAGGGGGTGGAGAAGGTGGTGGTGTGATG<br>CTGTTCTCTACGGGGAGCAGGGCCACCCCTGGGGTCGCTTTGGGGCGGCTCTGACAGTGCT<br>GGGGGATGTGAATGGGGACAAGCTGACAGACGTGGTCATCGGGGCCCCAGGAGAGGAGGAG<br>AACCGGGGTGCTGTCTACCTGTTTCACGGAGTCTTGGGACCCAGCATCAGCCCCTCCCACA<br>GCCAGCGGATCGCGGGCTCCCAGCTCTCCTCCAGGCTGCAGTATTTTGGGCAGGCACTGAG<br>CGGGGGTCAAGACCTCACCCAGGATGGACTGGTGGACCTGGCTGTGGGGGCCCGGGGCCAG<br>GTGCTCCTGCTCAGGACCAGACCTGTGCTCTGGGTGGGGGTGAGCATGCAGTTCATACCTG<br>CCGAGATCCCCAGGTCTGCGTTTGAGTGTCGGGAGCAGGTGGTCTCTGAGCAGACCCTGGT<br>ACAGTCCAACATCTGCCTTTACATTGACAAACGTTCTAAGAACCTGCTTGGGAGCCGTGAC<br>CTCCAAAGCTCTGTGACCTTGGACCTGGCCCTCGACCCTGGCCGCCTGAGTCCCCGTGCCA<br>CCTTCCAGGAAACAAAGAACCGGAGTCTGAGCCGAGTCCGAGTCCTCGGGCTGAAGGCACA<br>CTGTGAAAACTTCAACCTGCTGCTCCCGAGCTGCGTGGAGGACTCTGTGACCCCCATTACC<br>TTGCGTCTGAACTTCACGCTGGTGGGCAAGCCCCTCCTTGCCTTCAGAAACCTGCGGCCTA<br>TGCTGGCCGCACTGGCTCAGAGATACTTCACGGCCTCCCTACCCTTTGAGAAGAACTGTGG<br>AGCCGACCATATCTGCCAGGACAATCTCGGCATCTCCTTCAGCTTCCCAGGCTTGAAGTCC<br>CTGCTGGTGGGGAGTAACCTGGAGCTGAACGCAGAAGTGATGGTGTGGAATGACGGGGAAG<br>ACTCCTACGGAACCACCATCACCTTCTCCCACCCCGCAGGACTGTCCTACCGCTACGTGGC<br>AGAGGGCCAGAACAAGGGCAGCTGCGTTCCCTGCACCTGACATGTGACAGCGCCCCAGTT<br>GGGAGCCAGGGCACCTGGAGCACCAGCTGCAGAATCAACCACCTCATCTTCCGTGGCGGCG<br>CCCAGATCACCTTCTTGGCTACCTTTGACGTCTCCCCCAAGGCTGTCCTGGGAGACCGGCT<br>GCTTCTGACAGCCAATGTGAGCAGTGAGAACAACACTCCCAGGACCAGCAAGACCACCTTC<br>CAGCTGGAGCTCCCGGTGAAGTATGCTGTCTACACTGTGGTTAGCAGCCACGAACAATTCA<br>CCAAATACCTCAACTTCTCAGAGTCTGAGGAGAAGGAAAGCCATGTGGCCATGCACAGATA | hCD11c<br>GenBank:<br>M81695.1 |

FIGURE 8 cont.

| | | |
|---|---|---|
| | CCAGGTCAATAACCTGGGACAGAGGGACCTGCCTGTCAGCATCAACTTCTGGGTGCCTGTG<br>GAGCTGAACCAGGAGGCTGTGTGGATGGATGTGGAGGTCTCCCACCCCCAGAACCCATCCC<br>TTCGGTGCTCCTCAGAGAAAATCGCACCCCCAGCATCTGACTTCCTGGCGCACATTCAGAA<br>GAATCCCGTGCTGGACTGCTCCATTGCTGGCTGCCTGCGGTTCCGCTGTGACGTCCCCTCC<br>TTCAGCGTCCAGGAGGAGCTGGATTTCACCCTGAAGGGCAACCTCAGCTTTGGCTGGGTCC<br>GCCAGATATTGCAGAAGAAGGTGTCGGTCGTGAGTGTGGCTGAAATTACGTTCGACACATC<br>CGTGTACTCCCAGCTTCCAGGACAGGAGGCATTTATGAGAGCTCAGACGACAACGGTGCTG<br>GAGAAGTACAAGGTCCACAACCCCACCCCCCTCATCGTAGGCAGCTCCATTGGGGGTCTGT<br>TGCTGCTGGCACTCATCACAGCGGTACTGTACAAAGTTGGCTTCTTCAAGCGTCAGTACAA<br>GGAAATGATGGAGGAGGCAAATGGACAAATTGCCCCAGAAAACGGGACACAGACCCCCAGC<br>CCGCCCAGTGAGAAATGATCCCTCTTTGCCTTGGACTTCTTCTCCCGCGATTTTCCCCACT<br>TACTTACCCTCACCTGTCAGGCTGACGGGGAGGAACCACTGCACCACCGAGAGAGGCTGGG<br>ATGGGCCTGCTTCCTGTCTTTGGGAGAAAACGTCTTGCTTGGGAAGGGGCCTTTGTCTTGT<br>CAAGGTTCCAACTGGAAACCCTTAGGACAGGGTCCCTGCTGTGTTCCCCAAAAGGACTTGA<br>CTTGCAATTTCTACCTAGAAATACATGGACAATACCCCCAGGCCTCAGTCTCCCTTCTCCC<br>ATGAGGCACGAATGATCTTTCTTTCCTTTCCTTTTTTTTTTTTTCTTTTCTTTTTTTTTTT<br>TTTTTGAGACGGAGTCTCGCTCTGTCACCCAGGCTGGAGTGCAATGGCGTGATCTCGGCTC<br>GCTGCAACCTCCGCCTCCCGGGTTCAAGTAATTCTGCTGTCTCAGCCTCCTGCGTAGCTGG<br>GACTACAGGCACACGCCACCTCGCCCGGCCCGATCTTTCTAAAATACAGTTCTGAATATGC<br>TGCTCATCCCCACCTGTCTTCAACAGCTCCCCATTACCCTCAGGACAATGTCTGAACTCTC<br>CAGCTTCGCGTGAGAAGTCCCCTTCCATCCCAGAGGGTGGGCTTCAGGGCGCACAGCATGA<br>GAGCCTCTGTGCCCCATCACCCTCGTTTCCAGTGAATTAGTGTCATGTCAGCATCAGCTC<br>AGGGCTTCATCGTGGGGCTCTCAGTTCCGATTCCCCAGGCTGAATTGGGAGTGAGATGCCT<br>GCATGCTGGGTTCTGCACAGCTGGCCTCCCGCGGTTGGGTCAACATTGCTGGCCTGGAAGG<br>GAGGAGCGCCCTCTAGGGAGGGACATGGCCCCGGTGCGGCTGCAGCTCACCAGCCCCAGGG<br>GCAGAAGAGACCCAACCACTTCCTATTTTTTGAGGCTATGAATATAGTACCTGAAAAAATG<br>CCAAGCACTAGATTATTTTTTTAAAAAGCGTACTTTAAATGTTTGTGTTAATACACATTAA<br>AACATCGCACAAAAACGATGCATCTACCGCTCCTTGGGAAATAATCTGAAAGGTCTAAAAA<br>TAAAAAAGCCTTCTGTGG | |
| 35 | MTRTRAALLLFTALATSLGFNLDTEELTAFRVDSAGFGDSVVQYANSWVVVGAPQKITAAN<br>QTGGLYQCGYSTGACEPIGLQVPPEAVNMSLGLSLASTTSPSQLLACGPTVHHECGRNMYL<br>TGLCFLLGPTQLTQRLPVSRQECPRQEQDIVFLIDGSGSISSRNFATMMNFVRAVISQFQR<br>PSTQFSLMQFSNKFQTHFTFEEFRRTSNPLSLLASVHQLQGFTYTATAIQNVVHRLFHASY<br>GARRDATKILIVITDGKKEGDSLDYKDVIPMADAAGIIRYAIGVGLAFQNRNSWKELNDIA<br>SKPSQEHIFKVEDFDALKDIQNQLKEKIFAIEGTETTSSSSFELEMAQEGFSAVFTPDGPV<br>LGAVGSFTWSGGAFLYPPNMSPTFINMSQENVDMRDSYLGYSTELALWKGVQSLVLGAPRY<br>QHTGKAVIFTQVSRQWRMKAEVTGTQIGSYFGASLCSVDVDTGSTDLVLIGAPHYYEQTR<br>GGQVSVCPLPRGWRRWWCDAVLYGEQGHPWGRFGAALTVLGDVNGDKLTDVVIGAPGEEEN<br>RGAVYLFHGVLGPSISPSHSQRIAGSQLSSRLQYFGQALSGGQDLTQDGLVDLAVGARGQV<br>LLLRTRPVLWVGVSMQFIPAEIPRSAFECREQVVSEQTLVQSNICLYIDKRSKNLLGSRDL<br>QSSVTLDLALDPGRLSPRATFQETKNRSLSRVRVLGLKAHCENFNLLLPSCVEDSVTPITL<br>RLNFTLVGKPLLAFRNLRPMLAALAQRYFTASLPFEKNCGADHICQDNLGISFSFPGLKSL<br>LVGSNLELNAEVMVWNDGEDSYGTTITFSHPAGLSYRYVAEGQKQGQLRSLHLTCDSAPVG<br>SQGTWSTSCRINHLIFRGGAQITFLATFDVSPKAVLGDRLLLTANVSSENNTPRTSKTTFQ<br>LELPVKYAVYTVVSSHEQFTKYLNFSESEEKESHVAMHRYQVNNLGQRDLPVSINFWVPVE<br>LNQEAVWMDVEVSHPQNPSLRCSSEKIAPPASDFLAHIQKNPVLDCSIAGCLRFRCDVPSF<br>SVQEELDFTLKGNLSFGWVRQILQKKVSVVSVAEITFDTSVYSQLPGQEAFMRAQTTTVLE<br>KYKVHNPTPLIVGSSIGGLLLLALITAVLYKVGFFKRQYKEMMEEANGQIAPENGTQTPSP<br>PSEK | hCD11c<br>GI: 487830 |
| 36 | CTGTGCTCTGTCCCCAACCTTCCACTTCCCCTCAACGCGCTGCTCAGGGATGACCTTCGGC<br>ACTGTGCTTCTTCTGAGTGTCCTGGCTTCTTATCATGGATTCAACCTGGATGTGGAGGAGC<br>CTACGATCTTCCAGGAGGATGCAGGCGGCTTTGGGCAGAGCGTGGTGCAGTTCGGTGGATC<br>TCGACTCGTGGTGGGAGCACCCCTGGAGGTGGTGGCGGCCAACCAGACGGGACGGCTGTAT<br>GACTGCGCAGCTGCCACCGGCATGTGCCAGCCCATCCCCTGCACATCCGCCCTGAGGCCG<br>TGAACATGTCCTTGGGCCTGACCCTGGCAGCCTCCACCAACGGCTCCCGGCTCCTGGCCTG<br>TGGCCCGACCCTGCACAGAGTCTGTGGGGAGAACTCATACTCAAAGGGTTCCTGCCTCCTG<br>CTGGGCTCGCGCTGGGAGATCATCCAGACAGTCCCCGACGCCACGCCAGAGTGTCCACATC<br>AAGAGATGGACATCGTCTTCCTGATGGCTCTGGAAGCATTGACCAAAATGACTTTAA<br>CCAGATGAAGGGCTTTGTCCAAGCTGTCATGGGCCAGTTTGAGGGCACTGACACCCTGTTT<br>GCACTGATGCAGTACTCAAACCTCCTGAAGATCCACTTCACCTTCACCCAATTCCGGACCA<br>GCCCGAGCCAGCAGAGCCTGGTGGATCCCATCGTCAACTGAAAGGCCTGACGTTCACGGC<br>CACGGGCATCCTGACAGTGGTGACACAGCTATTTCATCATAAGAATGGGGCCCGAAAAAGT | hCD11d<br>NCBI<br>Reference<br>Sequence:<br>NM_005353.<br>2 |

FIGURE 8 cont.

|    | | |
|---|---|---|
| | GCCAAGAAGATCCTCATTGTCATCACAGATGGGCAGAAGTACAAAGACCCCCTGGAATACA<br>GTGATGTCATCCCCCAGGCAGAGAAGGCTGGCATCATCCGCTACGCTATCGGGGTGGGACA<br>CGCTTTCCAGGGACCCACTGCCAGGCAGGAGCTGAATACCATCAGCTCAGCGCCTCCGCAG<br>GACCACGTGTTCAAGGTGGACAACTTTGCAGCCCTTGGCAGCATCCAGAAGCAGCTGCAGG<br>AGAAGATCTATGCAGTTGAGGGAACCCAGTCCAGGGCAAGCAGCTCCTTCCAGCACGAGAT<br>GTCCCAAGAAGGCTTCAGCACAGCCCTCACAATGGATGGCCTCTTCCTGGGGGCTGTGGGG<br>AGCTTTAGCTGGTCTGGAGGTGCCTTCCTGTATCCCCCAAATATGAGCCCCACCTTCATCA<br>ACATGTCTCAGGAGAATGTGGACATGAGGGACTCTTACCTGGGTTACTCCACCGAGCTAGC<br>CCTGTGGAAGGGGGTACAGAACCTGGTCCTGGGGGCCCCCCGCTACCAGCATACCGGGAAG<br>GCTGTCATCTTCACCCAGGTGTCCAGGCAATGGAGGAAGAAGGCCGAAGTCACAGGGACGC<br>AGATCGGCTCCTACTTCGGGGCCTCCCTCTGCTCCGTGGATGTGGACAGCGATGGCAGCAC<br>CGACCTGATCCTCATTGGGGCCCCCCATTACTATGAGCAGACCCGAGGGGGCCAGGTGTCC<br>GTGTGTCCCCTTGCCTAGGGGGAGGGTGCAGTGGCAGTGTGACGCTGTTCTCCGTGGTGAGC<br>AGGGCCACCCCTGGGGCCGCTTTGGGGCAGCCCTGACAGTGTTGGGGGATGTGAATGAGGA<br>CAAGCTGATAGACGTGGCCATTGGGGCCCCGGGAGAGCAGGAGAACCGGGGTGCTGTCTAC<br>CTGTTTCACGGAGCCTCAGAATCCGGCATCAGCCCTCCCACAGCCAGCGGATTGCCAGCT<br>CCCAGCTCTCCCCCAGGCTGCAGTATTTTGGGCAGGCGCTGAGTGGGGGTCAGGACCTCAC<br>CCAGGATGGACTGATGGACCTGGCCGTGGGGGCCCGGGGCCAGGTGCTCCTGCTCAGGAGT<br>CTGCCGGTGCTGAAAGTGGGGGTGGCCATGAGATTCAGCCCTGTGGAGGTGGCCAAGGCTG<br>TGTACCGGTGCTGGGAAGAGAAGCCCAGTGCCCTGGAAGCTGGGGACGCCACCGTCTGTCT<br>CACCATCCAGAAAAGCTCACTGGACCAGCTAGGTGACATCCAAAGCTCTGTCAGGTTTGAT<br>CTGGCACTGGACCCAGGTCGTCTGACTTCTCGTGCCATTTTCAATGAAACCAAGAACCCCA<br>CTTTGACTCGAAGAAAAACCCTGGGACTGGGGATTCACTGTGAAACCCTGAAGCTGCTTTT<br>GCCAGATTGTGTGGAGGATGTGGTGAGCCCCATCATTCTGCACCTCAACTTCTCACTGGTG<br>AGAGAGCCCATCCCCTCCCCCCAGAACCTGCGTCCTGTGCTGGCCGTGGGCTCACAAGACC<br>TCTTCACTGCTTCTCTCCCCTTCGAGAAGAACTGTGGGCAAGATGGCCTCTGTGAAGGGGA<br>CCTGGGTGTCACCCTCAGCTTCTCAGGCCTGCAGACCCTGACCGTGGGGAGCTCCCTGGAG<br>CTCAACGTGATTGTGACTGTGTGGAACGCAGGTGAGGATTCCTACGGAACCGTGGTCAGCC<br>TCTACTATCCAGCAGGGCTGTCGCACCGACGGGTGTCAGGAGCCCAGAAGCAGCCCCATCA<br>GAGTGCCCTGCGCCTGGCATGTGAGACAGTGCCCACTGAGGATGAGGGCCTAAGAAGCAGC<br>CGCTGCAGTGTCAACCACCCCATCTTCCATGAGGGCTCTAACGGCACCTTCATAGTCACAT<br>TCGATGTCTCCTACAAGGCCACCCTGGGAGACAGGATGCTTATGAGGGCCAGTGCAAGCAG<br>TGAGAACAATAAGGCTTCAAGCAGCAAGGCCACCTTCCAGCTGGAGCTCCCGGTGAAGTAT<br>GCAGTCTACACCATGATCAGCAGGCAGGAAGAATCCACCAAGTACTTCAACTTTGCAACCT<br>CCGATGAGAAGAAAATGAAAGAGGCTGAGCATCGATACGTGTGAATAACCTCAGCCAGCG<br>AGATCTGGCCATCAGCATTAACTTCTGGGTTCCTGTCCTGCTGAACGGGTGGCTGTGTGG<br>GATGTGGTCATGGAGGCCCCATCTCAGAGTCTCCCCTGTGTTTCAGAGAGAAAACCTCCCC<br>AGCATTCTGACTTCCTGACCCAGATTTCAAGAAGTCCCATGCTGGACTGCTCCATTGCTGA<br>CTGCCTGCAGTTCCGCTGTGACGTCCCCTCCTTCAGCGTCCAGGAGGAGCTGGATTTCACC<br>CTGAAGGGCAATCTCAGTTTCGGCTGGGTCCGCGAGACATTGCAGAAGAAGGTGTTGGTCG<br>TGAGTGTGGCTGAAATTACGTTGCACACATCCGTGTACTCCCAGCTTCCAGGACAGGAGGC<br>ATTTATGAGAGCTCAGATGGAGATGGTGCTAGAAGAAGACGAGGTCTACAATGCCATTCCC<br>ATCATCATGGGCAGCTCTGTGGGGCTCTGCTACTGCTGGCGCTCATCACAGCCACACTGT<br>ACAAGCTTGGCTTCTTCAAACGCCACTACAAGGAAATGCTGGAGGACAAGCCTGAAGACAC<br>TGCCACATTCAGTGGGGACGATTTCAGCTGTGTGGCCCCAAATGTGCCTTTGTCCTAATAA<br>TCCACTTTCCTGTTTATCTCTACCACTGTGGGCTGGACTTGCTTGCAACCATAAATCAACT<br>TACATGGAAACAACTTCTGCATAGATCTGCACTGGCCTAAGCAACCTACCAGGTGCTAAGC<br>ACCTTCTCGGAGAGATAGAGATTGTAATGTTTTTACATATCTGTCCATCTTTTTCAGCAAT<br>GACCCACTTTTTACAGAAGCAGGCATGGTGCCAGCATAAATTTTCATATGCTTAAGAATTG<br>TCACATGAAATGAGGATGTTTATAGCACACTTTCCTTGCGTGGAAGAGCTATAACCCAGGG<br>ACCTGAGTGCCTCTCTGGGAATAGTCGGGGGAACCTATTTGTGGGCATTGAAAAAGTTTTT<br>TCACTTTC | |
| 37 | MTFGTVLLLSVLASYHGFNLDVEEPTIFQEDAGGFGQSVVQFGGSRLVVGAPLEVVAANQT<br>GRLYDCAAATGMCQPIPLHIRPEAVNMSLGLTLAASTNGSRLLACGPTLHRVCGENSYSKG<br>SCLLLGSRWEIIQTVPDATPECPHQEMDIVFLIDGSGSIDQNDFNQMKGFVQAVMGQFEGT<br>DTLFALMQYSNLLKIHFTFTQFRTSPSQQSLVDPIVQLKGLTFTATGILTVVTQLFHHKNG<br>ARKSAKKILIVITDGQKYKDPLEYSDVIPQAEKAGIIRYAIGVGHAFQGPTARQELNTISS<br>APPQDHVFKVDNFAALGSIQKQLQEKIYAVEGTQSRASSSFQHEMSQEGFSTALTMDGLFL<br>GAVGSFSWSGGAFLYPPNMSPTFINMSQENVDMRDSYLGYSTELALWKGVQNLVLGAPRYQ<br>HTGKAVIFTQVSRQWRKKAEVTGTQIGSYFGASLCSVDVDSDGSTDLILIGAPHYYEQTRG<br>GQVSVCPLPRGRVQWQCDAVLRGEQGHPWGRFGAALTVLGDVNEDKLIDVAIGAPGEQENR<br>GAVYLFHGASESGISPSHSQRIASSQLSPRLQYFGQALSGGQDLTQDGLMDLAVGARGQVL | hCD11d<br>GI: 62548866 |

FIGURE 8 cont.

| | | |
|---|---|---|
| | LLRSLPVLKVGVAMRFSPVEVAKAVYRCWEEKPSALEAGDATVCLTIQKSSLDQLGDIQSS VRFDLALDPGRLTSRAIFNETKNPTLTRRKTLGLGIHCETLKLLLPDCVEDVVSPIILHLN FSLVREPIPSPQNLRPVLAVGSQDLFTASLPFEKNCGQDGLCEGDLGVTLSFSGLQTLTVG SSLELNVIVTVWNAGEDSYGTVVSLYYPAGLSHRRVSGAQKQPHQSALRLACETVPTEDEG LRSSRCSVNHPIFHEGSNGTFIVTFDVSYKATLGDRMLMRASASSENNKASSSKATFQLEL PVKYAVYTMISRQEESTKYFNFATSDEKKMKEAEHRYRVNNLSQRDLAISINFWVPVLLNG VAVWDVVMEAPSQSLPCVSERKPPQHSDFLTQISRSPMLDCSIADCLQFRCDVPSFSVQEE LDFTLKGNLSFGWVRETLQKKVLVVSVAEITFDTSVYSQLPGQEAFMRAQMEMVLEEDEVY NAIPIIMGSSVGALLLLALITATLYKLGFFKRHYKEMLEDKPEDTATFSGDDFSCVAPNVP LS | |
| 38 | TCAGCCTGGAGTCACCTGCTCCTTCTCTCCACAGGACATGCTGGGCCCACACTCACTGCTG CTTGCCCTAGCTGGACTGTTCTTCCTGGGATCTGCTGTGTCCCAGGAATGCACCAAGTACA AAGTCAGCAGTTGCCGGGACTGTATCCAGTCGGGGCCTGGCTGTTCCTGGTGCCAGAAGCT GAACTTCACTGGACCAGGAGAACCTGACTCCTTGCGCTGTGACACACGGGCACAGCTGCTG CTGAAGGGTTGTCCAGCCGATGATATCATGGACCCCAGGAGCATCGCTAATCCTGAGTTCG ACCAACGGGGGCAACGGAAACAGCTATCTCCACAAAAAGTGACACTTTACTTGCGACCAGG ACAGGCTGCCGCATTCAATGTGACTTTCCGGCGGGCAAGGGATACCCCATTGATCTGTAC TACCTCATGGATCTCTCCTACTCCATGCTTGATGACCTCAACAACGTCAAGAAGCTGGGCG GGGACTTGCTGCAGGCCCTCAACGAGATCACCGAGTCTGGCCGCATCGGCTTTGGGTCGTT TGTGGACAAGACGGTGCTGCCTTTTGTTAACACCCATCCTGAGAAGCTGAGGAACCCATGT CCCAACAAGGAGAAGGCCTGCCAGCCCCCATTTGCCTTTCGGCACGTGCTCAAGTTAACCG ACAACTCCAACCAGTTTCAGACAGAGGTCGGCAAGCAACTGATTTCCGGAAACCTGGACGC CCCTGAGGGTGGGCTGGATGCCATAATGCAAGTTGCTGCATGTCCGGAGGAAATTGGCTGG CGCAATGTCACGAGGCTGCTGGTGTTTGCCACAGACGATGGCTTCCACTTTGCTGGTGATG GCAAACTGGGTGCCATCCTGACCCCCAATGATGGCCGCTGCCACCTGGAGGATAACATGTA CAAGAGGAGCAATGAGTTCGACTACCCATCCGTGGGTCAGCTGGCACACAAACTTTCCGAG AGCAACATCCAGCCCATCTTTGCGGTGACAAAGAAGATGGTGAAAACGTATGAGAAACTCA CGGAGATCATCCCCAAGTCAGCAGTGGGGGAACTGTCTGACGACTCCAGCAACGTGGTGCA GCTCATCAAGAATGCCTACTATAAACTCTCCTCTAGAGTCTTCCTGGACCACAGCACCCTC CCGGACACCCTGAAAGTCACCTATGACTCCTTCTGCAGTAATGGAGCATCGAGTATAGGCA AATCCCGTGGGGACTGTGATGGCGTACAGATCAACAACCCGGTCACCTTCCAGGTAAAGGT CATGGCTTCCGAGTGTATCCAGGAGCAGTCCTTTGTCATCCGGGCACTGGGTTTCACGGAT ACAGTGACCGTGCAGGTCCGTCCCCAGTGTGAGTGTCAGTGCCGGGACCAGAGTCGGGAGC AGAGTCTCTGTGGAGGCAAGGGAGTCATGGAGTGTGGTATCTGCAGGTGTGAGTCTGGCTA CATTGGGAAAAACTGTGAGTGCCAGACTCAGGGTCGGAGCAGCCAGGAGCTGGAGAGAAAC TGTCGGAAGGACAATAGTTCCATCGTGTGCTCAGGGCTTGGGGACTGCATCTGTGGGCAGT GTGTATGCCATACCAGTGACGTCCCCAACAAAGAGATCTTTGGGCAATACTGCGAGTGTGA CAATGTCAACTGTGAGAGATATAACAGCCAAGTCTGCGGTGGCTCAGATCGGGGTTCCTGC AACTGTGGCAAATGTAGTTGCAAGCCCGGTTACGAGGGCTCGGCCTGCCAGTGTCAGAGGT CCACCACGGGCTGTCTGAATGCACGGCTGGTAGAGTGCAGTGGCCGTGGCCACTGCCAATG CAACAGGTGCATATGTGACGAAGGCTACCAGCCACCGATGTGTGAGGATTGTCCCAGCTGT GGCTCGCACTGCAGGGACAACCACACCTCTTGTGCCGAGTGCCTGAAGTTTGATAAGGGCC CTTTTGAGAAGAACTGTAGTGTTCAGTGTGCTGGTATGACGCTGCAGACTATCCCTTTGAA GAAAAAGCCCTGCAAGGAGAGGGACTCGGAAGGCTGTTGGATAACTTACACTTTGCAGCAG AAGGACGGAAGGAACATTTACAACATCCATGGAGGACAGTCTAGAGTGTGTGAAGGGCC CCAATGTGGCTGCCATCGTAGGGGCACCGTGGTAGGTGTCGTACTGATTGGTGTCCTCCT CCTGGTCATCTGGAAGGCCCTGACCCACCTGACTGACCTCAGGGAGTACAGGCGCTTTGAG AAGGAGAAACTCAAGTCCCAATGGAACAATGACAACCCCCTCTTCAAGAGTGCTACGACAA CGGTCATGAACCCCAAGTTTGCTGAAAGCTAGAGCATGAGTTATCATAATCAAGCAGATGT GACCCCCTCAGACCACGCCTCCTCCCCTCTGCAAACACA | mCD18 GenBank: BC145644.1 |
| 39 | MLGPHSLLLALAGLFFLGSAVSQECTKYKVSSCRDCIQSGPGCSWCQKLNFTGPGEPDSLR CDTRAQLLLKGCPADDIMDPRSIANPEFDQRGQRKQLSPQKVTLYLRPGQAAAFNVTFRRA KGYPIDLYYLMDLSYSMLDDLNNVKKLGGDLLQALNEITESGRIGFGSFVDKTVLPFVNTH PEKLRNPCPNKEKACQPPFAFRHVLKLTDNSNQFQTEVGKQLISGNLDAPEGGLDAIMQVA ACPEEIGWRNVTRLLVFATDDGFHFAGDGKLGAILTPNDGRCHLEDNMYKRSNEFDYPSVG QLAHKLSESNIQPIFAVTKKMVKTYEKLTEIIPKSAVGELSDDSSNVVQLIKNAYYKLSSR VFLDHSTLPDTLKVTYDSFCSNGASSIGKSRGDCDGVQINNPVTFQVKVMASECIQEQSFV IRALGFTDTVTVQVRPQCECQCRDQSREQSLCGGKGVMECGICRCESGYIGKNCECQTQGR SSQELERNCRKDNSSIVCSGLGDCICGQCVCHTSDVPNKEIFGQYCECDNVNCERYNSQVC GGSDRGSCNCGKCSCKPGYEGSACQCQRSTTGCLNARLVECSGRGHCQCNRCICDEGYQPP MCEDCPSCGSHCRDNHTSCAECLKFDKGPFEKNCSVQCAGMTLQTIPLKKKPCKERDSEGC | mCD18 GI: 148877486 |

FIGURE 8 cont.

| | | |
|---|---|---|
| | WITYTLQQKDGRNIYNIHVEDSLECVKGPNVAAIVGGTVVGVVLIGVLLLVIWKALTHLTD LREYRRFEKEKLKSQWNNDNPLFKSATTTVMNPKFAES | |
| 40 | CCTAAGCGCAGATGAGTTTCCGGATTGCGGGCCCCAGACTTTTGCTACTGGGACTCCAGCT GTTTGCCAAGGCCTGGAGCTACAACCTGGACACACGGCCTACGCAGAGCTTCTTGGCACAA GCTGGAAGACATTTTGGGTACCAGGTCTTGCAGATTGAAGATGGGGTTGTCGTGGGAGCCC CAGGTGAGGGGGACAACACGGGAGGCCTCTATCACTGCCGAACAAGCAGCGAGTTCTGCCA GCCAGTCAGCCTACATGGTTCTAACCATACCTCCAAGTACTTGGGAATGACGCTGGCAACA GATGCCGCCAAGGGAAGCCTTTTGGCCTGTGACCCTGGACTGTCTCGGACATGCGATCAGA ACACTTACCTCAGTGGCCTCTGCTACCTCTTCCCCCAGAGTCTGGAGGGACCTATGTTACA AAATCGTCCCGCCTATCAGGAATGTATGAAGGGCAAAGTCGACCTGGTGTTTCTGTTCGAT GGCTCACAGAGCTTGGATAGAAAGGACTTTGAAAAAATCCTGGAATTCATGAAGGATGTGA TGAGGAAGCTCAGCAATACTTCCTACCAGTTTGCTGCCGTCCAGTTCTCCACAGACTGCAG AACAGAATTTACTTTCTTGGACTACGTTAAGCAGAACAAGAACCCCGATGTTCTGCTAGGC AGCGTGCAGCCCATGTTCTTGCTGACCAATACCTTTCGTGCCATCAACTATGTGGTGGCAC ACGTGTTCAAAGAAGAGTCTGGTGCCAGGCCTGATGCTACCAAGGTGCTTGTCATCATTAC AGACGGGGAGGCAAGTGATAAAGGCAACATCAGTGCGGCCCACGACATAACCCGCTACATC ATCGGGATTGGCAAGCATTTTGTGAGCGTACAAAAGCAAAAGACGCTCCACATATTTGCCT CAGAACCTGTAGAGGAATTTGTGAAGATTCTGGACACCTTTGAGAAGCTGAAGGATCTTTT TACTGACCTGCAGAGGAGGATTTATGCTATTGAGGGCACAAACAGACAGGACCTGACATCC TTTAACATGGAACTCTCCTCCAGCGGGATCAGCGCAGACCTCAGCAAGGGCCATGCAGTTG TGGGAGCTGTTGGGGCTAAGGATTGGGCCGGGGGCTTTCTGGACCTGCGTGAAGACCTGCA GGGTGCCACATTTGTTGGGCAGGAACCGCTGACCTCAGATGTGAGAGGGGGCTACCTGGGT TACACTGTGGCCTGGATGACCTCCCGGAGCTCCAGACCCCTGCTGGCAGCAGGAGCCCCAC GGTACCAGCATGTGGGACAAGTACTGCTTTTCCAAGCCCCAGAGGCTGGAGGACGTTGGAA CCAAACCCAGAAGATAGAAGGGACTCAGATCGGATCTTACTTTGGTGGGGAACTATGTAGT GTTGACCTGGACCAAGATGGCGAGGCAGAGCTGCTGCTGATTGGAGCACCCTGTTCTTTG GGGAGCAGAGAGGAGGCCGAGTGTTCACTTACCAGAGAAGACAGTCGCTGTTTGAAATGGT CTCAGAGCTACAGGGTGACCCTGGCTACCCGCTTGGTCGGTTTGGAGCCGCCATAACTGCC CTGACGGACATCAATGGGATAGGCTGACTGATGTGGCTGTGGGAGCCCCTTTGGAGGAGC AGGGTGCTGTGTACATCTTCAATGGGAAGCTGGTGGGCTCAGTCCCCAGCCAAGCCAGCG TATACAAGGAGCCCAGGTGTTCCCAGGAATCCGGTGGTTTGGCCGCTCCATCCATGGGGTG AAGGACCTTGGAGGGGACAGGCTGGCAAATGTGGTTGTAGGACCTGAGGGTCGGGTGGTTG TGCTGAGCTCCAGGCCGGTGGTGGATGTGGTCACTGAGCTGTCGTTCTCCCCAGAGGAAAT CCCAGTGCACGAGGTGGAGTGCTCCTACTCAGCCAGGGAGGAGCAGAAACACGGAGTCAAG CTCAAGGCATGCTTCCGGATCAAGCCCCTCACGCCACAGTTTCAAGGTCGCCTGCTTGCCA ACCTCAGCTACACCCTGCAGCTGGATGGCCATCGGATGAGGAGCCGAGGGTTGTTCCCAGA TGGAAGCCACGAGCTCAGTGGAAACACCTCCATCACCCCAGATAAATCCTGCTTGGACTTC CACTTCCACTTCCCGATCTGCATTCAAGACCTCATCTCCCCTATCAATGTCTCCCTGAATT TCTCTCTTTTGGAGGAAGAAGGAACACCAAGGGACCAAAAGGGCAGGGCCATGCAGCCTAT CCTGAGACCTTCAATCCACACAGTGACTAAGGAGATCCCTTTTTGAGAAGAAACTGTGGTGAA GATAAGAAGTGTGAGGCAAACCTGACCCTGTCATCCCCTGCCAGATCTGGACCCCTGCGTC TGATGTCCTCTGCCAGCCTTGCTGTGGAGTGGACACTGAGCAACTCAGGGGAAGATGCCTA CTGGGTGCGATTAGACCTGGACTTCCCTCGGGGACTCTCCTTCCGGAAAGTGGAGATGCTT CAGCCACACAGCCGAATGCCTGTGAGCTGCGAGGAGCTCACCGAGGGGTCAAGTCTCCTGA CTAAGACACTGAAATGCAATGTAAGCTCTCCCATCTTCAAAGCAGGCCAGGAGGTGAGCCT CCAGGTGATGTTTAACACGCTACTCAACAGCTCCTGGGAAGACTTCGTCGAGCTGAATGGC ACTGTGCACTGTGAGAATGAGAACTCAAGCCTCCAGGAGGACAACTCAGCCGCCACCCACA TTCCTGTCCTGTACCCTGTCAACATCCTTACTAAGGAGCAGGAGAACTCCACCCTCTATAT CAGTTTCACCCCTAAAGGTCCCAAGACCCAACAAGTCCAGCATGTCTACCAGGTGAGGATT CAGCCATCTGCCTATGACCACAACATGCCCACACTAGAGGCCTTGGTTGGGGTGCCCCGGC CTCACAGTGAGGACCTCATCACATACACATGGAGTGTACAAGGCGGATCCCCTTGTCACTTG CCACAGCGAGGACCTGAAGAGGCCGTCCAGCGAAGCTGAGCCTTGTCTGCCTGGAGTCCAG TTCCGCTGTCCAATTGTCTTCAGGTGGGAGATCCTCATCCAAGTGACGGGGACCGTGGAAC TCTCCAAGGAAATCAAGGCCTCCTCCACACTCAGCCTCTGCAGCTCACTCTCCGTCTCCTT CAACAGCAGCAAGCATTTCCATTTGTATGGCAGCAAAGCCTCTGAGGCCCAGGTCCTCGTG AAGGTTGACCTGATCCACGAGAAGGAGATGCTTCACGTGTACGTGCTCAGCGGCATTGGGG GCCTCGTGCTTCTGTTCCTGATTTTCCTGGCGCTCTACAAGGTTGGCTTCTTCAAACGGAA CCTGAAGGAGAAGATGGAGGCTGATGGAGGTGTTCCAAATGGAAGCCCTCCAGAAGACACT GACCCTCTGGCCAGTACCTGGGGAAGAGACCAAAGATATGGGCTGTCTAGAGCCCCTCCGGG AGAGTGACAAGGACTAAGGCCTAGGTCTGATACACTGACAGCCCAGGAATAGACTTGAGAG CCCTGGCTCTGACCAGCTTCAGTCACATGCCAC | mCD11a<br>GenBank:<br>AF065901.1 |

FIGURE 8 cont.

| 41 | MSFRIAGPRLLLLGLQLFAKAWSYNLDTRPTQSFLAQAGRHFGYQVLQIEDGVVVGAPGEG
DNTGGLYHCRTSSEFCQPVSLHGSNHTSKYLGMTLATDAAKGSLLACDPGLSRTCDQNTYL
SGLCYLFPQSLEGPMLQNRPAYQECMKGKVDLVFLFDGSQSLDRKDFEKILEFMKDVMRKL
SNTSYQFAAVQFSTDCRTEFTFLDYVKQNKNPDVLLGSVQPMFLLTNTFRAINYVVAHVFK
EESGARPDATKVLVIITDGEASDKGNISAAHDITRYIIGIGKHFVSVQKQKTLHIFASEPV
EEFVKILDTFEKLKDLFTDLQRRIYAIEGTNRQDLTSFNMELSSSGISADLSKGHAVVGAV
GAKDWAGGFLDLREDLQGATFVGQEPLTSDVRGGYLGYTVAWMTSRSSRPLLAAGAPRYQH
VGQVLLFQAPEAGGRWNQTQKIEGTQIGSYFGGELCSVDLDQDGEAELLLIGAPLFFGEQR
GGRVFTYQRRQSLFEMVSELQGDPGYPLGRFGAAITALTDINGDRLTDVAVGAPLEEQGAV
YIFNGKPGGLSPQPSQRIQGAQVFPGIRWFGRSIHGVKDLGGDRLANVVVGPEGRVVVLSS
RPVVDVVTELSFSPEEIPVHEVECSYSAREEQKHGVKLKACFRIKPLTPQFQGRLLANLSY
TLQLDGHRMRSRGLFPDGSHELSGNTSITPDKSCLDFHFHFPICIQDLISPINVSLNFSLL
EEEGTPRDQKGRAMQPILRPSIHTVTKEIPFEKNCGEDKKCEANLTLSSPARSGPLRLMSS
ASLAVEWTLSNSGEDAYWVRLDLDFPRGLSFRKVEMLQPHSRMPVSCEELTEGSSLLTKTL
KCNVSSPIFKAGQEVSLQVMFNTLLNSSWEDFVELNGTVHCENENSSLQEDNSAATHIPVL
YPVNILTKEQENSTLYISFTPKGPKTQQVQHVYQVRIQPSAYDHNMPTLEALVGVPRPHSE
DLITYTWSVQTDPLVTCHSEDLKRPSSEAEPCLPGVQFRCPIVFRWEILIQVTGTVELSKE
IKASSTLSLCSSLSVSFNSSKHFHLYGSKASEAQVLVKVDLIHEKEMLHVYVLSGIGGLVL
LFLIFLALYKVGFFKRNLKEKMEADGGVPNGSPPEDTDPLAVPGEETKDMGCLEPLRESDK
D | mCD11a
GI: 4587848 |
| 42 | ATGCTGGGCCTGCGCCCCTCACTGCTGCTTGCCCTAGCTGGACTGTTCTTCCTGGGATCTG
CTGTGTCCCAGGAATGCACCAAGTACAAAGTCAGCAGTTGCCGGGACTGTATCCAGTCGGG
GCCTGGCTGTTCCTGGTGCCAGAAGCTGAACTTCACTGGACCAGGAGAACCTGACTCCTTG
CGCTGTGACACACGGGCACAGCTGCTGCTGAAGGGTGTCCAGCCGATGATATCATGGACC
CCAGGAGCATCGCTAATCCTGAGTTCGACCAACGGGGGCAACGGAAACAGCTATCTCCACA
AAAAGTGACACTTTACTTGCGACCAGGACAGGCTGCCGCATTCAATGTGACTTTCCGGCGG
GCCAAGGGATACCCCATTGATCTGTACTACCTCATGGATCTCTCCTACTCCATGCTTGATG
ACCTCAACAACGTCAAGAAGCTGGGCGGGGACTTGCTGCAGGCCCTCAACGAGATCACCGA
GTCTGGCCGCATCGGCTTTGGGTCGTTTGTGGACAAGACGGTGCTGCCTTTTGTTAACACC
CATCCTGAGAAGCTGAGGAACCCATGTCCCAACAAGGAGAAGGCCTGCCAGCCCCCATTTG
CCTTTCGGCACGTGCTCAAGTTAACCGACAACTCCAACCAGTTTCAGACAGAGGTCGGCAA
GCAACTGATTTCCGGAAACCTGGACGCCCCTGAGGGTGGGCTGGATGCCATAATGCAAGTT
GCTGCATGTCCGGAGGAAATTGGCTGGCGCAATGTCACGAGGCTGCTGGTGTTTGCCACAG
ACGATGGCTTCCACTTTGCTGGTGATGGCAAACTGGGTGCCATCCTGACCCCCAATGATGG
CCGCTGCCACCTGGAGGATAACATGTACAAGAGGAGCAATGAGTTCGACTACCCATCCGTG
GGTCAGCTGGCACACAAACTTTCCGAGAGCAACATCCAGCCCATCTTTGCGGTGACAAAGA
AGATGGTGAAAACGTATGAGAAACTCACGGAGATCATCCCCAAGTCAGCAGTGGGGAACT
GTCTGACGACTCCAGCAACGTGGTGCAGCTCATCAAGAATGCCTACTATAAACTCTCCTCT
AGAGTCTTCCTGGACCACAGCACCCTCCCGGACACCCTGAAAGTCACCTATGACTCCTTCT
GCAGTAATGGAGCATCGAGTATAGGCAAATCCCGTGGGGACTGTGATGGCGTACAGATCAA
CAACCCGGTCACCTTCCAGGTAAAGGTCATGGCTTCCGAGTGTATCCAGGAGCAGTCCTTT
GTCATCCGGGCACTGGGTTTCACGGATACAGTGACCGTGCAGGTCCGTCCCCAGTGTGAGT
GTCACTGCCGGGACCAGAGTCGGGAGCAGAGTCTCTGTGGAGGCAAGGGAGTCATGGAGTG
TGGTATCTGCAGGTGTGAGTCTGGCTACATTGGGAAAAACTGTGAGTGCCAGACTCAGGGT
CGGAGCAGCCAGGAGCTGGAGAGAAACTGTCGGAAGGACAATAGTTCCATCGTGTGCTCAG
GGCTTGGGGACTGCATCTGTGGGCAGTGTGTATGCCATACCAGTGACGTCCCCAACAAAGA
GATCTTTGGGCAATACTGCGAGTGTGACAATGCTAACTGTGAGAGATATAACAGCCAAGTC
TGCGGTGGCTCAGATCGGGGTTCCTGCAACTGTGGCAAATGTAGTTGCAAGCCCGGTTACG
AGGGCTCGGCCTGCCAGTGTCAGAGGTCCACCACGGGCTGTCTGAATGCACGGCTGGTAGA
GTGCAGTGGCCGTGCCACTGCCAATGCAACAGGTGCATATGTGACGAAGGCTACCAGCCA
CCGATGTGTGAGGATTGTCCCAGCTGTGGCTCGCACTGCAGGGACAACCACACCTCTTGTG
CCGAGTGCCTGAAGTTTGATAAGGGCCCTTTTGAGAAGAACTGTAGTGTTCAGTGTGCTGG
TATGACGCTGCAGACTATCCCTTTGAAGAAAAGCCCTGCAAGGAGAAGGACTCGGAAGGC
TGTTGGATAACTTACACTTTGCAGCAGAAGGACGGAAGGAACATTTACAACATCCATGTGG
AGGACAGTCTAGAGTGTGTGAAGGGCCCCAATGTGGCTGCCATCGTAGGGGGCACCGTGGT
AGGTGTCGTACTGATTGGTGTCCTCCTCCTGGTCATCTGGAAGGCCCTGACCCACCTGACT
GACCTCAGGGAGTACAGGCGCTTTGAGAAGGAGAAACTCAAGTCCCAATGGAACAATGACA
ACCCCCTCTTCAAGAGTGCTACGACAACGGTCATGAACCCCAAGTTTGCTGAAAGCTAGAG
CATGAGTTATCATAATCAAGCAGATGTGACCCCCTCAGACCACGCCTCCTCCCCTCTGCAA
ACACAACGTGGCTTACAGCTCACCCCAGTGCTGCCAAGGATCCAAAAGCCTGCTCGGTTTC
TTNCCGCCATTATATCAAG | mCD11b
GenBank:
M31039.1 |

FIGURE 8 cont.

| 43 | MLGLRPSLLLALAGLFFLGSAVSQECTKYKVSSCRDCIQSGPGCSWCQKLNFTGPGEPDSL<br>RCDTRAQLLLKGCPADDIMDPRSIANPEFDQRGQRKQLSPQKVTLYLRPGQAAAFNVTFRR<br>AKGYPIDLYYLMDLSYSMLDDLNNVKKLGGDLLQALNEITESGRIGFGSFVDKTVLPFVNT<br>HPEKLRNPCPNKEKACQPPFAFRHVLKLTDNSNQFQTEVGKQLISGNLDAPEGGLDAIMQV<br>AACPEEIGWRNVTRLLVFATDDGFHFAGDGKLGAILTPNDGRCHLEDNMYKRSNEFDYPSV<br>GQLAHKLSESNIQPIFAVTKKMVKTYEKLTEIIPKSAVGELSDDSSNVVQLIKNAYYKLSS<br>RVFLDHSTLPDTLKVTYDSFCSNGASSIGKSRGDCDGVQINNPVTFQVKVMASECIQEQSF<br>VIRALGFTDTVTVQVRPQCECHCRDQSREQSLCGGKGVMECGICRCESGYIGKNCECQTQG<br>RSSQELERNCRKDNSSIVCSGLGDCICGQCVCHTSDVPNKEIFGQYCECDNVNCERYNSQV<br>CGGSDRGSCNCGKCSCKPGYEGSACQCQRSTTGCLNARLVECSGRGHCQCNRCICDEGYQP<br>PMCEDCPSCGSHCRDNHTSCAECLKFDKGPFEKNCSVQCAGMTLQTIPLKKKPCKEKDSEG<br>CWITYTLQQKDGRNIYNIHVEDSLECVKGPNVAAIVGGTVVGVVLIGVLLLVIWKALTHLT<br>DLREYRRFEKEKLKSQWNNDNPLFKSATTTVMNPKFAES | mCD11b<br>GI: 198435 |
|---|---|---|
| 44 | GCAGCTGTCTCCAAGTTGCTCAGAGCCTGCTTCTGTTCTCCAGTCATGAGCTGTACCTGGA<br>TAGCCTTTCTTCTGCTGTTGGGGTTTGTTTCTTGTCTTGGCTTCAACTTGGATGCAGAGAA<br>GCCGACACATTTTCACATGGACGGTGCTGAGTTCGGACACAGTGTGCTCCAGTATGATAGT<br>TCCTGGGTGGTGGTTGGAGCACCAAAGGAAATAAAAGCCACTAACCAAATAGGTGGCCTCT<br>ACAAATGTGGCTATCACACAGGCAACTGTGAGCCCATCTTCCTCCAGGTGCCCCCAGAGGC<br>TGTGAACATGTCCCTGGGCCTGTCCCTTGCTGCTGCCACCAACCCTTCCTGGCTGTTGGCT<br>TGTGGTCCTACTGTGCACCACACATGCAGAGAGAATATATACTTGACAGGGCTCTGCTTTC<br>TACTGAGTTCATCATTCAAGCAGAGCCAGAACTTCCCAACTGCACAGCAGGAGTGTCCAA<br>GCAAGACCAAGACATCGTGTTCCTGATTGATGGCTCGGGTAGCATCAGTTCCACAGATTTT<br>GAAAAAATGCTGGACTTTGTTAAAGCTGTGATGAGCCAGCTTCAGAGACCTAGCACACGGT<br>TCTCCCTGATGCAGTTCTCTGATTACTTCCGAGTACATTTTACTTTCAACAACTTCATCTC<br>CACGTCAAGCCCTTTAAGTCTGTTGGATTCTGTAAGGCAGCTAAGAGGGTACACATACACA<br>GCCTCGGCTATCAAGCATGTCATAACAGAACTGTTCACCACCCAAAGTGGAGCTCGGCAAG<br>ATGCCACCAAGGTCCTCATTGTCACTGATGGGAGAAAACAAGGGGACAACTTGAGTTA<br>TGATAGTGTCATCCCCATGGCAGAGGCTGCAAGCATCATTCGTTATGCAATTGGGGTAGGA<br>CACAAAGATGGTTTCCCACCACTTCCTCCTGTAACTTCCTCTTGAAGCAACTTCCTCTAAA<br>GGTAGAAAGCACTTTTCTCATCTCCTGCTGCCTTAGATATATGGAACCAGGGGAGGCTCCT<br>TCAGCCTGGGAACCTGTGACCCAATTGCTTCAACTCCCTAATGTTATTTGAGCCTCATTTA<br>GAAAGAATCTCCAAGGCTGATTGAAGAGTTTTGGGTGACAGTGTAGGTGATACCTTAGCCA<br>TGTTTGCCTCATTGTAGTAAAAGCATCCAACATAAAAAAAAAAAAAAA | mCD11c<br>GenBank:<br>BC057200.1 |
| 45 | MSCTWIAFLLLLGFVSCLGFNLDAEKPTHFHMDGAEFGHSVLQYDSSWVVVGAPKEIKATN<br>QIGGLYKCGYHTGNCEPIFLQVPPEAVNMSLGLSLAAATNPSWLLACGPTVHHTCRENIYL<br>TGLCFLLSSSFKQSQNFPTAQQECPKQDQDIVFLIDGSGSISSTDFEKMLDFVKAVMSQLQ<br>RPSTRFSLMQFSDYFRVHFTFNNFISTSSPLSLLDSVRQLRGYTYTASAIKHVITELFTTQ<br>SGARQDATKVLIVITDGRKQGDNLSYDSVIPMAEAASIIRYAIGVGHKDGFPPLPPVTSS | mCD11c<br>GI: 34980918 |
| 46 | GCAGGCTCTACAGCTCTCTACTTCCTAATGCACTGCTCAGCTATGGTCCGTGGAGTTGTGA<br>TCCTCCTGTGTGGCTGGGCCCTGGCTTCCTGTCATGGGTCTAACCTGGATGTGGAGAAGCC<br>CGTCGTGTTCAAAGAGGATGCAGCCAGCTTCGGACAGACTGTGGTGCAGTTTGGTGGATCT<br>CGACTCGTGGTGGGAGCCCCTCTGGAGGCGGTGGCAGTCAACCAAACAGGACAGTTGTATG<br>ACTGTGCGCCTGCCACTGGCGTGTGCCAGCCCATCTTACTGCACATTCCCCTAGAGGCAGT<br>GAACATGTCCCTGGGCCTGTCTCTGGTGGCTGACACCAATAACTCCCAGTTGCTGGCTTGT<br>GGTCCAACTGCACAGAGAGCTTGTGCAAAGAACATGTATGCAAAAGGTTCCTGCCTCCTTC<br>TGGGCTCCAGCTTGCAGTTCATCCAGGCAATCCCTGCTACCATGCCAGAGTGTCCAGGACA<br>AGAGATGGACATTGCTTTCCTGATTGATGGCTCCGGCAGCATTGATCAAAGTGACTTTACC<br>CAGATGAAGGACTTCGTCAAAGCTTTGATGGGCCAGTTGGCGAGCACCAGCACCTCGTTCT<br>CCCTGATGCAATACTCAAACATCCTGAAGACTCATTTTACCTTCACGGAATTCAAGAGCAG<br>CCTGAGCCCTCAGAGCCTGGTGGATGCCATCGTCCAGCTCCAAGGCCTGACTACACAGCC<br>TCGGGCATCCAGAAAGTGGTAGACAGCAACAGGCTCCTTCTTCTACGTGTCTGGTCAGCAC<br>TGAAGCCAGGTTGCCACTACAACACTCACATGCCATGGTGGGTCTGGCAGAGGGTACGGTT<br>CTCCTGGAAAGAGCTATTTCATAGCAAGAATGGGCCGAAAAGTGCCAAGAAGATACTA<br>ATTGTCATCACAGATGGGCAGAAATTCAGAGACCCCTGGAGTATAGACATGTCATCCCTG<br>AAGCAGAGAAAGCTGGGATCATTCGCTATGCTATAGGGGTGGGAGATGCCTTCCGGGAACC<br>CACTGCCCTACAGGAGCTGAACACCATTGGCTCAGCTCCCTCGCAGGACCACGTGTTCAAG<br>GTGGGCAATTTTGTAGCACTTCGCAGCATCCAGCGGCAAATTCAGGAGAAAATCTTTGCCA<br>TTGAAGGAACCGAATCAAGGTCAAGTAGTTCCTTTCAGCACGAGATGTCACAAGAAGGTTT<br>CAGCTCAGCTCTCTCAATGGATGGACCAGTTCTGGGGGCTGTGGGAAGCTTCAGCTGCTCT<br>GGAGGTGCCTTCTTGTACCCCTCAAATATGAGATCCACCTTCATCAACATGTCTCAGGAGA<br>ACGAGGATATGAGGGACGCTTACCTGGGTTACTCCACCGCACTGGCCTTTTGGAAGGGGGT<br>CCACAGCCTGATCCTGGGGGCCCCTCGCCACCAGCACACGGGGAAGGTTGTCATCTTTACC | mCD11d<br>NCBI<br>Reference<br>Sequence:<br>NM_0010298<br>72.3 |

FIGURE 8 cont.

| | | |
|---|---|---|
| | CAGGAATCCAGGCACTGGAGGCCCAAGTCTGAAGTCAGAGGGACACAGATCGGCTCCTACT<br>TTGGGGCATCTCTCTGTTCTGTGGACATGGATAGAGATGGCAGCACTGACCTGGTCCTGAT<br>TGGAGTCCCCCATTACTATGAGCACACCCGAGGGGGGCAGGTGTCGGTGTGCCCCATGCCT<br>GGTGTGAGGAGCAGGTGGCATTGTGGGACCCATCCTCCATGGGGAGCAGGGCCATCCTTGGG<br>GCCGCTTTGGGGCGGCTCTGACAGTGCTAGGGGACGTGAATGGGGACAGTCTGGCGGATGT<br>GGCTATTGGTGCACCCGGAGAGGAGGAGAACAGAGGTGCTGTCTACATATTTCATGGAGCC<br>TCGAGACAGGACATCGCTCCCTCGCCTAGCCAGCGGGTCACTGGCTCCCAGCTCTTCCTGA<br>GGCTCCAATATTTTGGGCAGTCATTAAGTGGGGGTCAGGACCTTACACAGGATGGCCTGGT<br>GGACCTGGCCGTGGGAGCCCAGGGGCACGTGCTGCTGCTTAGGAGTCTGCCTTTGCTGAAA<br>GTGGGGATCTCCATTAGATTTGCCCCCTCAGAGGTGGCAAAGACTGTGTACCAGTGCTGGG<br>GAAGGACTCCCACTGTCCTCGAAGCTGGAGAGGCCACCGTCTGTCTCACTGTCCGCAAAGG<br>TTCACCTGACCTGTTAGGTGATGTCCAAAGCTCTGTCAGGTATGATCTGGCGTTGGATCCG<br>GGCCGTCTGATTTCTCGTGCCATTTTTGATGAGACGAAGAACTGCACTTTGACCCGAAGGA<br>AGACTCTGGGGCTTGGTGATCACTGCGAAACAATGAAGCTGCTTTTGCCAGACTGTGTGGA<br>GGATGCAGTGACCCCTATCATCCTGCGCCTTAACTTATCCCTGGCAGGGGACTCTGCTCCA<br>TCCAGGAACCTTCGTCCTGTGCTGGCTGTGGGCTCACAAGACCATGTAACAGCTTCTTTCC<br>CGTTTGAGAAGAACTGTAAGCAGGAGCTCCTGTGTGAGGGAACCTGGGCGTCAGCTTCAA<br>CTTCTCAGGCCTGCAGGTCTTGGAGGTAGGAAGCTCCCCAGAGCTCACTGTGACAGTAACA<br>GTTTGGAATGAGGGTGAGGACAGCTATGGAACCTTAATCAAGTTCTACTACCCAGCAGAGC<br>TATCTTACCGACGGGTGACAAGAGCCCAGCAACCTCATCCGTACCCACTACGCCTGGCATG<br>TGAGGCTGAGCCCACGGGCCAGGAGAGCCTGAGGAGCAGCAGCTGTAGCATCAATCACCCC<br>ATCTTCCGAGAAGGTGCCAAGGCCACCTTCATGATCACATTTGATGTCTCCTACAAGGCCT<br>TCCTGGGAGACAGGTTGCTTCTGAGGGCCAGCGCAAGCAGTGAGAATAATAAGCCTGAAAC<br>CAGCAAGACTGCCTTCCAGCTGGAGCTTCCGGTGAAGTACACGGTCTATACCGTGATCAGT<br>AGGCAGGAAGATTCTACCAAGCATTTCAACTTCTCATCTTCCCACGGGGAGAGACAGAAAG<br>AGGCCGAACATCGATATCGTGTGAATAACCTGAGTCCATTGACGCTGGCCATCAGCGTTAA<br>CTTCTGGGTCCCCATCCTTCTGAATGGTGTGGCCGTGTGGGATGTGACTCTGAGGAGCCCA<br>GCACAGGGTGTCTCCTGTGTGTCACAGAGGGAACCTCCTCAACATTCCGACCTTCTGACCC<br>AGATCAAGGACGCTCTGTGCTGGACTGCGCCATCGCCGACTGCCTGCACCTCCGCTGTGA<br>CATCCCCTCCTTGGGCACCCTGGATGAGCTTGACTTCATTCTGAAGGGCAACCTCAGCTTC<br>GGCTGGATCAGTCAGACATTGCAGAAAAAGGTGTTGCTCCTGAGTGAGGCTGAAATCACAT<br>TCAACACATCTGTGTATTCCCAGCTGCCGGGACAGGAGGCATTTCTGAGAGCCCAGGTGTC<br>AACGATGCTAGAAGAATACGTGGTCTATGAGCCCGTCTTCCTCATGGTGTTCAGCTCAGTG<br>GGAGGTCTGCTGTTACTGGCTCTCATCACTGTGGCGCTGTACAAGCTTGGCTTCTTCAAAC<br>GTCAGTATAAAGAGATGCTGGATCTACCATCTGCAGATCCTGACCCAGCCGGCCAGGCAGA<br>TTCCAACCATGAGACTCCTCCACATCTCACGTCCTAGGAATCTACTTTCCTGTATATCTCC<br>ACAATTACGAGATTGGTTTTGCTTTTGCCTATGAATCTACTGGCATGGGAACAAGTTCTCT<br>TCAGCTCTGGGCTAGCCTGGGAAACTTCCCAGAAATGATGCCCTACCTCCTGAGCTGGGAG<br>ATTTTTATGGTTTGCCCATGTGTCAGATTTCAGTGCTGATCCACTTTTTTTGCAAGAGCAG<br>GAATGGGGTCAGCATAAATTTACATATGGATAAGAACTAACACAAGACTGAGTAATATGCT<br>CAATATTCAATGTATTGCTTGTATAAATTTTTAAAAAATAAAATGAAAATGCAGGTGGAAA<br>AAAAAAAAA | |
| 47 | MHCSAMVRGVVILLCGWALASCHGSNLDVEKPVVFKEDAASFGQTVVQFGGSRLVVGAPLE<br>AVAVNQTGQLYDCAPATGVCQPILLHIPLEAVNMSLGLSLVADTNNSQLLACGPTAQRACA<br>KNMYAKGSCLLLGSSLQFIQAIPATMPECPGQEMDIAFLIDGSGSIDQSDFTQMKDFVKAL<br>MGQLASTSTSFSLMQYSNILKTHFTFTEFKSSLSPQSLVDAIVQLQGLTYTASGIQKVVDS<br>NRLLLLRVWSALKPGCHYNTHMPWWVWQRVRFSWKELFHSKNGARKSAKKILIVITDGQKF<br>RDPLEYRHVIPEAEKAGIIRYAIGVGDAFREPTALQELNTIGSAPSQDHVFKVGNFVALRS<br>IQRQIQEKIFAIEGTESRSSSSFQHEMSQEGFSSALSMDGPVLGAVGSFSWSGGAFLYPSN<br>MRSTFINMSQENEDMRDAYLGYSTALAFWKGVHSLILGAPRHQHTGKVVIFTQESRHWRPK<br>SEVRGTQIGSYFGASLCSVDMDRDGSTDLVLIGVPHYYEHTRGGQVSVCPMPGVRSRWHCG<br>TTLHGEQGHPWGRFGAALTVLGDVNGDSLADVAIGAPGEEENRGAVYIFHGASRQDIAPSP<br>SQRVTGSQLFLRLQYFGQSLSGGQDLTQDGLVDLAVGAQGHVLLLRSLPLLKVGISIRFAP<br>SEVAKTVYQCWGRTPTVLEAGEATVCLTVRKGSPDLLGDVQSSVRYDLALDPGRLISRAIF<br>DETKNCTLTRRKTLGLGDHCETMKLLLPDCVEDAVTPIILRLNLSLAGDSAPSRNLRPVLA<br>VGSQDHVTASFPFEKNCKQELLCEGNLGVSFNFSGLQVLEVGSSPELTVTVTVWNEGEDSY<br>GTLIKFYYPAELSYRRVTRAQQPHPYPLRLACEAEPTGQESLRSSSCSINHPIFREGAKAT<br>FMITFDVSYKAFLGDRLLLRASASSENNKPETSKTAFQLELPVKYTVYTVISRQEDSTKHF<br>NFSSSHGERQKEAEHRYRVNNLSPLTLAISVNFWVPILLNGVAVWDVTLRSPAQGVSCVSQ<br>REPPQHSDLLTQIQGRSVLDCAIADCLHLRCDIPSLGTLDELDFILKGNLSFGWISQTLQK<br>KVLLLSEAEITFNTSVYSQLPGQEAFLRAQVSTMLEEYVVYEPVFLMVFSSVGGLLLLALI<br>TVALYKLGFFKRQYKEMLDLPSADPDPAGQADSNHETPPHLTS | mCD11d<br>GI:<br>294997269 |

EXPRESSION OF ANTIBODY OR A FRAGMENT THEREOF IN LACTOBACILLUS

CROSS-REFERENCE TO RELATED APPLICATIONS

This application is a US national stage entry of PCT/US2011/046670 filed on Aug. 4, 2011, which claims the benefit of United Kingdom Patent Application No.: 1013216.5; filed on Aug. 5, 2010 under 35 USC §365(b), both of which are incorporated herein by reference in their entirety.

BACKGROUND OF THE INVENTION

A Generally Regarded As Safe for humans (GRAS) microorganism is a Food and Drug Administration (FDA) designation for a microorganism regarded as safe for consumption. *Lactobacilli* are Gram positive bacteria that are currently used in food fermentation and preservation. *Lactobacilli* are also normal constituents of human microbiota and are classified as GRAS organisms. *Lactobacilli* are useful system for delivery of therapeutic and prophylactic bio-molecules.

Some infectious diseases are transmitted through the passage of mucosal layer into the cell environment in which the infectious agent multiplies. Blocking the passage through the mucosal layer can be an effective measure against an infection.

A therapeutic product combined with a vehicle capable of safe and long-term delivery of the therapeutic product is useful: it reduces hospital visits, economic cost of administration and can provide prevention of a disease. For example, a drug-containing stent has been used for long-term release of a drug at the site of implantation.

In addition to delivery capability, a vehicle that can produce therapeutics is useful for continuous delivery of the therapeutics. A genetically modified microorganism is suitable to produce biological therapeutics, such as nucleic acids or proteins, and can deliver the biological therapeutics continuously.

SUMMARY OF THE INVENTION

A composition comprising a *Lactobacillus*, comprising one or more exogenous nucleic acid sequences encoding a camelid single chain antibody or a fragment thereof, wherein said antibody or a fragment thereof binds to ICAM-1, CD18 or CD11, wherein said one or more exogenous nucleic acid sequences is integrated into a chromosome of said *Lactobacillus*, wherein said chromosome comprises an exogenous apf gene. In one embodiment, said *Lactobacillus* is a food-grade *Lactobacillus*. In one embodiment, said *Lactobacillus* is a vaginal floral strain. In one embodiment, said *Lactobacillus* is a *Lactobacillus paracasei*. In one embodiment, said *Lactobacillus* is a *Lactobacillus rhamnosus*. In one embodiment, said *Lactobacillus* is a *Lactobacillus rhamnosus* GR-1. In one embodiment, said *Lactobacillus* is a *Lactobacillus reuteri* RC-14. In one embodiment, said *Lactobacillus* is a *Lactobacillus iners*. In one embodiment, said *Lactobacillus* is a *Lactobacillus crispatus*. In one embodiment, said *Lactobacillus* is a *Lactobacillus gasseri*. In one embodiment, said *Lactobacillus* is a *Lactobacillus jensenei*. In one embodiment, said antibody or a fragment thereof binds to ICAM-1. In one embodiment, said antibody or a fragment thereof binds to CD18. In one embodiment, said antibody or a fragment thereof binds to CD11a or CD11b. In one embodiment, said one or more antibodies or a fragment thereof is presented on the surface of said *Lactobacillus*. In one embodiment, said one or more antibodies or a fragment thereof is anchored on the surface of said *Lactobacillus*. In one embodiment, said one or more antibodies or a fragment thereof is secreted from said *Lactobacillus*. In one embodiment, said one or more antibodies or a fragment thereof is expressed as an aggregation-promoting factor (APF) fusion protein. In one embodiment, at least one of said one or more antibodies or a fragment thereof is a single-chain camelid antibody or a fragment thereof. In one embodiment, said antibody or a fragment thereof is a VHH or VNAR antibody or a fragment thereof. In one embodiment, at least one of said one or more antibodies or a fragment thereof is a scFv antibody or a fragment thereof. A composition described herein further comprises one or more exogenous nucleic acid sequences encoding another antibody or a fragment thereof that binds to a pathogen.

Described herein is a use of the *Lactobacillus* for the treatment or prevention of infection in a mammal by a pathogen in a mammal comprising, administering said *Lactobacillus* to said mammal and inhibiting transepithelial viral transmission or cell adhesion to an epithelial layer so as to inhibit the infection of said mammal by said pathogen. Described herein is a use of the *Lactobacillus* for the treatment or prevention of infection in a mammal by a pathogen comprising, administering said *Lactobacillus* to said mammal and binding said antibody or a fragment thereof to at least one of a host mammal's cell surface molecules so as to inhibit the infection of said mammal by said pathogen. In one embodiment, said administering comprises delivery of said *Lactobacillus* to a nose of a human subject. In one embodiment, said administering comprises delivery of said *Lactobacillus* to an eye of a human subject. In one embodiment, said administering comprises delivery of said *Lactobacillus* to a vagina of a human subject. In one embodiment, said administering comprises delivery of said *Lactobacillus* to a rectum of a human subject. In one embodiment, said administering comprises delivery of said *Lactobacillus* to a urethra of a human subject. In one embodiment, said administering comprises delivery of said *Lactobacillus* to a mouth of a human subject. In one embodiment, said administering comprises delivery of said *Lactobacillus* is administered by intranasal delivery. In one embodiment, said administering comprises rectal delivery of said *Lactobacillus*. In one embodiment, said administering comprises vaginal delivery of said *Lactobacillus*. In one embodiment, said administering comprises urethral delivery of said *Lactobacillus*. In one embodiment, said administering comprises intravascular delivery of said *Lactobacillus*. In one embodiment, said administering comprises oral delivery of said *Lactobacillus*. In one embodiment, said administering comprises delivery of said *Lactobacillus* in a carrier. In one embodiment, said carrier comprises a lubricant. In one embodiment, said carrier comprises a surfactant. In one embodiment, said carrier comprises a gel. In one embodiment, said carrier comprises an organic solvent. In one embodiment, said carrier comprises an emulsifier. In one embodiment, said carrier comprises a gelling agent. In one embodiment, said carrier comprises a moisturizer. In one embodiment, said carrier comprises a stabilizer. In one embodiment, said carrier comprises a wetting agent. In one embodiment, said carrier comprises a time release agent. In one embodiment, said administering comprises delivery of said *Lactobacillus* is administered in a carrier comprising a sequestering agent. In one embodiment, said carrier comprises a dye. In one embodiment, said carrier comprises a perfume. In one embodiment, said carrier comprises a cream. In one embodiment, said carrier comprises a foam. In one embodiment, said carrier comprises a vaginal wash. In one embodiment, said carrier comprises a vaginal douche. In one embodiment, said carrier comprises an oral solution. In one embodiment, said carrier comprises a suppository. In one embodiment, said carrier comprises a breast milk supplement. In one embodiment, said carrier comprises an infant formula. In one embodiment, said administering comprises delivery of said *Lactobacillus* in conjunction with a contraceptive. In one embodiment, said contraceptive is a condom. In one embodiment, said contraceptive is a sponge. In one embodiment, said contraceptive is an intrauterine device. In one embodiment, said contraceptive is a cervical ring. In one embodiment, said contraceptive is a diaphragm. In one embodiment, said contraceptive is a cerivical cap. In one embodiment, said pathogen is an HIV virus. In one embodiment, said pathogen is an HPV virus. In one embodiment, said pathogen is an HSV virus. In one embodiment, said inhibition is complete blocking. In one embodiment, said inhibition is partial blocking. In one embodiment, said viral infection is sexually transmitted. In one embodiment, said mammal is a human. In one embodiment, said *Lactobacillus* is used prophylaticly for said treatment or prevention of a viral infection in said mammal. The use of a bacteria comprising one or more exogenous nucleic acid sequences integrated into a bacterial chromosome that encodes an antibody or a fragment thereof, wherein said bacteria expresses an antibody or a fragment thereof to ICAM-1, CD-18 or CD-11, comprising administering to a woman a cream, gel, vaginal wash or vaginal douche that comprises said bacteria to treat or prevent HIV infection in said woman. An expression cassette comprising a polynucleotide sequence of SEQ. ID No. 23. An expression cassette comprising a polynucleotide sequence of SEQ. ID No. 24. An expression cassette comprising a polynucleotide sequence of SEQ. ID No. 25. An expression cassette comprising a polynucleotide sequence of SEQ. ID No. 26. An expression cassette comprising a polynucleotide sequence of SEQ. ID No. 27.

Described herein is a host cell comprising the expression cassette of compositions described herein.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 3A is a demonstration of non-covalent attachment of scFv to the surface of *L. paracasei* pAF400 by Western Blot. (i) The bacterial pellet was treated with LiCl 5M to remove surface proteins and Western Blot of the cell extract was performed. (ii) Wild type *L. paracasei* was incubated with the culture supernatant of wild type *L. paracasei*, *L. paracasei* pAF100, and *L. paracasei* pAF400 to evaluate the binding of scFv. FIG. 3B shows flow cytometry analysis of *Lactobacillus* transformants producing surface anchored scFv anti-SAI/II antibody or a fragment thereof. The production of scFv on the surface was shown by detecting the E-tag using a mouse anti-E-tag antibody and Cy-2 conjugated goat anti-mouse immunoglobulin.

FIG. 4A shows a Western Blot analysis of *Lactobacilli* producing scFv anti-ICAM-1, ARP1 anti-rotavirus, and VHH anti-SAI/II (S36). FIG. 4B shows the flow cytometry analysis of *Lactobacillus* transformants producing surface anchored scFv anti-human ICAM-1 and VHH antibody or a fragment thereof.

FIG. 6A shows the production of scFv anti-SAI/II by Western Blot analysis of supernatant and cell extract. FIG. 6B shows the flow cytometry analysis of *L. paracasei* producing surface anchored scFv anti-human SAI/II using plasmid—(*L. paracasei* pAF900, black line) and chromosomally-integrated (*L. paracasei* EM181, grey line) based expression system. Non-transformed *Lactobacilli* (black filled). The production of scFv on the surface was shown by detecting the E-tag using a mouse anti-E-tag antibody and Cy-2 conjugated goat anti-mouse immunoglobulin. FIG. 6C shows the binding activity of scFv antibody or a fragment thereof produced by plasmid- and chromosomally integrated-based expression systems to SAI/II antigen using supernatant and bacterial cell suspension in ELISA.

FIG. 7A shows production and binding activity of *Lactobacilli* producing surface anchored ARP1 using plasmid—(*L. paracasei* pAF900-ARP1) and chromosomally integrated—(*L. paracasei* EM233) based expression system. FIG. 7B shows flow cytometry analysis showing the display of ARP1 on the surface by detecting the E-tag using a mouse anti-E-tag antibody and Cy-2 conjugated goat anti-mouse immunoglobulin. FIG. 7C shows binding activity of *Lactobacilli* producing surface anchored ARP1 to rotavirus measured by flow cytometry. Modified *Lactobacilli* were incubated with rotavirus and stained with rabbit anti-rotavirus serum and anti-rabbit PE conjugate antibody. FIG. 7D shows binding activity of modified *Lactobacilli* producing surface anchored ARP1 to rotavirus measured by ELISA. Plates coated with RRV rotavirus particles were incubated with serial dilutions of intact bacterial cells. The bound bacteria were detected using a mouse anti-E-tag antibody, an anti-mouse IgG alkaline phosphatase-conjugated and p-nitrophenyl phosphate substrate.

FIG. 8 illustrates nucleotide and amino acid sequences of human or mouse CD18, CD11a, CD11b, CD11c, and CD11d.

DETAILED DESCRIPTION OF THE INVENTION

Figure 1:
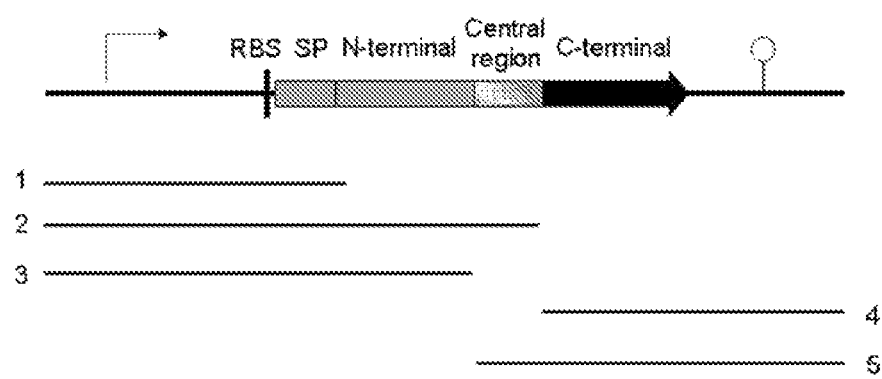
FIG. 1 illustrates amplified PCR fragments used for the construction of the different expression cassettes.

Provided herein are methods and compositions for a delivery system for delivering a therapeutic product to a target area for treating a disease. A delivery system includes, but is not limited to, a delivery vehicle; a therapeutic product; methods of producing a delivery vehicle, methods of delivering the vehicle to a target area; methods of carrying a therapeutic product by a delivery vehicle; methods of releasing therapeutic product by a delivery vehicle; and methods of treating diseases with the delivery system.

Delivery Vehicle

In one aspect a delivery vehicle is disclosed. In one embodiment, a delivery vehicle is a microorganism. In one embodiment, a microorganism is a naturally occurring microorganism, a genetically engineered microorganism, or an artificially evolved organism.

In one embodiment the microorganism expresses one or more exogenous proteins. In one embodiment the one or more exogenous proteins treats or prevents a pathogenic infection. In one embodiment the pathogen is a virus. In another embodiment the pathogen is an HIV, HSV or HPV virus. In one embodiment the one or more exogenous proteins inhibits transepithelial migration by a virus. In another embodiment the one or more exogenous proteins inhibits mammalian cell adhesion to an epithelial layer of said mammal. In another embodiment the one or more exogenous proteins binds to a host cell protein. In one embodiment the host cell protein is expressed on the cell surface. In another embodiment the one or more exogenous proteins binds to ICAM-1 (CD54), LFA-1, or Mac-1. In another embodiment the one or more exogenous proteins binds to CD18, or CD11. In another embodiment the one or more exogenous proteins binds to CD18 or CD11, and ICAM-1. In another embodiment the one or more exogenous proteins binds to CD11a, CD11b, CD11c or CD11d. In another embodiment the one or more proteins comprises one or more antibodies. In another embodiment the one or more antibodies comprises heavy and light chains. In one embodiment the one or more antibodies are single chain antibodies. In one embodiment the one or more antibodies are scFv antibodies. In one embodiment the one or more antibodies are camelid antibodies. In another embodiment the one or more antibodies are VHH antibodies. In another embodiment the one or more antibodies are VNAR antibodies.

In one embodiment, a CD18 protein is mammalian protein. In one embodiment, a CD18 protein is a human protein encoded by a nucleotide SEQ. ID. No. 28 or a homolog thereof. In another embodiment, a CD18 protein is a human protein comprising the sequence of SEQ. ID. No. 29 or a homolog thereof. In another embodiment, a CD18 protein is a human protein having the sequence of SEQ. ID. No. 29 or a homolog thereof. In another embodiment, a CD18 protein is a mouse protein encoded by a nucleotide SEQ. ID. No. 38 or a homolog thereof. In another embodiment, a CD18 protein is a mouse protein comprising the sequence of SEQ. ID. No. 39 or a homolog thereof. In another embodiment, a CD18 protein is a mouse protein having the sequence of SEQ. ID. No. 39 or a homolog thereof. As used herein, a homolog refers to a nucleotide or amino acid sequence having about 90% or higher sequence similarities to the sequences described herein.

In one embodiment, a CD11a protein is a human protein encoded by a nucleotide SEQ. ID. No. 30 or a homolog thereof. In another embodiment, a CD11a protein is a human protein comprising the sequence of SEQ. ID. No. 31 or a homolog thereof. In another embodiment, a CD11a protein is a human protein having the sequence of SEQ. ID. No. 31 or a homolog thereof. In another embodiment, a CD11a protein is a mouse protein encoded by the polynucleotide sequence SEQ. ID. No. 40 or a homolog thereof. In another embodiment, a CD11a protein is a mouse protein comprising the sequence of SEQ. ID. No. 41 or a homolog thereof. In another embodiment, a CD11a protein is a mouse protein having the sequence of SEQ. ID. No. 41 or a homolog thereof. As used herein, a homolog refers to a nucleotide or amino acid sequence having about 90% or higher sequence similarities to the sequences described herein.

In one embodiment, a CD11b protein is a human protein encoded by a nucleotide SEQ. ID. No. 32 or a homolog thereof. In another embodiment, a CD11b protein is a human protein comprising the sequence of SEQ. ID. No. 33 or a homolog thereof. In another embodiment, a CD11b protein is a human protein having the sequence of SEQ. ID. No. 33 or a homolog thereof. In another embodiment, a CD11b protein is a mouse protein encoded by a nucleotide SEQ. ID. No. 42 or a homolog thereof. In another embodiment, a CD11b protein is a mouse protein comprising the sequence of SEQ. ID. No. 43 or a homolog thereof. In another embodiment, a CD11b protein is a mouse protein having the sequence of SEQ. ID. No. 43 or a homolog thereof. As used herein, a homolog refers to a nucleotide or amino acid sequence having about 90% or higher sequence similarities to the sequences described herein.

In one embodiment, a CD11c protein is a human protein encoded by a nucleotide SEQ. ID. No. 34 or a homolog thereof. In another embodiment, a CD11c protein is a human protein comprising the sequence of SEQ. ID. No. 35 or a homolog thereof. In another embodiment, a CD11c protein is a human protein having the sequence of SEQ. ID. No. 35 or a homolog thereof. In another embodiment, a CD11c protein is a mouse protein encoded by a nucleotide SEQ. ID. No. 44 or a homolog thereof. In another embodiment, a CD11c protein is a mouse protein comprising the sequence of SEQ. ID. No. 45 or a homolog thereof. In another embodiment, a CD11c protein is a mouse protein having the sequence of SEQ. ID. No. 45 or a homolog thereof. As used herein, a homolog refers to a nucleotide or amino acid sequence having about 90% or higher sequence similarities to the sequences described herein.

In one embodiment, a CD11d protein is a human protein encoded by a nucleotide SEQ. ID. No. 36 or a homolog thereof. In another embodiment, a CD11d protein is a human protein comprising the sequence of SEQ. ID. No. 37 or a homolog thereof. In another embodiment, a CD11d protein is a human protein having the sequence of SEQ. ID. No. 37 or a homolog thereof. In another embodiment, a CD11d protein is a mouse protein encoded by a nucleotide SEQ. ID. No. 46 or a homolog thereof. In another embodiment, a CD11d protein is a mouse protein comprising the sequence of SEQ. ID. No. 47 or a homolog thereof. In another embodiment, a CD11d protein is a mouse protein having the sequence of SEQ. ID. No. 47 or a homolog thereof. As used herein, a homolog refers to a nucleotide or amino acid sequence having about 90% or higher sequence similarities to the sequences described herein.

In one embodiment, a delivery vehicle is a Gram-positive bacterium. In another embodiment, a delivery vehicle is a Gram-negative bacterium. In another embodiment, a microorganism is a GRAS (generally recognized as safe) organism. In another embodiment, a microorganism is produced as a food-grade microorganism. In another embodiment, a microorganism is produced as a Gram-positive GLP-grade microorganism. In another embodiment, a delivery vehicle is a *Lactobacillus* microorganism or a genetically engineered microorganism derived from a *Lactobacillus*. In another embodiment, a delivery vehicle is *L. paracasei* or a genetically engineered microorganism derived from *L. paracasei*. In another embodiment, a delivery vehicle is a pharmaceutical grade microorganism. In another embodiment, the pharmaceutical grade microorganism is a Good Manufacturing Practices (GMP)—certified pharmaceutical grade microorganism.

A Gram-positive bacterium includes, but is not limited to, a species of *Staphylococcus aureus, Staphylococcus saprophyticus, Enterococcus* spp., *Enterococcus faecalis, Enterococcus faecium, Streptococcus pneumoniae*, Group A *Streptococcus, Bacillus subtilis, Bacillus cereus, Bacillus circulans, Bacillus licheniformis, Paenibacillus alvei, Rhodococcus* spp., *Rhodococcus equi, Gordona bronchialis, Gordona sputi, Listeria monocytogenes, Corynebacterium diphtheriae, Nocardia asteroides, Norcardia jarcinica, Lactobacillus* spp., *Lactococcus lactis, Bifidobacterium* spp, *Arcanobacterium haemolyticum* or *Gardnerella vaginalis*.

A Gram-negative bacterium includes, but is not limited to, a species of *Escherichia coli, Salmonella, Shigella, Enterobacteriaceae, Psudomonas, Moraxella, Helicobacter, Stenotrophomonas, Bdellovibrio, Legionella, Wolbachia, cyanobacteria, Spirochaetes*, or *Coccobacilli*.

A GRAS organism refers to an organism recognized by the Food and Drug Administration as generally safe. A GRAS organism has been found in a variety of microorganisms such as bacteria, yeast, brown algae, or red algae. Examples of GRAS organism includes, but is not limited to, *Saccharomyces cerevisiae, Saccharomyces fragilis*, dried torula yeast, *Candida utilis, Candida guilliermondii, Candida lipolytica, Candida pseudotropicalis, Analipus japonicus, Eisenia bicyclis, Hizikia fusiforme, Kjellmaniella gyrata, Laminaria angustata, Laminaria longirruris, Laminaria longissima, Laminaria ochotensis, Laminaria claustonia, Laminaria saccharina, Laminaria digitata, Laminaria japonica, Macrocystis pyrifera, Petalonia fascia, Scytosiphon lome, Gloiopeltis furcata, Porphyra crispata, Porhyra deutata, Porhyra perforata, Porhyra suborbiculata, Porphyra tenera, Rhodymenis palmata, Lactobacillus acidophilus, Lactobacillus bulgaricus* and *Streptococcus thermophillus, Kluyveromyces lactis*, and *Lactobacillus paracasei*.

The United Nations' Food and Agricultural Organization accepts certain microorganism as a food-grade microorganism. A food-grade microorganism is an organism as a probiotic nutrients, i.e., safe to consume as a live form. A probiotic organism can be modified to a vehicle as described herein. A probiotic organism includes, but is not limited to, a member of the genera *Lactobacillus* or *Bifidobacterium*. A probiotic organism can be derived from a natural or commercially available strains including, but is not limited to, *Bifidobacterium* LAFT B94, *Lactobacillus acidophilus, Lactobacillus acidophilus* LAFTI L10, *Lactobacillus casei, Lactobacillus casei* LAFTI L26, *Bifidobacterium animalis* subsp. *Bifidobacterium lactis, Bifidobacterium lactis* BB-12, *Bifidobacterium lactis* HN019, *Bifidobacterium breve, Bifidobacterium breve* Yakult, *Bifidobacterium infantis Bifidobacterium, Bifidobacterium infantis* 35624, *Bifidobacterium longum, Bifidobacterium longum* BB536, *Bifidobacterium bifidum* BB012, *E. coli* M-17, *E. coli* Nissle 1917, *Baccillus coagulans*, and *Streptococcus thermophilus, Lactobacillus acidophilus* DDS-1, *Lactobacillus acidophilus* LA-5, *Lactobacillus acidophilus* NCFM, *Lactobacillus acidophilus* NCFM, *Lactobacillus acidophilus* CD 1285, *Lactobacillus casei* 431, *Lactobacillus casei* F19, *Lactobacillus casei* Shirota, *Lactobacillus paracasei, Lactobacillus paracasei* St11, *Lactobacillus johnsonii, Lactobacillus johnsonii* La1, *Lactobacillus lactis, Lactobacillus lactis* L1A, *Lactobacillus plantarum, Lactobacillus plantarum* 299v, *Lactobacillus reuteri, Lactobacillus reuteri* ATTC 55730, *Lactobacillus rhamnosus, Lactobacillus rhamnosus* ATCC 53013, *Lactobacillus rhamnosus* LB21, *Lactobacillus rhamnosus* GR-1, *Lactobacillus reuteri* RC-14-*Lactobacillus rhamnosus* R011, *Lactobacillus helveticus*, and *Lactobacillus helveticus* R0052. Generally, any *Lactobacillus* or *Bifidobacterium* strain can be usefulfor methods disclosed herein. The strains include, but are not limited to, *Lactobacillus acetotolerans, Lactobacillus acidipiscis, Lactobacillus acidophilus, Lactobacillus agilis, Lactobacillus algidus, Lactobacillus alimentarius, Lactobacillus amylolyticus, Lactobacillus amylophilus, Lactobacillus amylovorus, Lactobacillus animalis, Lactobacillus arizonensis, Lactobacillus aviarius, Lactobacillus bifermentans, Lactobacillus brevis, Lactobacillus buchneri, Lactobacillus casei, Lactobacillus coelohominis, Lactobacillus collinoides, Lactobacillus coryniformis* subsp. *coryniformis, Lactobacillus coryniformis* subsp. *torquens, Lactobacillus crispatus, Lactobacillus curvatus, Lactobacillus cypricasei, Lactobacillus delbrueckii* subsp. *bulgaricus, Lactobacillus delbrueckii* subsp *delbrueckii, Lactobacillus delbrueckii* subsp. *lactis, Lactobacillus durianus, Lactobacillus equi, Lactobacillus farciminis, Lactobacillus ferintoshensis, Lactobacillus fermentum, Lactobacillus formicalis, Lactobacillus fructivorans, Lactobacillus frumenti, Lactobacillus fuchuensis, Lactobacillus gallinarum, Lactobacillus gasseri, Lactobacillus graminis, Lactobacillus hamsteri, Lactobacillus helveticus, Lactobacillus helveticus* subsp. *jugurti, Lactobacillus heterohiochii, Lactobacillus hilgardii, Lactobacillus homohiochii, Lactobacillus iners, Lactobacillus intestinalis, Lactobacillus japonicus, Lactobacillus jensenii, Lactobacillus johnsonii, Lactobacillus kefiri, Lactobacillus kimchii, Lactobacillus kunkeei, Lactobacillus leichmannii, Lactobacillus letivazi, Lactobacillus lindneri, Lactobacillus malefermentans, Lactobacillus mali, Lactobacillus maltaromicus, Lactobacillus manihotivorans, Lactobacillus mindensis, Lactobacillus mucosae, Lactobacillus murinus, Lactobacillus nagelii, Lactobacillus oris, Lactobacillus panis, Lactobacillus pantheri, Lactobacillus parabuchneri, Lactobacillus paracasei* subsp. *paracasei, Lactobacillus paracasei* subsp. *pseudoplantarum, Lactobacillus paracasei* subsp. *tolerans, Lactobacillus parakefiri, Lactobacillus paralimentarius, Lactobacillus paraplantarum, Lactobacillus pentosus, Lactobacillus perolens, Lactobacillus plantarum, Lactobacillus pontis, Lactobacillus psittaci, Lactobacillus reuteri, Lactobacillus rhamnosus, Lactobacillus ruminis, Lactobacillus sakei, Lactobacillus salivarius, Lactobacillus salivarius* subsp. *salicinius, Lactobacillus salivarius* subsp. *salivarius, Lactobacillus sanfranciscensis, Lactobacillus sharpeae, Lactobacillus suebicus, Lactobacillus thermophilus, Lactobacillus thermotolerans, Lactobacillus vaccinostercus, Lactobacillus vaginalis, Lactobacillus versmoldensis, Lactobacillus vitulinus, Lactobacillus vermiforme, Lactobacillus zeae, Bifidobacterium adolescentis, Bifidobacterium aerophilum, Bifidobacterium angulatum, Bifidobacterium animalis, Bifidobacterium asteroides, Bifidobacterium bifidum, Bifidobacterium boum, Bifidobacterium breve, Bifidobacterium catenulatum, Bifidobacterium choerinum, Bifidobacterium coryneforme, Bifidobacterium cuniculi, Bifidobacterium dentium, Bifidobacterium gallicum, Bifidobacterium gallinarum, Bifidobacterium indicum, Bifidobacterium longum, Bifidobacterium longum* subsp. *longum, Bifidobacterium longum* subsp. *infantis, Bifidobacterium longum* subsp. *suis, Bifidobacterium magnum, Bifidobacterium merycicum, Bifidobacterium minimum, Bifidobacterium pseudocatenulatum, Bifidobacterium pseudolongum, Bifidobacterium pseudolongum* subsp. *globosum, Bifidobacterium pseudolongum* subsp. *pseudolongum, Bifidobacterium psychroaerophilum, Bifidobacterium pullorum, Bifidobacterium ruminantium, Bifidobacterium saeculare, Bifidobacterium scardovii*,

*Bifidobacterium subtile, Bifidobacterium thermoacidophilum, Bifidobacterium thermoacidophilum* subsp. *suis*, *Bifidobacterium thermophilum*, or *Bifidobacterium urinalis*.

In one embodiment, an intestinal microorganism grows on food ingested by a host, fluid secreted from the intestinal tube and/or mucus covering the intestinal wall. Intestinal microorganisms are composed of different kinds and amounts. They also differ by portions of the gastrointestinal tracts they occupy. A group of intestinal microorganisms occupying an area or a section of intestine is referred to as an intestinal microflora. In one embodiment intestinal microflora is bacterial flora. In one embodiment human intestinal bacterial flora comprises anaerobic bacteria. In one embodiment human intestinal bacterial flora comprises aerobic bacteria In one embodiment the intestinal bacterial flora occupies a human colon. The colon tissue contacting the intestinal normal bacterial flora is a mucosal layer comprising epithelium, crypt cells, lamina propria and muscularis mucosa. In one embodiment a microorganism found in the intestinal microflora is used as a delivery vehicle. In another embodiment, a strain of microorganism that can colonize the stomach is utilized as a delivery vehicle. For example, *Helicobacter pylori* can be used as a delivery vehicle. In one embodiment, a strain of microorganism that can colonize the intestine is utilized as a delivery vehicle.

In another embodiment, a strain of microorganism that can colonize a vagina is utilized as a delivery vehicle. For example, a species of *Lactobacillus* or *Bifidobacterium* can be utilized as a delivery vehicle for colonization of the vagina. In one embodiment a human vagina is colonized with a microorganism that express one or more exogenous proteins. In another embodiment, a strain of microorganism that can colonize a urethra is utilized as a delivery vehicle. In another embodiment, a strain of microorganism that can colonize a nose is utilized as a delivery vehicle. In another embodiment, a strain of microorganism that can colonize an eye or orbital socket is utilized as a delivery vehicle. In another embodiment, a strain of microorganism that can colonize mouth is utilized as a delivery vehicle. In another embodiment, a strain of microorganism that can colonize the throat is utilized as a delivery vehicle.

Production of Delivery Vehicle

In another aspect methods and compositions described herein are related to producing a delivery vehicle. To use as a delivery vehicle, a non-pathogenic microorganism for human use is employed as a delivery vehicle. In one embodiment, the microorganism is a non-pathogenic organism. In another embodiment, the microorganism is naturally occurring, non-pathogenic organism. In another embodiment, the microorganism is rendered non-pathogenic, such as by genetic modification or by artificial evolution. A microorganism that can be used as a delivery vehicle either naturally or by genetic modification includes, but is not limited to, Chaetomiaceae such as the genera *Chaetomium* e.g. the species *Chaetomidium fimeti*; Choanephoraceae such as the genera *Blakeslea*, *Choanephora* e.g. the species *Blakeslea trispora*, *Choanephora cucurbitarum* or *Choanephora infundibulifera* var. *cucurbitarum*; Cryptococcaceae such as the genera *Candida*, *Crytococcus*, *Rhodotorula*, *Torulopsis* e.g. the species *Candida albicans, Candida albomarginata, Candida antarctica, Candida bacarum, Candida bogoriensis, Candida boidinii, Candida bovina, Candida brumptii, Candida cacaoi, Candida cariosilignicola, Candida catenulate, Candida chalmersii, Candida ciferrii, Candida cylindracea, Candida edax, Candida ernobii, Candida famata, Candida freyschussii, Candida friedrichii, Candida glabrata, Candida guiffiermondii, Candida haemulonii, Candida humicola, Candida inconspicua, Candida ingens, Candida intermedia, Candida kefir, Candida krusei, Candida lactiscondensi, Candida lambica, Candida lipolytica, Candida lusitaniae, Candida macedoniensis, Candida magnoliae, Candida membranaefaciens, Candida mesenterica, Candida multigemmis, Candida mycoderma, Candida nemodendra, Candida nitratophila, Candida norvegensis, Candida norvegica, Candida parapsilosis, Candida pelliculosa, Candida peltata, Candida pini, Candida pseudotropicalis, Candida pulcherrima, Candida punicea, Candida pustula, Candida ravautii, Candida reukaufii, Candida rugosa, Candida sake, Candida silvicola, Candida solani, Candida sp., Candida spandovensis, Candida succiphila, Candida tropicalis, Candida utilis, Candida valida, Candida versatilis, Candida vini, Candida zeylanoides, Cryptococcus albidus, Cryptococcus curvatus, Cryptococcus flavus, Cryptococcus humicola, Cryptococcus hungaricus, Cryptococcus kuetzingii, Cryptococcus laurentii, Cryptococcus macerans, Cryptococcus neoformans, Cryptococcus tereus, Cryptococcus uniguttulatus, Rhodotorula acheniorum, Rhodotorula bacarum, Rhodotorula bogoriensis, Rhodotorula flava, Rhodotorula glutinis, Rhodotorula macerans, Rhodotorula minuta, Rhodotorula mucilaginosa, Rhodotorula pilimanae, Rhodotorula pustula, Rhodotorula rubra, Rhodotorula tokyoensis, Torulopsis colliculosa, Torulopsis dattila* or *Torulopsis neoformans*; Cunninghamellaceae such as the genera *Cunninghamella* e.g. the species *Cunninghamella blakesleeana, Cunninghamella echinulata, Cunninghamella echinulata* var. *elegans, Cunninghamella elegans* or *Cunninghamella hornothaffica*; Demetiaceae such as the genera *Alternaria, Bipolaris, Cercospora, Chalara, Cladosporium, Curvularia, Exophilia, Helicosporium, Helminthosporium, Orbimyces, Philalophora, Pithomyces, Spilocaea, Thielaviopsis, Wangiella* e.g. the species *Curvularia affinis, Curvularia clavata, Curvularia fallax, Curvularia inaequalis, Curvularia indica, Curvularia lunata, Curvularia pallescens, Curvularia verruculosa* or *Helminothosporium* sp.; Moniliaceae such as the genera *Arthrobotiys, Aspergillus, Epidermophyton, Geotrichum, Gliocladium, Histoplasma, Microsporum, Monilia, Oedocephalum, Oidium, Penicillium, Trichoderma, Trichophyton, Thrichoteclum, Verticillium* e.g. the species *Aspergillus aculeatus, Aspergillus albus, Aspergillus alliaceus, Aspergillus asperescens, Aspergillus awamori, Aspergillus candidus, Aspergillus carbonarius, Aspergillus carneus, Aspergillus chevalieri, Aspergillus chevalieri* var. *intermedius, Aspergillus clavatus, Aspergillus ficuum, Aspergillus flavipes, Aspergillus flavus, Aspergillus foetidus, Aspergillus fumigatus, Aspergillus giganteus, Aspergillus humicola, Aspergillus intermedius, Aspergillus japonicus, Aspergillus nidulans, Aspergillus niger, Aspergillus niveus, Aspergillus ochraceus, Aspergillus oryzae, Aspergillus ostianus, Aspergillus parasiticus, Aspergillus parasiticus* var. *globosus, Aspergillus penicillioides, Aspergillus phoenicis, Aspergillus rugulosus, Aspergillus sclerotiorum, Aspergillus sojae* var. *gymnosardae, Aspergillus sydowii, Aspergillus tamarii, Aspergillus terreus, Aspergillus terricola, Aspergillus toxicarius, Aspergillus unguis, Aspergillus ustus, Aspergillus versicolor, Aspergillus vitricolae, Aspergillus wentii, Penicillium adametzi, Penicillium albicans, Penicillium arabicum, Penicillium arenicola, Penicillium argillaceum, Penicillium arvense, Penicillium asperosporum, Penicillium aurantiogriseum, Penicillium avellaneum, Penicillium baarnense, Penicillium baciffisporum, Penicillium brasilianum, Penicillium brevicompactum, Penicillium camemberti, Penicillium canadense, Penicillium canescens, Penicillium caperatum, Penicillium capsulatum, Penicillium caseicolum, Penicillium chrysogenum, Penicillium citreoni-*

*grum, Penicillium citrinum, Penicillium claviforme, Penicillium commune, Penicillium corylophilum, Penicillium corymbiferum, Penicillium crustosum, Penicillium cyclopium, Penicillium daleae, Penicillium decumbens, Penicillium dierckxii, Penicillium digitatum, Penicillium digitatum var. latum, Penicillium divaricatum, Penicillium diversum, Penicillium duclauxii, Penicillium echinosporum, Penicillium expansum, Penicillium fellutanum, Penicillium frequentans, Penicillium funiculosum, Penicillium glabrum, Penicillium gladioli, Penicillium griseofulvum, Penicillium hirsutum, Penicillium hispanicum, Penicillium islandicum, Penicillium italicum, Penicillium italicum var. avellaneum, Penicillium janczewskii, Penicillium janthinellum, Penicillium japonicum, Penicillium lavendulum, Penicillium lilacinum, Penicillium lividum, Penicillium martensii, Penicillium megasporum, Penicillium miczynskii, Penicillium nalgiovense, Penicillium nigricans, Penicillium notatum, Penicillium ochrochloron, Penicillium odoratum, Penicillium oxalicum, Penicillium paraherquei, Penicillium patulum, Penicillium pinophilum, Penicillium piscarium, Penicillium pseudostromaticum, Penicillium puberulum, Penicillium purpurogenum, Penicillium raciborskii, Penicillium roqueforti, Penicillium rotundum, Penicillium rubrum, Penicillium sacculum, Penicillium simplicissimum, Penicillium sp., Penicillium spinulosum, Penicillium steckii, Penicillium stoloniferum, Penicillium striatisporum, Penicillium striatum, Penicillium tardum, Penicillium thomii, Penicillium turbatum, Penicillium variabile, Penicillium vermiculatum, Penicillium vermoesenii, Penicillium verrucosum, Penicillium verrucosum var. corymbiferum, Penicillium verrucosum var. cyclopium, Penicillium verruculosum, Penicillium vinaceum, Penicillium violaceum, Penicillium viridicatum, Penicillium vulpinum, Trichoderma hamatum, Trichoderma harzianum, Trichoderma koningii, Trichoderma longibrachiatum, Trichoderma polysporum, Trichoderma reesei, Trichoderma virens* or *Trichoderma viride*; Mortierellaceae such as the genera *Mortierella* e.g. the species *Mortierella isabellina, Mortierella polycephala, Mortierella ramanniana, Mortierella vinacea* or *Mortierella zonata*; Mucoraceae such as the genera *Actinomucor, Mucor, Phycomyces, Rhizopus, Zygorhynchus* e.g. the species *Mucor amphibiorum, Mucor circinelloides f. circinelloides, Mucor circinelloides var. griseocyanus, Mucor flavus, Mucor fuscus, Mucor griseocyanus, Mucor heterosporus, Mucor hiemalis, Mucor hiemalis f. hiemalis, Mucor inaequisporus, Mucor indicus, Mucor javanicus, Mucor mucedo, Mucor mucilagineus, Mucor piriformis, Mucor plasmaticus, Mucor plumbeus, Mucor racemosus, Mucor racemosus f. racemosus, Mucor racemosus f. sphaerosporus, Mucor rouxianus, Mucor rouxii, Mucor sinensis, Mucor sp., Mucor spinosus, Mucor tuberculisporus, Mucor variisporus, Mucor variosporus, Mucor wosnessenskii, Phycomyces blakesleeanus, Rhizopus achlamydosporus, Rhizopus arrhizus, Rhizopus chinensis, Rhizopus delemar, Rhizopus formosaensis, Rhizopus japonicus, Rhizopus japonicus, Rhizopus microsporus, Rhizopus microsporus var. chinensis, Rhizopus microsporus var. oligosporus, Rhizopus microsporus var. rhizopodiformis, Rhizopus nigricans, Rhizopus niveus, Rhizopus oligosporus, Rhizopus oryzae, Rhizopus pygmaeus, Rhizopus rhizopodiformis, Rhizopus semarangensis, Rhizopus sontii, Rhizopus stolonifer, Rhizopus thermosus, Rhizopus tonkinensis, Rhizopus tritici* or *Rhizopus usamii*; Pythiaceae such as the genera *Phytium, Phytophthora* e.g. the species *Pythium debaryanum, Pythium intermedium, Pythium irregulare, Pythium megalacanthum, Pythium paroecandrum, Pythium sylvaticum, Pythium ultimum, Phytophthora cactorum, Phytophthora cinnamomi, Phytophthora citricola, Phytophthora citrophthora, Phytophthora cryptogea, Phytophthora drechsleri, Phytophthora erythroseptica, Phytophthora lateralis, Phytophthora megasperma, Phytophthora nicotianae, Phytophthora nicotianae var. parasitica, Phytophthora palmivora, Phytophthora parasitica* or *Phytophthora syringae*; Sacharomycetaceae such as the genera *Hansenula, Pichia, Saccharomyces, Saccharomycodes, Yarrowia* e.g. the species *Hansenula anomala, Hansenula californica, Hansenula canadensis, Hansenula capsulata, Hansenula Hansenula glucozyma, Hansenula henricii, Hansenula holstii, Hansenula minuta, Hansenula nonfermentans, Hansenula philodendri, Hansenula polymorphs, Hansenula saturnus, Hansenula subpelliculosa, Hansenula wickerhamii, Hansenula wingei, Pichia alcoholophila, Pichia angusta, Pichia anomala, Pichia bispora, Pichia burtonii, Pichia canadensis, Pichia capsulata, Pichia carsonii, Pichia cellobiosa, Pichia ciferrii, Pichia farinosa, Pichia fermentans, Pichia finlandica, Pichia glucozyma, Pichia guilliermondii, Pichia haplophila, Pichia henricii, Pichia holstii, Pichia jadinii, Pichia lindnerii, Pichia membranaefaciens, Pichia methanolica, Pichia minuta var. minuta, Pichia minuta var. nonfermentans, Pichia norvegensis, Pichia ohmeri, Pichia pastoris, Pichia philodendri, Pichia pini, Pichia polymorphs, Pichia quercuum, Pichia rhodanensis, Pichia sargentensis, Pichia stipitis, Pichia strasburgensis, Pichia subpelliculosa, Pichia toletana, Pichia trehalophila, Pichia vini, Pichia xylosa, Saccharomyces aceta, Saccharomyces bailii, Saccharomyces bayanus, Saccharomyces bisporus, Saccharomyces capensis, Saccharomyces carlsbergensis, Saccharomyces cerevisiae, Saccharomyces cerevisiae var. ellipsoideus, Saccharomyces chevalieri, Saccharomyces delbrueckii, Saccharomyces diastaticus, Saccharomyces drosophilarum, Saccharomyces elegans, Saccharomyces ellipsoideus, Saccharomyces fermentati, Saccharomyces florentinus, Saccharomyces fragilis, Saccharomyces heterogenous, Saccharomyces hienipiensis, Saccharomyces inusitatus, Saccharomyces italicus, Saccharomyces kiuyveri, Saccharomyces krusei, Saccharomyces lactis, Saccharomyces marxianus, Saccharomyces microellipsoides, Saccharomyces montanus, Saccharomyces norbensis, Saccharomyces oleaceus, Saccharomyces paradoxus, Saccharomyces pastorianus, Saccharomyces pretoriensis, Saccharomyces rosei, Saccharomyces rouxii, Saccharomyces uvarum, Saccharomycodes ludwigii* or *Yarrowia lipolytica*; Saprolegniaceae such as the genera *Saprolegnia* e.g. the species *Saprolegnia ferax*; Schizosacharomycetaceae such as the genera *Schizosaccharomyces* e.g. the species *Schizosaccharomyces japonicus var. japonicus, Schizosaccharomyces japonicus var. versatilis, Schizosaccharomyces malidevorans, Schizosaccharomyces octosporus, Schizosaccharomyces pombe var. malidevorans* or *Schizosaccharomyces pombe var. pombe*; Sodariaceae such as the genera *Neurospora, Sordaria* e.g. the species *Neurospora africana, Neurospora crassa, Neurospora intermedia, Neurospora sitophila, Neurospora tetrasperma, Sordaria fimicola* or *Sordaria macrospora*; Tuberculariaceae such as the genera *Epicoccum, Fusarium, Myrothecium, Sphacelia, Starkeyomyces, Tubercularia* e.g. the species *Fusarium acuminatum, Fusarium anthophilum, Fusarium aquaeductuum, Fusarium aquaeductuum var. medium, Fusarium avenaceum, Fusarium buharicum, Fusarium camptoceras, Fusarium cerealis, Fusarium chlamydosporum, Fusarium ciliatum, Fusarium coccophilum, Fusarium coeruleum, Fusarium concolor, Fusarium crookwellense, Fusarium culmorum, Fusarium dimerum, Fusarium diversisporum, Fusarium equiseti, Fusarium equiseti var. bullatum, Fusarium eumartii, Fusarium flocciferum, Fusarium fujikuroi, Fusarium graminearum, Fusarium graminum, Fusarium het-* erosporum, Fusarium incarnatum, Fusarium inflexum, Fusarium javanicum, Fusarium lateritium, Fusarium lateritium var. majus, Fusarium longipes, Fusarium melanochlorum, Fusarium merismoides, Fusarium merismoides var. chlamydosporale, Fusarium moniliforme, Fusarium moniliforme var. anthophilum, Fusarium moniliforme var. subglutinans, Fusarium nivale, Fusarium nivale var. majus, Fusarium oxysporum, Fusarium oxysporum f. sp. aechmeae, Fusarium oxysporum f. sp. cepae, Fusarium oxysporum f. sp. conglutinans, Fusarium oxysporum f. sp. cucumerinum, Fusarium oxysporum f. sp. cyclaminis, Fusarium oxysporum f. sp. dianthi, Fusarium oxysporum f. sp. lycopersici, Fusarium oxysporum f. sp. melonis, Fusarium oxysporum f. sp. passiflorae, Fusarium oxysporum f. sp. pisi, Fusarium oxysporum f. sp. tracheiphilum, Fusarium oxysporum f. sp. tuberosi, Fusarium oxysporum f. sp. tulipae, Fusarium oxysporum f. sp. vasinfectum, Fusarium pallidoroseum, Fusarium poae, Fusarium proliferatum, Fusarium proliferatum var. minus, Fusarium redolens, Fusarium redolens f. sp. dianthi, Fusarium reticulatum, Fusarium roseum, Fusarium sacchari var. elongatum, Fusarium sambucinum, Fusarium sambucinum var. coeruleum, Fusarium semitectum, Fusarium semitectum var. majus, Fusarium solani, Fusarium solani f. sp. pisi, Fusarium sporotrichioides, Fusarium sporotrichioides var. minus, Fusarium sublunatum, Fusarium succisae, Fusarium sulphureum, Fusarium tabacinum, Fusarium tricinctum, Fusarium udum, Fusarium ventricosum, Fusarium verticillioides, Fusarium xylarioides or Fusarium zonatum; Sporobolomycetaceae such as the genera Bullera, Sporobolomyces, Itersonilia e.g. the species Sporobolomyces holsaticus, Sporobolomyces odorus, Sporobolomyces puniceus, Sporobolomyces salmonicolor, Sporobolomyces singularis or Sporobolomyces tsugae; Adelotheciaceae such as the genera e.g. the species Physcomitrella patens; Dinophyceae such as the genera Ciypthecodinium, Phaeodactylum e.g. the species Crypthecodinium cohnii or Phaeodactylum tricornutum; Ditrichaceae such as the genera Ceratodon, Pleuridium, Astomiopsis, Ditrichum, Philibertiella, Ceratodon, Distichium, Skottsbergia e.g. the species Ceratodon antarcticus, Ceratodon purpureus, Ceratodon purpureus ssp. convolutes or Ceratodon purpureus ssp. stenocarpus; Prasinophyceae such as the genera Nephroselmis, Prasinococcus, Scherffelia, Tetraselmis, Mantoniella, Ostreococcus e.g. the species Nephroselmis olivacea, Prasinococcus capsulatus, Scherffelia dubia, Tetraselmis chui, Tetraselmis suecica, Mantoniella squamata or Ostreococcus tauri; Actinomycetaceae such as the genera Actinomyces, Actinobaculum, Arcanobacterium, Mobiluncus e.g. the species Actinomyces bernardiae, Actinomyces bovis, Actinomyces bowdenii, Actinomyces canis, Actinomyces cardiffensis, Actinomyces catuli, Actinomyces coleocanis, Actinomyces denticolens, Actinomyces europaeus, Actinomyces funkei, Actinomyces georgiae, Actinomyces gerencsehae, Actinomyces hordeovulnehs, Actinomyces howellii, Actinomyces humiferus, Actinomyces hyovaginalis, Actinomyces israelii, Actinomyces marimammavum, Actinomyces meyeri, Actinomyces naeslundii, Actinomyces nasicola, Actinomyces neuii subsp. anitratus, Actinomyces neuii subsp. neuii, Actinomyces odontolyticus, Actinomyces oricola, Actinomyces pyogenes, Actinomyces radicidentis, Actinomyces radingae, Actinomyces slackii, Actinomyces suimastitidis, Actinomyces suis, Actinomyces turicensis, Actinomyces urogenitalis, Actinomyces vaccimaxillae, Actinomyces viscosus, Actinobaculum schaalii, Actinobaculum suis, Actinobaculum urinale, Arcanobacterium bernardiae, Arcanobacterium haemolyticum, Arcanobactehum hippocoleae, Arcanobacterium phocae, Arcanobacterium pluranimalium, Arcanobacterium pyogenes, Mobiluncus curtisii subsp. curtisii, Mobiluncus curtisii subsp. holmesii or Mobiluncus mulieris; Bacillaceae such as the genera Amphibacillus, Anoxybacillus, Bacillus, Exiguobacterium, Gracilibacillus, Holobacillus, Saccharococcus, Salibacillus, Virgibacillus e.g. the species Amphibacillus fermentum, Amphibacillus tropicus, Amphibacillus xylanus, Anoxybacillus flavithermus, Anoxybacillus gonensis, Anoxybacillus pushchinoensis, Bacillus acidocaldarius, Bacillus acidoterrestris, Bacillus aeolius, Bacillus agaradhaerens, Bacillus agri, Bacillus alcalophilus, Bacillus alginolyticus, Bacillus alvei, Bacillus amyloliquefaciens, Bacillus amylolyticus, Bacillus aneurinilyticus, Bacillus aquimaris, Bacillus arseniciselenatis, Bacillus atrophaeus, Bacillus azotofixans, Bacillus azotoformans, Bacillus badius, Bacillus barbaricus, Bacillus benzoevorans, Bacillus borstelensis, Bacillus brevis, Bacillus carboniphilus, Bacillus centrosporus, Bacillus cereus, Bacillus chitinolyticus, Bacillus chondroitinus, Bacillus choshinensis, Bacillus circulars, Bacillus clarkii, Bacillus clausii, Bacillus coagulans, Bacillus cohnii, Bacillus curdlanolyticus, Bacillus cycloheptanicus, Bacillus decolorationis, Bacillus dipsosauri, Bacillus edaphicus, Bacillus ehimensis, Bacillus endophyticus, Bacillus fastidiosus, Bacillus firmus, Bacillus flexus, Bacillus formosus, Bacillus fumarioli, Bacillus funiculus, Bacillus fusiformis, Bacillus sphaericus subsp. fusiformis, Bacillus galactophilus, Bacillus globisporus, Bacillus globisporus subsp. marinus, Bacillus glucanolyticus, Bacillus gordonae, Bacillus halmapalus, Bacillus haloalkaliphilus, Bacillus halodenitrificans, Bacillus halodurans, Bacillus halophilus, Bacillus horikoshii, Bacillus horti, Bacillus infernos, Bacillus insolitus, Bacillus jeotgali, Bacillus kaustophilus, Bacillus kobensis, Bacillus krulwichiae, Bacillus laevolacticus, Bacillus larvae, Bacillus laterosporus, Bacillus lautus, Bacillus lentimorbus, Bacillus lentus, Bacillus licheniformis, Bacillus luciferensis, Bacillus macerans, Bacillus macquariensis, Bacillus marinus, Bacillus marisflavi, Bacillus marismortui, Bacillus megaterium, Bacillus methanolicus, Bacillus migulanus, Bacillus mojavensis, Bacillus mucilaginosus, Bacillus mycoides, Bacillus naganoensis, Bacillus nealsonii, Bacillus neidei, Bacillus niacini, Bacillus okuhidensis, Bacillus oleronius, Bacillus pabuli, Bacillus pallidus, Bacillus pantothenticus, Bacillus parabrevis, Bacillus pasteurii, Bacillus peoriae, Bacillus polymyxa, Bacillus popilliae, Bacillus pseudalcaliphilus, Bacillus pseudofirmus, Bacillus pseudomycoides, Bacillus psychrodurans, Bacillus psychrophilus, Bacillus psychrosaccharolyticus, Bacillus psychrotolerans, Bacillus pulvifaciens, Bacillus pumilus, Bacillus pycnus, Bacillus reuszeri, Bacillus salexigens, Bacillus schlegelii, Bacillus selenitireducens, Bacillus silvestris, Bacillus simplex, Bacillus siralis, Bacillus smithii, Bacillus sonorensis, Bacillus sphaericus, Bacillus sporothermodurans, Bacillus stearothermophilus, Bacillus subterraneus, Bacillus subtilis subsp. spizizenii, Bacillus subtilis subsp. subtilis, Bacillus thermantarcticus, Bacillus thermoaerophilus, Bacillus thermoamylovorans, Bacillus thermoantarcticus, Bacillus thermocatenulatus, Bacillus thermocloacae, Bacillus thermodenitrificans, Bacillus thermoglucosidasius, Bacillus thermoleovorans, Bacillus thermoruber, Bacillus thermosphaericus, Bacillus thiaminolyticus, Bacillus thuringiensis, Bacillus tusciae, Bacillus validus, Bacillus vallismortis, Bacillus vedderi, Bacillus vulcani, Bacillus weihenstephanensis, Exiguobacterium acetylicum, Exiguobacterium antarcticum, Exiguobacterium aurantiacum, Exiguobacterium undae, Gracilibacillus dipsosauri, Gracilibacillus halotolerans, Halobacillus halophilus, Halobacillus karajensis, Halobacillus litoralis, Halobacillus salinus, Halobacillus trueperi, Saccharococcus caldoxylosilyticus, *Saccharococcus thermophilus, Salibacillus marismortui, Salibacillus salexigens, Virgibacillus carmonensis, Virgibacillus marismortui, Virgibacillus necropolis, Virgibacillus pantothenticus, Virgibacillus picturae, Virgibacillus proomii* or *Virgibacillus salexigens*, Brevibacteriaceae such as the genera *Brevibacterium* e.g. the species *Brevibacterium acetylicum, Brevibacterium albidum, Brevibacterium ammoniagenes, Brevibacterium avium, Brevibacterium casei, Brevibacterium citreum, Brevibacterium divahcatum, Brevibacterium epidermidis, Brevibacterium fermentans, Brevibacterium frigoritolerans, Brevibacterium halotolerans, Brevibacterium imperiale, Brevibacterium incertum, Brevibacterium iodinum, Brevibacterium linens, Brevibacterium liquefaciens, Brevibacterium lutescens, Brevibacterium luteum, Brevibacterium lyticum, Brevibacterium mcbrellneri, Brevibacterium otitidis, Brevibacterium oxydans, Brevibacterium paucivorans, Brevibacterium protophormiae, Brevibacterium pusillum, Brevibacterium saperdae, Brevibacterium stationis, Brevibacterium testaceum* or *Brevibacterium vitaeruminis*; Corynebacteriaceae such as the genera *Corynebacterium* e.g. the species *Corynebacterium accolens, Corynebacterium afermentans* subsp. *afermentans, Corynebacterium afermentans* subsp. *lipophilum, Corynebacterium ammoniagenes, Corynebacterium amycolatum, Corynebacterium appendicis, Corynebacterium aquilae, Corynebacterium argentoratense, Corynebacterium atypicum, Corynebacterium aurimucosum, Corynebacterium auris, Corynebacterium auriscanis, Corynebacterium betae, Corynebacterium beticola, Corynebacterium bovis, Corynebacterium callunae, Corynebacterium camporealensis, Corynebacterium capitovis, Corynebacterium casei, Corynebacterium confusum, Corynebacterium coyleae, Corynebacterium cystitidis, Corynebacterium durum, Corynebacterium efficiens, Corynebacterium equi, Corynebacterium falsenii, Corynebacterium fascians, Corynebacterium felinum, Corynebacterium flaccumfaciens, Corynebacterium flavescens, Corynebacterium freneyi, Corynebacterium glaucum, Corynebacterium glucuronolyticum, Corynebacterium glutamicum, Corynebacterium hoagii, Corynebacterium ilicis, Corynebacterium imitans, Corynebacterium insidiosum, Corynebacterium iranicum, Corynebacterium jeikeium, Corynebacterium kroppenstedtii, Corynebacterium kutscheri, Corynebacterium lilium, Corynebacterium lipophiloflavum, Corynebacterium macginleyi, Corynebacterium mastitidis, Corynebacterium matruchotii, Corynebacterium michiganense, Corynebacterium michiganense* subsp. *tessellarius, Corynebacterium minutissimum, Corynebacterium mooreparkense, Corynebacterium mucifaciens, Corynebacterium mycetoides, Corynebacterium nebraskense, Corynebacterium oortii, Corynebacterium paurometabolum, Corynebacterium phocae, Corynebacterium pilosum, Corynebacterium poinsettiae, Corynebacterium propinquum, Corynebacterium pseudodiphtheriticum, Corynebacterium pseudotuberculosis, Corynebacterium pyogenes, Corynebacterium rathayi, Corynebacterium renale, Corynebacterium riegelii, Corynebacterium seminale, Corynebacterium sepedonicum, Corynebacterium simulans, Corynebacterium singulare, Corynebacterium sphenisci, Corynebacterium spheniscorum, Corynebacterium striatum, Corynebacterium suicordis, Corynebacterium sundsvallense, Corynebacterium terpenotabidum, Corynebacterium testudinoris, Corynebacterium thomssenii, Corynebacterium tritici, Corynebacterium ulcerans, Corynebacterium urealyticum, Corynebacterium variabile, Corynebacterium vitaeruminis* or *Corynebacterium xerosis*; Enterobacteriacae such as the genera *Alterococcus, Arsenophonus, Brenneria, Buchnera, Budvicia, Buttiauxella, Calymmatobacterium, Cedecea, Citrobacter, Edwardsiella, Enterobacter, Erwinia, Escherichia, Ewingella, Hafnia, Klebsiella, Kluyvera, Leclercia, Leminorella, Moellerella, Morganella, Obesumbacterium, Pantoea, Pectobacterium, Photorhabdus, Plesiomonas, Pragia, Proteus, Providencia, Rahnella, Saccharobacter, Salmonella, Shigella, Serratia, Sodalis, Tatumella, Trabulsiella, Wigglesworthia, Xenorhabdus. Yersinia* and *Yokenella* e.g. the species *Arsenophonus nasoniae, Brenneria alni, Brenneria nigrifluens, Brenneria quercina, Brenneria rubrifaciens, Brenneria salicis, Budvicia aquatica, Buttiauxella agrestis, Buttiauxella brennerae, Buttiauxella ferragutiae, Buttiauxella gaviniae, Buttiauxella izardii, Buttiauxella noackiae, Buttiauxella warmboldiae, Cedecea davisae, Cedecea lapagei, Cedecea neteri, Citrobacter amalonaticus, Citrobacter diversus, Citrobacter freundii, Citrobacter genomospecies, Citrobacter gillenii, Citrobacter intermedium, Citrobacter koseri, Citrobacter murliniae, Citrobacter* sp., *Edwardsiella hoshinae, Edwardsiella ictaluri, Edwardsiella tarda, Erwinia alni, Erwinia amylovora, Erwinia ananatis, Erwinia aphidicola, Erwinia billingiae, Erwinia cacticida, Erwinia cancerogena, Erwinia carnegieana, Erwinia carotovora* subsp. *atroseptica, Erwinia carotovora* subsp. *betavasculorum, Erwinia carotovora* subsp. *odohfera, Erwinia carotovora* subsp. *wasabiae, Erwinia chrysanthemi, Erwinia cypripedii, Erwinia dissolvers, Erwinia herbicola, Erwinia mallotivora, Erwinia milletiae, Erwinia nigrifluens, Erwinia nimipressuralis, Erwinia persicina, Erwinia psidii, Erwinia pyrifoliae, Erwinia quercina, Erwinia rhapontici, Erwinia rubrifaciens, Erwinia salicis, Erwinia stewartii, Erwinia tracheiphila, Erwinia uredovora, Escherichia adecarboxylata, Escherichia anindolica, Escherichia aurescens, Escherichia blattae, Escherichia coli, Escherichia coli* var. *communior, Escherichia coli-mutabile, Escherichia fergusonii, Escherichia hermannii, Escherichia* sp., *Escherichia vulneris, Ewingella americana, Hafnia alvei, Klebsiella aerogenes, Klebsiella edwardsii* subsp. *atlantae, Klebsiella ornithinolytica, Klebsiella oxytoca, Klebsiella planticola, Klebsiella pneumoniae, Klebsiella pneumoniae* subsp. *pneumoniae, Klebsiella* sp., *Klebsiella terrigena, Klebsiella trevisanii, Kluyvera ascorbata, Kluyvera citrophila, Kluyvera cochleae, Kluyvera cryocrescens, Kluyvera georgiana, Kluyvera noncitrophila, Kluyvera* sp., *Leclercia adecarboxylata, Leminorella grimontii, Leminorella richardii, Moellerella wisconsensis, Morganella morganii, Morganella morganii* subsp. *morganii, Morganella morganii* subsp. *sibonii, Obesumbaterium proteus, Pantoea agglomerans, Pantoea ananatis, Pantoea citrea, Pantoea dispersa, Pantoea punctata, Pantoea stewartii* subsp. *stewartii, Pantoea terrea, Pectobacterium atrosepticum, Pectobacterium carotovorum* subsp. *atrosepticum, Pectobacterium carotovorum* subsp. *carotovorum, Pectobacterium chrysanthemi, Pectobacterium cypripedii, Photorhabdus asymbiotica, Photorhabdus luminescens, Photorhabdus luminescens* subsp. *akhurstii, Photorhabdus luminescens* subsp. *laumondii, Photorhabdus luminescens* subsp. *luminescens, Photorhabdus* sp., *Photorhabdus temperata, Plesiomonas shigelloides, Pragia fontium, Proteus hauseri, Proteus ichthyosmius, Proteus inconstans, Proteus mirabilis, Proteus morganii, Proteus myxofaciens, Proteus penneri, Proteus rettgeri, Proteus shigelloides, Proteus vulgaris, Providencia alcalifaciens, Providencia friedericiana, Providencia heimbachae, Providencia rettgeri, Providencia rustigianii, Providencia stuartii, Rahnella aquatilis, Salmonella abony, Salmonella arizonae, Salmonella bongori, Salmonella choleraesuis* subsp. *arizonae, Salmonella choleraesuis* subsp. *bongori, Salmonella choleraesuis* subsp. *cholereasuis, Salmonella choleraesuis* subsp. *diarizonae,*

*Salmonella choleraesuis* subsp. *houtenae*, *Salmonella choleraesuis* subsp. *indica*, *Salmonella choleraesuis* subsp. *salamae*, *Salmonella daressalaam*, *Salmonella enterica* subsp. *houtenae*, *Salmonella enterica* subsp. *salamae*, *Salmonella entehtidis*, *Salmonella gallinarum*, *Salmonella heidelberg*, *Salmonella panama*, *Salmonella senftenberg*, *Salmonella typhimurium*, *Serratia entomophila*, *Serratia ficaria*, *Serratia fonticola*, *Serratia grimesii*, *Serratia liquefaciens*, *Serratia marcescens*, *Serratia marcescens* subsp. *marcescens*, *Serratia marinorubra*, *Serratia odorifera*, *Serratia plymouthensis*, *Serratia plymuthica*, *Serratia proteamaculans*, *Serratia proteamaculans* subsp. *quinovora*, *Serratia quinivorans*, *Serratia rubidaea*, *Shigella boydii*, *Shigella flexneri*, *Shigella paradysenteriae*, *Shigella sonnei*, *Tatumella ptyseos*, *Xenorhabdus beddingii*, *Xenorhabdus bovienii*, *Xenorhabdus luminescens*, *Xenorhabdus nematophila*, *Xenorhabdus nematophila* subsp. *beddingii*, *Xenorhabdus nematophila* subsp. *bovienii*, *Xenorhabdus nematophila* subsp. *poinarii* or *Xenorhabdus poinarii*; Gordoniaceae such as the genera *Gordonia*, *Skermania* e.g. the species *Gordonia aichiensis*, *Gordonia alkanivorans*, *Gordonia amarae*, *Gordonia amicalis*, *Gordonia bronchialis*, *Gordonia desulfuricans*, *Gordonia hirsuta*, *Gordonia hydrophobica*, *Gordonia namibiensis*, *Gordonia nitida*, *Gordonia paraffinivorans*, *Gordonia polyisoprenivorans*, *Gordonia rhizosphere*, *Gordonia rubripertincta*, *Gordonia sihwensis*, *Gordonia sinesedis*, *Gordonia sputi*, *Gordonia terrae* or *Gordonia westfalica*; Micrococcaceae such as the genera *Micrococcus*, *Arthrobacter*, *Kocuria*, *Nesterenkonia*, *Renibacterium*, *Rothia*, *Stomatococcus* e.g. the species *Micrococcus agilis*, *Micrococcus antarcticus*, *Micrococcus halobius*, *Micrococcus kristinae*, *Micrococcus luteus*, *Micrococcus lylae*, *Micrococcus nishinomiyaensis*, *Micrococcus roseus*, *Micrococcus sedentarius*, *Micrococcus varians*, *Arthrobacter agilis*, *Arthrobacter albus*, *Arthrobacter atrocyaneus*, *Arthrobacter aurescens*, *Arthrobacter chlorophenolicus*, *Arthrobacter citreus*, *Arthrobacter creatinolyticus*, *Arthrobacter crystallopoietes*, *Arthrobacter cumminsii*, *Arthrobacter duodecadis*, *Arthrobacter flavescens*, *Arthrobacter flavus*, *Arthrobacter gandavensis*, *Arthrobacter globiformis*, *Arthrobacter histidinolovorans*, *Arthrobacter ilicis*, *Arthrobacter koreensis*, *Arthrobacter luteolus*, *Arthrobacter methylotrophus*, *Arthrobacter mysorens*, *Arthrobacter nasiphocae*, *Arthrobacter nicotianae*, *Arthrobacter nicotinovorans*, *Arthrobacter oxydans*, *Arthrobacter pascens*, *Arthrobacter picolinophilus*, *Arthrobacter polychromogenes*, *Arthrobacter protophormiae*, *Arthrobacter psychrolactophilus*, *Arthrobacter radiotolerans*, *Arthrobacter ramosus*, *Arthrobacter rhombi*, *Arthrobacter roseus*, *Arthrobacter siderocapsulatus*, *Arthrobacter simplex*, *Arthrobacter sulfonivorans*, *Arthrobacter sulfureus*, *Arthrobacter terregens*, *Arthrobacter tumescens*, *Arthrobacter uratoxydans*, *Arthrobacter ureafaciens*, *Arthrobacter variabilis*, *Arthrobacter viscosus*, *Arthrobacter woluwensis*, *Kocuria erythromyxa*, *Kocuria kristinae*, *Kocuria palustris*, *Kocuria polaris*, *Kocuria rhizophila*, *Kocuria rosea*, *Kocuria varians*, *Nesterenkonia halobia*, *Nesterenkonia lacusekhoensis*, *Renibacterium salmoninarum*, *Rothia amarae*, *Rothia dentocariosa*, *Rothia mucilaginosa*, *Rothia nasimurium* or *Stomatococcus mucilaginosus*; Mycobacteriaceae such as the genera *Mycobacterium* e.g. the species *Mycobacterium africanum*, *Mycobacterium agri*, *Mycobacterium aichiense*, *Mycobacterium alvei*, *Mycobacterium asiaticum*, *Mycobacterium aurum*, *Mycobacterium austroafricanum*, *Mycobacterium bohemicum*, *Mycobacterium botniense*, *Mycobacterium brumae*, *Mycobacterium chelonae* subsp. *abscessus*, *Mycobacterium chitae*, *Mycobacterium chlorophenolicum*, *Mycobacterium chubuense*, *Mycobacterium confluentis*, *Mycobacterium cookii*, *Mycobacterium diernhoferi*, *Mycobacterium doricum*, *Mycobacterium duvalii*, *Mycobacterium fallax*, *Mycobacterium farcinogenes*, *Mycobacterium flavescens*, *Mycobacterium frederiksbergense*, *Mycobacterium gadium*, *Mycobacterium gilvum*, *Mycobacterium gordonae*, *Mycobacterium hassiacum*, *Mycobacterium hiberniae*, *Mycobacterium hodleri*, *Mycobacterium holsaticum*, *Mycobacterium komossense*, *Mycobacterium lacus*, *Mycobacterium madagascariense*, *Mycobacterium mageritense*, *Mycobacterium montefiorense*, *Mycobacterium moriokaense*, *Mycobacterium murale*, *Mycobacterium neoaurum*, *Mycobacterium nonchromogenicum*, *Mycobacterium obuense*, *Mycobacterium palustre* *Mycobacterium parafortuitum*, *Mycobacterium peregrinum*, *Mycobacterium phlei*, *Mycobacterium pinnipedii*, *Mycobacterium poriferae*, *Mycobacterium pulveris*, *Mycobacterium rhodesiae*, *Mycobacterium shottsii*, *Mycobacterium sphagni*, *Mycobacterium terrae, Mycobacterium thermoresistibile, Mycobacterium tokaiense, Mycobacterium triviale, Mycobacterium tusciae* or *Mycobacterium vanbaalenii*; Nocardiaceae such as the genera *Nocardia, Rhodococcus* e.g. the species *Nocardia abscessus, Nocardia africana, Nocardia amarae, Nocardia asteroides, Nocardia autotrophica, Nocardia beijingensis, Nocardia brasiliensis, Nocardia brevicatena, Nocardia caishijiensis, Nocardia calcarea, Nocardia carnea, Nocardia cellulans, Nocardia cerradoensis, Nocardia coeliaca, Nocardia corynebacterioides, Nocardia crassostreae, Nocardia cummidelens, Nocardia cyriacigeorgica, Nocardia farcinica, Nocardia flavorosea, Nocardia flumina, Nocardia globerula, Nocardia hydrocarbonoxydans, Nocardia ignorata, Nocardia mediterranei, Nocardia nova, Nocardia orientalis, Nocardia otitidis-caviarum, Nocardia otitidiscaviarum, Nocardia paucivorans, Nocardia petroleophila, Nocardia pinensis, Nocardia pseudobrasiliensis, Nocardia pseudovaccinii, Nocardia purls, Nocardia restricta, Nocardia rugosa, Nocardia salmonicida, Nocardia saturnea, Nocardia seriolae, Nocardia soli, Nocardia sulphurea, Nocardia transvalensis, Nocardia uniformis, Nocardia vaccinii, Nocardia veterana* or *Nocardia vinacea*; Pseudomonaceae such as the genera *Azomonas, Azotobacter, Cellvibrio, Chryseomonas, Flaviomonas, Lampropedia, Mesophilobacter, Morococcus, Oligella, Pseudomonas, Rhizobacter, Rugamonas, Serpens, Thermoleophilum, Xylophilus* e.g. the species *Azomonas agilis, Azomonas insignis, Azomonas macrocytogenes, Azotobacter agilis, Azotobacter agilis* subsp. *armeniae, Azotobacter armeniacus, Azotobacter beijerinckii, Azotobacter chroococcum, Azotobacter indicum, Azotobacter macrocytogenes, Azotobacter miscellum, Azotobacter nigricans* subsp. *nigricans, Azotobacter paspali, Azotobacter salinestris, Azotobacter* sp., *Azotobacter vinelandii, Flavimonas oryzihabitans, Mesophilobacter marinus, Oligella urethralis, Pseudomonas acidovorans, Pseudomonas aeruginosa, Pseudomonas agarici, Pseudomonas alcaligenes, Pseudomonas aminovorans, Pseudomonas amygdali, Pseudomonas andropogonis, Pseudomonas anguilliseptica, Pseudomonas antarctica, Pseudomonas antimicrobica, Pseudomonas antimycetica, Pseudomonas aptata, Pseudomonas arvilla, Pseudomonas asplenii, Pseudomonas atlantica, Pseudomonas atrofaciens, Pseudomonas aureofaciens, Pseudomonas avellanae, Pseudomonas azelaica, Pseudomonas azotocolligans, Pseudomonas balearica, Pseudomonas barkers, Pseudomonas bathycetes, Pseudomonas beijerinckii, Pseudomonas brassicacearum, Pseudomonas brenneri, Pseudomonas butanovora, Pseudomonas carboxydoflava, Pseudomonas carboxydohydrogena, Pseudomonas carboxydovorans, Pseudomonas carrageeno-* vora, *Pseudomonas caryophylli, Pseudomonas cepacia, Pseudomonas chlohtidismutans, Pseudomonas chlororaphis, Pseudomonas cichorii, Pseudomonas citronellolis, Pseudomonas cocovenenans, Pseudomonas compransoris, Pseudomonas congelans, Pseudomonas coronafaciens, Pseudomonas corrugata, Pseudomonas dacunhae, Pseudomonas delafieldii, Pseudomonas delphinii, Pseudomonas denitrificans, Pseudomonas desmolytica, Pseudomonas diminuta, Pseudomonas doudoroffii, Pseudomonas echinoides, Pseudomonas elongata, Pseudomonas extorquens, Pseudomonas extremorientalis, Pseudomonas facilis, Pseudomonas ficuserectae, Pseudomonas flava, Pseudomonas flavescens, Pseudomonas fluorescens, Pseudomonas fragi, Pseudomonas frederiksbergensis, Pseudomonas fulgida, Pseudomonas fuscovaginae, Pseudomonas gazotropha, Pseudomonas gladioli, Pseudomonas glathei, Pseudomonas glumae, Pseudomonas graminis, Pseudomonas halophila, Pseudomonas helianthi, Pseudomonas huttiensis, Pseudomonas hydrogenothermophila, Pseudomonas hydrogenovora, Pseudomonas indica, Pseudomonas indigofera, Pseudomonas iodinum, Pseudomonas kilonensis, Pseudomonas lachrymans, Pseudomonas lapsa, Pseudomonas lemoignei, Pseudomonas lemonnieri, Pseudomonas lundensis, Pseudomonas luteola, Pseudomonas maltophilia, Pseudomonas marginalis, Pseudomonas marginata, Pseudomonas marina, Pseudomonas meliae, Pseudomonas mendocina, Pseudomonas mesophilica, Pseudomonas mixta, Pseudomonas monteilii, Pseudomonas morsprunorum, Pseudomonas multivorans, Pseudomonas natriegens, Pseudomonas nautica, Pseudomonas nitroreducens, Pseudomonas oleovorans, Pseudomonas oryzihabitans, Pseudomonas ovalis, Pseudomonas oxalaticus, Pseudomonas palleronii, Pseudomonas paucimobilis, Pseudomonas phaseolicola, Pseudomonas phenazinium, Pseudomonas pickettii, Pseudomonas pisi, Pseudomonas plantarii, Pseudomonas plecoglossicida, Pseudomonas poae, Pseudomonas primulae, Pseudomonas proteolytica, Pseudomonas pseudoalcaligenes, Pseudomonas pseudoalcaligenes* subsp. *konjaci, Pseudomonas pseudoalcaligenes* subsp. *pseudoalcaligenes, Pseudomonas pseudoflava, Pseudomonas putida, Pseudomonas putida* var. *naraensis, Pseudomonas putrefaciens, Pseudomonas pyrrocinia, Pseudomonas radiora, Pseudomonas reptilivora, Pseudomonas rhodesiae, Pseudomonas rhodos, Pseudomonas hboflavina, Pseudomonas rubescens, Pseudomonas rubrisubalbicans, Pseudomonas ruhlandii, Pseudomonas saccharophila, Pseudomonas savastanoi, Pseudomonas savastanoi* pvar. *glycinea, Pseudomonas savastanoi* pvar. *phaseolicola, Pseudomonas solanacearum, Pseudomonas* sp., *Pseudomonas spinosa, Pseudomonas stanieri, Pseudomonas stutzeri, Pseudomonas syringae, Pseudomonas syringae* pvar. *aptata, Pseudomonas syringae* pvar. *atrofaciens, Pseudomonas syringae* pvar. *coronafaciens, Pseudomonas syringae* pvar. *delphinii, Pseudomonas syringae* pvar. *glycinea, Pseudomonas syringae* pvar. *helianthi, Pseudomonas syringae* pvar. *lachrymans, Pseudomonas syringae* pvar. *lapsa, Pseudomonas syringae* pvar. *morsprunorum, Pseudomonas syringae* pvar. *phaseolicola, Pseudomonas syringae* pvar. *primulae, Pseudomonas syringae* pvar. *syringae, Pseudomonas syringae* pvar. *tabaci, Pseudomonas syringae* pvar. *tomato, Pseudomonas syringae* subsp. *glycinea, Pseudomonas syringae* subsp. *savastanoi, Pseudomonas syringae* subsp. *syringae, Pseudomonas syzygii, Pseudomonas tabaci, Pseudomonas taeniospiralis, Pseudomonas testosteroni, Pseudomonas thermocarboxydovorans, Pseudomonas thermotolerans, Pseudomonas thivervalensis, Pseudomonas tomato, Pseudomonas trivialis, Pseudomonas veronii, Pseudomonas vesicularis, Pseudomonas viridiflava, Pseudomonas viscogena, Pseudomonas woodsii, Rhizobacter dauci, Rhizobacter daucus* or *Xylophilus ampelinus*; Rhizobiaceae such as the genera *Agrobacterium, Carbophilus, Chelatobacter, Ensifer, Rhizobium, Sinorhizobium* e.g. the species *Agrobacterium atlanticum, Agrobacterium ferrugineum, Agrobacterium gelatinovorum, Agrobacterium larrymoorei, Agrobacterium meteors, Agrobacterium radiobacter, Agrobacterium rhizogenes, Agrobacterium rubi, Agrobacterium stellulatum, Agrobacterium tumefaciens, Agrobacterium vitis, Carbophilus carboxidus, Chelatobacter heintzii, Ensifer adhaerens, Ensifer arboris, Ensifer fredii, Ensifer kostiensis, Ensifer kummerowiae, Ensifer medicae, Ensifer meliloti, Ensifer saheli, Ensifer terangae, Ensifer xinjiangensis, Rhizobium ciceri Rhizobium etli, Rhizobium fredii, Rhizobium galegae, Rhizobium gallicum, Rhizobium giardinii, Rhizobium hainanense, Rhizobium huakuii, Rhizobium huautlense, Rhizobium indigoferae, Rhizobium japonicum, Rhizobium leguminosarum, Rhizobium loessense, Rhizobium loti, Rhizobium lupini, Rhizobium mediterraneum, Rhizobium meliloti, Rhizobium mongolense, Rhizobium phaseoli, Rhizobium radiobacter, Rhizobium rhizogenes, Rhizobium rubi, Rhizobium sullae, Rhizobium tianshanense, Rhizobium trifolii, Rhizobium tropici, Rhizobium undicola, Rhizobium vitis, Sinorhizobium adhaerens, Sinorhizobium arboris, Sinorhizobium fredii, Sinorhizobium kostiense, Sinorhizobium kummerowiae, Sinorhizobium medicae, Sinorhizobium meliloti, Sinorhizobium morelense, Sinorhizobium saheli* or *Sinorhizobium xinjiangense*; Streptomycetaceae such as the genera *Kitasatosprora, Streptomyces, Streptoverticillium* e.g. the species *Streptomyces abikoensis, Streptomyces aburaviensis, Streptomyces achromogenes* subsp. *achromogenes, Streptomyces achromogenes* subsp. *rubradiris, Streptomyces acidiscabies, Streptomyces acrimycini, Streptomyces aculeolatus, Streptomyces afghaniensis, Streptomyces alanosinicus, Streptomyces albaduncus, Streptomyces albiaxialis, Streptomyces albidochromogenes, Streptomyces albidoflavus, Streptomyces albireticuli, Streptomyces albofaciens, Streptomyces alboflavus, Streptomyces albogriseolus, Streptomyces albolongus, Streptomyces alboniger, Streptomyces albospinus, Streptomyces albosporeus* subsp. *albosporeus, Streptomyces albosporeus* subsp. *labilomyceticus, Streptomyces alboverticillatus, Streptomyces albovinaceus, Streptomyces alboviridis, Streptomyces albulus, Streptomyces albus* subsp. *albus, Streptomyces albus* subsp. *pathocidicus, Streptomyces almquistii, Streptomyces althioticus, Streptomyces amakusaensis, Streptomyces ambofaciens, Streptomyces aminophilus, Streptomyces anandii, Streptomyces anthocyanicus, Streptomyces antibioticus, Streptomyces antimycoticus, Streptomyces anulatus, Streptomyces arabicus, Streptomyces ardus, Streptomyces arenae, Streptomyces argenteolus, Streptomyces armeniacus, Streptomyces asiaticus, Streptomyces asterosporus, Streptomyces atratus, Streptomyces atroaurantiacus, Streptomyces atroolivaceus, Streptomyces atrovirens, Streptomyces aurantiacus, Streptomyces aurantiogriseus, Streptomyces aureocirculatus, Streptomyces aureofaciens, Streptomyces aureorectus, Streptomyces aureoversilis, Streptomyces aureoverticillatus, Streptomyces aureus, Streptomyces avellaneus, Streptomyces avermectinius Streptomyces avermitilis, Streptomyces avidinii, Streptomyces azaticus, Streptomyces azureus, Streptomyces baarnensis, Streptomyces bacillaris, Streptomyces badius, Streptomyces baldaccii, Streptomyces bambergiensis, Streptomyces beijiangensis, Streptomyces bellus, Streptomyces bikiniensis, Streptomyces biverticillatus, Streptomyces blastmyceticus, Streptomyces bluensis, Streptomyces bobili, Streptomyces bottropensis, Streptomyces brasiliensis, Strep-* tomyces bungoensis, Streptomyces cacaoi subsp. asoensis, Streptomyces cacaoi subsp. cacaoi, Streptomyces caelestis, Streptomyces caeruleus, Streptomyces californicus, Streptomyces calvus, Streptomyces canaries, Streptomyces candidus, Streptomyces canescens, Streptomyces cangkringensis, Streptomyces caniferus, Streptomyces cavus, Streptomyces capillispiralis, Streptomyces capoamus, Streptomyces carpaticus, Streptomyces carpinensis, Streptomyces catenulae, Streptomyces caviscabies, Streptomyces cavourensis subsp. cavourensis, Streptomyces cavourensis subsp. washingtonensis, Streptomyces cellostaticus, Streptomyces celluloflavus, Streptomyces cellulolyticus, Streptomyces cellulosae, Streptomyces champavatii, Streptomyces chartreuses, Streptomyces chattanoogensis, Streptomyces chibaensis, Streptomyces chrestomyceticus, Streptomyces chromofuscus, Streptomyces chryseus, Streptomyces chiysomallus subsp. chiysomallus, Streptomyces chiysomallus subsp. fumigatus, Streptomyces cinereorectus, Streptomyces cinereoruber subsp. cinereoruber, Streptomyces cinereoruber subsp. fructofermentans, Streptomyces cinereospinus, Streptomyces cinereus, Streptomyces cinerochromogenes, Streptomyces cinnabarinus, Streptomyces cinnamonensis, Streptomyces cinnamoneus, Streptomyces cinnamoneus subsp. albosporus, Streptomyces cinnamoneus subsp. cinnamoneus, Streptomyces cinnamoneus subsp. lanosus, Streptomyces cinnamoneus subsp. sparsus, Streptomyces cirratus, Streptomyces ciscaucasicus, Streptomyces citreofluorescens, Streptomyces clavifer, Streptomyces clavuligerus, Streptomyces cochleatus, Streptomyces coelescens, Streptomyces coelicoflavus, Streptomyces coelicolor, Streptomyces coeruleoflavus, Streptomyces coeruleofuscus, Streptomyces coeruleoprunus, Streptomyces coeruleorubidus, Streptomyces coerulescens, Streptomyces collinus, Streptomyces colombiensis, Streptomyces corchorusii, Streptomyces costaricanus, Streptomyces cremeus, Streptomyces oystallinus, Streptomyces curacoi, Streptomyces cuspidosporus, Streptomyces cyaneofuscatus, Streptomyces cyaneus, Streptomyces cyanoalbus, Streptomyces cystargineus Streptomyces daghestanicus, Streptomyces diastaticus subsp. ardesiacus, Streptomyces diastaticus subsp. diastaticus, Streptomyces diastatochromogenes, Streptomyces distallicus, Streptomyces djakartensis, Streptomyces durhamensis, Streptomyces echinatus, Streptomyces echinoruber, Streptomyces ederensis, Streptomyces ehimensis, Streptomyces endus, Streptomyces enissocaesilis, Streptomyces erumpens, Streptomyces erythraeus, Streptomyces erythrogriseus, Streptomyces eurocidicus, Streptomyces europaeiscabiei, Streptomyces eurythermus, Streptomyces exfoliates, Streptomyces felleus, Streptomyces fervens, Streptomyces fervens subsp. fervens, Streptomyces fervens subsp. melrosporus, Streptomyces filamentosus, Streptomyces filipinensis, Streptomyces fimbriatus, Streptomyces fimicarius, Streptomyces finlayi, Streptomyces flaveolus, Streptomyces flaveus, Streptomyces flavidofuscus, Streptomyces flavidovirens, Streptomyces flaviscleroticus, Streptomyces flavofungini, Streptomyces flavofuscus, Streptomyces flavogriseus, Streptomyces flavopersicus, Streptomyces flavotricini, Streptomyces flavovariabilis, Streptomyces flavovirens Streptomyces flavoviridis, Streptomyces flocculus, Streptomyces floridae, Streptomyces fluorescens, Streptomyces fradiae, Streptomyces fragilis, Streptomyces fulvissimus, Streptomyces fulvorobeus, Streptomyces fumanus, Streptomyces fumigatiscleroticus, Streptomyces galbus, Streptomyces galilaeus, Streptomyces gancidicus, Streptomyces gardneri, Streptomyces gelaticus, Streptomyces geysiriensis, Streptomyces ghanaensis, Streptomyces gibsonii, Streptomyces glaucescens, Streptomyces glaucosporus, Streptomyces glaucus, Streptomyces globisporus subsp. caucasicus, Streptomyces globisporus subsp. flavofuscus, Streptomyces globisporus subsp. globisporus, Streptomyces globosus, Streptomyces glomeratus, Streptomyces glomeroaurantiacus, Streptomyces gobitricini, Streptomyces goshikiensis, Streptomyces gougerotii, Streptomyces graminearus, Streptomyces graminofaciens, Streptomyces ghseinus, Streptomyces griseoaurantiacus, Streptomyces griseobrunneus, Streptomyces griseocarneus, Streptomyces griseochromogenes, Streptomyces griseoflavus, Streptomyces griseofuscus, Streptomyces griseoincarnatus, Streptomyces griseoloalbus, Streptomyces griseolosporeus, Streptomyces griseolus, Streptomyces griseoluteus, Streptomyces griseomycini, Streptomyces griseoplanus, Streptomyces griseorubens, Streptomyces griseoruber, Streptomyces griseorubiginosus, Streptomyces griseosporeus, Streptomyces griseostramineus, Streptomyces griseoverticillatus, Streptomyces griseoviridis, Streptomyces griseus subsp. alpha, Streptomyces griseus subsp. cretosus, Streptomyces griseus subsp. griseus, Streptomyces griseus subsp. solvifaciens, Streptomyces hachijoensis, Streptomyces halstedii, Streptomyces hawaiiensis, Streptomyces heliomycini, Streptomyces helvaticus, Streptomyces herbaricolor, Streptomyces hiroshimensis, Streptomyces hirsutus, Streptomyces humidus, Streptomyces humiferus, Streptomyces hydrogenans, Streptomyces hygroscopicus subsp. angustmyceticus, Streptomyces hygroscopicus subsp. decoyicus, Streptomyces hygroscopicus subsp. glebosus, Streptomyces hygroscopicus subsp. hygroscopicus, Streptomyces hygroscopicus subsp. ossamyceticus, Streptomyces iakyrus, Streptomyces indiaensis, Streptomyces indigoferus, Streptomyces indonesiensis, Streptomyces intermedius, Streptomyces inusitatus, Streptomyces ipomoeae, Streptomyces janthinus, Streptomyces javensis, Streptomyces kanamyceticus, Streptomyces kashmirensis, Streptomyces kasugaensis, Streptomyces katrae, Streptomyces kentuckensis, Streptomyces kifunensis, Streptomyces kishiwadensis Streptomyces kunmingensis, Streptomyces kurssanovii, Streptomyces labedae, Streptomyces laceyi, Streptomyces ladakanum, Streptomyces lanatus, Streptomyces lateritius, Streptomyces laurentii, Streptomyces lavendofoliae, Streptomyces lavendulae subsp. grasserius: Streptomyces lavendulae subsp. lavendulae, Streptomyces lavenduligriseus, Streptomyces lavendulocolor, Streptomyces levis, Streptomyces libani subsp. libani, Streptomyces libani subsp. rufus, Streptomyces lienomycini, Streptomyces lilacinus, Streptomyces limosus, Streptomyces lincolnensis, Streptomyces lipmanii, Streptomyces litmocidini, Streptomyces lomondensis, Streptomyces longisporoflavus, Streptomyces longispororuber, Streptomyces longisporus, Streptomyces longwoodensis, Streptomyces lucensis, Streptomyces luridiscabiei, Streptomyces luridus, Streptomyces lusitanus, Streptomyces luteireticuli, Streptomyces luteogriseus, Streptomyces luteosporeus, Streptomyces luteoverticillatus, Streptomyces lydicus, Streptomyces macrosporus, Streptomyces malachitofuscus, Streptomyces malachitospinus, Streptomyces malaysiensis, Streptomyces mashuensis, Streptomyces massasporeus, Streptomyces matensis, Streptomyces mauvecolor, Streptomyces mediocidicus, Streptomyces mediolani, Streptomyces megasporus, Streptomyces melanogenes, Streptomyces melanosporofaciens, Streptomyces mexicanus, Streptomyces michiganensis, Streptomyces microflavus, Streptomyces minutiscleroticus, Streptomyces mirabilis, Streptomyces misakiensis, Streptomyces misionensis, Streptomyces mobaraensis, Streptomyces monomycini, Streptomyces morookaensis, Streptomyces murinus, Streptomyces mutabilis, Streptomyces mutomycini, Streptomyces naganishii, Streptomyces narbonensis, Streptomyces nashvillensis, Streptomyces netropsis, Streptomyces neyagawaensis, Streptomyces niger, Streptomyces nigrescens, *Streptomyces nigrifaciens*, *Streptomyces nitrosporeus*, *Streptomyces niveiciscabiei*, *Streptomyces niveoruber*, *Streptomyces niveus*, *Streptomyces noboritoensis*, *Streptomyces nodosus*, *Streptomyces nogalater*, *Streptomyces nojiriensis*, *Streptomyces noursei*, *Streptomyces novaecaesareae*, *Streptomyces ochraceiscleroticus*: *Streptomyces odorifer*, *Streptomyces olivaceisderoticus*, *Streptomyces olivaceovihdis*, *Streptomyces olivaceus*, *Streptomyces olivochromogenes*, *Streptomyces olivomycini*, *Streptomyces olivoreticuli*, *Streptomyces olivoreticuli* subsp. *cellulophilus*, *Streptomyces olivoreticuli* subsp. *olivoreticuli*, *Streptomyces olivoverticillatus*, *Streptomyces olivoviridis*, *Streptomyces omiyaensis*, *Streptomyces orinoci*, *Streptomyces pactum*, *Streptomyces paracochleatus*, *Streptomyces paradoxus*, *Streptomyces parvisporogenes*, *Streptomyces parvulus*, *Streptomyces parvus*, *Streptomyces peucetius*, *Streptomyces phaeochromogenes*, *Streptomyces phaeofaciens*, *Streptomyces phaeopurpureus*, *Streptomyces phaeoviridis*, *Streptomyces phosalacineus*, *Streptomyces pilosus*, *Streptomyces platensis*, *Streptomyces plicatus*, *Streptomyces pluricolorescens*, *Streptomyces polychromogenes*, *Streptomyces poonensis*, *Streptomyces praecox*, *Streptomyces prasinopilosus*, *Streptomyces prasinosporus*, *Streptomyces prasinus*, *Streptomyces prunicolor*, *Streptomyces psammoticus*, *Streptomyces pseudoechinosporeus*, *Streptomyces pseudogriseolus*, *Streptomyces pseudovenezuelae*, *Streptomyces pulveraceus*, *Streptomyces puniceus*, *Streptomyces puniciscabiei*, *Streptomyces purpeofuscus*, *Streptomyces purpurascens*, *Streptomyces purpureus*, *Streptomyces purpurogeneisderoticus*, *Streptomyces racemochromogenes*, *Streptomyces rameus*, *Streptomyces ramulosus*, *Streptomyces rangoonensis*, *Streptomyces recifensis*, *Streptomyces rectivertidllatus*, *Streptomyces rectiviolaceus*, *Streptomyces regensis*, *Streptomyces resistomycificus*, *Streptomyces reticuliscabiei*, *Streptomyces rhizosphaericus*, *Streptomyces rimosus* subsp. *paromomycinus*, *Streptomyces rimosus* subsp. *rimosus*, *Streptomyces rishiriensis*, *Streptomyces rochei*, *Streptomyces roseiscleroticus*, *Streptomyces roseodiastaticus*, *Streptomyces roseoflavus*, *Streptomyces roseofulvus*, *Streptomyces roseolilacinus*, *Streptomyces roseolus*, *Streptomyces roseosporus*, *Streptomyces roseoverticillatus*, *Streptomyces roseoviolaceus*, *Streptomyces roseoviridis*, *Streptomyces rubber*, *Streptomyces rubiginosohelvolus*, *Streptomyces rubiginosus*, *Streptomyces rubrogriseus*, *Streptomyces rutgersensis* subsp. *castelarensis*, *Streptomyces rutgersensis* subsp. *rutgersensis*, *Streptomyces salmonis*, *Streptomyces sampsonii*, *Streptomyces sanglieri*, *Streptomyces sannanensis*, *Streptomyces sapporonensis*, *Streptomyces scabiei*, *Streptomyces sclerotialus*, *Streptomyces scopiformis*, *Streptomyces seoulensis*, *Streptomyces septatus*, *Streptomyces setae*, *Streptomyces setonii*, *Streptomyces showdoensis*, *Streptomyces sindenensis*, *Streptomyces sioyaensis*, *Streptomyces somaliensis*, *Streptomyces sparsogenes*, *Streptomyces spectabilis*, *Streptomyces speibonae*, *Streptomyces speleomycini*, *Streptomyces spheroids*, *Streptomyces spinoverrucosus*, *Streptomyces spiralis*, *Streptomyces spiroverticillatus*, *Streptomyces spitsbergensis*, *Streptomyces sporocinereus*, *Streptomyces sporoclivatus*, *Streptomyces spororaveus*, *Streptomyces sporoverrucosus*, *Streptomyces stelliscabiei*, *Streptomyces stramineus*, *Streptomyces subrutilus*, *Streptomyces sulfonofaciens*, *Streptomyces sulphurous*, *Streptomyces syringium*, *Streptomyces tanashiensis*, *Streptomyces tauricus*, *Streptomyces tendae*, *Streptomyces termitum*, *Streptomyces thermoalcalitolerans*, *Streptomyces thermoautotrophicus*, *Streptomyces thermocarboxydovorans*, *Streptomyces thermocarboxydus*, *Streptomyces thermocoprophilus*, *Streptomyces thermodiastaticus*, *Streptomyces thermogriseus*, *Streptomyces thermolineatus*, *Streptomyces thermonitrificans*, *Streptomyces thermospinosisporus*, *Streptomyces thermoviolaceus* subsp. *apingens*, *Streptomyces thermoviolaceus* subsp. *thermoviolaceus*, *Streptomyces thermovulgaris*, *Streptomyces thioluteus*, *Streptomyces torulosus*, *Streptomyces toxytricini*, *Streptomyces tricolor*, *Streptomyces tubercidicus*, *Streptomyces tuirus*, *Streptomyces turgidiscabies*, *Streptomyces umbrinus*, *Streptomyces variabilis*, *Streptomyces variegates*, *Streptomyces varsoviensis*, *Streptomyces vastus*, *Streptomyces venezuelae*, *Streptomyces vinaceus*, *Streptomyces vinaceusdrappus*, *Streptomyces violaceochromogenes*, *Streptomyces violaceolatus*, *Streptomyces violaceorectus*, *Streptomyces violaceoruber*, *Streptomyces violaceorubidus*, *Streptomyces violaceus* *Streptomyces violaceusniger*, *Streptomyces violarus*, *Streptomyces violascens*, *Streptomyces violatus*, *Streptomyces violens*, *Streptomyces virens*, *Streptomyces virginiae*, *Streptomyces viridiflavus*, *Streptomyces viridiviolaceus*, *Streptomyces viridobrunneus*, *Streptomyces viridochromogenes*, *Streptomyces viridodiastaticus*, *Streptomyces viridosporus*, *Streptomyces vitaminophileus*, *Streptomyces vitaminophilus*, *Streptomyces wedmorensis*, *Streptomyces werraensis*, *Streptomyces willmorei*, *Streptomyces xanthochromogenes* *Streptomyces xanthocidicus*, *Streptomyces xantholiticus*, *Streptomyces xanthophaeus*, *Streptomyces yatensis*, *Streptomyces yerevanensis*, *Streptomyces yogyakartensis*, *Streptomyces yokosukanensis*, *Streptomyces yunnanensis*, *Streptomyces zaomyceticus*, *Streptoverticillium abikoense*, *Streptoverticillium albireticuli*, *Streptoverticillium alboverticillatum*, *Streptoverticillium album*, *Streptoverticillium ardum*, *Streptoverticillium aureoversale*, *Streptoverticillium aureoversile*, *Streptoverticillium baldaccii*, *Streptoverticillium biverticillatum*, *Streptoverticillium blastmyceticum*, *Streptoverticillium cinnamoneum* subsp. *albosporum*, *Streptomyces cinnamoneus* subsp. *albosporus*, *Streptoverticillium cinnamoneum* subsp. *cinnamoneum*, *Streptoverticillium cinnamoneum* subsp. *lanosum*, *Streptoverticillium cinnamoneum* subsp. *sparsum*, *Streptoverticillium distallicum*, *Streptoverticillium ehimense*, *Streptoverticillium eurocidicum*, *Streptoverticillium fen/ens* subsp. *fervens*, *Streptoverticillium fervens* subsp. *melrosporus*, *Streptoverticillium flavopersicum*, *Streptoverticillium griseocarneum*, *Streptoverticillium griseoverticillatum*, *Streptoverticillium hachijoense*, *Streptoverticillium hiroshimense*, *Streptoverticillium kashmirense*, *Streptoverticillium kentuckense*, *Streptoverticillium kishiwadense*, *Streptoverticillium ladakanum*, *Streptoverticillium lavenduligriseum*, *Streptoverticillium lilacinum*, *Streptoverticillium luteoverticillatum*, *Streptoverticillium mashuense*, *Streptoverticillium mobaraense*, *Streptoverticillium morookaense*, *Streptoverticillium netropsis*, *Streptoverticillium olivomycini*, *Streptomyces olivomycini*, *Streptoverticillium olivoreticuli* subsp. *cellulophilum*, *Streptoverticillium olivoreticuli* subsp. *olivoreticuli*, *Streptoverticillium olivoreticulum*, *Streptoverticillium olivoreticulum* subsp. *cellulophilum*, *Streptoverticillium olivoverticillatum*, *Streptoverticillium orinoci*, *Streptoverticillium parvisporogenes*, *Streptoverticillium parvisporogenum*, *Streptoverticillium rectiverticillatum*, *Streptoverticillium reticulum* subsp. *protomycicum*, *Streptoverticillium roseoverticillatum*, *Streptoverticillium salmonis*, *Streptoverticillium sapporonense*, *Streptoverticillium septatum*, *Streptoverticillium syringium*, *Streptoverticillium thioluteum*, *Streptoverticillium verticillium* subsp. *quantum*, *Streptoverticillium verticillium* subsp. *tsukushiense* and *Streptoverticillium viridoflavum*. In one embodiment a delivery vehicle is made by the methods disclosed in Appl Environ Microbiol. 2011 March; 77(6):2174-9), which is herein incorporated by reference in tis entirety. In another embodiment a deliver vehicle has one or more attributes disclosed in Appl Environ Microbiol. 2011 March; 77(6):2174-9), which is herein incorporated by reference in tis entirety.

Delivering a Vehicle to Target Area

In one aspect, methods and compositions described herein relate to delivering a delivery vehicle to a target area. In one embodiment, a delivery vehicle is a microorganism. In one embodiment, a microorganism is delivered to a target area by directly applying the delivery vehicle to the target area. Methods of delivery include, but are not limited to, ingestion, inhalation, injection, sprays, and topical application. In one embodiment, a microorganism is delivered in a pharmaceutical composition, such as a foam, cream, patch, gel, powder, solution, liquid, oil, oral solution, vaginal wash, vaginal douche, breast milk supplement, infant formula or petroleum jelly. In another embodiment, a microorganism is delivered in a pharmaceutical composition formulated as a suppository, as an aerosol, as a liquid, as a tampon, or as a tablet. Routes of administration include, but are not limited to, intranasal, rectal, vaginal, intraperitoneal, intravascular, hypodermic, oral, intraurethral, intraocular, inhalation, or other routes known in the art as medically safe route of administration. In another embodiment, a microorganism is delivered to a mammal by a medical device. In one embodiment the medical device is a syringe, catheter, eye dropper, pills, spreader, speculum, or other invasive instruments.

In one embodiment, a delivery vehicle is provided as a delayed release delivery system. In another embodiment a delivery vehicle is provided is provided with a contraceptive device, such as a cervical ring diaphragm, sponge, condom, intrauterine device, or capsule. In another embodiment, a delivery vehicle is co-administered with a chemical contraceptive, such as estradiol, progesterone, nonoyxnol-9, octoxynol-9, benzalkonium chloride, sodium chlorate, or analogs thereof. In another embodiment, a composition comprises a delivery vehicle and one or more lubricants. In one embodiment, the lubricant is water-based, oil-based, or silicone-based. In one embodiment the lubricant is water, glycerin, propylene glycol, polyquaternium 15, methylparaben, propylparaben, propylene glycol, glycerin, methylparaben, butylene glycol, xylitol, cyclomethiocone, or cyclopentasiloxane. In one embodiment, the delivery vehicle comprises antibiotics.

In another embodiment, the delivery vehicle is provided as part of a stent, delivering therapeutic products as disclosed herein at the site of implantation of the stent. In another embodiment, the delivery vehicle can be packaged as part of a hollow tube that does not block a lumen but expanded to fit along the circumference of a tubal lumen.

In one embodiment, a delivery vehicle described herein is provided as a prophylactic composition. In one embodiment, a prophylactic composition comprises a delivery vehicle and a contraceptive chemical or device.

In another embodiment, a prophylactic composition comprises a delivery vehicle co-administered with a lubricant.

In one embodiment, a kit is provided that comprises a delivery vehicle and a contraceptive device and optionally directions for use. In one embodiment the contraceptive device comprises a sponge, condom, intrauterine devices, a diaphragm, cervical cap, an expandable body or another physical barrier contraceptive. In another embodiment the contraceptive device comprises a foaming agent.

In one embodiment the kit comprises a delivery vehicle provided in a container separate from the contraceptive device. In one embodiment the delivery vehicle is provided in a lyophilized composition. In another embodiment the delivery vehicle is provided in a liquid, gel or cream composition.

In anther embodiment the kit comprises a delivery vehicle provided in the same container as the contraceptive device.

In one embodiment the kit comprises directions that explain how to use the delivery vehicle in conjunction with the contraceptive device in order to reduce the risk of infection. In one embodiment the directions explain how to use the delivery vehicle in conjunction with the contraceptive device in order to reduce the risk of pregnancy and infection. In one embodiment the directions contain graphical illustrations.

In one embodiment, a pharmaceutical composition comprises a delivery vehicle. In another embodiment, a pharmaceutical composition comprises a delivery vehicle and maltodextrin beads. In one embodiment the delivery vehicle is a microorganism. In one embodiment the medicament is manufactured using a fluid bed dryer. In one embodiment the fluid bed dryer has a sterilized component assembled for use. In one embodiment maltodextrin beads are placed into the fluid bed dryer and are dried at about 30° C. to 33° C. until sufficiently dry. A suspension of microorganisms is sprayed onto the beads using a peristaltic pump. After about half of the microorganism suspension is sprayed onto the maltodextrin beads, the heat is increased to about 35° C. to 38° C. After all of the microorganism suspension has been sprayed onto the beads, the coated beads are then allowed to dry at about 37° C. to 38° C. for about 15-30 additional minutes. The coated maltodextrin beads can be frozen, stored as a powder, placed into gelatin capsules, or pressed into tablets. In one embodiment the coated maltodextrin beads are used as a vaginal medicament. In another embodiment, the coated maltodextrin beads are used in an oral tablet. In another embodiment, the coated maltodextrin beads are used in a suppository. In another embodiment, the coated maltodextrin beads are used in a suspension for delivery to a target surface on a mammal.

In another embodiment, a pharmaceutical composition comprises a delivery vehicle and maltodextrin/dextrose co-agglomerates. In another embodiment, a pharmaceutical composition comprises a delivery vehicle and maltodextrin/sucrose co-agglomerates. In another embodiment, a pharmaceutical composition comprises a delivery vehicle and maltodextrin/fructose co-agglomerates. In another embodiment, sorbitol, mannitol, glycerol, or another dextrose equivalent is used for preparing a pharmaceutical composition comprising a delivery vehicle.

In one embodiment, a vaginal cream is provided that comprises a delivery vehicle. In one embodiment, the vaginal cream comprises one or more ingredients such as a stabilizer, pharmaceutically acceptable excipient, stiffening agent, oil, solvent, emulsifier, humectant, buffering agent, or emollient. In some embodiment, vaginal cream is a vaginal ointment, or vaginal emulsion. A pharmaceutically acceptable excipient includes a substance, or mixture of substances, that is used in the formulation of vaginal cream compositions to give desirable physical characteristics to the formulation. Examples of those compounds, materials, compositions, and/or dosage forms are, within the scope of sound medical judgment, suitable for contact with the tissues of human and animals without excessive toxicity, irritation, allergic response, or other complications. In some embodiments pharmaceutically acceptable excipients are those approved by a regulatory agency of the Federal or a state government or listed in the U.S. Pharmacopeia or other generally recognized international pharmacopeia for use in animals, and more particularly in humans. Various pharmaceutically acceptable excipients can be used. In one embodiment, a pharmaceutically acceptable excipient is a carrier for active pharmaceutical ingredient. In some embodiments, the pharmaceutically acceptable excipient or a carrier can be, but is not limited to, a stiffening agent, oil, a solvent, an emulsifier, a humectant, a buffering agent, a filler, an emollient, a stabilizer, a lubricant, a surfactant, gel, an organic solvent, a gelling agent, a moisturizer, an wetting agent, a time release agent, a sequestering agent, a dye, a perfume or combinations thereof.

In one embodiment a stabilizer comprises a substance that keeps a formulation chemically stable. F In one embodiment a stabilizer protects a formulation from instability caused by light, moisture, heat, or oxidation. In some embodiments, the stabilizer is lipophilic. In some embodiments, the stabilizer is hydrophilic. In some embodiments, the stabilizer can prevent or retard the oxidation of an oil. In some embodiments, the stabilizer is butylated hydroxyanisole (BHA), butylated hydroxytoluene (BHT), ascorbic acid and its esters, vitamin E and its esters, e.g., vitamin E acetate, sodium bisulfite, sodium metabisulfite, 3-dehydroshikimic acid (DHS), tocopherols and their esters, alkyl gallates, chelating agents, EDTA (ethylenediaminetetraacetic acid; edetate disodium), citric acid, benzyl alcohol, or a combination thereof. In some embodiments, the stabilizer is edetate disodium, butylated hydroxyanisole, butylated hydroxytoluene, or a combination thereof.

In one embodiment a stiffening agent comprises a substance, or mixture of substances, added to make a cream composition more viscous at room temperature. In one embodiment the cream is a vaginal cream. In some embodiments, a stiffening agent is any substance that promotes formation of a formulation having a semi-solid consistency. The stiffening agent can be hydrophilic (e.g., carbopol, carboxymethylcellulose, hydroxypropylmethylcellulose, alginate, polyethylene glycol). In some embodiments, the stiffening agent has low hydrophilic-lipophilic balance (HLB). In some embodiments, the HLB value is less than 7. In some embodiments, the HLB value is less than 5. In some embodiments, the HLB value is about 4. Examples of suitable stiffening agents include, but are not limited to, hydrogenated vegetable oil, cetyl alcohol, cetyl esters wax, microcrystalline wax, paraffin, stearyl alcohol, lauryl alcohol, myristal alcohol, cetostearyl alcohol, white wax, yellow wax, beeswax, candelilla wax, cotton wax, carnauba wax, bayberry wax, rice-bran wax, and combinations thereof. In some embodiments, the stiffening agent is a mixture of cetyl esters wax, cetyl alcohol, and beeswax.

In one embodiment an oil includes any pharmaceutically acceptable hydrophobic liquid. In some embodiments, oil is an ester of glycerol (1,2,3-propanetriol) and fatty acids. Each of the fatty acid hydrocarbon chain can contain greater than 8 carbons. In some embodiments, each hydrocarbon chain can contain from about 12 to about 36 carbon atoms. In some embodiments, the hydrocarbon chains can contain a variety of functional groups. In some embodiments, the hydrocarbon chain can be branched. In some embodiments, the hydrocarbon chains are unsaturated or polyunsaturated. In some embodiments, the hydrocarbon chains are saturated. The degree of saturation can affect the physical state, for example viscosity, of the oil. In some embodiments, the oil can be, but is not limited to, vegetable, nut, and seed oils (e.g., almond oil, castor oil, coconut oil, corn oil, cotton seed oil, jojoba oil, linseed oil, grape seed oil, rape seed oil, mustard oil, olive oil, palm and palm kernel oil, peanut oil, safflower oil, sesame oil, soybean oil, sunflower-seed oil, *crambe* oil, wheat germ oil, and cocoa butter), hydrocarbon and petroleum oils (e.g., petrolatum, mineral oil, and liquid paraffin). In some embodiments, the term "oil" refers to higher fatty acids (e.g., lauric acid, myristic acid, palmitic acid, stearic acid, behenic acid, oleic acid, 12-hydroxystearic acid, undecylenic acid, tall acid, lanolin fatty acid, isostearic acid, linoleic acid, and linolenic acid) and combinations thereof. In some embodiments, the oil is not an ester of glycerol, e.g., mineral oil and silicone oil.

In one embodiment a solvent comprises a substance capable of dissolving or dispersing one or more of the therapeutic product or the excipients of the present invention. The solvent can be aqueous or non-aqueous. In some embodiments, the solvent is hydrophilic, and is 10% to 75% by weight, or 20% to 60% by weight, of the total composition. In some embodiments, the solvent is lipophilic, and is 20% to 60% by weight, or 25% to 50% by weight, of the total composition. In some embodiments, the solvent is water, a polyol (e.g., glycerol) or combinations thereof. In some embodiments, the solvent is oil as described above.

In one embodiment an emulsifier comprises a substance that promotes formation and stabilization of an emulsion or suspension. In some embodiments, the emulsifier includes, but is not limited to, sodium lauryl sulfate, propylene glycol monostearate, methyl stearate, glyceryl monostearate, and combinations thereof.

In one embodiment a humectant comprises a substance that promotes retention of moisture in the composition of the present invention. In some embodiments, the humectant includes, but is not limited to, polyethylene glycol, propylene glycol, glycerin, polyol, polyol derivatives, and combinations thereof.

In one embodiment a buffering agent comprises a substance capable of neutralizing both acids and bases and thereby maintaining the desired pH of the composition. In some embodiments, the buffering agent affects the emulsifying properties. For example, different buffering agents can be provided to increase or decrease the emulsification of a formulation. In some embodiments, the buffer can be, but is not limited to, Tris buffers (Tris EDTA (TE), Tris acetate (TAE), Tris phosphate (TPE), Tris glycine), phosphate buffers (e.g., sodium phosphate, potassium phosphate), bicarbonate buffers, acetate buffers (e.g., sodium acetate), ammonium buffers, citrate buffers, and derivatives and combinations thereof. In some embodiments, an organic acid buffer is used. In some embodiments, an acetate buffer, a phosphate buffer, or a citrate buffer can be used. In some embodiments, a zwitterionic buffer can be used. In some embodiments, the buffering agent is a phosphate buffer (e.g., sodium phosphate dibasic).

The pH of a composition of the invention can be physiologically compatible and/or sufficient to maintain stability of a composition or a delivery vehicle contained therein. In some embodiments, the composition of the present invention can have a pH of 5 to 9 (such as about pH 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8, or 9), or a pH of 6.5 to 8. An emollient includes any substance that moisturizes and increases the pliability of the vaginal epithelium. In some embodiments, the emollient is lanolin, isopropyl myristate, palmitate, oleyl alcohol, beeswax, mineral oil, silicone oil, or combinations thereof.

In one embodiment, a gel comprises a delivery vehicle. In one embodiment the gel is a vaginal gel. In one embodiment, a vaginal gel comprises a pharmaceutically acceptable excipient, a gelling agent such as glycerin, water, hydroxyethylcellulose, methylcellulose, a buffering agent such as glucono-delta-lactone, citric acid, sodium bicarbonate, a diluents for GRAS organism such as magnesium stearate, or mannitol.

In some embodiments, a delivery vehicles described herein is provided as a kit comprising a delivery vehicle in a storage medium and a contraceptive. In one embodiment, the kit comprises a temperature-controlled container. In one embodiment, the kit comprises a moisture-controlled container. In another embodiment, the kit comprises an air-tight container. In one embodiment, a storage medium comprises a buffered solution safe for human use. In another embodiment, a buffered solution comprises glycerin. In one embodiment the concentration of glycerin can be about 5%, 7%, 10%, 13%, 15%, 18%, 20%, 23%, 27%, 30%, 35%, 50%, 55%, 60%, 65%, 70%, 75%, 80%, 85% 90%, 95%, or 99% of the storage solution. In another embodiment, a buffered solution comprises dimethyl sulfoxide. In one embodiment the concentration of dimethyl sulfoxide can be about 5%, 7%, 10%, 13%, 15%, 18%, 20%, 23%, 27%, or 30% of the storage solution. In one embodiment, the contraceptive is a condom. In another embodiment, the condom is a male condom. In another embodiment, the condom is a female condom. In another embodiment, the condom is a latex condom. In another embodiment, the condom is a silicone-based condom. In another embodiment, the condom is polyurethane-based condom. In another embodiment, the condom is nitrile-based condom. In another embodiment the condom is biological material-based condom (e.g., sheep skin). In one embodiment, the contraceptive vaginal ring. In another embodiment, the vaginal ring comprises an ethylene vinylacetate copolymer. In another embodiment, the vaginal ring comprises magnesium stearate. In another embodiment, the vaginal ring comprises chemical contraceptives such as progestin or estradiol analogs. In one embodiment, the contraceptive is a diaphragm. In another embodiment, the diaphragm comprises plastic. In another embodiment, the contraceptive is a sponge. In another embodiment, the sponge comprises an expandable polymer, such as polyurethane. In another embodiment, a sponge is impregnated with a delivery vehicle described herein. In another embodiment, a sponge is impregnable with delivery vehicles described herein. In another embodiment, a sponge is immersible in a solution comprising water.

In one embodiment, a pharmaceutical composition comprises a microorganism described herein which is lyophilized or freeze-dried. In another embodiment, a pharmaceutical composition comprises a microorganism described herein which has undergone sporulation or is present as a spore. In one embodiment, a pharmaceutical composition described herein are formulated by directly mixing lyophilized microorganisms with one or more excipients. In another embodiment, a pharmaceutical composition described is formulated by resuspending lyophilized microorganisms in a suitable solution and mixing the resuspended solution with one or more excipients. In one embodiment, a suitable solution is phosphate-buffered saline. In another embodiment, a suitable solution is water. In one embodiment, an the pharmaceutical composition is a foam, cream, patch, gel, powder, solution, liquid, oil, oral solution, vaginal wash, vaginal douche, breast milk supplement, infant formula, petroleum jelly, a suppository, an aerosol, a liquid, tampon component, or a tablet.

In one embodiment a pharmaceutical composition comprises a sufficient amount of microorganism described herein (such as a *Lactobacilli* strain) to deliver number of colony-forming units (CFU) of the microorganism so that an adequate amount of therapeutic product is expressed in a subject. In one embodiment the pharmaceutical composition comprises $10^4$ to $10^{18}$ CFU/g of composition. In another embodiment the pharmaceutical composition comprises $10^5$ to $10^{16}$ CFU/g of composition. In another embodiment the pharmaceutical composition comprises $10^6$ to $10^{12}$ CFU/g of composition. In another embodiment the pharmaceutical composition comprises $10^4$, $10^5$, $10^6$, $10^7$, $10^8$, $10^9$, $10^{10}$, $10^{11}$, $10^{12}$, $10^{13}$, $10^{14}$, $10^{15}$, $10^{16}$, $10^{17}$, or $10^{18}$ CFU/g of composition. In another embodiment the pharmaceutical composition comprises $10^4$ to $10^{18}$ CFU/ml of composition. In another embodiment the pharmaceutical composition comprises $10^5$ to $10^{16}$ CFU/ml of composition. In another embodiment the pharmaceutical composition comprises $10^6$ to $10^{12}$ CFU/ml of composition. In another embodiment the pharmaceutical composition comprises $10^4$, $10^5$, $10^6$, $10^7$, $10^8$, $10^9$, $10^{10}$, $10^{11}$, $10^{12}$, $10^{13}$, $10^{14}$, $10^{15}$, $10^{16}$, $10^{17}$, or $10^{18}$ CFU/ml of composition.

In one embodiment a microorganism is suitably freeze-dried so as to provide live microorganisms upon reconstitution. In one embodiment a pharmaceutical composition is provided, comprising a freeze-dried microorganism obtained as described in Korean patents KR429494B or KR 429495 B, the contents of which are incorporated herein by reference in their entirety. In another embodiment a microorganism may be dried by spray drying or fluid bed drying. In one embodiment the dried microorganism can have a coating, such as a gastric juice resistant coating. In one embodiment a dried microorganism used in a blending or compacting step has a coating or is embedded in matrix material. In one embodiment a freeze-dried preparation of a microorganism can be obtained by treatment of a cell suspension of the microorganism with compounds such as proteins (whey, milk, others), sugars (maltose, trehalose, lactose, sucrose), starch, cellulose, and optionally, other stabilizing or freeze protecting agents like ascorbic acid. In another embodiment, the cell suspension is treated with proteins, maltodextrins, trehalose, and optionally, other stabilizing or freeze protecting agents like ascorbic acid to form a viscous paste, which is submitted to freeze-drying. The so-obtained material can be ground to a size of about 10 µM to about 800 µM. In one embodiment, the microorganism is coated by or embedded within a salt of a medium or long-chain fatty acid, wherein the microorganism optionally has a first coating layer below the coating by the salt of the medium or long-chain fatty acid. In one embodiment a pharmaceutical composition is prepared using the methods of US20090214647 (which is herein incorporated by reference in its entirety), such as to prepare an enteric tablet.

Other methods of lyophilizing live microorganisms for use in a pharmaceutical composition known in the art can be used with the microorganisms described herein. For example, AU 2005251397, which is herein incorporated by reference in its entirety, describes methods of lyophilizing live bacteria for use in cancer treatment. Remington: The Science and Practice of Pharmacy ($21^{st}$ edition, Lippincott Williams & Wilkins, 2005), which is herein incorporated by reference in its entirety, describes methods of formulating a medicament containing microorganism.

In another embodiment a pharmaceutical composition comprising a microorganism described herein is formulated for administration to the vagina, such as the formulations described in US 20050276836, which is herein incorporated by reference in its entirety. In one embodiment the pharmaceutical composition is a Suppository-Type Vaginal Pellet. In one embodiment the pellet is formulated with polyethylene glycol, a lyophilized microorganism described herein, one or more excipients, (such as Povidone K29) and optionally citric acid and sodium bicarbonate.

In another embodiment a lyophilized vaginal foam is provided. In one embodiment the vaginal foam is prepared as follows: about 20 g of a microorganism described herein (such as a *lactobacillus* that expresses one or more antibodies of interest) with at least $10^6$ cfu/mL and supplemented with one or more of p-aminobenzoic acid, D-pantothenic acid, niacinamide, riboflavin, thiamine, L-arginine, L-cystine, L-tyrosine, L-tryptophane, or L-aspartic acid is combined with about 20 mL of a solution containing alginic acid, sodium salt, and PEG 400 in distilled water. Aliquots of about 5 mL of the suspension are filled into plastic syringes and subjected to a complete freezing process for about 12 h at −80.degree. C. The samples are removed from the syringe mold and lyophilized to yield a vaginal foam devices.

In one embodiment a pharmaceutical composition of the invention is prepared in the form of a suspension, spray, gel, cream, powder, capsule, solution for lavages, ovules, a vaginal insert, tablets or a microencapsulated product employing excipients and formulation techniques know to those skilled in the art. In one embodiment the formulation is one described in formulations described in US 20050220776, which is herein incorporated by reference in its entirety.

In one embodiment a pharmaceutical composition is formulated to adhere to a mucosal membrane. In one embodiment mucous adhesive excipients may be added to comprise up to about 10% of the pharmaceutical composition. In one embodiment the mucous adhesive excipient is a hydrocolloid, more preferably the hydrocolloid is selected from the group comprising xanthan gum, locust bean gum alginate and most preferably the hydrocolloid is xanthan gum.

*Candida albicans* are not able to ferment lactitol, this may also be the case for *E. coli* or other Gram negative bacteria. In one embodiment a prebiotic substrate which is not fermented by *Candida albicans* or by pathogenic bacteria is employed in a vaginal pharmaceutical composition formulations comprising a microorganism described herein (such as a *Lactobacilli* strain) in order to suppress the growth of *Candida albicans*. In one embodiment prebiotic substrate can be an oligosaccharide, such as lactitol, oligofructose or lactulose. In one embodiment the substrate is lactitol.

In another embodiment of the present invention, a pharmaceutical composition that is a absorbent product is provided comprising a microorganism described herein (such as a *Lactobacilli* strain). The microorganism is incorporated into absorbent products in order to allow the convenient administration of the microorganism during use of the absorbent product.

In one embodiment the absorbent product is a feminine hygiene diaper, sanitary napkin, impregnated tampon, panty guard or an incontinence guard comprising a microorganism described herein (such as a *Lactobacilli* strain). In one embodiment the microorganism employed in the absorbent product is used in a bacterial concentrations of $10^5$ to $10^{13}$ CFU/g. In another embodiment the microorganism (such as a *Lactobacilli* strain) employed in the absorbent product is used in a bacterial concentrations of $10^6$ to $10^{12}$ CFU/g. In another embodiment the microorganism (such as a *Lactobacilli* strain) employed in the absorbent product is used in a bacterial concentrations of $10^4$, $10^5$, $10^6$, $10^7$, $10^8$, $10^9$, $10^{10}$, $10^{11}$, $10^{12}$, $10^{13}$, $10^{14}$, $10^{15}$, $10^{16}$, $10^{17}$, or $10^{18}$ CFU/g of absorbent product.

In one embodiment a microorganism described herein (such as a *Lactobacilli* strain) is mixed with one ore more protective solutions to increase the survival rate of live microorganism through the formulation process. In one embodiment, a protective solution is oil. In another embodiment, a protective solution is a long-chain fatty acid. In another embodiment, a protective solution is a salt-containing medium. In one embodiment, a microorganism is first mixed with a protective solution prior to drying, compaction, granulation or grinding. In another embodiment, microorganism is mixed with protective solution, compacted, granulated and then processed for further coating. In another embodiment, a mixture of microorganism and protective solution is converted to a powder in which the powder is added to the coating process.

In one embodiment, long-chain fatty acid useful for formulations described herein is C10 to C30 fatty acid. In one embodiment, the fatty acid is a stearate. In another embodiment, the fatty acid is a palmitate.

In one embodiment, the salt useful for formulations described herein is non-toxic salt. In one embodiment, the salt is calcium salt. In another embodiment, the sale is magnesium salt.

In one embodiment, oil useful for formulation described herein is edible oil. In one embodiment, the oil is tocopherol. In another embodiment, the oil is soy oil, palm oil, or sunflower oil.

In one embodiment, the amount of salt, fatty acid or oil can be from about 5 to about 90% of the dried weight of the formulation.

In one embodiment a microorganism described herein (such as a *Lactobacilli* strain) is coated. In one embodiment the coating material suitable for formulations containing microorganism is a water-soluble material. In one embodiment, the water-soluble material is carbohydrate. In another embodiment, the water-soluble material renders the solution viscous. In one embodiment carbohydrates useful for coating include but are not limited to oligosaccharides, disaccharides or monosaccharides. In another embodiment carbohydrates useful for coating include but are not limited to alginate, pectin, starch, modified starch, maltodextrin, carrageenan, gum arabic, guar gum, xanthan, cellulose or cellulose derivatives, such as hydroxypropyl methylcellulose, hydroxypropyl methylcellulose phthalate or acetate-succinate. In another embodiment, a protein such as gelatin is used in coating process.

In another embodiment the treatment schedule of a subject with a pharmaceutical composition comprising a microorganism described herein (such as a *Lactobacilli* strain) depends on the product in question and the route of administration. In one embodiment the route of administration of a pharmaceutical composition comprising a microorganism described herein (such as a *Lactobacilli* strain) is intranasal, rectal, vaginal, intraperitoneal, intravascular, hypodermic, oral, intraurethral, intraocular, or by inhalation. In one embodiment the subject is administered a pharmaceutical composition comprising a microorganism described herein (such as a *Lactobacilli* strain) one to six times a day (such as 1, 2, 3, 4, 5, or 6 times a day). In one embodiment the subject is administered a pharmaceutical composition comprising a microorganism described herein (such as a *Lactobacilli* strain) from 1 to 90 days (such as 1, 2, 3, 4, 5, 6, 7, 8, 9, 10 11, 12, 13, 14, 15, 16, 17, 18, 19, 20, 21, 22, 23, 24, 25, 26 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 88, 83, 84, 85, 86, 87, 88, 89, or 90 days). In another embodiment the subject is administered a pharmaceutical composition comprising a microorganism described herein (such as a *Lactobacilli* strain) from 1 to 60 days. In another embodiment the subject is administered a pharmaceutical composition comprising a microorganism described herein (such as a *Lactobacilli* strain) from 1 to 30 days. In another embodiment the subject is administered a pharmaceutical composition comprising a microorganism described herein (such as a *Lactobacilli* strain) from 1 to 14 days. In another embodiment the subject is administered a pharmaceutical composition comprising a microorganism described herein (such as a *Lactobacilli* strain) from 1 to 7 days. In another embodiment the subject is administered a pharmaceutical composition comprising a microorganism described herein (such as a *Lactobacilli* strain) about each day on a continuous basis. In another embodiment the subject is administered a pharmaceutical composition comprising a microorganism described herein (such as a *Lactobacilli* strain) prior to, during or after sexual intercourse. In one embodiment the microorganism described herein (such as a *Lactobacilli* strain) is administered to specific mucosal layer (such as an oral, anal, vaginal or urethral mucosal layer) prior to, during or after sexual intercourse.

In another embodiment the subject is administered a pharmaceutical composition comprising a microorganism described herein (such as a *Lactobacilli* strain) once a day for 1 to 30 days. In another embodiment the subject is administered a pharmaceutical composition comprising a microorganism described herein (such as a *Lactobacilli* strain) twice a day for 1 to 30 days. In another embodiment the subject is administered a pharmaceutical composition comprising a microorganism described herein (such as a *Lactobacilli* strain) three times a day for 1 to 30 days. In another embodiment the subject is administered a pharmaceutical composition comprising a microorganism described herein (such as a *Lactobacilli* strain) four times a day for 1 to 30 days.

In another embodiment a pharmaceutical composition comprising a microorganism described herein (such as a *Lactobacilli* strain) is administered to a subject in sufficient quantities and at sufficient intervals so as to maintain a stable population of the microorganism in the subject in vivo. In one embodiment the microorganism described herein (such as a *Lactobacilli* strain) is maintained in a subject in sufficient numbers to express an amount of a therapeutic product sufficient to inhibit infection of the subject by a pathogen. In one embodiment the pathogen is HIV. In another embodiment the therapeutic product is an anti-CD18 or anti-CD11 antibody.

Target Area

In one aspect a target area is a biological area accessible by a delivery vehicle. A target area includes, but is not limited to the skin, dermis, epithelium, vascular surface, interstitial fluid, extracellular matrix, mucosal layer, cuticle, or a subcutaneous layer. In one embodiment, a target area is an oral cavity. In another embodiment, a target area is a vaginal cavity. In another embodiment, a target area is a vaginal epithelium. In another embodiment, a target area is a uterine wall. In another embodiment, a target area is an endometrium. In another embodiment, a target area is a perimetrium. In another embodiment, a target area is a myometrium. In another embodiment, a target area is a cervix. In another embodiment, a target area is a uterine tube. In another embodiment, a target area is a vaginal wall. In another embodiment, a target area is a sinus cavity. In another embodiment, a target area is an anus. In another embodiment, a target area is a colon. In another embodiment, a target area is a urethra. In another embodiment, a target area is an airway. In another embodiment, a target area is an ear canal. In another embodiment, a target area is an ocular cavity. In another embodiment, a target area is an eye. In another embodiment, a target area is an oral mucosa. In another embodiment, a target area is a stomach. In another embodiment, a target area is a rectum or a portion of a gastrointestinal tract.

Therapeutic Product

In one aspect, a delivery vehicle expresses a therapeutic product. In one embodiment the delivery vehicle is a microorganism. In one embodiment a therapeutic product is biological material. Biological material includes, but is not limited to, an antibody or a fragment thereof, a polypeptide, a protein, a glycoprotein, a carbohydrate, a co-factor of an enzyme such as vitamin, flavin, a fatty acid, or a nucleic acid. In one embodiment, a therapeutic product is a protein. In another embodiment, a therapeutic product is a glycoprotein. In another embodiment, a therapeutic product is a polypeptide.

In one embodiment, a therapeutic product is an antibody or a fragment thereof. An antibody or a fragment thereof includes, but is not limited to an antibody that comprises one or more light chains and one or more heavy chains, a single-chain antibody, a VHH antibody (variable domain of a heavy chain), a VNAR antibody, or a scFv antibody (a single-chain Fv fragment). In another embodiment, a therapeutic product is a VHH or VNAR antibody or a fragment thereof. In one embodiment, a single-chain antibody is a single heavy-chain antibody that forms a homodimer. In another embodiment, a single heavy-chain antibody is a camelid antibody. In another embodiment, a single heavy-chain antibody is a camel antibody. In another embodiment, a VHH antibody is a llama antibody. In another embodiment, a therapeutic product is a scFv antibody or a fragment thereof. In one embodiment, an antibody or a fragment there of is a human antibody. In another embodiment, an antibody or a fragment there of is a humanized antibody. In another embodiment, a therapeutic product is an antibody or a fragment thereof fused to a polypeptide that is not an antibody or a fragment derived from an antibody. In another embodiment, a therapeutic product is a single heavy-chain antibody or a fragment thereof.

In one embodiment, a single heavy chain antibody is a VNAR antibody (see US 20080206233, which is herein incorporated by reference in its entirety. It has been shown that sharks also have a single VH-like domain in their antibodies termed VNAR (Nuttall et al. "Isolation and characterization of an IgNAR variable domain specific for the human mitochondrial translocase receptor Tom70" Eur. J. Biochem. (2003) 270, 3543-3554; Dooley et al. "Selection and characterization of naturally occurring single-domain (IgNAR) antibody fragments from immunized sharks by phage display" Molecular Immunology (2003) 40, 25-33; Nuttall et al. "Selection and affinity maturation of IgNAR variable domains targeting *Plasmodium falciparum* AMA1" Proteins: Structure, Function and Bioinformatics (2004) 55, 187-197). Each IgNAR contains a single variable domain (VNAR) and five constant domains (CNAR). VNAR and VHH domains both contain disulfide bonds and have binding affinities in the nanomolar range. In another embodiment a VNAR-type immunoglobulin or fragments thereof can be expressed by a microorganism described herein.

In one embodiment, a delivery vehicle described herein express full-length IgNAR or a fragment thereof. In one embodiment, a delivery vehicle described herein express a single VNAR domain. In another embodiment, a delivery vehicle described herein express a VNAR domain and one or more CNAR domains. In one embodiment, the sequence of VNAR domain is humanized.

In one embodiment, a baby shark is immunized with a polypeptide binding target such as CD18, CD11a, or ICAM-1 to obtain IgNAR. The immunization procedure has been described (for example, Suran et al., J. Immunology, 99:679-686, 1967). In one embodiment, the polypeptide is dissolved in keyhole limpet hemocyanin (KLH) supplemented with complete Freund's adjuvant and then injected intramuscularly. Booster shots are administered as necessary. In one embodiment, booster shots are administered in every two weeks for four weeks after the initial injection is administered. After immunization, blood is withdrawn from the shark and the total IgG is precipitated from the blood. In one embodiment, fractions binding to the polypeptide are separated from the total IgG through affinity chromatography methods. The purified, polypeptide-binding antibodies are sequenced.

In another embodiment, lymphocytes are isolated from immunized shark blood. RNAs purified from the lymphocytes are reverse-transcribed. PCR primers are prepared based on sequence information generated by amino acid sequencing and used to amplify cDNAs expressing antigen-specific IgNAR. In one embodiment, the amplified sequence is cloned to an expression vector to recombinantly express antigen-specific IgNAR or a fragment thereof.

In another embodiment, a fragment of IgNAR is chemically synthesized by digesting isolated antigen-specific IgNAR. In one embodiment, controlled digestion utilizing proteolytic enzyme, such as trypsin, is performed for a limited digestion of the full-length IgNAR. Resulting fragments are tested for antigen-binding in a conventional laboratory protein-protein binding assay. In one embodiment, testing is performed by affinity chromatography using the antigen polypeptide as bait protein. In another embodiment, testing is performed in a pull-down assay using a bead-antigen conjugate as bait protein. In one embodiment, a fragment retaining the antigen-specific binding is sequenced. In another embodiment, the sequence information is utilized to express the fragment in a microorganism described herein.

In one embodiment, a VNAR domain or a fragment thereof is secreted. In another embodiment, a VNAR domain or a fragment thereof is anchored to the surface of a delivery vehicle described herein. In one embodiment, a VNAR domain or a fragment thereof is covalently linked to a scFv. In another embodiment, a VNAR domain or a fragment thereof is covalently linked to a scFv recognizing SAI/II adhesion. In another embodiment, a VNAR domain or a fragment thereof is fused with the APF protein. In another embodiment, a VNAR domain or a fragment thereof is covalently linked to scFv and the APF protein. In another embodiment, scFv is fused to the APF protein via a VNAR domain or a fragment thereof. In one embodiment, a region of the APF protein is selected for expression and secretion of a VNAR domain or a fragment thereof.

A domain refers to a folded protein structure that retains its tertiary structure independently of the rest of the protein. Generally, domains are responsible for discrete functional properties of proteins, and in many cases may be added, removed, or transferred to other proteins without loss of function of the remainder of the protein and/or of the domain. An antibody domain is a folded polypeptide domain which comprises a sequence characteristic of immunoglobulin variable domains and which specifically binds an antigen, including complete antibody variable domains as well as modified variable domains, such as one or more loops have been replaced by sequences which are not characteristic of antibody variable domains or antibody variable domains.

In one embodiment, an antibody produced from a camelid species is devoid of any light chains. In another embodiment a camelid antibody is devoid of any light chains and comprises one or more heavy chains. In one embodiment the one or more heavy chains have variable domains with properties differing from the variable domains of four-chain immunoglobulins. As used herein, this variable domain is called VHH to distinguish it from the classical VH of four-chain immunoglobulins. The variable domain has no normal interaction sites with the VL or with the CH1 domain which do not exist in the heavy-chain immunoglobulins.

In camelid species, the heavy chain variable region, referred to as VHH, forms the entire antigen-binding domain. Differences between camelid VHH variable regions and those derived from conventional antibodies ($V_H$) include; (a) more hydrophobic amino acids in the light chain contact surface of $V_H$ as compared to the corresponding region in VHH; (b) a longer CDR3 in VHH; and (c) the frequent occurrence of a disulfide bond between CDR1 and CDR3 in VHH. A nucleotide sequence of camel VHH was produced by Muyldermans et al., WO2009150539.

TABLE 1

Camel VHH Sequence

| SEQ. ID. No. | Sequence |
|---|---|
| 1 | GATGTGCAGCTGGTGGAGTCTGGGGGAGGCTCGGTGCAGACTGGAGGGTCTCTGAGACTCTCCTGCTT AGCCTCTGGATACACCTATCGTAGTTACTGTCGAGGGTGGTTCCGCCGGCCTCCAGGGAAGGAGCGTG AGGCGGTCGCGATTATAAATAGCCTTGGTCAAACGATCTATGTCGCCGACCCCGTGAAGGGCCGATTC TCCATCTCCCAAGACAACGCCAAGGACACGGTGTATCTGCAAATGAACAGCCTGAAACTTAACGACAC GGCCATGTATTACTGTGCGGTAGCCAATGGTGGTTGTGGTGAGTCGTGGCGCCCTGATTACGTCGGCC AGGGGACCCAGGTCACCGTCTCCTCACACCACCATCACCATCACTAA |

The VHH produced in camelid species can also be generated in a cell by genetic engineering or by chemical synthesis. In one embodiment, a cell is a microorganism. In one embodiment, the microorganism is a delivery vehicle. In another embodiment, the microorganism is non-pathogenic. In one embodiment, the microorganism is a strain of *Lactobacillus*. In another embodiment, the microorganism is a GRAS microorganism. In another embodiment, the microorganism is a food-grade edible microorganism. In another embodiment, a GRAS microorganism is a GLP-certified grade microorganism. In another embodiment, the microorganism is a pharmaceutical grade microorganism. In another embodiment, the pharmaceutical grade microorganism is a Good Manufacturing Practices (GMP)—certified pharmaceutical grade microorganism.

In one embodiment, a delivery vehicle delivers an antibody or antigen-binding fragment, variant, or derivative thereof. In one embodiment the antibody or antigen-binding fragment, variant, or derivative thereof is a polyclonal, monoclonal, multispecific, single chain antibody, or epitope-binding fragment. In another embodiment the antibody or antigen-binding fragment, variant, or derivative thereof is an Fab, Fab' and F(ab')$_2$, Fd, Fvs, single-chain Fvs (scFv), single-chain antibody, disulfide-linked Fvs (sdFv), a fragment comprising either a $V_L$ or $V_H$ domain, a fragment produced by a Fab expression library, or an anti-idiotypic (anti-Id) antibody (e.g., anti-Id antibody to TNF-alpha antibody). scFv molecules are described, e.g., in U.S. Pat. No. 5,892,019. In one embodiment an antibody is an IgG, IgE, IgM, IgD, IgA, or IgY antibody. In another embodiment an antibody is a IgG1, IgG2, IgG3, IgG4, IgA1 or IgA2 antibody. In one embodiment the antibody or antigen-binding fragment, variant, or derivative thereof is human. In one embodiment the antibody or antigen-binding fragment, variant, or derivative thereof is humanized. In one embodiment the antibody or antigen-binding fragment, variant, or derivative thereof is camelid. In another embodiment an antibody or fragment thereof is a single chain antibody or fragment thereof.

An antibody or a fragment thereof including a single-chain antibody can comprise variable region(s) alone or in combination with the entirety or a portion of the following: hinge region, $C_{H1}$, $C_{H2}$, or $C_{H3}$ domains. An antigen-binding fragment can also comprise any combination of variable region(s) with a hinge region, $C_{H1}$, $C_{H2}$, or $C_{H3}$ domains. An antibody or an immunospecific fragment thereof includes humanized or fully human antibodies, antibodies where at least all of the CDRs within the variable domain(s) have the amino acid sequence of a human immunoglobulin variable domain or the amino acid sequence of a human immunoglobulin CDR. In one embodiment, the non-CDR regions of an antibody is from any animal origin such as a bird or a mammal and can comprise primate, murine, donkey, rabbit, goat, guinea pig, camel, llama, horse, or chicken non-CDR immunoglobulin region.

In one embodiment, a heavy chain portion of an antibody includes amino acid sequences derived from an immunoglobulin heavy chain. In one embodiment, a polypeptide comprising a heavy chain portion comprises at least one of: a $C_{H1}$ domain, a hinge (e.g., upper, middle, and/or lower hinge region) domain, a $C_{H2}$ domain, a $C_{H3}$ domain, or a variant or fragment thereof. In another embodiment, a binding polypeptide comprises a polypeptide chain comprising a $C_{H1}$ domain; a polypeptide chain comprising a $C_{H1}$ domain, at least a portion of a hinge domain, and a $C_{H2}$ domain; a polypeptide chain comprising a $C_{H1}$ domain and a $C_{H3}$ domain; a polypeptide chain comprising a $C_{H1}$ domain, at least a portion of a hinge domain, and a $C_{H3}$ domain; or a polypeptide chain comprising a $C_{H1}$ domain, at least a portion of a hinge domain, a $C_{H2}$ domain, and a $C_{H3}$ domain. In another embodiment, a polypeptide comprises a polypeptide chain comprising a $C_{H3}$ domain. In another embodiment, a binding polypeptide can lack at least a portion of a $C_{H2}$ domain (e.g., all or part of a $C_{H2}$ domain). In another embodiment, an antibody domain (e.g., the heavy chain portions) is modified such that they vary in amino acid sequence from the naturally occurring immunoglobulin domains.

In one embodiment, a therapeutic product is a polypeptide that binds to cell surface molecule. In another embodiment, a therapeutic product is a polypeptide that binds to a cell surface molecule and blocks a pathogen from binding to the surface molecule. In one embodiment the polypeptide is an antibody or a fragment thereof. In another embodiment, the polypeptide binds to ICAM-1. In another embodiment, the polypeptide binds to CD18. In another embodiment, the polypeptide binds to CD11. In another embodiment, a polypeptide is not an antibody or a fragment thereof. In another embodiment, a pathogen is a virus, bacteria or a fungus.

In one embodiment, a therapeutic product that binds to a cell surface molecule is identified by screening with a high-throughput screening method. In one embodiment, the high-throughput screening method is phage display. An example of a suitable phage display technique is described in U.S. Patent Application No. 2004000940, which is herein incorporated by reference in its entirety. Other high-throughput screening techniques for identifying protein-protein interactions, such as cDNA library screening, yeast-two hybridization, or affinity column chromatography can be used for screening.

In one embodiment, a therapeutic product is that binds to a cell surface molecule is further screened for an ability to block one or more pathogens from interacting with the cell surface molecule. In one embodiment, the screening method is a transwell assay system where pathogens bound to cell surface are identified by relative location in a transwell in comparison to unbound pathogens. In another embodiment, the screening method is a competition assay where the therapeutic product is bound to a cell surface, and in a subsequent step the amount of freed therapeutic product is measured in relation to increasing concentration of a pathogen. In one embodiment, a dissociation constant of a polypeptide capable of binding to CD11 is measured in a competition assay against an HIV virus. In another embodiment, a dissociation constant of a polypeptide that binds to CD18 is measured in a competition assay against an HIV virus. In another embodiment, a dissociation constant of a polypeptide capable of binding to ICAM-1 is measured in a competition assay against an HIV virus.

In one embodiment, an antibody therapeutic product is an antibody or a fragment thereof that binds to a cell surface molecule. In one embodiment, the cell surface molecule is ICAM. In another embodiment, the cell surface molecule is CD18. In another embodiment, the cell surface molecule is CD11. In another embodiment, the cell surface molecule is ICAM-1. In another embodiment, the cell surface molecule is CD60b, CD1a, CD1b, CD1c, CD1d, CD1e, CD2, CD3, CD3d, CD3e, CD3g, CD4, CD5, CD6, CD7, CD8a, CD8b, CD9, CD10, CD11a, CD11b, CD11c, CD11d, CDW12, CD13, CD14, CD15, CD16a, CD16b, CD17, CD18, CD19, CD20, CD21, CD22, CD23, CD24, CD25, CD26, CD27, CD28, CD29, CD30, CD31, CD32a, CD32b, CD32c, CD33, CD34, CD35, CD36, CD37, CD38, CD39, CD40, CD41, CD42a, CD42b, CD42c, CD42d, CD43, CD44, CD45, CD45RA, CD45RB, CD45RC, CD45RO, CD46, CD47, CD48, CD49a, CD49b, CD49c, CD49d, CD49e, CD49f, CD50, CD51, CD52, CD53, CD54, CD55, CD56, CD57, CD58, CD59, CD60a, CD60b, CD60c, CD61, CD62E, CD62L, CD62P, CD63, CD64a, CD65, CD65s, CD66a, CD66b, CD66c, SynCAMs, NCAMs, VCAM01, L1, CHL1, MAG, Nectin or a nectin-like molecules.

The "CD" notation for cell surface molecules described herein mean one or more molecules collectively known as or assigned to a particular "CD" number. For example, CD11 means molecules and subunits known as cluster of differentiation 11 such as CD11a, CD11b, or CD11c. CD designated molecules are also known by common names. For example, CD54 is also known as ICAM-1. CD11a is also known as lymphocyte function associated antigen 1 alpha polypeptide, integrin alpha L or ITGAL. Each molecule described herein by its commonly known name refers to human nucleotide or polypeptide sequence in public sequence databases that can be identified by the commonly known name.

In one embodiment, VHH or VNAR or antibody sequences recognizing a cellular or viral protein are obtained by immunizing a transgenic mammal capable of expressing heavy chain antibodies. In one embodiment, heavy chain antibody includes heavy chain antibodies with single variable domain, such as human single variable domains, Camelid single variable domains or shark single variable domains, synthetic or semi-synthetic single variable domains. Animals, such as a mouse, with a confirmed immune response can be used to obtain nucleic acid sequence to clone the antibody with the VHH or VNAR sequence. In another embodiment, phage display techniques known in the art (e.g., McCafferty et al, Phage display of peptides and proteins. Academic Press, San Diego, 1996) can be used to screen for antibodies recognizing a cellular protein (such as CD18, CD11a, b, c, or d) or viral protein. In another embodiment, a llama can be immunized with a human cell surface protein or a viral protein as described herein. From the immunized llama, lymphocytes can be harvested from a blood sample to test and screen for antibody response.

In one embodiment, an antibody therapeutic product is an antibody or a fragment thereof that binds to a viral molecule. In one embodiment, the viral molecule is a viral envelope protein. In one embodiment, the envelope protein is HIV gp120. In another embodiment, the area recognized by the antibody is CD4 binding site of gp120. In another embodiment, the area recognized by the antibody is the co-receptor binding site on gp 120. In another embodiment, the area recognized by the antibody is V3 loop of gp120. In another embodiment, the area recognized by the antibody is the glycans on gp120. In another embodiment, the envelope protein is HIV gp 41. In another embodiment, the area recognized by the antibody is membrane proximal external region of gp 41. In one embodiment, the area recognized by the antibody is glycoprotein C of HSV-1. In another embodiment, the area recognized by the antibody is ICPS major capsid protein of HSV. In another embodiment, the area recognized by the antibody is glycoprotein D of HSV-2. In one embodiment, the area recognized by the antibody is Hepatitis B core antigen (HBcAg). In another embodiment, the area recognized by the antibody is Hepatitis B surface antigen (HBsAg).

In one embodiment, an antibody therapeutic product is an antibody or a fragment thereof that binds to a virus. A virus includes, but is not limited to, Adenovirus, Astrovirus, Avian influenza virus, Coxsackievirus, Dengue virus, Ebola virus, Echovirus, Enteric adenovirus, Enterovirus, Hantaviruses, Hepatitis A virus, Hepatitis B virus, Hepatitis C virus, Hepatitis D virus, Hepatitis E virus, Herpes simplex virus (HSV), Human cytomegalovirus, Human immunodeficiency virus (HIV), Human papillomavirus (HPV), Influenza virus, Japanese encephalitis virus (JEV), Lassa virus, Marburg virus, Measles virus, Mumps virus, Norovirus, Parainfluenza virus, Poliovirus, Rabies virus, Respiratory syncytial virus, Rotavirus, Rubella virus, SARS coronavirus, Tick-borne encephalitis virus (TBEV), Variola virus, West Nile virus, and Yellow fever virus.

In one embodiment, a therapeutic product is a nucleic acid. In one embodiment, a nucleic acid is a DNA or a RNA molecule capable of interacting with a cell surface molecule. In another embodiment, a nucleic acid is selected for its ability to interact with ICAM-1. In another embodiment, a nucleic acid is selected for its ability to interact with CD18. In another embodiment, a nucleic acid is selected for its ability to interact with CD11.

In one embodiment, a therapeutic product is an aptamer. In one aspect, an aptamer is an oligonucleotide aptamer. In one embodiment, an oligonucleotide aptamer is a DNA aptamer. In another embodiment, an oligonucleotide aptamer is a RNA aptamer. In another embodiment, an oligonucleotide aptamer is selected by an in vitro selection process, such as SELEX (systematic evolution of ligands by exponential enrichment). In another embodiment, an oligonucleotide aptamer is selected for its ability to bind to a cell surface antigen. In another embodiment, an oligonucleotide aptamer is selected for its ability to bind to ICAM-1. In another embodiment, an oligonucleotide aptamer is selected for its ability to bind to CD18. In another embodiment, an oligonucleotide aptamer is selected for its ability to bind to CD11. In another aspect, an aptamer is a peptide aptamer. In one embodiment, a peptide aptamer is selected by an in vitro method, such as yeast-two-hybrid. In another embodiment, a peptide aptamer is selected for its ability to bind to a cell surface antigen. In another embodiment, an oligonucleotide aptamer is selected for its ability to bind to ICAM-1. In another embodiment, an oligonucleotide aptamer is selected for its ability to bind to CD18. In another embodiment, an oligonucleotide aptamer is selected for its ability to bind to CD11.

In one embodiment, a therapeutic product is a ligand. In one embodiment, a ligand is selected for its ability to interact with a cell surface molecule. In another embodiment, a ligand is selected for its ability to interact with ICAM-1. In another embodiment, a ligand is selected for its ability to interact with CD18. In another embodiment, a ligand is selected for its ability to interact with CD11. In one aspect, a ligand, upon binding to one or more cell surface molecules, prevents other molecules from interacting with the cell surface molecule. In another aspect, a ligand is a competitive ligand that displaces other molecules already bound to a cell surface molecule.

Production of Therapeutic Product

In one embodiment, a therapeutic product is produced in a delivery vehicle. In one embodiment, the delivery vehicle is a microorganism. In one embodiment, a microorganism delivers a polypeptide. In one embodiment, the polypeptide is encoded by a nucleic acid sequence in the microorganism. In one embodiment, the polypeptide is produced from a plasmid transcribed and translated by the microorganism. In another embodiment, the polypeptide is encoded by an exogenous nucleic acid sequence integrated into the microorganism's genome. In one embodiment, a therapeutic product is produced within a vehicle from a plasmid or other vector. In another embodiment, a therapeutic product is produced within a vehicle by a nucleic acid sequence integrated to the chromosome. In one embodiment the microorganism is a *Lactobacillus*. Chromosomal integration of recombinant DNA ensures stable expression of heterologous antigens both in vitro and in vivo. Various systems have previously been developed to stably integrate a heterologous gene into the chromosome, generating food grade expression systems devoid of antibiotic selection genes. One of these systems is based on the site-specific integration apparatus of temperate bacteriophage A2 of *Lactobacillus*. In another embodiment, an antibody or its fragment is produced from a chromosomally integrated nucleic acids sequence encoding the antibody or a fragment thereof.

Methods of chromosomal integration include, but are not limited to, homologous recombination or use of insertion sequences (e.g., a transposon). In one embodiment, two-chain antibody production in a microorganism involves a heterodimerization and/or post-translational modification of polypeptide. In another embodiment, a microorganism produces a single heavy-chain antibody. In one embodiment, a nucleic sequence encoding an antibody is modified by introducing changes in the length of nucleotide introduced into a microorganism's chromosome, adjusting codon usage to suit the microorganism, such as by replacing an amino acid codon with another amino acid, or adjusting various transcription-controlling sequences (such as operator, promoter, enhancer, Shine-Dalgarno, or Kozak sequences) to find right codon for expression.

In one aspect, a chromosomal integration system further comprises a safety switch. In one embodiment the safety switch returns the genetically engineered microorganism to substantially natural state, renders the microorganism incapable of producing a therapeutic product, renders the microorganism incapable of reproduction or cell division, or kills the microorganism. In one embodiment, the safety switch comprises a system capable of removing foreign gene inserted into the chromosome upon external stimulus. In one embodiment, the system is a Cre-loxP system in which foreign genes flanked by two loxP sequences are removed from the genome by Cre recombinase. In one embodiment, the Cre recombinase is a part of the foreign gene inserted but controlled under an inducible promoter. In another embodiment, a purified Cre recombinase is applied to sites that therapeutic product is produced. In another embodiment, the safety switch comprises a sensitivity gene that renders the microorganism susceptible to an exogenous compound or energy source, such as an antibiotic or radiation. In another embodiment, the safety switch comprises an inducible promoter that requires the presence of an exogenous compound before it allows expression of a gene of interest (such as an antibody or fragment thereof).

In one aspect, methods and use of compositions for integrating and producing antibody or a fragment thereof in a microorganism are provided. In one embodiment, the microorganism is a Lactobacillus. In one embodiment, antibody production is based on a system utilizing the APF protein of L. crispatus M247 to direct the expression and secretion of an antibody or its fragments.

In one embodiment, an antibody or fragment thereof is expressed as an APF-fusion protein. APF can be divided into N- and C-terminal domains separated by a central region rich in asparagine, glutamine, threonine and alanine. The APF protein is positively charged. It can interact electrostatically with the negatively charged cell envelope teichoic acid. In one embodiment, antibodies are secreted as an APF-fusion protein. In another embodiment, APF-fusion proteins located within bacterial cell membrane that are in the process of being secreted can be extracted by treating the cell with 5 M LiCl.

In one embodiment, the APF system utilizes a site-specific integration apparatus of the temperate bacteriophage A2 of Lactobacillus. In one embodiment, the APF protein is expressed and present in homofermentative Lactobacilli. In another embodiment, the APF protein is expressed and secreted from heterofermentative Lactobacilli or other Gram positive bacteria. In another embodiment, the APF protein is expressed and present in culture medium. In another embodiment, the APF protein is expressed and present on the surface of a Lactobacillus. In one embodiment, an antibody or a fragment thereof is covalently linked to a scFv. In another embodiment, an antibody or a fragment thereof is covalently linked to a scFv recognizing SAI/II adhesion. In another embodiment, an antibody or a fragment thereof is fused with the APF protein. In another embodiment, an antibody or a fragment thereof is covalently linked to scFv and the APF protein. In another embodiment, scFv is fused to the APF protein via an antibody or a fragment thereof. In one embodiment, a region of the APF protein is selected for expression and secretion of an antibody or a fragment thereof. In one embodiment, an APF protein is an APF protein of Lactobacillus crispatus. In one embodiment, an APF protein of Lactobacillus crispatus is an APF of strain M247 or Mu5 (Table 2).

TABLE 2

Sequence of APF

| SEQ. ID. No. | Sequence |
|---|---|
| 2 | TTGAAAATTAAATCTATCTTAGTTAAGTCAATTGCAGTAACTGCTTTATCAGTTACAGGTTTAGTAGCAG CTAATAACAACACTAATACTGCTCAAGCTGCTATTGTAGAAAACGATACAGCTGTTGTAACAGTTAAGAA CGTTTCAGACAACGCAATCACTGTTTACAACAGCTACAAGAATCCAGAGGCTACTGGCCAAACTTTGGCA AGCAACACCTCATGGAAAGTAATTAAGACTGCTTACGATGCCAAAGGTCACAAGTGGTATGACTTAGGCA AGAACCAATGGGTTCGTGCTAAGTATGTAACTCGCGGCTACCACACTCAAGCTGCTGTAACCCAAGCTCC AGTACAACACCAAACTCAAACTGAAAATACTAATTCTGCAGCAACTACTACTGCAGCAAATAACACCAAC ACTCAAACTACTACTTCAACTGTAAGTGGTTCAGAAGCTAGTGCTAAGGAATGGATTGCCGGTAGAGAAT CTGGTGGCTCATACGGTGCTTCAAATGGTCAATACGTTGGTAAATACCAACTTTCAGCTTCATACTTGAA TGGTGACTATTCAGCAGCTAACCAAGAGCGAGTAGCTGATAACTATGTCAAAGGTCGTTATGGCTCATGG ACTGCTGCTAAGGCATTCTGGCAAGCAAACGGCTGGTACTAA |

In one embodiment, a fusion protein of an antibody or a fragment thereof is produced with the N-terminal portion of the APF protein. In another embodiment, a fusion protein of antibody or a fragment thereof is produced by fusing an scFv antibody or a fragment thereof to the middle region and C-terminal part of APF. In another embodiment, fusions with the middle region and C-terminal part of APF are produced to attach antibody or a fragment thereof to the surface of a bacterium.

In one embodiment, in order to produce antibody or a fragment thereof covalently bound to the cell surface via the carboxyterminal LPXTG, scFv is fused to the anchoring signal sequence of the L. casei prtP gene. In one embodiment, an antibody, either attached to a cell or cell-free form, is detected by flow cytometry. In another embodiment, varying amounts of covalent surface anchored proteins are detected in the supernatant.

In one embodiment, three expression cassettes are selected based on the amount of scFv produced and the location of the scFv (supernatant only, cell surface and supernatant, cell wall anchored). In another embodiment, expression cassettes are used to produce scFvs against ICAM-1 as well as VHHs against rotavirus and the SAI/II adhesion of S. mutans. In another embodiment, the scFv anti-ICAM-1 produced by Lactobacilli has a higher binding activity than the scFv anti-SAI/II. In another embodiment, fusion to the C-terminal APF part increases the level of antibody secretion. In another embodiment, a sequence is inserted between the middle region of APF and the antibody or a fragment thereof to elongate the fusion protein and to improve the display of antibody or a fragment thereof.

In one embodiment, the pEM76 delivery system is used to catalyze the integration of the fusion between the apf gene and the gene encoding the scFv directed against the SAI/II adhesion of S. mutans into the attB site of L. paracasei. In another embodiment, the system uses site-specific integration apparatus of temperate bacteriophage A2 of Lactobacillus. In another embodiment, the system creates integration of expression cassettes mediating secretion, secretion and attachment, and surface anchoring of the scFv.

In one embodiment, a gene encoding a surface anchored VHH antibody is integrated to the genome of a microorganism. In one embodiment, a gene encoding a surface anchored VNAR antibody is integrated to the genome of a microorganism. In another embodiment, a gene encoding a surface anchored scFv is integrated to the microorganism.

In another embodiment, up to about 1000 antibody molecules are displayed on the surface of a microorganism. In another embodiment, up to about 2000 antibody molecules are displayed on the surface of a microorganism. The number of antibody molecules that are displayed on the surface of a microorganism includes, but is not limited to, up to about 10,000, 20,000, 30,000, 40,000, 50,000, 75,000, 100,000, 200,000, 500,000, 750,000, and 1,000,000. In another embodiment, the integrated VHH or VNAR gene is stable over 50 generations. In another embodiment, the integrated VHH or VNAR sequence is stable over 100 generations.

In one aspect, integration and expression methods described herein is applied to other lactic acid bacteria, including *L. lactis*. In one embodiment, the apf promoter originally from *L. crispatus* is used in *L. paracasei*. In another embodiment, antibody or a fragment thereof is produced in *L. rhamnosus* GG using the cassettes described herein. In one embodiment, sequence of the attB site is utilized for the application in *L. lactis*.

In one aspect, two or more expression cassettes encoding antibodies of different specificities are integrated. In one embodiment, a first cassette encodes and expresses and ICAM-specific antibody. In another embodiment, a first cassette encodes and expresses a CD18-specific antibody. In another embodiment, a first cassette encodes and expresses a CD11-specific antibody. In another embodiment, a cassette encodes and expresses an ICAM-specific and a CD18-specific antibody. In another embodiment, a cassette encodes and expresses an ICAM-specific, a CD11-specific and a CD18-specific antibody.

In addition to APF system, a cell surface, cell wall, or secreted protein of a microorganism can be used as a fusion partner to express, display or secrete the antibodies or fragments thereof at the delivered sites. Examples of bacterial proteins that can be useful for methods disclosed herein include, but are not limited to, periplasmic ABC-type metal ion transport system, component/surface adhesion lemA protein FmtB surface protein sixty seven kDa Myosin-crossreactive streptococcal antigen, Myosin-crossreactive antigen, Sortase, Mucus binding protein precursor, Mucus binding protein, Mucus binding protein precursor, Steroid binding protein, Surface exclusion protein, Tropomyosin-like protein, Biofilm-associated surface protein, Aggregation promoting protein, Aggregation promoting protein, Fibrinogen-binding protein, Surface layer protein, Autolysin; amidase, Cell shape-determining protein (MreB), Cell shape-determining protein (MreB), Cell shape-determining protein (MreC), Cell shape-determining protein (MreD), Rod shape-determining protein (RodA), UDP-N-acetylmuramate-alanine ligase, UDP-N-acetylmuramyl tripeptide synthetase, UDP-N-acetylmuramoyl-L-alanyl-D-glutamyl-lysine ligase, UDP-N-acetylmuroylalanine-D-glutamate ligase, p-N-acetylmuramoyl-pentapeptide-transferase, p-N-acetylmuramoyl-pentapeptide-transferase, N-acetylmuramidase, d-alanine-d-alanine ligase, Permease, d-ala-d-ala adding enzyme, d-alanyl-d-alanine carboxypeptidase, UDP-N-acetylglucosamine 1-carboxyvinyltransferase, UDP-N-acetylglucosamine pyrophosphorylase, Undecaprenyl pyrophosphate synthetase, Undecaprenyl-phosphate N-acetylglucosaminyltransferase, Penicillin binding protein, Penicillin binding protein 1A, Penicillin binding protein-related factor A, Penicillin binding protein 2B, DltA D-alanine-D-alanyl carrier protein ligase, DltB basic membrane protein, DltC D-alanyl carrier protein, DltD extramembranal transfer protein, Oligosaccharide repeat unit transporter (EpsI), UDP-galactopyranose mutase, Polysaccharide polymerase, Glycosyltransferase, Galactosyl transferase, Phospho-glucosyltransferase (EpsE), EpsD, EpsC, EpsB, EpsA, GTP-binding protein, Cell wall-associated hydrolase, Guanylate kinase, Cell surface, cell membrane or secreted protein, Membrane protein, Cell surface, cell membrane or secreted protein, Ribonucleotide reductase (NrdI), Ribonucleotide reductase, Cell surface, cell membrane or secreted protein, Cell surface, cell membrane or secreted protein, Cell surface, cell membrane or secreted protein, ABC transporter component, ABC transporter, ATPase component of ABC transporter, Acetyltransferase, Transcriptional regulator, Polysaccharide transporter, EpsV, EpsU, EpsA, Capsular polysaccharide biosynthesis protein J (capJ), Cap5P, Cap5P, CpsIVN, Lipopolysaccharide biosynthesis protein, Cellulose synthase, Sucrose phosphorylase, Polysaccharide transporter, LPS biosynthesis protein, Oligo-1,6-glucosidase, Alpha-glucosidase, Glucan 1,6-alpha-glucosidase, Alpha-glucosidase II, Dextran glucosidase, 1,4-alpha-glucan branching enzyme, Neopullulanase, Pullulanase, Amylopullulanase, Cyclomaltodextrin transport membrane protein, bacterial cell division membrane protein, Membrane protein, Membrane protein, DNA methylase, tRNA (guanine-N1)-methyltransferase, Theronyl-tRNA synthetase, Surface protein, Transport accessory protein, Methionine synthase, Autoinducer-2 production protein (LuxS), or Cell division protein (cdpA) or Biofilm-associated surface protein.

In one embodiment, methods and compositions for producing ICAM-1 antibody in a microorganism are described. In one embodiment, the microorganism is a *Lactobacillus* strain. In another embodiment, the microorganism is a *Lactobacillus paracasei*. In one embodiment, a *Lactobacillus* APF protein directs the expression and secretion of antibody or a fragment thereof. In another embodiment, a site-specific integration apparatus of the temperate bacteriophage A2 is used to mediate chromosomal integration of exogenous nucleic acid sequence that encodes an ICAM-1 antibody or a fragment thereof. In one embodiment, a fusion between the antibody or a fragment thereof and the apf gene is generated to optimize the level of expression, secretion and location of the antibody or a fragment thereof. In one embodiment, non-covalent and covalent anchoring systems are used for expression. In one embodiment, an expression cassette is integrated in the chromosome using site-specific integration vectors, generating food grade *Lactobacilli* producing antibody or a fragment thereof.

In one embodiment, a microorganism is used to produce CD18-specific antibody or a fragment thereof. In one embodiment, the microorganism is *Lactobacillus paracasei*. In one embodiment, a *Lactobacillus* APF protein directs the expression and secretion of antibody or a fragment thereof. In one embodiment, the expression utilizes site-specific integration apparatus of the temperate bacteriophage A2 to mediate chromosomal integration for CD18 antibody expression. In one embodiment, a fusion between the antibody or a fragment thereof and the apf gene is generated to optimize the level of expression, secretion and location of the antibody or a fragment thereof. In one embodiment, non-covalent and covalent anchoring systems are used for expression. In one embodiment, an expression cassette is integrated in the chromosome using site-specific integration vectors, generating food grade *Lactobacilli* producing antibody or a fragment thereof.

In one embodiment, a microorganism is used to produce a CD11-specific antibody or a fragment thereof. A CD11 antibody as used herein can be a CD11a, CD11b, CD11c or CD11d antibody. In one embodiment the CD11-specific antibody is a human antibody. In another embodiment the CD11- specific antibody is a humanized antibody. In another embodiment the CD11-specific antibody is a camelid antibody. In another embodiment the CD11-specific antibody is a VHH or VNAR antibody. In one embodiment, the microorganism is *Lactobacillus paracasei*. In one embodiment, a *Lactobacillus* APF protein directs the expression and secretion of antibody or a fragment thereof. In one embodiment, the expression utilizes site-specific integration apparatus of the temperate bacteriophage A2 to mediate chromosomal integration for CD11 antibody expression. In one embodiment, a fusion between the antibody or a fragment thereof and the apf gene is generated to optimize the level of expression, secretion and location of the antibody or a fragment thereof. In one embodiment, non-covalent or covalent anchoring systems are used for expression. In one embodiment, an expression cassette is integrated in the chromosome using site-specific integration vectors, generating food grade *Lactobacilli* producing antibody or a fragment thereof.

Delivery of a Therapeutic Product

In one aspect, methods and compositions described herein are related to expression of a therapeutic product by a delivery vehicle. In one embodiment, a therapeutic product is expressed intracellularly. In another embodiment, a therapeutic product is anchored on the surface of the delivery vehicle. The anchoring can be enabled by fusing the therapeutic product to a known cell surface protein of the delivery vehicle. Various fusion combinations between the fusion partner and the heterologous gene can be performed to obtain production of the protein at different cellular locations and to optimize expression and secretion. In one embodiment, to achieve cell surface display of heterologous proteins in *Lactobacilli*, cell wall sorting and covalent anchoring mechanisms of the M protein and prtP proteases is used. In another embodiment, anchoring comprises the cell wall spanning (CWS) domain of the *Lactococcus lactis* protein PrtP or a functional part thereof, derivative and/or analogue thereof. In another embodiment, anchoring comprises AcmA or AcmD type protein anchors, the AcmA and AcmD-type carbohydrate binding domains, or their homologs thereof. In another embodiment, therapeutic products are fused to anchoring system of S-layer and Sep proteins.

In one embodiment a therapeutic product comprises one or more antibodies that bind to a human ICAM-1, CD18, or CD11 (e.g. CD11a, CD11b, CD11c or CD11d subunits). In one embodiment the one or more antibodies are single chain antibodies. In another embodiment the one or more antibodies are camelid or camelid modified antibodies. In another embodiment the one or more antibodies are VHH or VNAR antibodies.

Releasing Therapeutic Product at Target Area

In one aspect, methods and compositions described herein are related to releasing of a therapeutic product by a delivery vehicle. In one embodiment, a method of releasing a therapeutic product comprises a constitutive release. A method of producing a therapeutic product comprises an inductive release. In one embodiment, releasing includes, but is not limited to, secretion, active transport, exocytosis, phagocytosis, and passive diffusion. In one embodiment, a therapeutic product is diffused out from a vehicle. In another embodiment, a therapeutic product is exported from a vehicle. In another embodiment, a therapeutic product is secreted from a vehicle.

Disease

In one aspect, methods and compositions described herein are related to methods of treating or preventing a disease with a delivery system. In one embodiment, a system comprises a delivery vehicle, a therapeutic product, medical devices or chemicals employed in delivering the vehicle to a target area. In another embodiment, the system is used for treating or preventing a medical condition.

In one embodiment, a treatment includes medical treatment upon observing a condition in situ. In one embodiment, a medical disease or a condition is prevented by employing a delivery system described herein. In another embodiment, the system produces a therapeutic product that prevents infection by a pathogen.

In one embodiment, a disease is an pathogenic infection or disease. In another embodiment, an infection is a viral infection. In another embodiment, a viral infection is a human immunodeficiency virus infection. In another embodiment, a viral infection is human papilloma virus infection. In another embodiment, a viral infection is herpes virus infection. In another embodiment, a viral infection is sexually transmitted infection. In another embodiment, a disease is bacterial infection. In another embodiment, a disease is a fungal infection. In another embodiment, a disease is infection by a prion. In another embodiment, a disease is parasitic infection. In another embodiment, a disease is a condition of the immune system. In another embodiment, a disease is a cancer. In another embodiment, a cancer is a cervical cancer.

An infectious or parasitic disease includes, but is not limited to, intestinal infectious diseases, tuberculosis, zoonotic bacterial diseases, other bacterial diseases, human immunodeficiency virus (HIV) infection, poliomyelitis and other non arthropod borne viral diseases of central nervous system, viral diseases accompanied by exanthem, arthropod borne viral diseases, other diseases due to viruses and chlamydiae, rickettsioses and other arthropod borne diseases, syphilis and other venereal diseases, other spirochetal diseases, mycoses, helminthiases, other infectious and parasitic diseases, and late effects of infectious and parasitic diseases.

Intestinal infectious diseases include, but are not limited to cholera, typhoid and paratyphoid fevers, *salmonella* gastroenteritis, shigellosis, shigellosis, staphylococcal food poisoning, amoebiasis, acute amoebic dysentery without mention of abscess, chronic intestinal amoebiasis without mention of abscess, amoebic nondysenteric colitis, amoebic liver abscess, amoebic lung abscess, amoebic brain abscess, amoebic skin ulceration, amoebic infection of other sites, amoebiasis, balantidiasis, giardiasis, coccidiosis, intestinal trichomoniasis, cryptosporidiosis, cyclosporiasis, protozoal intestinal disease, intestinal infections due to other organisms, enteritis due to rotavirus, enteritis due to other viral enteritis, intestinal infection due to other organism not elsewhere classified, ill defined intestinal infections, colitis enteritis and gastroenteritis of presumed infectious origin.

Tuberculosis includes, but is not limited to primary tuberculous infection, pulmonary tuberculosis, tuberculosis of meninges and central nervous system, tuberculosis of intestines, peritoneum, and mesenteric glands, tuberculosis of bones and joints, tuberculosis of vertebral column, pott's disease, tuberculosis of genitourinary system, tuberculosis of other organs, erythema nodosum with hypersensitivity reaction in tuberculosis, bazin disease, tuberculosis of peripheral lymph nodes, scrofula, and miliary tuberculosis.

Zoonotic bacterial diseases includes, but is not limited to plague, bubonic plague, tularemia, anthrax, brucellosis, glanders, melioidosis, rat bite fever, listeriosis, *erysipelothrix* infection, and pasteurellosis.

Other bacterial diseases include, but are not limited to leprosy, diseases due to other mycobacteria, diphtheria, whooping cough, streptococcal sore throat and scarlatina, strep throat, scarlet fever, erysipelas, meningococcal meningitis, tetanus, septicemia, pneumococcal septicemia, gram negative septicemia, septicemia, and actinomycotic infections.

A human immunodeficiency virus infection includes, but is not limited to human immunodeficiency virus infection with specified conditions, human immunodeficiency virus infection causing other specified, and other human immunodeficiency virus infection.

A poliomyelitis and other non arthropod borne viral diseases of central nervous system include, but are not limited to acute poliomyelitis, slow virus infection of central nervous system, kuru, creutzfeld jakob disease, Prion diseases, meningitis due to enterovirus, other enterovirus diseases of central nervous system, and other non arthropod borne viral diseases of central nervous system.

Viral diseases accompanied by exanthem include, but are not limited to smallpox, cowpox and paravaccinia, chickenpox, herpes zoster, herpes simplex, genital herpes, herpetic gingivostomatitis, herpetic disease, uncomplicated, measles, rubella, other viral exanthemata, fifth disease, viral exanthems, roseola infantum, other human herpesvirus encephalitis, other human herpesvirus infections, other poxvirus infections, other orthopoxvirus infections, monkeypox, other parapoxvirus infections, bovine stomatitis, sealpox, yatapoxvirus infections, tanapox, yaba monkey tumor virus, other poxvirus infections, and poxvirus infections.

Arthropod borne viral diseases include, but are not limited to yellow fever, dengue fever, mosquito borne viral encephalitis, encephalitis, tick borne viral encephalitis, viral encephalitis transmitted by other and arthropods, arthropod borne hemorrhagic fever, ebola hemorrhagic fever, other arthropod borne viral diseases, and west nile virus.

Other pathogenic diseases due to viruses and chlamydiae include, but are not limited to viral hepatitis, hepatitis a with hepatic coma, hepatitis a without coma, hepatitis b with hepatic coma, hepatitis b without coma, acute, other specified viral hepatitis with mention of hepatic coma, other specified viral hepatitis without mention of hepatic coma, viral hepatitis c, viral hepatitis c without hepatic coma, viral hepatitis c with hepatic coma, hepatitis, viral, rabies, mumps, mumps, uncomplicated, ornithosis, specific diseases due to coxsackie virus, herpangina, hand, foot, mouth disease, mononucleosis, trachoma, other diseases of conjunctiva due to viruses and chlamydiae, other diseases due to viruses and chlamydiae, molluscum contagiosum, warts, all sites, condyloma acuminata, sweating fever, cat scratch disease, foot and mouth disease, cmv disease, rhinovirus, HIV, HPV, and respiratory syncytial virus.

Rickettsioses and other arthropod borne diseases include, but are not limited to louse borne epidemic typhus, other typhus, tick borne rickettsioses, rocky mountain spotted fever, other rickettsioses, malaria, leishmaniasis, trypa omiasis, relapsing fever, other arthropod borne diseases, other specified arthropod borne diseases, lyme disease, and babesiosis.

Syphilis and other venereal diseases include, but are not limited to congenital syphilis, early syphilis, symptomatic, syphilis, primary, genital, early syphilis, latent, cardiovascular syphilis, neurosyphilis, other forms of late syphilis, with symptoms, late syphilis, latent, other and syphilis, gonococcal infections, gonorrhoea, acute, lower GU tract, gonococcal conjunctivitis, and nongonococcal urethritis.

Other spirochetal diseases include, but are not limited to leptospirosis, vincent's angina, yaws, and pinta.

Mycoses include, but are not limited to dermatophytosis, dermatophytosis of scalp/beard, onychomycosis, dermatophytosis of hand, tinea cruris, tinea pedis, tinea corporis, dermatomycosis, tinea versicolor, dermatomycosis, candidiasis, moniliasis, oral, moniliasis, vulva/vagina, monilial balanitis, moniliasis, skin/nails, coccidioidomycosis, histoplasmosis, *histoplasma* infection, blastomycotic infection, other mycoses, and opportunistic mycoses.

Helminthiases include, but are not limited to schistosomiasis bilharziasis, other trematode infections, echinococcosis, other cestode infection, trichi is, filarial infection and dracontiasis, ancylostomiasis and necatoriasis, other intestinal helminthiases, *ascariasis*, anisakiasis, strongyloidiasis, trichuriasis, enterobiasis, capillariasis, trichostrongyliasis, helminthiases, intestinal parasitism.

Other pathogenic diseases include, but are not limited to toxoplasmosis, toxoplasmosis, trichomoniasis, urogenital trichomoniasis, trichomonal vaginitis, trichomoniasis, urethritis, pediculosis and phthirus infestation, pediculosis, head lice, pediculosis, body lice, pediculosis, pubic lice, pediculosis, acariasis, scabies, chiggers, sarcoidosis, ainhum, behcet's syndrome, pneumocystosis, psorospermiasis, and sarcosporidiosis.

Late effects of infectious and parasitic diseases include, but are not limited to late effects of tuberculosis, and late effects of polio.

A pathogenic infection or disease can arise from bacterial, viral, fungal, or other parasitic infection. A bacterial pathogen includes, but is not limited to *Acinetobacter baumannii, Bacillus anthracia, Bartonella, Bordetella pertussis, Borrelia, Brucella, Chlamydia pneumoniae, Chlamydia trachomatis, Clostridium botulinum, Clostridium difficile, Corynebacterium diphtheriae, Coxiella burnetii, Ehrlichia, Enterococci, Enterovirulent Escherichia coli, Francisella tularensis, Haemophilus ducreyi, Helicobacter pylori, Klebsiella pneumoniae, Legionella pneumophila, Leptospira interrogans, Mycobacterium tuberculosis, Mycoplasma genitalium, Mycoplasma pneumoniae, Neisseria gonorrhoeae, Neisseria meningitidis, Orientia tsutsugamushi, Pseudomonas aeruginosa, Rickettsia, Salmonella, Shigella, Staphylococcus aureus, Streptococcus pneumoniae, Streptococcus pyogenes, Treponema pallidum, Ureaplasma urealyticum, Vibrio cholerae, Vibrio vulnificus,* and *Yersinia pestis.*

A viral pathogen includes, but is not limited to Adenovirus, Astrovirus, Avian influenza virus, Coxsackievirus, Dengue virus, Ebola virus, Echovirus, Enteric adenovirus, Enterovirus, Hantaviruses, Hepatitis A virus, Hepatitis B virus, Hepatitis C virus, Hepatitis D virus, Hepatitis E virus, Herpes simplex virus (HSV), Human cytomegalovirus, Human immunodeficiency virus (HIV), Human papillomavirus (HPV), Influenza virus, Japanese encephalitis virus (JEV), Lassa virus, Marburg virus, Measles virus, Mumps virus, Norovirus, Parainfluenza virus, Poliovirus, Rabies virus, Respiratory syncytial virus, Rotavirus, Rubella virus, SARS coronavirus, Tick-borne encephalitis virus (TBEV), Variola virus, West Nile virus, and Yellow fever virus.

A fungal pathogen includes, but is not limited to *Candida albicans.*

A parasitic pathogen includes, but is not limited to *Plasmodium, Schistosoma mansoni,* and *Trichomonas vaginalis.*

In one embodiment, a pathogenic infection is an HIV infection. An HIV infection can be caused by any infectious HIV type or subtype, such as HIV-1, HIV-2, or HIV-3, or HIVs with various envelop proteins such as group M (subtypes A, B, C, D, E [A/E], F, G, H, I [A/G/I or A/G/H/K/] J, K, or circulating recombinant forms), group N, group O, or group P.

In another embodiment, a pathogenic infection is an HPV (human papilloma virus) infection. An HPV infection can be caused by any infectious HPV type or subtype, such as HPV- 1, HPV-2, HPV-3, HPV-4, HPV-6, HPV-7, HPV-10, HPV-11, HPV-16, HPV-18, HPV-31, HPV-32, HPV-33, HPV-39, HPV-42, HPV-44, HPV-45, HPV-51, HPV-52, HPV-53, HPV-56, HPV-58, HPV-59, HPV-66, HPV-68, HPV-73, or HPV-82. In one embodiment, a disease is HPV-16 infection. In another embodiment, a disease is HPV-18 infection. In another embodiment, a disease is HPV-31 infection. In another embodiment, a disease is HPV-45 infection. In another embodiment, a disease is HPV-6 infection. In another embodiment, a disease is HPV-11 infection.

In another embodiment, a pathogenic infection is an HSV (herpes simplex virus) infection. An HSV infection can be caused by any infectious HSV type or subtype, such as HSV-1, HSV-2, HHV-1 (Human herpes virus), or HHV-2.

In another embodiment, a pathogenic infection is an infection by a virus in the genus of Parvovirus. A virus in the genus of Parvovirus includes, but is not limited to, Canine parvovirus, Chicken parvovirus, Feline panleukopenia virus, Feline parvovirus, HB virus, H-1 virus, Kilham rat virus, Lapine parvovirus, LUIII virus, Mink enteritis virus, Minute virus of mice, Murine parvovirus 1, Porcine parvovirus, Raccoon parvovirus, RT parvovirus, and Tumor virus X.

In another embodiment, a pathogenic infection is an infection by a virus in the family of Parvoviridae. A virus in the family of Parvoviridae includes, but is not limited to, parvovirus B19, and Adeno-associated virus 2. In another embodiment, an infection is rotavirus infection.

In one embodiment, a delivery vehicle is used to treat or prevent infection by a pathogen. In another embodiment, a delivery vehicle is used to provide passive immunization against infectious disease. In another embodiment, a delivery vehicle described herein is used for providing a preventive measure against prolonged infection. In another embodiment, a delivery vehicle described herein is used for providing a preventive measure against reentry of infectious virus. In another embodiment, a delivery vehicle described herein is used for providing a preventive measure against virus passing through an epithelial layer of an animal, such as gut epithelia or vaginal epithelia. In another embodiment, a delivery vehicle described herein is used for inhibiting transmigration of virus through an epithelial layer. In another embodiment, a delivery vehicle described herein is used for inhibiting transmigration of virus through a vaginal epithelial layer. In another embodiment, a delivery vehicle described herein is used for inhibiting transmigration of virus through a rectal epithelial layer. In another embodiment, a delivery vehicle described herein is used for inhibiting transmigration of virus through an oral epithelial layer. In another embodiment, a delivery vehicle described herein is used for inhibiting transmigration of virus through an ocular epithelial layer. In another embodiment, a delivery vehicle described herein is used for inhibiting transmigration of virus through a gastrointestinal epithelial layer. In one embodiment, the transmigration of virus through an epithelial layer is completely blocked by a delivery vehicle described herein. In another embodiment, the transmigration of virus is partially blocked by a delivery vehicle described herein. In another embodiment, a delivery vehicle described herein blocks up to about 10%, 20%, 30%, 40%, 50%, 60%, 70%, 80%, or 90% of virus capable of transmigration from transmigration. In another embodiment, a virus that can transmigrate through an epithelial layer is collected in a laboratory transwell migration assay and its quantity is measured by an enzyme-linked immunoabsorbent assay (ELISA). In another embodiment, a delivery vehicle described herein is used for preventing cell adhesion and/or internalization of a virus. In another embodiment, a delivery vehicle described herein is used to prevent cell adhesion. In another embodiment, a delivery vehicle described herein is used to prevent cell adhesion to an epithelial layer of a mammal. In another embodiment, a delivery vehicle described herein is used for preventing virus adhering to cell surface molecules. In another embodiment, a delivery vehicle described herein is used for preventing virus from binding to a host cell or cells. In another embodiment, a delivery vehicle described herein is used for preventing virus from gaining entry into the bloodstream. In another embodiment, a delivery vehicle described herein is used for preventing virus from attaching to a host cell that expresses a cell surface molecule recognized by virus. In another embodiment, a delivery vehicle described herein is used for preventing viral entry and neutralizing a virus. In one embodiment the virus is an HIV, HPV or HSV virus. In one embodiment the delivery vehicle comprises a recombinant microorganism (such as a *Lactobacillus*) that expresses an antibody or fragment thereof that inhibits transepithelial migration of a virus through an epithelial layer. In one embodiment the recombinant microorganism comprises one or more polynucleotides that encode one or more antibodies or fragments thereof. In one embodiment the one or more polynucleotides are integrated into a chromosome of the recombinant microorganism. In another embodiment the one or more polynucleotides are not integrated into a chromosome of the recombinant microorganism.

In one embodiment a *Lactobacillus* comprises an exogenous nucleic acid integrated into a chromosome of the *Lactobacillus* that encodes an antibody or fragment thereof. In another embodiment a *Lactobacillus* comprises more than one exogenous nucleic acid integrated into a chromosome of the *Lactobacillus* that encodes an antibody or fragment thereof. In one embodiment the *Lactobacillus* expresses the antibody or fragment thereof. In one embodiment the antibody or fragment thereof binds to human CD18, CD11, ICAM-1 or a subunit thereof. In another embodiment the *Lactobacillus* expresses two or more antibodies or fragments thereof that bind to human CD18, CD11, ICAM-1 or a subunit thereof. In one embodiment the *Lactobacillus* is administered to a human to treat or prevent infection from a pathogen. In one embodiment the pathogen is a virus. In one embodiment the virus is a HIV, HPV or HSV. In another embodiment the virus is HIV. In one embodiment the human is a man. In one embodiment the *Lactobacillus* is administered to the man's genitals. In another embodiment the *Lactobacillus* is administered to the man's rectum. In another embodiment the *Lactobacillus* is administered to the man's urethra. In another embodiment the *Lactobacillus* is administered to a man in conjunction with a contraceptive. In another embodiment the *Lactobacillus* is administered to a man in conjunction with a prophylactic. In another embodiment the human is a woman. In one embodiment the *Lactobacillus* is administered to the woman's genitals. In another embodiment the *Lactobacillus* is administered to the woman's vagina. In another embodiment the *Lactobacillus* is administered to the woman's urethra. In another embodiment the *Lactobacillus* is administered to the woman's rectum. In one embodiment the *Lactobacillus* administered to the woman's vagina expresses an antibody or fragment thereof bind to human CD18, CD11, ICAM-1 which inhibits viral transmigration through an epithelial layer. In one embodiment the inhibited virus is a HIV, HPV or HSV virus. In one embodiment the inhibited virus is a HIV.

In one embodiment treatment of a human population with a *Lactobacillus* that comprises an exogenous nucleic acid integrated into a chromosome of the *Lactobacillus* encodes an antibody or fragment thereof that binds to human CD18, CD11, ICAM-1 and expresses said antibody or fragment thereof decreases the rate of HIV infection in said human population by 1-100%, such as 10-90% or 20-80% or 30-70& or 40-60% or 50% compared to a human population that is not treated with said *Lactobacillus*. In another embodiment the rate of decrease is 1, 2, 3, 4, 5, 6, 7, 8, 9, 10 11, 12, 13, 14, 15, 16, 17, 18, 19, 20, 21, 22, 23, 24, 25, 26 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 88, 83, 84, 85, 86, 87, 88, 89, 90, 91, 92, 93, 94, 95, 96, 97, 98, 99, or 100%. In one embodiment the human population comprises males and females. In another embodiment the human population consists of females. In another embodiment the human population consists of males. In another embodiment the human population comprises humans from newborns to those that are 80 years old. In another embodiment the human population comprises humans from newborns to those that are 10 years old. In another embodiment the human population comprises humans from newborns to those that are 20 years old. In another embodiment the human population comprises humans from newborns to those that are 10 years old.

Blocking Transmission of Cell-Associated HIV-1 Across a Cervical Epithelial Monolayer It has been previously shown that commercially available free anti CD18 or anti-ICAM-1 antibodies block transmission of cell-associated HIV-1 across a cervical epithelial monolayer (U.S. Pat. No. 6,566,095 and US 20090317404, which are herein incorporated by reference in their entirety). Anti-ICAM-1 (clone MT-M5), anti-CD18 (clone H52), or isotype control mouse IgG1 were added to HIV-infected PBMC immediately prior to their addition to the apical chamber of cervical epithelial transwell cultures (US 20090317404). PBMC were allowed to migrate for 24 hours and antibodies remained present for the duration of the assay. It was shown that both anti-ICAM-1 and anti-CD18 significantly reduced cell migration at all concentrations when tested over a range of 10-100 μg/ml when compared to both untreated and isotype controls. However, anti-CD 18 blocked cell migration significantly better than anti-ICAM-1 at all concentrations tested, further reducing the number of cells detected in the basal compartment when compared to blocking by the corresponding concentration of anti-ICAM-1. Further, it was observed that commercially available free antibodies to CD 18 and ICAM-1 when mixed at a 50:50 ratio successfully block transmigration of PBMC from infected cultures (US 20090317404). Increased efficacy was also observed at lower concentrations of anti-CD18 and anti-ICAM-1, in combination, than at higher concentrations of anti-CD18 and anti-ICAM-1, individually.

EXAMPLES

Example 1

The aggregation-promoting factor (APF) protein of *Lactobacillus crispatus* was used as a vector molecule to deliver antibody or a fragment thereof. APF protein has useful characteristics such as high secretion level and non-covalent anchoring to the bacterium.

The integration vector contains the phage A2 integrase gene (A2-int) which catalyses the insertion of vector DNA containing the A2-attP site into an attB site present in the genome of all lactic acid bacteria tested so far. Subsequent expression of a β-recombinase catalyses the deletion of non "food grade" DNA (antibiotic resistance gene, *E. coli* DNA) located between two six sites. The system can generate stable integration without the use of selection markers and as it presents some flexibility with regard to the sequence of the attB site, it can be use for integration of heterologous genes in various lactic acid bacteria.

Bacterial Strains, Plasmids and Growth Conditions.

The bacterial strains and plasmids used are listed in Table 1. *Escherichia coli* DH5a was grown with shaking at 37° C. in Luria-Bertani (LB) medium. *Lactobacillus paracasei* (previously known as *L. casei* or *L. zeae* ATCC 393 pLZ15$^-$) was grown in MRS broth at 37° C. under static conditions (Difco™, Becton Dickinson, Sparks, Md.) and on MRS agar plates at 37° C. in anaerobic conditions. When appropriate, the concentration of antibiotics used was 100 μg/ampicillin or 300 μg/ml erythromycin for *E. coli* transformants and 5 μg/ml erythromycin for *L. paracasei* transformants.

TABLE 3

Strains and plasmids.

| Srains or plasmid | Relevant properties |
|---|---|
| STRAINS | |
| *E. coli* DH5α | |
| *L. paracasei* | Previously considered a plasmid free *L. casei* 393 |
| *L. paracasei* pAF100 | *L. paracasei* with pAF100 plasmid, secreted scFv anti-SAI/II |
| *L. paracasei* pAF400 | *L. paracasei* with pAF400 plasmid, secreted and attached scFv anti-SAI/II |
| *L. paracasei* pAF900 | *L. paracasei* with pAF900 plasmid, surface anchored scFv anti-SAI/II |
| *L. paracasei* pAF100-ICAM | *L. paracasei* with pAF100-ICAM plasmid, secreted scFv anti-ICAM-1 |
| *L. paracasei* pAF400-ICAM | *L. paracasei* with pAF400-ICAM plasmid, secreted and attached scFv anti-ICAM-1 |
| *L. paracasei* pAF900-ICAM | *L. paracasei* with pAF900-ICAM plasmid, surface anchored scFv anti-ICAM-1 |
| *L. paracasei* pAF100-ARP1 | *L. paracasei* with pAF100-ARP1 plasmid, secreted ARP1 anti-rotavirus |
| *L. paracasei* pAF400-ARP1 | *L. paracasei* with pAF400-ARP1 plasmid, secreted and attached ARP1 |
| *L. paracasei* pAF900-ARP1 | *L. paracasei* with pAF900-ARP1 plasmid, surface anchored ARP1 |
| *L. paracasei* pAF100-S36 | *L. paracasei* with pAF100-S36 plasmid, secreted S36-VHH anti-SAI/II |
| *L. paracasei* pAF400-S36 | *L. paracasei* with pAF400-S36 plasmid, secreted and attached S36-VHH |
| *L. paracasei* pAF900-S36 | *L. paracasei* with pAF900-S36 plasmid, surface anchored S36-VHH |
| *L. paracasei* EM171 | *L. paracasei* with integrated pAF400 cassette, secreted and attached scFv anti-SAI/II |
| *L. paracasei* EM181 | *L. paracasei* with integrated pAF900 cassette, surface anchored scFv anti-SAI/II |
| *L. paracasei* EM182 | *L. paracasei* with integrated pAF100 cassette, secreted scFv anti-SAI/II |
| pGEM-T | Apr, 3'T overhangs |
| pSP72 | Apr, multiple cloning region |
| pIAV7 | Broad range vector, Err, lacZ, pWV01 replication origin |
| pLP402-scFv-long anchor | Apr, Emr, scFv anti-SAI/II and prtP anchor region |

TABLE 3-continued

Strains and plasmids.

| Srains or plasmid | Relevant properties |
| --- | --- |
| psp72SalBamAS | pSP72 with Fragment 1 encoding the promoter region, the signal peptide (33 amino acids) and the first 4 amino acids of the N-terminal domain of the apf gene |
| psp72SalBamAS2 | pSP72 with Fragment 2 encoding the promoter region, the signal peptide (33 amino acids), the whole N-terminal domain (75 amino acids) and the middle region (37 amino acids) of the apf gene |
| psp72SalBamAS3 | pSP72 with Fragment 3 encoding the promoter region, the signal peptide and the whole N-terminal domain |
| pSP10 | pSP72SalBamAS with Fragment 4 encoding the C-terminal domain (last 78 amino acids) and the terminator region of the apf gene |
| pSP20 | pSP72SalBamAS2 with Fragment 4 |
| pSP30 | pSP72SalBamAS3 with Fragment 4 |
| pSP40 | pSP72SalBamAS with Fragment 5 encoding the middle region, the C-terminal domain and the terminator region of the apf gene |
| pSP50 | pSP72SalBamAS3 with Fragment 5 |
| pSP100 | pSP10 with scFv (anti-SAI/II)-E-tag gene followed by a stop codon |
| pSP200 | pSP20 with scFv (anti-SAI/II)-E-tag gene followed by a stop codon |
| pSP300 | pSP30 with scFv (anti-SAI/II)-E-tag gene followed by a stop codon |
| pSP400 | pSP40 with scFv (anti-SAI/II)-E-tag gene translationally fused to the downstream apf gene region |
| pSP500 | pSP50 with scFv (anti-SAI/II)-E-tag gene translationally fused to the downstream apf gene region |
| pSP600 | pSP10 with scFv (anti-SAI/II)-E-tag gene translationally fused to the downstream apf gene region |
| pSP700 | pSP20 with scFv (anti-SAI/II)-E-tag gene translationally fused to the downstream apf gene region |
| pSP800 | pSP30 with scFv (anti-SAI/II)-E-tag gene translationally fused to the downstream apf gene region |
| pSP900 | pSP600 with prtP anchored region encoding gene following the scFv (anti-SAI/II)-E-tag gene |
| pSP1000 | pSP700 with prtP anchored region encoding gene following the scFv (anti-SAI/II)-E-tag gene |
| pSP1100 | pSP800 with prtP anchored region encoding gene following the scFv (anti-SAI/II)-E-tag gene |
| pAF100 to pAF1100 series | pIAV7 with SalI and EcoRI fragment of pSP100 to pSP1100 series |
| pAF100-ICAM | pAF100 with scFv anti-human ICAM-1 |
| pAF400-ICAM | pAF400 with scFv anti-human ICAM-1 |
| pAF900-ICAM | pAF900 with scFv anti-human ICAM-1 |
| pAF100-ARP1 | pAF100 with ARP1 anti-rotavirus |
| pAF400-ARP1 | pAF400 with ARP1 anti-rotavirus |
| pAF900-ARP1 | pAF900 with ARP1 anti-rotavirus |
| pAF100-S36 | pAF100 with S36 anti-SAI/II |
| pAF400-S36 | pAF400 with S36 anti-SAI/II |
| pAF900-S36 | pAF900 with S36 anti-SAI/II |
| pEM76 | Integrative vector containing six1, A2 int, attP and six2 |
| pEM94 | Containing the β-recombinase gene in order to delete the non-food-grade DNA present in the integrated plasmids by site-specific recombination |
| pEM171 | pEM76 with expression cassette of pAF400 |
| pEM181 | pEM76 with expression cassette of pAF900 |
| pEM182 | pEM76 with expression cassette of pAF100 |

Construction of Expression Cassettes.

FIG. 1 illustrates an amplified PCR fragments used for the construction of the different expression cassettes. The APF proteins can be divided in three domains, N-terminal, C-terminal and a central region which is rich in asparagine, glutamine, threonine and alanine. PCR fragments are designated from 1 to 5 (see material and methods). Fragment 1: The region encoding the promoter region, the signal peptide (33 amino acids) and the 4 amino acid of the N-terminal domain. Fragment 2: The promoter region and the gene encoding the signal peptide (33 amino acids), the whole N-terminal domain (75 amino acid) and the middle region (37 amino acid). Fragment 3: The promoter region and the genes encoding the signal peptide and the whole N-terminal domain. Fragment 4: The gene encoding the C-terminal domain (last 78 amino acids) and the terminator region. Fragment 5: The gene encoding the middle region, the C-terminal domain and the terminator region. The apf gene of L. crispatus M247 encodes a 223 amino acid protein containing a signal peptide (33 amino acids), a N-terminal domain (75 amino acids), a central region rich in asparagine, glutamine, threonine and alanine (37 amino acids) and a C-terminal domain (the last 78 amino acids) (GeneBank AF492458) (FIG. 1). Eleven expression cassettes were generated by fusing a model scFv antibody or a fragment thereof directed against the SAI/II adhesion of S. mutans with the promoter region and the gene encoding the APF protein of L. crispatus M247. The expression cassettes differ by the APF region encoding gene fragments included (N-terminal domain, central region and C-terminal domain) or by the insertion of the anchored region of the prtP gene for covalent surface binding of the antibody or a fragment thereof.

Genomic DNA from L. crispatus M247 was purified and used as a template for amplification of five DNA fragments, 1 to 5, corresponding to different regions of the apf gene (FIG. 1). The sequences of the primers used for amplification are shown in Table 4.

TABLE 4

Primer sequences

| SEQ. ID. | Primer | SEQUENCE |
| --- | --- | --- |
| 3. | APFSalS | 5'-CGCGTCGACGGATAAGGCAGAATAATGGAATAA-3' |
| 4. | APFBamAS | 5'-CGGGATCCTTCTACAATAGCAGCTTGAGCAGT-3' |
| 5. | APFBamAS2 | 5'-CGGGATCCAGTAGTAGTTTGAGTGTTGGTGTT-3' |
| 6. | APFBamAS3 | 5'-CGGGATCCGTGGTAGCCGCGAGTTACATACT-3' |
| 7. | APFSacS | 5'-CGAGCTCTCAACTGTAAGTGGTTCAGAAGCT-3' |
| 8. | APFEcoAS2 | 5'-CGGAATTCCTTGAACCGTTTGTGGTGTCGTTT-3' |
| 9. | APFSacS2 | 5'-CGAGCTCTACCACACTCAAGCTGCTGTAACC-3' |
| 10. | scFvS | 5'-GCCCAGGTGAAACTGCAGGAGT-3' |
| 11. | E-tagAS | 5'-TGCGGCACGCGGTTCCAGCGGATCCGGATACGGCACC GGCGCACCTGCGGCCGCCGCCCGTTTTATTTCCAACT-3' |
| 12. | scFvBgl/Sfi/NcoIS | 5'-CATGAGATCTGCGGCCCAGCCGGCCATGGATGCCCAGGTGAAACTGCAG-3' |
| 13. | etagNhe/Sacstop | 5'-CCGGAGCTCCTCGCTAGCCTATGCGGCACGCGGTTCCAGCGGA-3' |
| 14. | etagNhe/Sac | 5'-CCGGAGCTCCTCGCTAGCTGCGGCACGCGGTTCCAGCGGA-3' |
| 15. | PrtPNheIS | 5'-GCTCTAGCTAGCAAGAAGACTTCGCTGCTTAACCAGT-3' |
| 16. | PrtPSacIAS | 5'-TAAGCGAGCTCCTATTCTTCACGTTGTTTCCGTT-3' |
| 17. | ICAM-NcoI | 5'-CATGCCATGGATGGGGTCAATTCAGAGGTTCAGCT-3' |
| 18. | ICAM-NotI | 5'-GCATGCGGCCGCTTTGATTTCCAGCTTGGTGCCT-3' |
| 19. | S36NcoI | 5'-AGCGGCCCAGCCGGCCATGGCCCAGGT-3' |
| 20. | S36NotI | 5'-TAAGCGGCCGCGGTGACCTGGGTTCCCTGGCCCGA-3' |
| 21. | VHH1NcoI | 5'-AGCGGCCCAGCCGGCCATGGCCCAGGT-3' |
| 22. | VHH1Not | 5'-TAAGCGGCCGCGGTGACCTGGGTTCCCTGGCCCGA-3' |

The 486-bp Fragment 1 containing the promoter region, the signal peptide (33 amino acids) and the first 4 amino acid of the N-terminal domain was amplified using primers APFSa1S and APFBamAS; the 810-bp Fragment 2, containing the promoter region and the gene segment encoding the signal peptide (33 amino acids), the whole N-terminal domain (75 amino acid) and the central region (37 amino acid), using primers APFSa1S and APFBamAS2; the 699-bp Fragment 3 containing the promoter region, the signal peptide and the whole N-terminal domain using primers APFSa1S and BamAS3; the 492-bp Fragment 4 containing the gene segment encoding the C-terminal domain (last 78 amino acids) and the terminator region using primers APFSacS and EcoAS2, and the 609-bp Fragment 5 containing the gene encoding the middle region, the C-terminal domain and the terminator region using primers APFSacS2 and EcoAS2.

Fragments 1 to 3 were digested with SalI and BamHI and ligated to a similarly digested pSP72 plasmid, generating psp72SalBamAS, psp72SalBamAS2 and psp72SalBamAS3, respectively. Fragment 4 was cloned between SacI and EcoRI sites in psp72SalBamAS, psp72SalBamAS2 and psp72SalBamAS3 vectors yielding pSP10, pSP20, and pSP30, respectively. Fragment 5 was also digested with SacI and EcoRI and ligated to similarly digested pSP72SalBamAS and pSP72SalBamAS3 vectors resulting in pSP40 and pSP50, respectively.

The gene encoding a scFv antibody or a fragment thereof directed against the SAI/II adhesion of S. mutans was amplified from the pLP402-scFv-long anchor vector using the primers scFvS and E-tagAS, thus introducing an E-tag gene downstream of the scFv and a NotI restriction site between the scFv and E-tag encoding genes. The PCR product was cloned in pGEM-T vector. The scFv-E-tag gene was further amplified using the primers scFvBgl/Sfi/NcoIS and etagNhe/Sac to introduce the restriction sites BglII, SfiI and NcoI upstream the scFv gene and the restriction site NheI and SacI downstream the E-tag gene. The PCR product was digested with BglII and SacI and cloned in pSP10, pSP20, pSP30, pSP40 and pSP50 generating pSP600, pSP700, pSP800, pSP400 and pSP500, respectively. The scFv-E-tag gene was also amplified using the primers scFvBgl/Sfi/NcoIS and etagNhe/Sacstop, introducing a stop codon after the E-tag. The PCR product was digested with BglII and SacI and cloned between BamHI and SacI in pSP10, pSP20, pSP30 yielding pSP100, pSP200 and pSP300, respectively.

Figure 2:
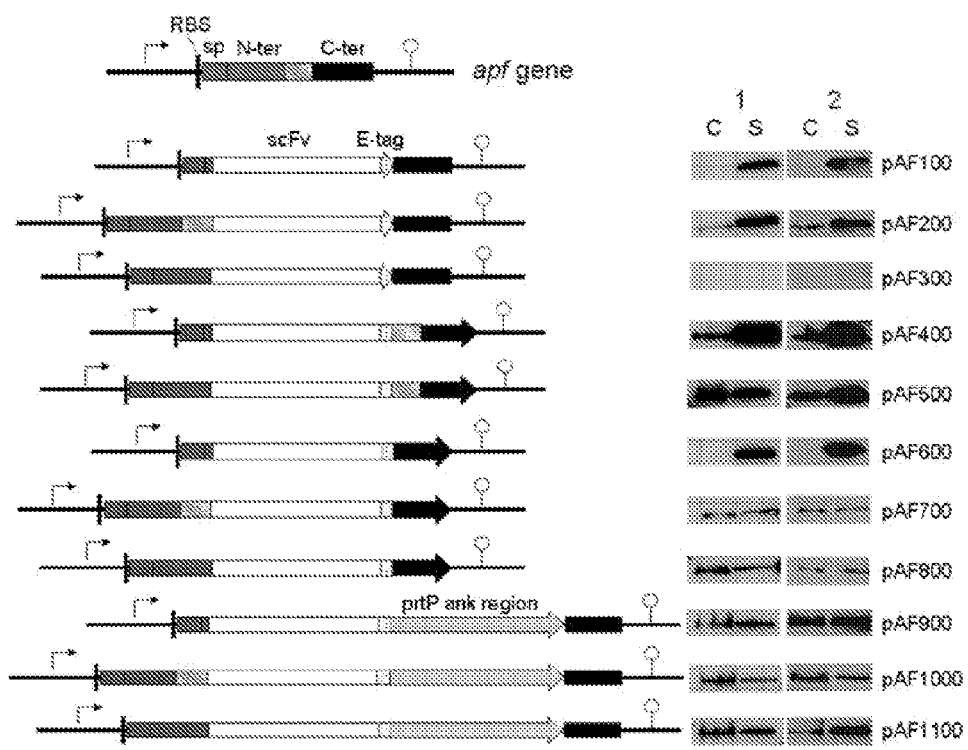
FIG. 2 illustrates scFv production by *Lactobacilli* transformed with plasmids containing different expression cassettes.

In order to mediate covalent attachment of the fusion protein to the cell surface, the prtP anchor region encoding gene was amplified from pLP401-scFv-long anchor using the primers PrtPNheIS and PrtPSacIAS. The PCR product was inserted between the NheI and SacI sites in psp600, psp700 and psp800 resulting in psp900, psp1000 and psp1100. The 11 expression cassettes were subsequently released from the pSP100 to pSP1100 vectors using SalI and EcoRI and ligated into a similarly digested shuttle E. coli/Lactobacillus vector pIAV7 resulting in the pAF plasmid series (pAF100 to pAF1100) (FIG. 2). The pAF plasmids were produced in *E. coli* and then introduced in *L. paracasei* by electroporation as previously described. FIG. 2 illustrates scFv production by *Lactobacilli* transformed with plasmids containing different expression cassettes. *L. paracasei* was transformed with the plasmids pAF100 to pAF1100. The scFv production in cell extract (C) and supernatant (S) was analyzed in two separate experiments (1 and 2). For each experiment, all transformants were analyzed at the same time. An equivalent of 125 µl supernatant and extract from $1 \times 10^8$ cells was loaded in each well.

Cloning of scFv Antibody or a Fragment Thereof Against Human ICAM-1 and VHH Fragments Against SAI/II Adhesion of *S. Mutans* and Rotavirus.

The scFv anti-ICAM-1 was derived from the mouse monoclonal antibody MTM5. Total RNA was extracted from the monoclonal antibody secreting hybridomas. Variable region encoding sequences of both the heavy (VH) and light (VK) chains were amplified using specific primers with a 5' RACE kit. The VH and VK sequences were fused together with a linker gene encoding the amino acid sequence $(G_4S)_3$ and cloned into a pGEM®-T vector after addition of overhang A using Taq DNA polymerase. The scFv anti-human ICAM-1 encoding gene was subsequently amplified using the primers ICAM-NcoI and reverse primers ICAM-NotI. The gene encoding S36-VHH directed against the SAI/II adhesion of *S. mutans* was amplified from the pUR5850S36 plasmid using the primers S36NcoI and S36NotI. The gene encoding ARP1 (previously called VHH1) directed against rotavirus was amplified from the pLP501-ARP1 plasmid using the primers VHH1NcoI and VHH1NotI. The amplified DNA fragments containing the antibody or a fragment thereof genes were digested with NcoI and NotI and cloned between the NcoI and NotI restriction sites into pAF100, pAF400 and pAF900 plasmids.

Chromosomal Integration of Expression Cassettes Containing the scFv Anti-SAI/II Gene and Anti-Rotavirus Genes.

The plasmid pEM171 was constructed in four steps: i) The 519-bp SalI-NcoI fragment of plasmid pAF400, containing the promoter, the signal peptide and the short N-terminal domain of the apf gene, was ligated with pGEM5Z digested with the same enzymes, to generate pEM157; ii) The 1415-bp NcoI-BglII fragment, containing the scFv gene and the C-terminal region of the apf gene, was obtained from pAF400 and inserted in pUC21 digested with the same enzymes, resulting in pEM158. iii) A XbaI (blunt-ended)-BglII insert from pEM158 was cloned into the Ecl1361'-BamHI sites of the integrative pEM76 vector thus yielding pEM170. iv) The NdeI-NcoI fragment of pEM157 was inserted into the same sites of pEM170 to yield pEM171.

Plasmids pEM181, pEM182 and pEM233 were constructed by interchange of the fragment NcoI-EcoRI of plasmid pEM171 by the corresponding fragments of pAF900, pAF100, and pAF900-ARP1, respectively.

The integrative plasmids pEM171, pEM181, pEM182, and pEM233 were independently introduced by electroporation into *L. paracasei*. Resulting strains were subsequently electro-transformed with pEM94, a replicative plasmid that carries the β-recombinase gene, in order to delete, by site-specific recombination, the non-food-grade DNA present in the integrated plasmids. After this depuration step, the strains were cultured at 37° C. to eliminate pEM94 (which carries a temperature sensitive origin of replication). The obtained strains were designated *L. paracasei* EM171 (secreted and attached scFv), *L. paracasei* EM181 (anchored scFv), *L. paracasei* EM182 (secreted scFv), and *L. paracasei* EM233 (anchored VHH1) respectively. Each step (integration, depuration, and curation) was confirmed by PCR analysis and by Southern blotting.

Western Blot.

Expression levels of scFv produced by the different *Lactobacillus* transformants were determined by Western Blot. The transformants were grown in MRS medium containing erythromycin (3 µg/ml) until $OD_{600}$ 0.8. Non-transformed *L. paracasei* were used as a negative control and grown in MRS only. The cultures were centrifuged at 3,200×g to separate the pellet from the supernatant. The supernatant was filter sterilized, pH adjusted to 7.3-7.6, dialyzed against 10 mM Tris (pH 8.0) and concentrated using Amicon Ultra-4 centrifugal filter units (10 kDa cut off, Millipore, Carrigtwohill, Co. Cork, Ireland). Concentrated supernatant was mixed with 2× Laemmli buffer and boiled for 5 min. The cell culture pellet was washed twice with PBS, resuspended in 200 µl Laemmli buffer and boiled for 5 min. The cell extract was centrifuged at 16,000×g to remove cell debris and the supernatant containing soluble proteins was saved. The supernatant and cell extract was run on a 10% SDS-polyacrylamide gel at 170 volts and the proteins were transferred onto a nitrocellulose membrane. The membrane was blocked with PBS-TM (PBS with 0.05% (v/v) Tween 20+5% (w/v) milk powder) and successively incubated with mouse anti-E-tag antibodies (1 µg/ml), and HRP (horse radish peroxidase) labelled goat antimouse antibodies. The signal was detected by chemiluminescence using the ECL Plus™ Western Blotting detection system.

Treatment with LiCl.

Non-transformed *Lactobacilli* and *Lactobacilli* containing the plasmid pAF400 and pAF900 ($2 \times 10^9$ bacteria) were washed three times with PBS and incubated with 10 ml LiCl 5M on a rocking table for 30 min at 4° C. The cells were pelleted at 8,000×g and resuspended in 200 µl loading buffer. The samples were run on SDS-PAGE and transferred on nitrocellulose as described above.

Quantification by Densitometry.

The amount of scFv in the supernatant and bacterial extract was estimated by Western Blot densitometry using a purified E-tag scFv as a standard. Two-fold dilutions of the standard scFv and dilutions of the supernatant and bacterial extract were loaded on a 10% polyacrylamide gel and Western Blot was performed as described above. The amount of scFv in the extract was calculated using the Gel Doc™ image analysis system and Quantity One® analysis software.

Flow Cytometry.

50 µl ($10^7$ bacteria) of each culture of *Lactobacillus* transformants grown until $OD_{600}$ of 0.8 were washed three times in PBS by centrifugation (10,000×g for 2 min) before resuspension in 100 µl of PBS. An equal amount of mouse anti-E-tag antibody diluted 1/100 was added and the samples were incubated on ice for 30 min. The washing procedure in PBS was repeated and the samples were resuspended in 100 µl PBS and mixed with 100 µl Cy-2 conjugated goat anti-mouse immunoglobulin (Jackson Immunoresearch Laboratories, West Grove, Pa.) (final dilution 1/200) and incubated on ice for 30 min. The *Lactobacilli* were fixed using 2% paraformaldehyde. After washing, the samples were resuspended in 1 ml of PBS and analysed in a FACS Calibur machine.

To ascertain binding to rhesus rotavirus (RRV), *Lactobacilli* grown to an OD of 0.8 were incubated with a 10-fold excess of RRV. This was followed by successive incubation with 1:200 dilution of rabbit anti-rotavirus serum (a generous gift from Dr Lennart Svensson, University of Linkoping) and a 1:200 dilution of donkey anti-rabbit PE conjugate antibody. All incubations were performed on ice for 30 min. The *Lac-*

*tobacilli* were fixed using 2% paraformaldehyde. After washing, the samples were resuspended in 1 ml of PBS and analysed in a FACS Calibur machine.

Fluid Based Assay.

The assay was similarly performed as for the flow cytometry but the anti-E-tag antibody bound to the bacteria was detected with an alkaline phosphatase conjugated rabbit anti-mouse antibody (1/1,000). Following incubation for 30 min on ice, the bacteria were resuspended in diethanolamine buffer (1 M, pH 10.0) and 100 µl of the bacterial suspension was added in duplicate to an ELISA plate. 100 µl of 2-fold concentrated p-nitrophenyl phosphate (pNPP) (2 mg/ml) was added to the wells. After 30 min incubation, the absorbance was read at 405 nm in a Varioskan Flash microplate reader.

Enzyme-Linked Immunosorbent Assay.

96-well plates were coated with 100 µl recombinant human ICAM-1/Fc, SAI/II antigen (1 µg/ml in PBS) or rotavirus overnight at 4° C. After washing with PBS containing 0.05% Tween 20 (PBS-T), dilutions of the supernatant from *L. paracasei* cultures secreting scFv anti-ICAM-1, ARP1 or S36 as well as bacterial cells of anchored constructs, were added and incubated at room temperature for 2 h. Supernatants and cells from culture of non-transformed *L. paracasei* were used as negative controls. Plates were washed twice and a mouse anti-E-tag antibody (1/1,000) was added to the wells. After 1 h incubation at room temperature, plates were washed twice and an alkaline phosphatase conjugated rabbit anti-mouse antibody (1/1,000) was added to the plates. Following incubation for 1 h at room temperature, diethanolamine buffer (1 M, pH 10.0) containing 1 mg/ml of pNPP was added to the wells. After 30 min incubation, the absorbance was read at 405 nm in a Varioskan Flash microplate reader.

Mouse Model of Rotavirus Infection.

Four-day-old BALB/c pups were used for the study. *Lactobacilli* ($10^8$) were administered to pups once daily in a 10-µl volume, starting on day −1 and continuing until day 3. Infections were made orally on day 0 using $2 \times 10^7$ ffu RRV (20 diarrhea doses (DD50)), a dose which causes diarrhea in more than 90% of inoculated animals. Occurrence and severity of diarrhea was recorded daily until day 4. Diarrhea in the pups was assessed on the basis of consistency of feces. Watery diarrhea was given a score of 2, loose stool a score of 1, and no stool or normal stool a score of 0. Severity was defined as the sum of diarrhea scores for each pup during the course of the experiment (severity=Σdiarrhea score [day 1+day 2+day 3+day 4]) and duration was defined as the total sum of days with diarrhea.

Statistical Analysis.

Both severity and duration were analyzed using Kruskal-Wallis and Dunn tests.

Comparison of Production of scFv Anti-SAI/II Using Different Expression Cassettes.

In order to optimize the production of antibody or a fragment thereof in *Lactobacilli*, eleven different expression cassettes were made using the secretion machinery of the APF protein of *L. crispatus* M247 and the scFv anti-SAI/II adhesion of *S. mutans*. In some of the cassettes, the gene encoding the Proteinase P (prtP) anchored region, which mediates covalent binding to the bacterial surface was fused to the antibody or a fragment thereof. The production of scFv by the modified *Lactobacilli* was compared by Western Blot in two different experiments (FIG. 2). *Lactobacilli* containing pAF100 and pAF600 show expression only in the supernatant while the other constructs showed expression both in the supernatant and cell extract. *L. paracasei* pAF400 produced the highest level of scFv in the supernatant while the lowest level was obtained with the *Lactobacillus* containing pAF300, pAF700 and pAF800. The amount of scFv produced by *L. paracasei* transformed with the three plasmids mediating surface anchoring of scFv (pAF900, pAF1000 and pAF1100) was shown to be similar. In these constructs, shedding of the fusion proteins into the supernatant was also observed.

Figure 3:
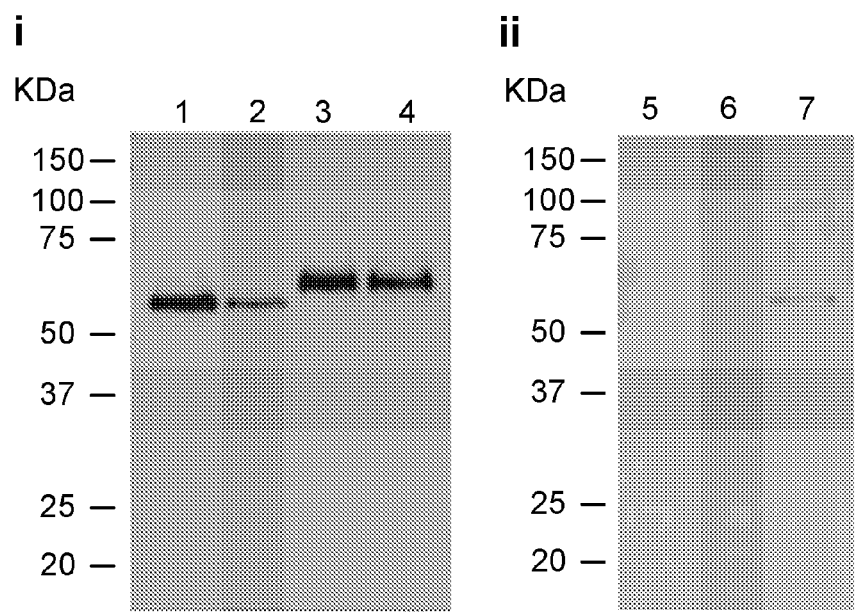
FIG. 3A and FIG. 3B illustrate evaluation of display of scFv to the surface of modified *L. paracasei*.
Figure 3:
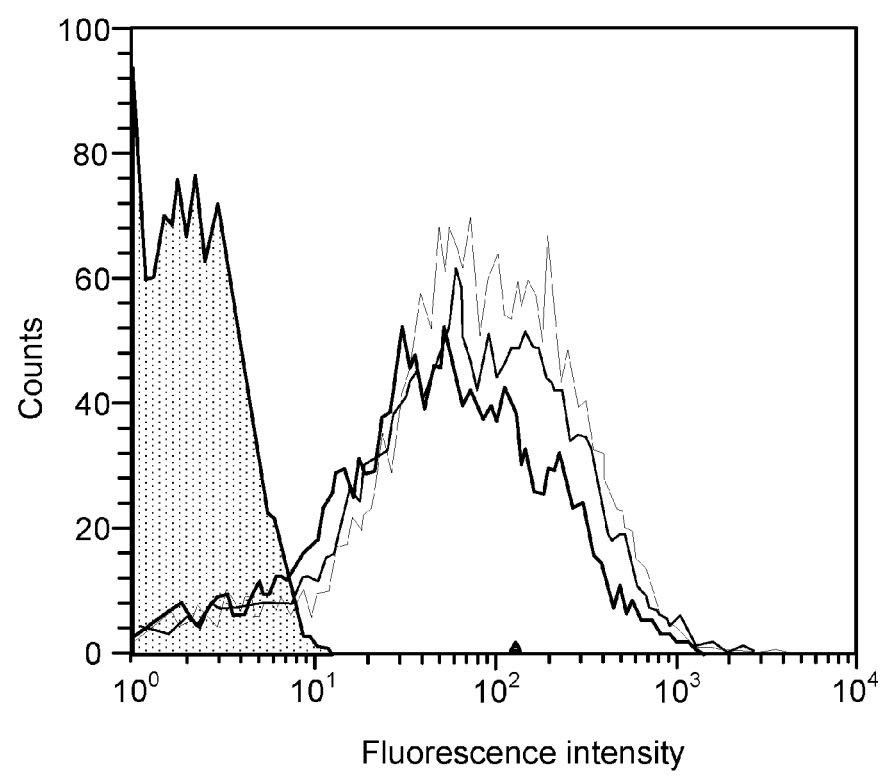

The conserved C-terminal part of APF may mediate non-covalent binding of the protein to the bacterial surface. FIG. 3 illustrates evaluation of display of scFv to the surface of modified *L. paracasei*. (A), demonstration of non-covalent attachment of scFv to the surface of *L. paracasei* pAF400 by Western Blot. (i) The bacterial pellet was treated with LiCl 5M to remove surface proteins and Western Blot of the cell extract was performed. Lane 1: *L. paracasei* pAF400, untreated pellet; lane 2: *L. paracasei* pAF400, LiCl treated pellet; lane 3: *L. paracasei* pAF900, untreated pellet; lane 4: *L. paracasei* pAF900, LiCl treated pellet. (ii) Wild type *L. paracasei* was incubated with the culture supernatant of wild type *L. paracasei* (lane 5), *L. paracasei* pAF100 (lane 6), and *L. paracasei* pAF400 (lane 7) to evaluate the binding of scFv. (B) Flow cytometry analysis of *Lactobacillus* transformants producing surface anchored scFv anti-SAI/II antibody or a fragment thereof. The production of scFv on the surface was shown by detecting the E-tag using a mouse anti-E-tag antibody and Cy-2 conjugated goat anti-mouse immunoglobulin. *L. paracasei* pAF900 (black line), *L. paracasei* pAF1000 (dark grey line), pAF1100 (light grey line), and non-transformed *L. paracasei* (black filled).

Fusion of scFv to both the middle region and C-terminal part of APF (*Lactobacillus* pAF400 and *Lactobacillus* pAF500) results in a higher amount of recombinant protein in the cell fraction. Since the APF was previously shown to be removed from the surface of *Lactobacilli* by LiCl treatment, the cell pellet of *L. paracasei* pAF400 was pretreated with 5M LiCl before protein extraction and Western Blot analysis. Pretreatment of the cell pellet with LiCl was shown to remove 75% of the scFv fusion protein (55-kDa band) in the cell pellet extract. In comparison, lower amounts of scFv were extracted from the surface of *L. paracasei* pAF900 (surface anchored scFv) (FIG. 3A). In addition, a 55-kDa band, corresponding to the scFv fusion protein, was observed in the cell extract of non-transformed *L. paracasei* pre-incubated for two hours with the culture supernatant of *L. paracasei* pAF400 (FIG. 3A). No band was detected when *L. paracasei* was previously incubated with the supernatant of *L. paracasei* pAF100 or non-transformed *Lactobacilli*. Although other mechanisms might be involved, these results suggest that the scFv can attach to the cell wall through the middle region and C-terminal part of the APF protein.

Surface expression of scFv by the transformed *Lactobacilli* was also analysed by flow cytometry using an anti-E-tag antibody. A positive signal was obtained with the *Lactobacillus* transformed with pAF900, pAF1000 and pAF1100 which display surface anchored scFv (FIG. 3B). No significant difference was observed in the level of expression between these three constructs. *L. paracasei* transformed with the plasmids pAF100 to pAF800 did not show any signal by flow cytometry. Although detected on the surface of *L. paracasei* pAF400 in Western Blot, the scFv attached on the surface of *Lactobacilli* can not be protrud sufficiently outside the bacterial surface to be recognised by the anti-E-tag in flow cytometry.

Quantification of scFv Anti-SAI/II Produced by Selected Expression Cassettes.

Expression cassettes producing fusion proteins with short APF N-terminals were utilized herein. The three selected plasmids were pAF100, generating secreted scFv only, pAF400, generating both secreted and cell wall attached scFv and pAF900, generating surface anchored scFv. The amount of scFv in the supernatant of L. paracasei pAF100 and L. paracasei pAF400 was shown to be 100 ng/ml and 1000 ng/ml, respectively. The amount of scFv present in the cell extract of L. paracasei pAF400 and pAF900 was estimated to be approximately 1000 and 2000 scFv fusion molecules/bacterium.

Expression of scFv Anti-ICAM-1 and VHHs in Selected Expression Cassettes.

Figure 4:
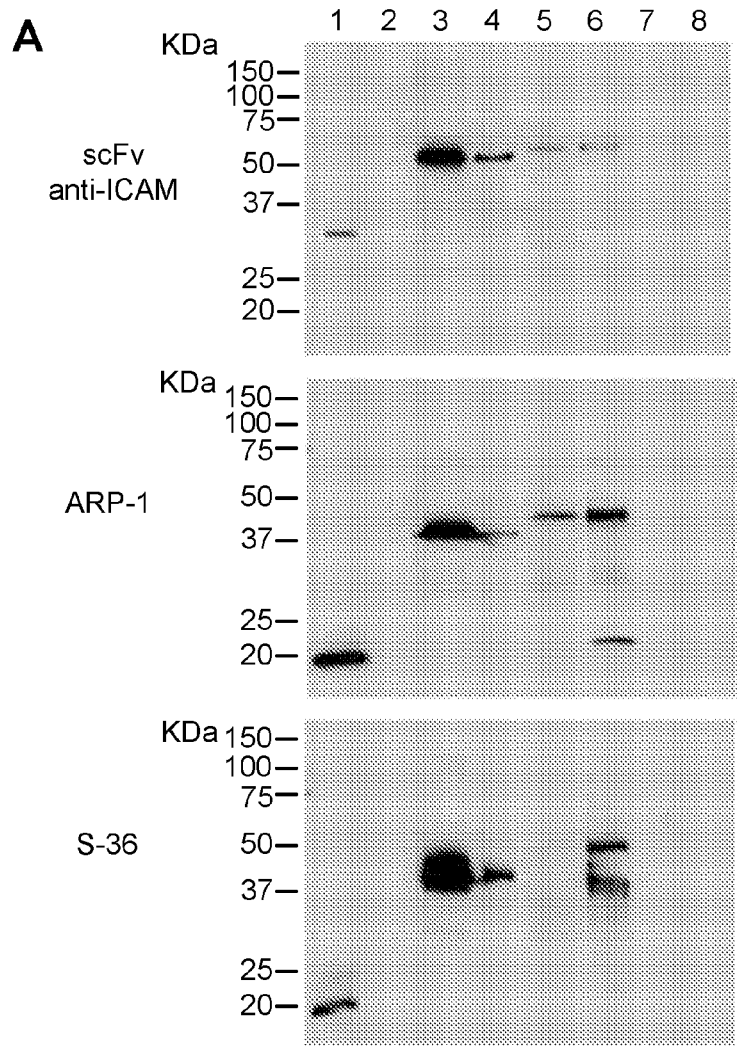
FIG. 4A and FIG. 4B illustrate production of scFv and VHH antibody or a fragment thereof by modified *Lactobacilli*.
Figure 4:
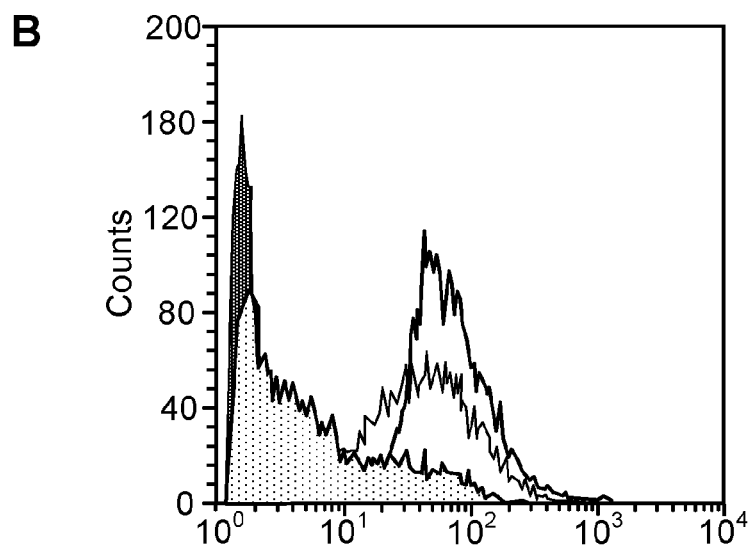

The plasmids pAF100, pAF400 and pAF900 were subsequently used for expression of a scFv directed against human ICAM-1 in L. paracasei generating L. paracasei pAF100-ICAM, pAF400-ICAM, and pAF900-ICAM. The same plasmids were also use for expression of VHH antibody or a fragment thereof against SAI/II (S36-VHH) (L. paracasei pAF100-S36, pAF400-S36, pAF900-S36) and rotavirus (ARP1) (L. paracasei pAF100-ARP1, pAF400-ARP1, pAF900-ARP1). scFv expression was analysed by immunoblotting supernatant or cell extract of L. paracasei-transformed strains using a mouse monoclonal anti-E-tag antibody. A band of 30 kDa was detected in the supernatant of L. paracasei pAF100-ICAM, which migrated at the expected size of the secreted scFv (FIG. 4A). The supernatant and cell extract of Lactobacilli pAF400-ICAM showed a band of 55 kDa which correspond to the scFv secreted in the supernatant and attached on the surface. The band is larger than the theoretical molecular weight (42 kDa), which could be related to posttranslational modification of the C-terminal part of APF. A 60 kDa-band was detected in the cell extract of the Lactobacilli transformed with pAF900-ICAM corresponding to the surface anchored scFv. For the VHHs against SAI/II and rotavirus, a protein near the predicted size (16.5 kDa) was detected in the supernatant of L. paracasei pAF100-ARP1 and pAF100-S36 (FIG. 4A). L. paracasei pAF400-ARP1 and L. paracasei pAF400-S36 showed a band of 40 kDa in both the supernatant and the cell extract which is higher than the predicted size of the fusion protein (29 kDa) (as previously observed for the similar scFv fusion). The cell extract of Lactobacilli transformed with pAF900-VHH and pAF900-S36 showed a major band at 47 kDa, corresponding to the theoretical molecular weight of the surface anchored VHHs. The additional bands detected in the cell extract are most probably degradation products or antibody or a fragment thereof linked to cell wall residues. FIG. 4 illustrates production of scFv and VHH antibody or a fragment thereof by modified Lactobacilli. (A) Western Blot analysis of Lactobacilli producing scFv anti-ICAM-1, ARP1 anti-rotavirus, and VHH anti-SAI/II (S36). Lane 1: pAF100, secreted, supernatant; lane 2: pAF100, secreted, cell extract; lane 3: pAF400, secreted and attached, supernatant; lane 4: pAF400, secreted and attached, cell extract; lane 5: pAF900, surface anchored, supernatant; lane 6: pAF900, surface anchored, cell extract; lane 7: L. paracasei, supernatant; lane 8: L. paracasei, cell extract. An equivalent of 40 µl supernatant and extract from $3.5 \times 10^7$ cells was loaded in each well. (B) Flow cytometry analysis of Lactobacillus transformants producing surface anchored scFv anti-human ICAM-1 and VHH antibody or a fragment thereof. The production of scFv on the surface was shown by detecting the E-tag using a mouse anti-E-tag antibody and Cy-2 conjugated goat anti-mouse immunoglobulin. L. paracasei pAF900-ICAM (grey filled), L. paracasei pAF900-ARP1 (black line), L. paracasei pAF900-S36 (grey line), and non-transformed L. paracasei (black filled).

The amount of scFv and VHH antibody or a fragment thereof was estimated by densitometry (Table 5). The level of scFv and VHH antibody or a fragment thereof in the supernatant was 7 and 4 times higher respectively, using the pAF400 than the pAF100 plasmid. In addition, the level of antibody expressed in the supernatant or in the cell extract was 7-10 times higher for VHH than for scFv.

TABLE 5

Amount of scFv and VHH antibody or a fragment thereof produced by the transformed Lactobacilli using densitometry[1]

| Construct | Location of antibody | anti-ICAM Supernatant[2] (ng/ml) | anti-ICAM Cell extract (molecules/ bacteria) | ARP1 Supernatant (ng/ml) | ARP1 Cell extract (molecules/ bacteria) | S36 Supernatant (ng/ml) | S36 Cell extract (molecules/ bacteria) |
|---|---|---|---|---|---|---|---|
| L. paracasei pAF100 | Secreted | 150 | ND[3] | 500 | ND | 700 | ND |
| L. paracasei pAF400 | Secreted and attached | 900 | 650 | 3000 | 330 | 5000 | 1300 |
| L. paracasei pAF900 | Surface anchored | ND | 650 | ND | 6000 | ND | 3000 |

[1]The amount of scFv in the supernatant and bacterial extract was estimated by Western Blot densitometry using a purified E-tag scFv as a standard.
[2]Supernatant from a culture grown until an $OD_{600}$ nm of 0.8.
[3]ND, not done.

Flow cytometry showed that the scFv and VHHs fragments fused to the prtP anchored region were displayed on the surface of Lactobacilli transformed with the pAF900 plasmids (FIG. 4B). However, as observed for the scFv anti-SAI/II, no signal was observed for the Lactobacilli transformed with pAF400 (secreted and attached antibody or a fragment thereof). In order to confirm cell attachment, the cells were treated as for the flow cytometry but detected using an enzyme-substrate reaction and the absorbance was read at 405 nm. In comparison to non-transformed Lactobacilli ($OD_{405}$ 0.249), antibody or a fragment thereof could be detected on the surface of Lactobacilli transformed with pAF400-ICAM ($OD_{405}$ 0.429), pAF400-ARP1 ($OD_{405}$ 0.478) and pAF400-S36 ($OD_{405}$ 1.086). The signal was equivalent to a 30-fold dilution of *Lactobacilli* expressing the corresponding surface anchored fragment.

Binding of scFv and VHH Antibody or a Fragment Thereof in ELISA.

Figure 5:
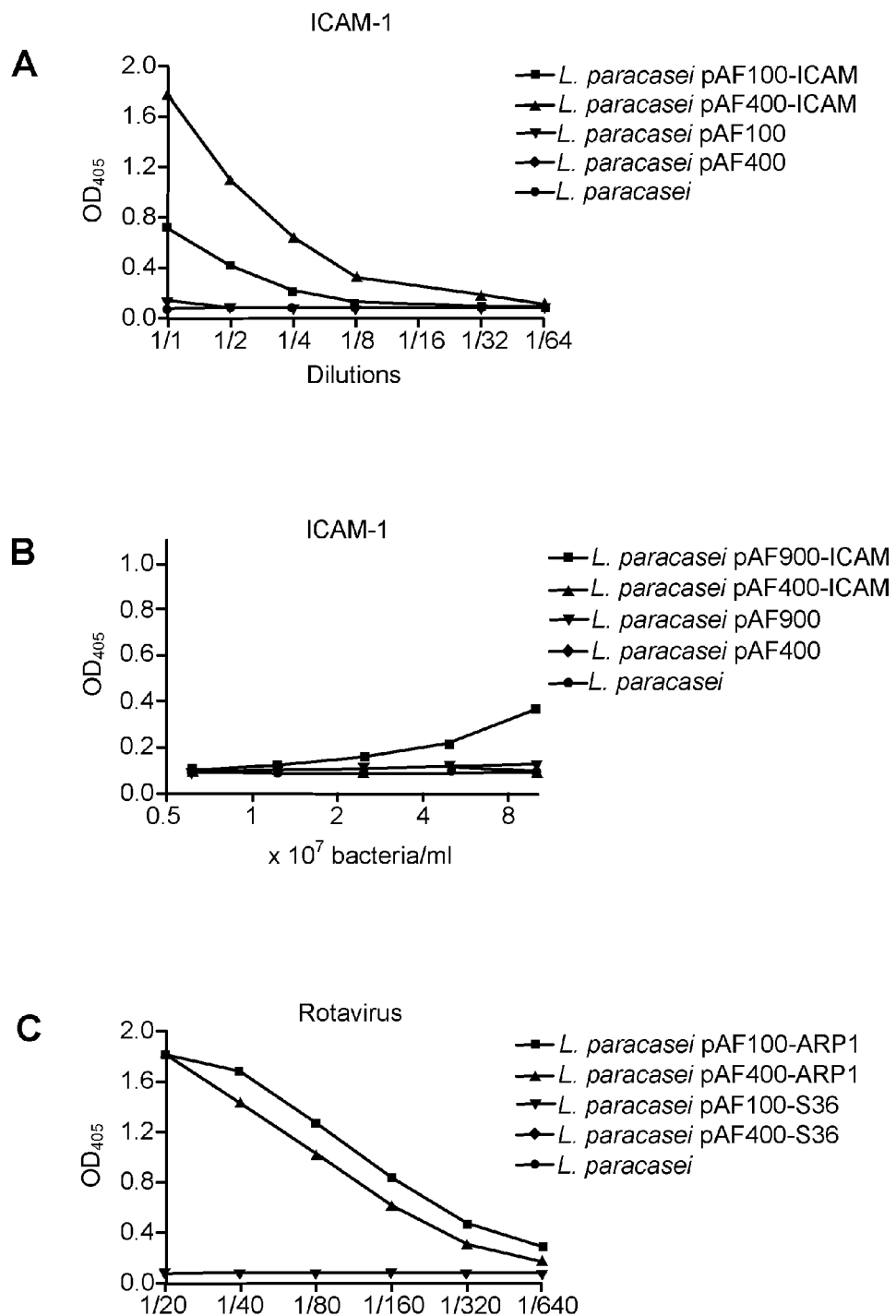
FIGS. 5A, 5B, 5C, 5D, 5E, and 5F illustrate binding activity of antibody or a fragment thereof to antigens in ELISA. Culture supernatant (FIGS. 5A, 5C, and 5E) or bacterial cells (FIGS. 5B, 5D, and 5F) were added to plates coated with human ICAM-1 (FIGS. 5A and 5B), SAI/II (FIGS. 5E, 5F) and rotavirus (FIGS. 5C, 5D). The binding activity of scFv and VHH antibody or a fragment thereof produced by *Lactobacilli*, secreted in the supernatant or expressed on the bacterial surface, was analysed by ELISA.
Figure 5:
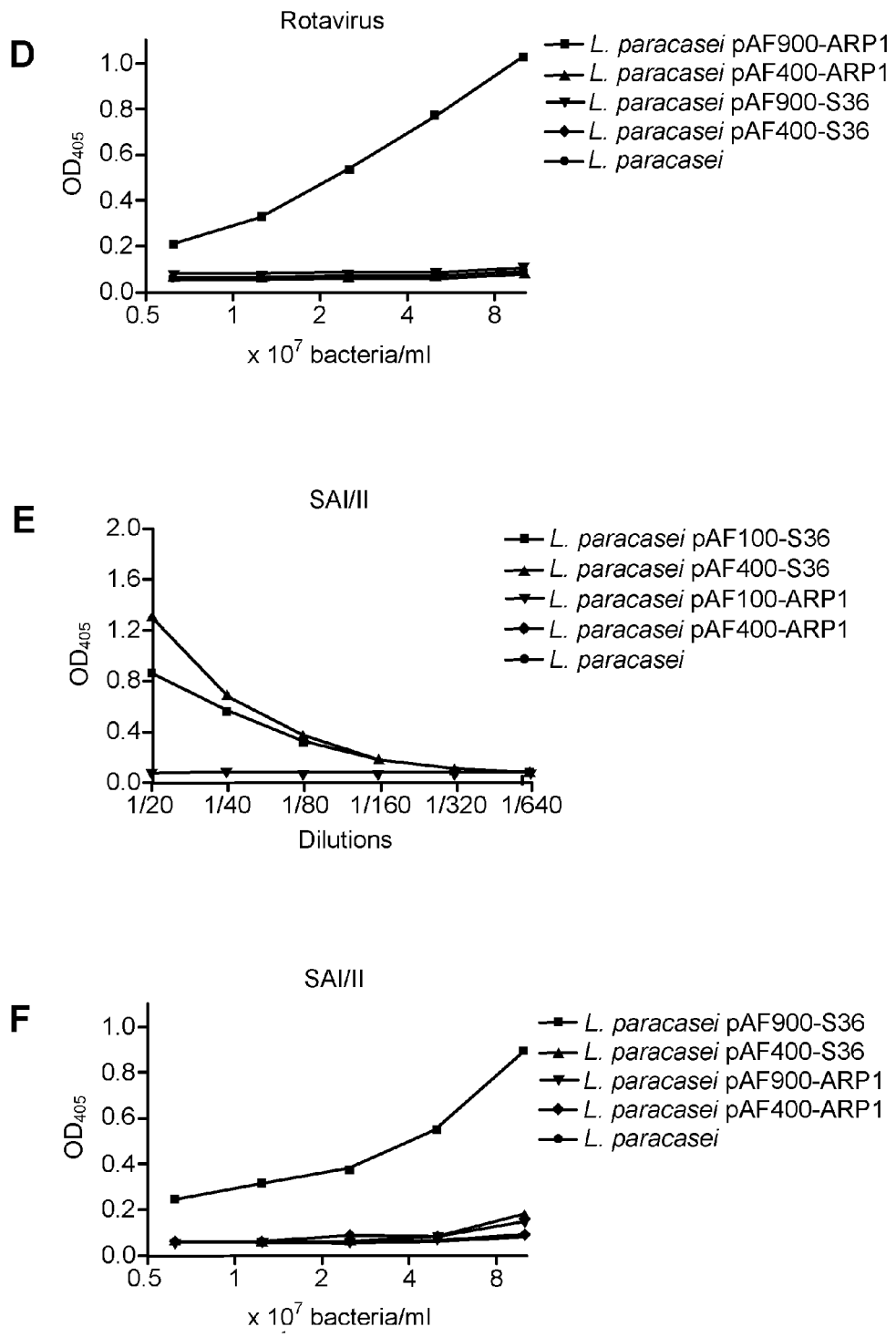

FIG. 5 illustrates binding activity of antibody or a fragment thereof to antigens in ELISA. Culture supernatant (A, C, E) or bacterial cells (B, D, F) were added to plates coated with human ICAM-1 (A,B), SAI/II (E, F) and rotavirus (C, D). The binding activity of scFv and VHH antibody or a fragment thereof produced by *Lactobacilli*, secreted in the supernatant or expressed on the bacterial surface, was analysed by ELISA (FIG. 5). Binding activity of scFv to recombinant human ICAM-1 was observed using the supernatant of *Lactobacilli* transformed with pAF 100-ICAM and pAF400-ICAM. A 4-fold higher binding activity was observed in the supernatant of *L. paracasei* pAF400-ICAM than *L. paracasei* pAF100-ICAM that correlates with the higher amount of scFv produced by the former (FIG. 5A, Table 3). Whole bacterial cells of *L. paracasei* pAF900-ICAM (surface anchored scFv) were also shown to bind to human ICAM-1 (FIG. 5B).

VHH fragments produced by *Lactobacilli* were shown to bind with higher activity than scFv antibody or a fragment thereof. The supernatant of *Lactobacilli* transformed with pAF100-ARP1 and pAF400-ARP1 (FIG. 5C) or whole cells of *L. paracasei* pAF900-ARP1 (FIG. 5D) showed good binding to rotavirus particles in ELISA. Transformed *Lactobacilli* producing S36-VHH also showed high binding activity to the SAI/II antigen (FIGS. 5E and 5F). The supernatant of *Lactobacilli* transformed with pAF400-ARP1 and pAF400-S36 only showed marginally higher binding activity than *Lactobacilli* transformed with the corresponding pAF100 plasmids.

No binding activity was observed using whole *Lactobacilli* transformed with pAF400-ICAM, pAF400-S36 and pAF400-ARP1. The latter could be due to that the E-tag is poorly detected when the antibody is attached to the cell through the C-terminal of APF as observed above. However, using BacLight™ Green-stained bacteria in a spectrofluorometric assay, binding to antigen coated plates by *Lactobacilli* transformed with pAF900 was observed but not with pAF400 plasmids.

To ascertain binding activity of *Lactobacilli* producing surface expressed ARP1, transformed *Lactobacilli* were pre-incubated with RRV and subsequently with rabbit anti-sera against rotavirus and donkey anti-rabbit PE conjugated antibodies. *Lactobacilli* producing surface anchored ARP1 were shown to bind to rotavirus as detected by flow cytometry.

Chromosomal Integration of the Gene Encoding the scFv Anti-SAI/II.

Figure 6:
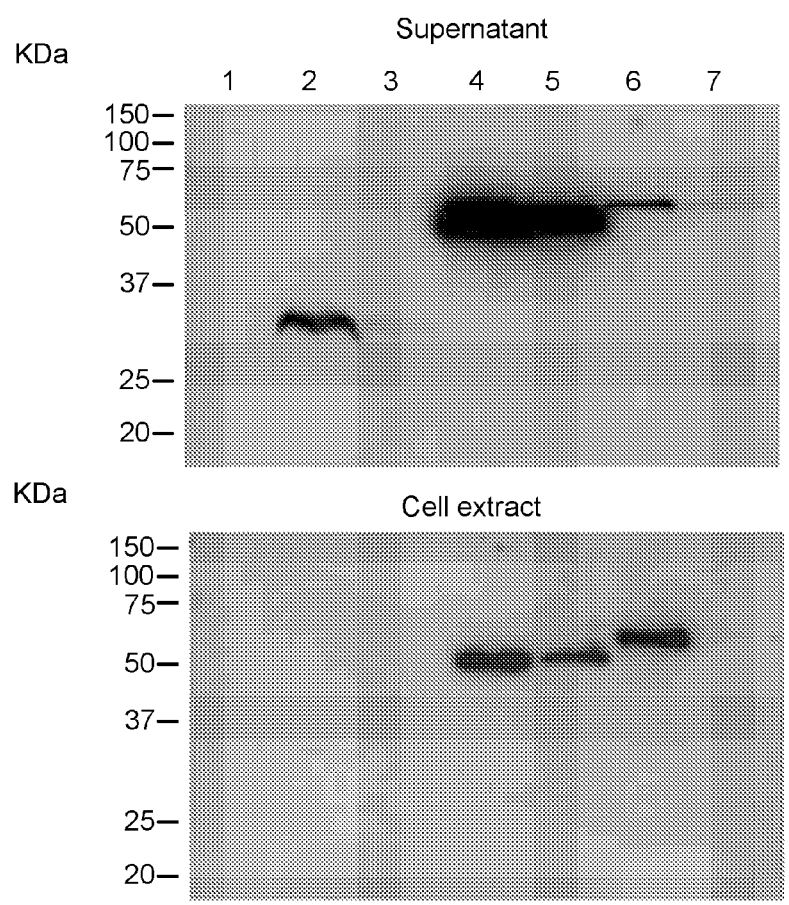
FIGS. 6A, 6B, and 6C illustrate production and binding activity of scFv using plasmid and chromosomal integration-based expression system.
Figure 6:
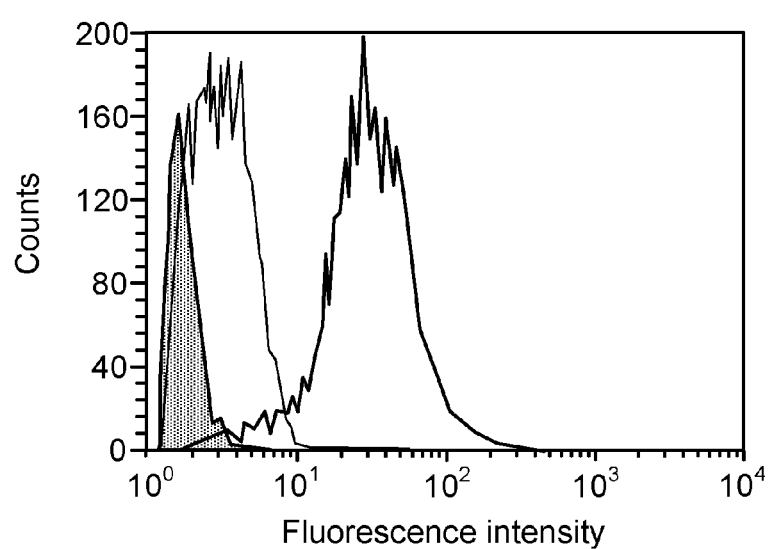
Figure 6:
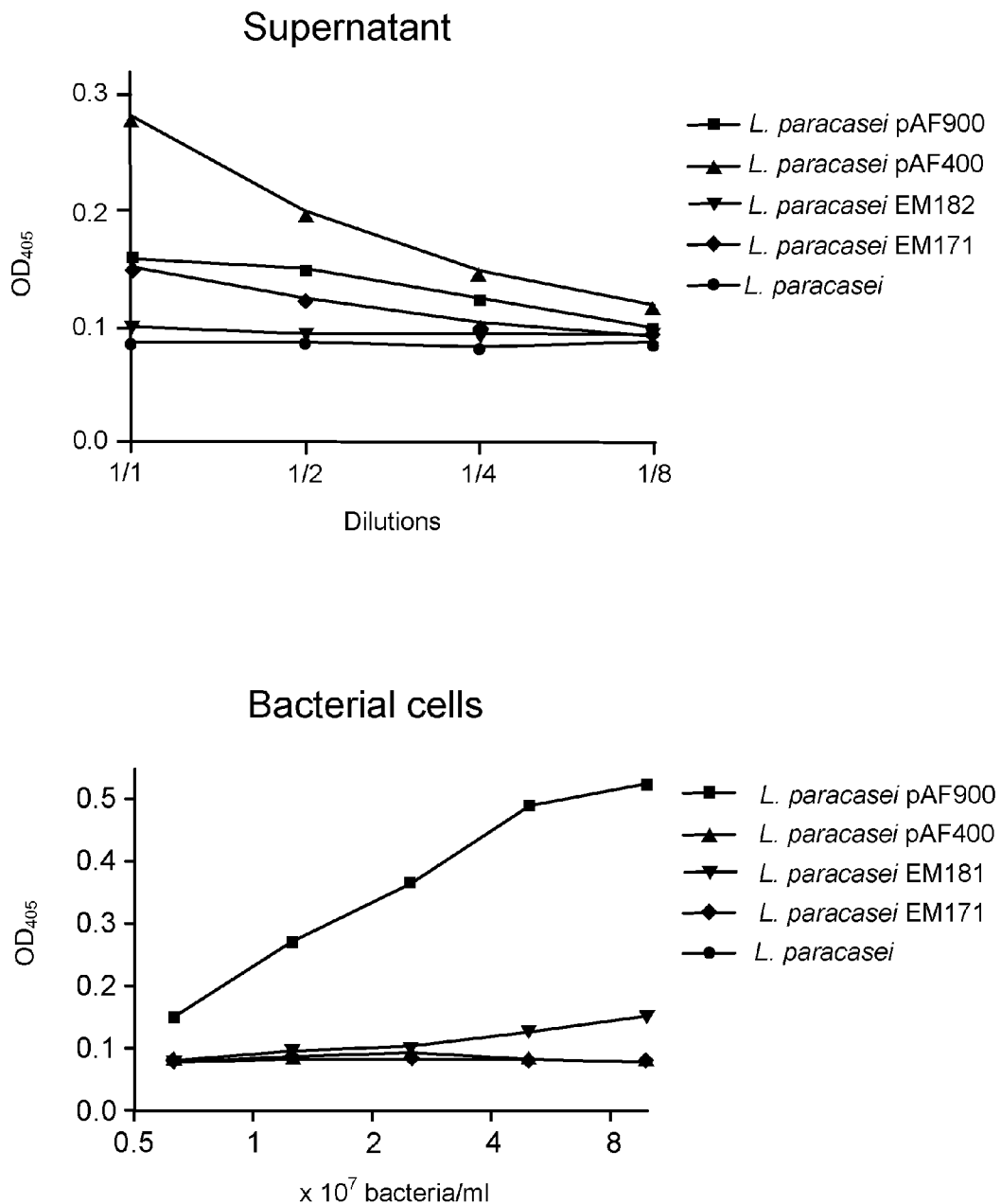

FIG. 6 illustrates production and binding activity of scFv using plasmid- and chromosomally integrated-based expression system. (A) Production of scFv anti-SAI/II by Western Blot analysis of supernatant and cell extract. Lane 1: *L. paracasei*; lane 2: *L. paracasei* pAF100, secreted; lane 3: *L. paracasei* EM182, secreted; lane 4: *L. paracasei* pAF400, secreted and attached; lane 5: *L. paracasei* EM171, secreted and attached; lane 6: *L. paracasei* pAF900, surface anchored; lane 7: *L. paracasei* EM181, surface anchored. An equivalent of 125 µl supernatant and extract from $1 \times 10^8$ cells was loaded in each well. (B) Flow cytometry analysis of *L. paracasei* producing surface anchored scFv anti-human SAI/II using plasmid—(*L. paracasei* pAF900, black line) and chromosomally-integrated (*L. paracasei* EM181, grey line) based expression system. Non-transformed *Lactobacilli* (black filled). The production of scFv on the surface was shown by detecting the E-tag using a mouse anti-E-tag antibody and Cy-2 conjugated goat anti-mouse immunoglobulin. (C) Binding activity of scFv antibody or a fragment thereof produced by plasmid- and chromosomally integrated-based expression systems to SAI/II antigen using supernatant and bacterial cell suspension in ELISA. The three selected cassettes fused to the gene encoding the scFv anti-SAI/II were integrated into the chromosome of *L. paracasei* using site-specific integration. scFv expression was analysed by immunoblotting (FIG. 6A) and the amount of scFv produced in the supernatant and cell extract was evaluated by densitometry. When integrated on the chromosome, the amount of scFv in the supernatant of *L. paracasei* EM182 (secreted scFv) and in the cell extract of *L. paracasei* EM181 (surface anchored scFv) was about 10-fold lower than when using the corresponding plasmid construct (respectively 12 ng/ml and 100 molecules/bacteria). A 10-fold decrease in fluorescence intensity was also observed by flow cytometry using an anti-E-tag antibody (FIG. 6B). The amount of scFv detected in the supernatant and cell extract of EM171 (secreted and attached scFv) was shown to be only 2-fold lower (450 ng/ml and 450 molecules/bacterium) than the plasmid system (1000 ng/ml and 1000 molecules/bacterium).

Binding activity against SAI/II antigen was observed using the supernatant and whole bacterial cells in ELISA but at a reduced level than when using the corresponding plasmid system (FIG. 6C). In the supernatant, a 4-fold reduction in binding activity was observed for the secreted and attached scFv (*L. paracasei* EM171) and at least, a 8-fold reduction for the secreted scFv (*L. paracasei* EM182). Whole bacterial cells of *L. paracasei* EM181 were binding at a level less than 16-fold lower than *L. paracasei* pAF900. No binding activity was observed using whole cells of transformed *Lactobacilli* producing attached scFv (*L. paracasei* pAF400 and *L. paracasei* EM171).

Chromosomal Integration of the ARP1 Anti-Rotavirus Gene.

Figure 7:
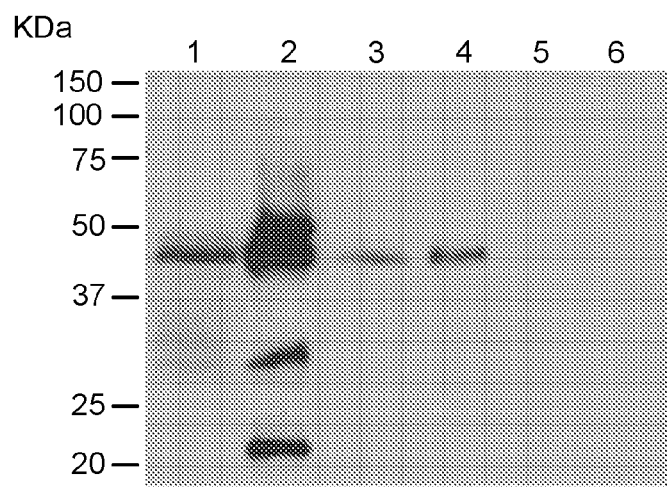
FIGS. 7A, 7B, 7C, and 7D illustrate production and binding activity of *Lactobacilli* producing surface-anchored ARP1 using plasmid pAF900-ARP1 and chromosomal integration based expression system (*L. paracasei* EM233).
Figure 7:
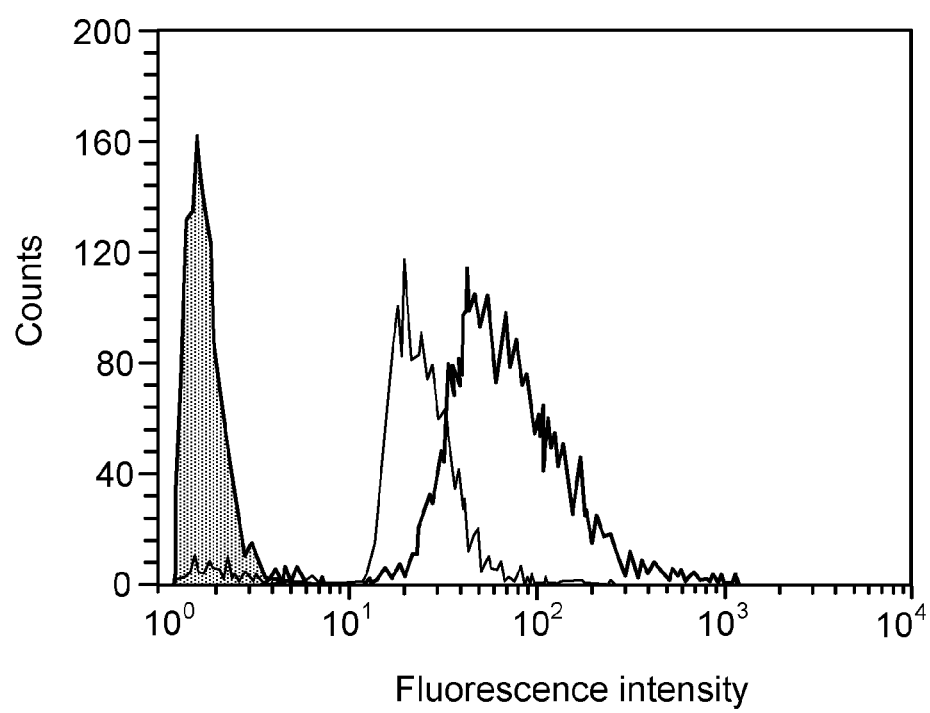
Figure 7:
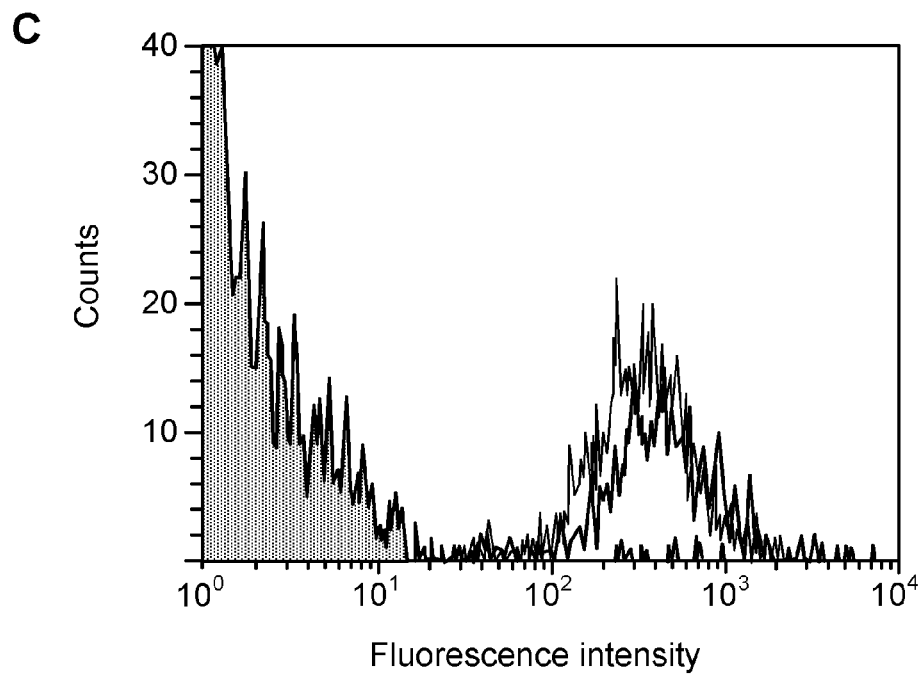
Figure 7:
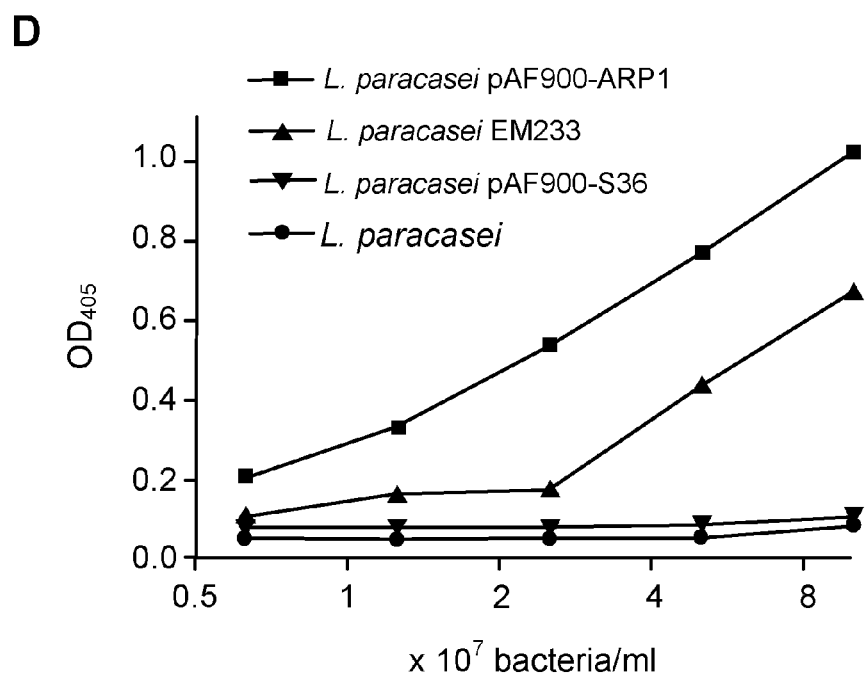

FIG. 7 illustrates A) Production and binding activity of *Lactobacilli* producing surface anchored ARP1 using plasmid—(*L. paracasei* pAF900-ARP1) and chromosomally integrated—(*L. paracasei* EM233) based expression system. (A) Production of ARP1 by Western Blot analysis of supernatant and cell extract. Lane 1: *L. paracasei* pAF900-ARP1, supernatant; lane 2: *L. paracasei* pAF900-ARP1, cell extract; lane 3: *L. paracasei* EM233, supernatant; lane 4: *L. paracasei* EM233, cell extract; lane 5: *L. paracasei*, supernatant; lane 6: *L. paracasei*, cell extract. An equivalent of 40 µA supernatant and extract from $3.5 \times 10^7$ cells was loaded in each well. (B) Flow cytometry analysis showing the display of ARP1 on the surface by detecting the E-tag using a mouse anti-E-tag antibody and Cy-2 conjugated goat anti-mouse immunoglobulin. *L. paracasei* pAF900-ARP1 (black line), *L. paracasei* EM233 (grey line), and non-transformed *Lactobacilli* (black filled). (C) Binding activity of *Lactobacilli* producing surface anchored ARP1 to rotavirus measured by flow cytometry. Modified *Lactobacilli* were incubated with rotavirus and stained with rabbit anti-rotavirus serum and anti-rabbit PE conjugate antibody. *L. paracasei* pAF900-ARP1 (black line), *L. paracasei* EM233 (grey line), non-transformed *Lactobacilli* (black filled). (D) Binding activity of modified *Lactobacilli* producing surface anchored ARP1 to rotavirus measured by ELISA. Plates coated with RRV rotavirus particles were incubated with serial dilutions of intact bacterial cells. The bound bacteria were detected using a mouse anti-E-tag antibody, an anti-mouse IgG alkaline phosphatase-conjugated and p-nitrophenyl phosphate substrate.

The cassette mediating surface anchoring of ARP1 was integrated on the chromosome of *L. paracasei*. In Western blot, the intensity of the bands was 10 times lower with the integrated construct corresponding to 600 molecules/bacteria (FIG. 7A). However, when evaluating the surface display of the ARP1 fragment on the surface of bacteria by flow cytometry using an anti-E-tag antibody, the fluorescence intensity was shown to be only 6-fold lower for *L. paracasei* EM233 than the corresponding plasmid construct, *L. paracasei* pAF900-ARP1 (FIG. 7B).

*L. paracasei* EM233 was also grown for 50 generations and fluorescence intensity was evaluated at generation 10, 20, 30, 40 and 50. No difference was observed in the fluorescence intensity between the different generations showing that the integrated gene is stable.

The binding of whole cells of *L. paracasei* EM233 to rotavirus was shown to be similar using flow cytometry (FIG. 7C) while using ELISA, whole cells of *L. paracasei* EM233 was shown to bind to rotavirus particles at a level about 3 times lower than the corresponding plasmid construct (FIG. 7D). Binding to rotavirus was also observed using immunofluorescence microscopy and the intensity was shown to be similar between both constructs (data not shown).

The transformed *Lactobacilli* were administered prophylactically to mice, one day before infection, and the treatment was continued once daily. *L. paracasei* pAF900-ARP1 and *L. paracasei* EM233 reduced the duration and severity of diarrhea to a similar level (Table 6).

TABLE 6

Duration and severity of rotavirus induced diarrhea in the different treatment groups.

| Group | Duration Mean ± SE, days | Severity Mean ± SE |
|---|---|---|
| *L. paracasei* pAF900-ARP1 | 1.00 ± 0.22 | 1.00 ± 0.22* |
| *L. paracasei* EM233 | 1.14 ± 0.14 | 1.14 ± 0.14* |
| *L. paracasei* | 1.43 ± 0.20 | 2.29 ± 0.36 |

*Statistically significant from *L. paracasei* group by Kruskal-Wallis (P = 0.007) and Dunn test (P < 0.05).

Example 2

Expression Cassettes

Expression cassettes comprising one or more sequences in Table 7 are made to express antibody fragments in a microorganism.

TABLE 7

Expression cassette sequences

| SEQ. ID. | Sequence | Remarks |
|---|---|---|
| 23 | AGGTCTAATTATTAGGGGGAGAAGGAGAGAGTAGCCCGAAAACTTTTAGTTGGCTTGGAC TGAACGAAGTGAGGGAAAGGCTACTAAAACGTCGAGGGGCAGTGAGAGCGAAGCGAACAC TTGATCTTTTAAGTTGCTATCTTTTATAGGTCAATAGAGTATACTTATTTGTCCTATTGA TTAGATAGCAGTATAATAGCTTTATAGAGTAGGTCATTTAAGTTGAGCATAATAGGAGGA TCAAGAATGAAAAAATTTATTTATCGAGTTTTAGAAAATGACGAAGTGGTGGCTATTTTT AATGAGCAAGAATATGCGCAAGATTTTATCGCTTACGAAAAGACAATTTCTGATAAGCAA TTTGAAATTGAAAAAGTAGCACTCGCAGATTGGTTATTGCAACCGAGAGAATTTTAGGGG TTGGTTGAAAATGGCTAAAATTGGTTATGCACGACTCTAGGGGAGCTCGAATTCGAAGCT TCTGCAGACGCGTCGACGTCATATGGATCCAAAATAAAAAGCGCCTACCCCACCGACCAA AGTGAATGGGTAGACGCCTAACAAATACTCGGAGCAACAAGGCTCTTTGTATACACATTT TTACACAGGAGGGCAATAATATGGCGGTATTCAAGCGAGCTAACCGAAAAGTAAGCCTT GGGGATTCCAGTATTCATACAAAGTGGATGGCATCTCCAAGCAGAAAACATCATTTTACA AAACAAGAAAAGAAGCTAAGGCTGCTGAGGCGAAGTACCTCGCTTCTACTGGCGGATCTG TAAAAATCGATCCAGTGATCACTTTCGCAGATTGGTATGACAAGTGGTTGCATACCTACA AGATACGTTCTGTTTCCGAACTGACGATGACCAAGTATGCAACTTCGGGTACAATCATCA GAAACTACTTCAAAGACCTTAAATTAATTGACTTAACGCGCATGATTTATCAACAGTTTA TTAACAACTATATTGATGACGGTTACGGCCACAAGCACGCAAGGCAATCAGTCCAGAAGC TACATTCACACGCTCATCAAGCAATTATGGCCGCAGCAGACGAAGGTTTGATTAGGCGCG ATTATGCCGCTCATGCAGAACTGGGTGGTACCGCAGGCAGATCAGAAGACACAAAATTTC TTGAAGCTGATCAGTTCGAGAAACTGCGAGATTATGTTGATCAATTTGCCAACCCGCAAC GAATTGCTCTCATGATGGTTCAAACGGCCATATACTCTGGCGCTCGGCTTGGAGAAATTG GTGGCTTAACGTGGGAAGATATTGATGAGAAGAAGAGCACCATCAGTATCGACAAGACCT TCAAGTACAGGTTTGTCATTCGTAACGCGGATGGTAGCTGGCCAGACCGTGAAAAAGTCT TCGGTCCGACCAAGACTCCTTCAAGTGTTCGTACTATCAAAGTAAGCCCAGTTCTTATCG CTAGCCTCCATAAGCTCATATTGGCTGACAGAATAAAAGCGATTAACAATCCGTACCATT TACTGTTTCTTGGGCCGACCGGCTTGCCAATATATAGCAATGGTGTCAACAAGGAACTTC GCCGCGCTCTCAAACATCTTGGTATTGAGCGTCCTGGGTTCGGTTTCCACGGATTGCGGC ACACGCATGGCAGCTACTTGCTTTATAAAGGCCTTGACATTCAGTATGTATCACATCGCC TCGGACACGAAAACGTTGGCATTACCACCAAGATCTATACACATCTGCTGGATGCGATGA CACAGAAGCAGGACGAGAAAGCAATGAATGTGTTGTGACTAAAAATCGAACCAGAGAAAG CGGCTCAATGTCAACTGCCACAAGGTTTACAGCACACATTCAATTTTCGATCACGAACCA TTTTCCTAAAAAATCGCAATTTCAGGCTATTTGGTTCGATGTGGTTCGATGGATTATATT TTTTAGGGGTTTTTCGGAGTTCAGATAAATGCAAGAATGCCGGTTTAAAGCCATTTCTGA GCACTAAAAAAGACCCTCTAGGGGGCTTTGATACCGGTGATCGGGGTATCACGGAATGTA TACGTACTGATATGATTGCATTTATGACAAAAAGTGGTTCGATGTGGTTCGATGCTTCAA ACGACAGCGACCAACAACACATCTCTATATAATAGGTAGAAATAGCTTTTAAGAGTTCAG AAATATGGGCACACAAGACCGGGGTCTAATTATTAGGGGGAGAAGGAGAGAGTAGCCCGA AAACTTTTAGTTGGCTTGGACTGAACGAAGTGAGGGAAAGGCTACTAAAACGTCGAGGGG CAGTGAGAGCGAAGCGAACACTTGATCTTTTAAGTTGCTATCTTTTATAGGTCAATAGAG TATACTTATTTGTCCTATTGATTAGATAGCAGTATAATAGCTTTATAGAGTAGGTCATTT AAGTTGAGCATAATAGGAGGATCAAGAATGAAAAAATTTATTTATCGAGTTTTAGAAAAT GACGAAGTGGTGGCTATTTTTAATGAGCAAGAATATGCGCAAGATTTTATCGCTTACGAA AAGACAATTTCTGATAAGCAATTTGAAATTGAAAAGTAGCACTCGCAGATTGGTTATTG CAACCGAGAGAATTTTAGGGGTTGGTTGAAAATGGCTAAAATTGGTTATGCACGACTC | Fragment six1-int-attP-six2 of integrative vector pEM76 |

TABLE 7-continued

Expression cassette sequences

| SEQ. ID. | Sequence | Remarks |
|---|---|---|
| 24 | AGGTCTAATTATTAGGGGGAGAAGGAGAGAGTAGCCCGAAAACTTTTAGTTGGCTTGGAC<br>TGAACGAAGTGAGGGAAAGGCTACTAAAACGTCGAGGGGCAGTGAGAGCGAAGCGAACAC<br>TTGATCTTTTAAGTTGCTATCTTTTATAGGTCAATAGAGTATACTTATTTTGTCCTATTGA<br>TTAGATAGCAGTATAATAGCTTTATAGAGTAGGTCATTTAAGTTGAGCATAATAGGAGGA<br>TCAAGAATGAAAAAATTTATTTATCGAGTTTTAGAAAATGACGAAGTGGTGGCTATTTTT<br>AATGAGCAAGAATATGCGCAAGATTTTATCGCTTACGAAAAGACAATTTCTGATAAGCAA<br>TTTGAAATTGAAAAAGTAGCACTCGCAGATTGGTTATTGCAACCGAGAGAATTTTAGGGG<br>TTGGTTGAAAATGGCTAAAATTGGTTATGCACGACTCTAGGGGAGCTAGAGCGGCCGCCA<br>CGGCGATATCGGATCCATATGGTCGACGGATAAGGCAGAATAATGGAATAAATTAATAAA<br>AAATTTGTGAGAATTAAAAAGAAAGAGGAAACTCTTTCTTTTTTCGTTTTGCAAAAGTG<br>TTTCAATATATTAAATGCGAACAAGCTTTTGCACATAGCAAATAAAAATTAAAAATCGAG<br>TTAAATGGCGATCTGATGCGGTTTTGTATCATCTGAATAAATTTACATAAATATTACAAT<br>TGTTACAATTTTGACATACTTTGCAATAGTTTCTTAATCTGCAGGTGATATTCCTGTTAT<br>AGTTCTGCAATTTAAGCAAGGTAGTATATGCTGTGTCAATTGAATGGGACGGACGAATAA<br>GGTGAAAATTCGTTACTTATGACTTTTAAAATTTTAAGGAGAGAATTTTTTGAAAATTA<br>AATCTATCTTAGTTAAGTCAATTGCAGTAACTGCTTTATCAGTTACAGGTTTAGTAGCAG<br>CTAATAACAACACTAATACTGCTCAAGCTGCTATTGTAGAAGGATCTGCGGCCCAGCCGG<br>CCATGGATGCCCAGGTGAAACTGCAGGAGTCTGGACCTGACCTGGTGAAACCTGGGGCCT<br>CAGTGAAGATATCCTGCAAGGCTTCTGGATACACATTCACTGACTACAACATACACTGGG<br>TGAAGCAGAGCCGTGGAAGAGCCTTGAGTGGATTGGATATATTTATCCTTACAATGGTA<br>ATACTTACTACAACCAGAAGTTCAAGAACAAGGCCACATTGACTGTAGACAATTCCTCCA<br>CCCTCAGCCTACATGGAGCTCCGCAGCCTGACACCTGAGGACTCTGCAGTCTATTACTGTG<br>CAACCTACTTTGACTACTGGGGCCAAGGCACCACGGTCACCGTCTCCTCAGGTGGAGGCG<br>GTTCAGGCGGAGGTGGCTCTGGCGGTGGCGGATCGGACATCGAGCTCACTCAGTCTCCA<br>CAATCATGTCTGCATCTCCAGGGGAGAAGGTCACCATAACCTGCAGTGCCAGCTCAAGTG<br>TAAGTTACATGCACTGGTTCCAGCAGAAGCCAGGCACTTCTCCCAAACTCTGGCTTTATA<br>GCACATCCAACCTGGCTTCTGGAGTCCCTGCTCGCTTCAGTGGCAGTGGATCTGGGACCT<br>CTTACTCTCTCACAATCAGCCGAATGGAGGCTGAAGATGCTGCCACTTATTACTGCCATC<br>AAAGGACTAGTTACCCGTACACGTTCGGAGGGGGGACAAAGTTGGAAATAAAACGGGCAG<br>CGGCCGCAGGTGCGCCGGTGCCGTATCCGGATCCGCTGGAACCGCGTGCCGCAGCTAGCG<br>AGGAGCTCTACCACACTCAAGCTGCTGTAACCCAAGCTCCAGTACAACACCAAACTCAAA<br>CTGAAAATACTAATTCTGCAGCAACTACTACTGCAGCAAATAACACCAACACTCAAACTA<br>CTACTTCAACTGTAAGTGGTTCAGAAGCTAGTGCTAAGGAATGGATTGCCGGTAGAGAAT<br>CTGGTGGCTCATACGGTGCTTCAAATGGTCAATACGTTGGTAAATACCAACTTTCAGCTT<br>CATACTTGAATGGTGACTATTCAGCAGCTAACCAAGAGCGAGTAGCTGATAACTATGTCA<br>AAGGTCGTTATGGCTCATGGACTGCTGCTAAGGCATTCTGGCAAGCAAACGGCTGGTACT<br>AAAAATAAACCTCTTTTCAAAACTAAATAAAATCAAACTAACTTAAAGGAGGCATGCTGT<br>CAAAATGATAGTGTGTCTCTTTTTGATTTTTTAATTAAATAAATACGATATAATTTAAA<br>TAACAAATATTAATAATCAAAACATACAGAAAGTGGAACAGCTATGAAGCAAAATTAAT<br>TGTGACTTTGTTGACTAGTGTTTGCCTGATGGGACGGCTAGTGTAATACACGAAACGAC<br>ACCACAAACGGTTCAAGGAATTCATCGATGATATCGATCCAAATAAAAAGCGCCTACC<br>CCACCGACCAAAGTGAATGGGTAGACGCCTAACAAATACTCGGAGCAACAAGGCTCTTTG<br>TATACACATTTTTACACAGGAGGGCAATAATATGGCGGTATTCAAGCGAGCTAACCGAAA<br>AAGTAAGCCTTGGGGATTCCAGTATTCATACAAAGTGGATGGCATCTCCAAGCAGAAAAC<br>ATCATTTTACAAAACAAGAAAAGAAGCTAAGGCTGCTGAGGCGAAGTACCTCGCTTCTAC<br>TGGCGGATCTGTAAAAATCGATCCAGTGATCACTTTCGCAGATTGGTATGACAAGTGGTT<br>GCATACCTACAAGATACGTTCTGTTTCCGAACTGACGATGACCAAGTATGCAACTTCGGG<br>TACAATCATCAGAAACTACTTCAAAGACCTTAAATTAATTGACTTAACGCGCATGATTTA<br>TCAACAGTTTATTAACAACTATATTGATGACGGTTACGGCCACAAGCACGCAAGGCAATC<br>AGTCCAGAAGCTACATTCACACGCTCATCAAGCAATTATGGCCGCAGCAGACGAAGGTTT<br>GATTAGGCGCGATTATGCCGCTCATGCAGAACTGGGTGGTACCGCAGGCAGATCAGAAGA<br>CACAAAATTTCTTGAAGCTGATCAGTTCGAGAAACTGCGAGATTATGTTGATCAATTTGC<br>CAACCCGCAACGAATTGCTCTCATGATGGTTCAAACGGCCATATACTCTGGCGCTCGGCT<br>TGGAGAAATTGGTGGCTTAACGTGGGAAGATATTGATGAGAAGAAGAGCACCATCAGTAT<br>CGACAAGACCTTCAAGTACAGGTTTGTCATTCGTAACGCGGATGGTAGCTGGCCAGACCG<br>TGAAAAGTCTTCGGTCCGACCAAGACTCCTTCAAGTGTTCGTACTATCAAAGTAAGCCC<br>AGTTCTTATCGCTAGCCTCCATAAGCTCATATTGGCTGACAGAATAAAAGCGATTAACAA<br>TCCGTACCATTTACTGTTTCTTGGGCCGACCGGCTTGCCAATATATAGCAATGGTGTCAA<br>CAAGGAACTTCGCCGCGCTCTCAAACATCTTGGTATTGAGCGTCCTGGGTTCGGTTTCCA<br>CGGATTGCGGCACACGCATGGCAGCTACTTGCTTTATAAAGGCCTTGACATTCAGTATGT<br>ATCACATCGCCTCGGACACGAAAACGTTGGCATTACCACCAAGATCTATACACATCTGCT<br>GGATGCGATGACACAGAAGCAGGACGAGAAAGCAATGAATGTGTTGTGACTAAAAATCAA<br>ACCAGAGAAAGCGGCTCAATGTCAACTGCCACAAGGTTTACAGCACACATTCAATTTTCG<br>ATCACGAACCATTTTCCTAAAAAATCGCAATTTCAGGCTATTTGGTTCGATGTGGTTCGA<br>TGGATTATATTTTTAGGGGTTTTTCGGAGTTCAGATAAATGCAAGAATGCCGGTTTAAA<br>GCCATTTCTGAGCACTAAAAAAGACCCTCTAGGGGGCTTTGATACCGGTGATCGGGGTAT<br>CACGGAATGTATACGTACTGATATGATTGCATTTATGACAAAAAGTGGTTCGATGTGGTT<br>CGATGCTTCAAACGACAGCGACCAACAACACATCTCTATATAATAGGTAGAAATAGCTTT<br>TAAGAGTTCAGAAATATGGGCACACAAGACCGGGGTCTAATTATTAGGGGAGAAGGAGA<br>GAGTAGCCCGAAAACTTTTAGTTGGCTGGACTGAACGAAGTGAGGGAAAGGCTACTAAAA<br>ACGTCGAGGGGCAGTGAGAGCGAAGCGAACACTTGATCTTTTAAGTTGCTATCTTTTATA<br>GGTCAATAGAGTATACTTATTTGTCCTATTGATTAGATAGCAGTATAATAGCTTTATAGA<br>GTAGGTCATTTAAGTTGAGCATAATAGGAGGATCAAGAATGAAAAATTTATTTATCGAG<br>TTTTAGAAAATGACGAAGTGGTGGCTATTTTTAATGAGCAAGAATATGCGCAAGATTTTA<br>TCGCTTACGAAAAGACAATTTCTGATAAGCAATTTGAAATTGAAAAAGTAGCACTCGCAG | Fragment six1-(cassette mediating expression of secreted/attached scFv anti-SAI/II)-int-attP-six2 of pEM171 |

TABLE 7-continued

Expression cassette sequences

| SEQ. ID. | Sequence | Remarks |
|---|---|---|
| | ATTGGTTATTGCAACCGAGAGAATTTTAGGGGTTGGTTGAAAATGGCTAAAATTGGTTAT<br>GCACGACTC | |
| 25 | AGGTCTAATTATTAGGGGGAGAAGGAGAGAGTAGCCCGAAAACTTTTAGTTGGCTTGGAC<br>TGAACGAAGTGAGGGAAAGGCTACTAAAACGTCGAGGGGCAGTGAGAGCGAAGCGAACAC<br>TTGATCTTTTAAGTTGCTATCTTTTATAGGTCAATAGAGTATACTTATTTGTCCTATTGA<br>TTAGATAGCAGTATAATAGCTTTATAGAGTAGGTCATTTAAGTTGAGCATAATAGGAGGA<br>TCAAGAATGAAAAAATTTATTTATCGAGTTTTAGAAAATGACGAAGTGGTGGCTATTTTT<br>AATGAGCAAGAATATGCGCAAGATTTTATCGCTTACGAAAAGACAATTTCTGATAAGCAA<br>TTTGAAATTGAAAAGTAGCACTCGCAGATTGGTTATTGCAACCGAGAGAATTTTAGGGG<br>TTGGTTGAAAATGGCTAAAATTGGTTATGCACGACTCTAGGGGAGCTAGAGCGGCCGCCA<br>CGGCACGATATCGGATCCATATGGTCGACGGATAAGGCAGAATAATGGAATAAATTAATAAA<br>AAATTTGTGAGAATTAAAAAAGAAAGAGGAAACTCTTTCTTTTTTCGTTTTGCAAAAGTG<br>TTTCAATATATTAAATGCGAACAAGCTTTTGCACATAGCAAATAAAAATTAAAAATCGAG<br>TTAAATGGCGATCTGATGCGGTTTTGTATCATCTGAATAAATTTACATAAATATTACAAT<br>TGTTACAATTTTGACATACTTTGCAATAGTTTCTTAATCTGCAGGTGATATTCCTGTTAT<br>AGTTCTGCAATTTAAGCAAGGTAGTATATGCTGTGTCAATTGAATGGGACGGACGAATAA<br>GGTGAAAATTCGTTACTTATGACTTTTAAAATTTTAAGGAGAGAATTTTTTTGAAAATTA<br>AATCTATCTTAGTTAAGTCAATTGCAGTAACTGCTTTATCAGTTACAGGTTTAGTAGCAG<br>CTAATAACAACACTAATACTGCTCAAGCTGCTATTGTAGAAGGATCTGCGGCCCAGCCGG<br>CCATGGATGCCCAGGTGAAACTGCAGGAGTCTGGACCTGACCTGGTGAAACCTGGGGCCT<br>CAGTGAAGATATCCTGCAAGGCTTCTGGATACACATTCACTGACTACAACATACACTGGG<br>TGAAGCAGAGCCGTGGAAAGAGCCTTGAGTGGATTGGATATATTTATCCTTACAATGGTA<br>ATACTTACTACAACCAGAAGTTCAAGAACAAGGCCACATTGACTGTAGACAATTCCTCCA<br>CCTCAGCCTACATGGAGCTCCGCAGCCTGACACCTGAGGACTCTGCAGTCTATTACTGTG<br>CAACCTACTTTGACTACTGGGGCCAAGGCACCACGGTCACCGTCTCCTCAGGTGGAGGCG<br>GTTCAGGCGGAGGTGGCTCTGGCGGTGGCGGATCGGACATCGAGCTCACTCAGTCTCCAG<br>CAATCATGTCTGCATCTCCAGGGGAGAAGGTCACCATAACCTGCAGTGCCAGCTCAAGTG<br>TAAGTTACATGCACTGGTTCCAGCAGAAGCCAGGCACTTCTCCCAAACTCTGGCTTTATA<br>GCACATCCAACCTGGCTTCTGGAGTCCCTGCTCGCTTCAGTGGCAGTGGATCTGGGACCT<br>CTTACTCTCTCACAATCAGCCGAATGGAGGCTGAAGATGCTGCCACTTATTACTGCCATC<br>AAAGGACTAGTTACCCGTACACGTTCGGAGGGGGGACAAAGTTGGAAATAAAACGGGCGG<br>CGGCCGCAGGTGCGCCGGTGCCGTATCCGGATCCGCTGGAACCGCGTGCCGCAGCTAGCA<br>AGAAGACTTCGCTGCTTAACCAGTTGCAATCTGTGAAGGCTGCGCTGGGAACGGACTTGG<br>GCAATCAAACTGATCCAAGCACTGGCAAAACATTTATGGCAGCGTTAGACGATCTAGTGG<br>CACAAGCTCAAGCAGGCACGCAAACGGCCGACCAGCTTCAAGCGAGTCTTGCCAAGGTAC<br>TTGATGCAGTATTAGCAAAACTTGCGGAGGGTATTAAAGCGGCAACACCGGCTGAGGTTG<br>GCAATGCTAAAGATGCTGCGACTGGCAAAACTTGGTATGCCGACATTGCTGACACATTGA<br>CGTCTGGTCAAGCCAGTGCTGATGCGTCTGACAAGCTTGCACATTTACAAGCTTTGCAAA<br>GTCTGAAAACGAAGGTGGCAGCTGCCGTTGAAGCGGCCAAGACAGCTGGTAAAGGCGACG<br>ATACAAGCGGTACTAGCGACAAAGGCGGCGGTCAAGGTACCCCGGCGCCCGCTCCAGGCG<br>ACACAGGTAAGAACAAAGGCGATGAGGGCAGCCAGCCTAGTTCTGGCGGTAATATCCCAA<br>CAAAGCCAGCCACAACGACGTCAACGAGCACGGATGATACGACTGATCGTAATGGTCAAC<br>ATACATCCGGTAAGGGAGCATTACCCAAGCAGCAGAGACAACTGAGCGGCCAGCGTTTG<br>GCTTCTTGGGTGTCATTGTGGTCAGTCTGATGGGGGTATTAGGATTGAAACGGAAACAAC<br>GTGAAGAATAGGAGCTCTCAACTGTAAGTGGTTCAGAAGCTAGTGCTAAGGAATGGATTG<br>CCGGTAGAGAATCTGGTGGCTCATACGGTGCTTCAAATGGTCAATACGTTGGTAAATACC<br>AACTTTCAGCTTCATACTTGAATGGTGACTATTCAGCAGCTAACCAAGAGCGAGTAGCTG<br>ATAACTATGTCAAAGGTCGTTATGGCTCATGGACTGCTGCTAAGGCATTCTGGCAAGCAA<br>ACGGCTGGTACTAAAAATAAACCTCTTTTCAAAACTAAATAAAATCAAACTAACTTAAAG<br>GAGGCATGCTGTCAAATGATAGTGTGTCTCTTTTTGATTTTTTTAATTAAATAAATACG<br>ATATAATTTAAATAACAAATATTAATAATCAAAACATACAGAAAGTGGAACAGCTATGAA<br>GCAAAAATTAATTGTGACTTTGTTGACTAGTGTTTGCCTGATGGGGACGGCTAGTGTAAT<br>ACACGAAACGACACCACAAACGGTTCAAGGAATTCATCGATGATATCAGATCCAAAATAA<br>AAAGCGCCTACCCCACCGACCAAAGTGAATGGGTAGACGCCTAACAAATACTCGGAGCAA<br>CAAGGCTCTTTGTATACACATTTTTACACAGGAGGGCAATAATATGGCGGTATTCAAGCG<br>AGCTAACCGAAAAAGTAAGCCTTGGGGATTCCAGTATTCATACAAAGTGGATGGCATCTC<br>CAAGCAGAAAACATCATTTTACAAAACAAGAAAAGAAGCTAAGGCTGCTGAGGCGAAGTA<br>CCTCGCTTCTACTGGCGGATCTGTAAAAATCGATCCAGTGATCACTTTCGCAGATTGGTA<br>TGACAAGTGGTTGCATACCTACAAGATACGTTCTGTTTCCGAACTGACGATGACCAAGTA<br>TGCAACTTCGGGTACAATCATCAGAAACTACTTCAAAGACCTTAAATTAATTGACTTAAC<br>GCGCATGATTTATCAACAGTTTATTAACAACTATATTGATGACGGTTACGGCCACAAGCA<br>CGCAAGGCAATCAGTCCAGAAGCTACATTCACACGCTCATCAAGCAATTATGGCCGCAGC<br>AGACGAAGGTTTGATTAGGCGCGATTATGCCGCTCATGCAGAACTGGGTGGTACCGCAGG<br>CAGATCAGAAGACACAAAATTTCTTGAAGCTGATCAGTTCGAGAAACTGCGAGATTATGT<br>TGATCAATTTGCCAACCCGCAACGAATTGCTCTCATGATGGTTCAAGCTTTGGCTGCCAT<br>GGCGCTCGGCTTGAGAAATTGGTGGCTTAACGTGGGAAGATATTGATGAGAAGAAGAG<br>CACCCATCAGTATCGACAAGACCTTCAAGTACAGGTTTGTCATTCGTAACGCGGATGGTAG<br>CTGGCCAGACCGTGAAAAGTCTTCGGTCCGACCAAGACTCCTTCAAGTGTTCGTACTAT<br>CAAAGTAAGCCAGTTCTTATCGCTAGCCTCCATAAGCTCAGCCTGTGACAGAATAAA<br>AGCGATTAACAATCCGTACCATTTACTGTTTCTTGGGCCGACCGGCTTGCCAATATATAG<br>CAATGGTGTCAACAAGGAACTTCGCCGCGCTCTCAAACATCTTGGTATTGAGCGTCCTGG<br>GTTCGGTTTCCACGGATTGCGGCACACGCATGGCAGCTACTTGCTTTATAAAGGCCTTGA<br>CATTCAGTATGTATCACATCGCCTCGGACACGAAAACGTTGGCATTACCACCAAGATCTA<br>TACACATCTGCTGGATGCGATGACACAGAAGCAGGACGAGAAAGCAATGAATGTGTTGTG | Fragment six1-<br>(cassette<br>mediating<br>expression of<br>anchored scFv<br>anti-SAI/II)-int-<br>attP-six2 of<br>pEM181 |

TABLE 7-continued

Expression cassette sequences

| SEQ. ID. | Sequence | Remarks |
|---|---|---|
| | ACTAAAAATCGAACCAGAGAAAGCGGCTCAATGTCAACTGCCACAAGGTTTACAGCACAC<br>ATTCAATTTTCGATCACGAACCATTTTCCTAAAAAATCGCAATTTCAGGCTATTTGGTTC<br>GATGTGGTTCGATGGATTATATTTTTTAGGGGTTTTTCGGAGTTCAGATAAATGCAAGAA<br>TGCCGGTTTAAAGCCATTTCTGAGCACTAAAAAAGACCCTCTAGGGGGCTTTGATACCGG<br>TGATCGGGGTATCACGGAATGTATACGTACTGATATGATTGCATTTATGACAAAAAGTGG<br>TTCGATGTGGTTCGATGCTTCAAACGACAGCGACCAACAACACATCTCTATATAATAGGT<br>AGAAATAGCTTTTAAGAGTTCAGAAATATGGGCACACAAGACCGGGGTCTAATTATTAGG<br>GGGAGAAGGAGAGAGTAGCCCGAAAACTTTTAGTTGGCTTGGACTGAACGAAGTGAGGGA<br>AAGGCTACTAAAACGTCGAGGGGCAGTGAGAGCGAAGCGAACACTTGATCTTTTAAGTTG<br>CTATCTTTTATAGGTCAATAGAGTATACTTATTTGTCCTATTGATTAGATAGCAGTATAA<br>TAGCTTTATAGAGTAGGTCATTTAAGTTGAGCATAATAGGAGGATCAAGAATGAAAAAT<br>TTATTTATCGAGTTTTAGAAAATGACGAAGTGGTGGCTATTTTTAATGAGCAAGAATATG<br>CGCAAGATTTTATCGCTTACGAAAAGACAATTTCTGATAAGCAATTTGAAATTGAAAAAG<br>TAGCACTCGCAGATTGGTTATTGCAACCGAGAGAATTTTAGGGGTTGGTTGAAATGGCT<br>AAAATTGGTTATGCACGACTC | |
| 26 | AGGTCTAATTATTAGGGGGAGAAGGAGAGAGTAGCCCGAAAACTTTTAGTTGGCTTGGAC<br>TGAACGAAGTGAGGGAAAGGCTACTAAAACGTCGAGGGGCAGTGAGAGCGAAGCGAACAC<br>TTGATCTTTTAAGTTGCTATCTTTTATAGGTCAATAGAGTATACTTATTTGTCCTATTGA<br>TTAGATAGCAGTATAATAGCTTTATAGAGTAGGTCATTTAAGTTGAGCATAATAGGAGGA<br>TCAAGAATGAAAAAATTTATTTATCGAGTTTTAGAAAATGACGAAGTGGTGGCTATTTTT<br>AATGAGCAAGAATATGCGCAAGATTTTATCGCTTACGAAAAGACAATTTCTGATAAGCAA<br>TTTGAAATTGAAAAAGTAGCACTCGCAGATTGGTTATTGCAACCGAGAGAATTTTAGGGG<br>TTGGTTGAAAATGGCTAAAATTGGTTATGCACGACTCTAGGGGAGCTAGAGCGGCCGCCA<br>CGGCGATATCGGATCCATATGGTCGACGGATAAGGCAGAATAATGGAATAAATTAATAAA<br>AAATTTGTGAGAATTAAAAAAGAAAGAGGGAAACTCTTTCTTTTTTCGTTTTGCAAAGTG<br>TTTCAATATATTAAATGCGAACAAGCTTTTGCACATAGCAAATAAAAATTAAAAATCGAG<br>TTAAATGGCGATCTGATGCGGTTTTGTATCATCTGAATAAATTTACATAAATATTACAAT<br>TGTTACAATTTTGACATACTTTGCAATAGTTTCTTAATCTGCAGGTGATATTCCTGTTAT<br>AGTTCTGCAATTTAAGCAAGGTAGTATATGCTGTGTCAATTGAATGGGACGGACGAATAA<br>GGTGAAAATTCGTTACTTATGACTTTTAAAATTTTAAGGAGAGAATTTTTTTGAAATTA<br>AATCTATCTTAGTTAAGTCAATTGCAGTAACTGCTTTATCAGTTACAGGTTTAGTAGCAG<br>CTAATAACAACACTAATACTGCTCAAGCTGCTATTGTAGAAGGATCTGCGGCCCAGCCGG<br>CCATGGATGCCCAGGTGAAACTGCAGGAGTCTGGACCTGACCTGGTGAAACCTGGGGCCT<br>CAGTGAAGATATCCTGCAAGGCTTCTGGATACACATTCACTGACTACAACATACACTGGG<br>TGAAGCAGAGCCGTGGAAAGAGCCTTGAGTGGATTGGATATATTTATCCTTACAATGGTA<br>ATACTTACTACAACCAGAAGTTCAAGAACAAGGCCACATTGACTGTAGACAATTCCTCCA<br>CCTCAGCCTACATGGAGCTCCGCAGCCTGACACCTGAGGACTCTGCAGTCTATTACTGTG<br>CAACCTACTTTGACTACTGGGGCCAAGGCACCACGGTCACCGTCTCCTCAGGTGGAGGCG<br>GTTCAGGCGGAGGTGGCTCTGGCGGTGGCGGATCGGACATCGAGCTCACTCAGTCTCCAG<br>CAATCATGTCTGCATCTCCAGGGGAGAAGGTCACCATAACCTGCAGTGCCAGCTCAAGTG<br>TAAGTTACATGCACTGGTTCCAGCAGAAGCCAGGCACTTCTCCCAAACTCTGGCTTTATA<br>GCACATCCAACCTGGCTTCTGGAGTCCCTGCTCGCTTCAGTGGCAGTGGATCTGGGACCT<br>CTTACTCTCTCACAATCAGCCGAATGGAGGCTGAAGATGCTGCCACTTATTACTGCCATC<br>AAAGGACTAGTTACCCGTACACGTTCGGAGGGGGGACAAAGTTGGAAATAAAACGGGCGG<br>CGGCCGCAGGTGCGCCGGTGCCGTATCCGGATCCGCTGGAACCGCGTGCCGCATAGGCTA<br>GCGAGGAGCTCTCAACTGTAAGTGGTTCAGAAGCTAGTGCTAAGGAATGGATTGCCGGTA<br>GAGAATCTGGTGGCTCATACGGTGCTTCAAATGGTCAATACGTTGGTAAATACCAACTTT<br>CAGCTTCATACTTGAATGGTGACTATTCAGCAGCTAACCAAGAGCGAGTAGCTGATAACT<br>ATGTCAAAGGTCGTTATGGCTCATGGACTGCTGCTAAGGCATTCTGGCAAGCAAACGGCT<br>GGTACTAAAAATAAACCTCTTTTCAAAACTAAATAAAATCAAACTAACTTAAAGGAGGCA<br>TGCTGTCAAAATGATAGTGTGTCTCTTTTTGATTTTTTTAATTAAATAAATACGATATAA<br>TTTAAATAACAAATATTAATAATCAAAACATACAGAAAGTGGAACAGCTATGAAGCAAAA<br>ATTAATTGTGACTTTGTTGACTAGTGTTTGCCTGATGGGGACGGCTAGTGTAATACACGA<br>AACGACACCACAAACGGTTCAAGGAATTCATCGATGATATCAGATCCAAAATAAAAGCG<br>CCTACCCCACCGACCAAAGTGAATGGGTAGACGCCTAACAAATACTCGGAGCAACAAGGC<br>TCTTTGTATACACATTTTTACACAGGAGGGCAATAATATGGCGGTATTCAAGCGAGCTAA<br>CCGAAAAAGTAAGCCTTGGGGATTCCAGTATTCATACAAAGTGGCATCTCCAAGCA<br>GAAAACATCATTTTACAAAACAAGAAAAGAAGCTAAGGCTGCTGAGGCGAAGTACCTCGC<br>TTCTACTGCGGATCTGTAAAAATCGATCCAGTGATCACTTTCGCAGATTGGTATGACAA<br>GTGGTTGCATACCTACAAGATACGTTCTGTTTCCGAACTGACGATGACCAAGTATGCAAC<br>TTCGGGTACAATCATCAGAAACTACTTCAAAGACCTTAAATTAATTGACTTAACGCGCAT<br>GATTTATCAACAGTTTATTAACAACTATATTGATGACGGTTACGGCCACAAGCACGCAAG<br>GCAATCAGTCCAGAAGCTACATTCACACGCTCATCAAGCAATTATGGCCGCAGCAGACGA<br>AGGTTTGATTAGGCGCGATTATGCCGCTCATGCAGAACTGGGTGGTACCGCAGGCAGATC<br>AGAAGACACAAAATTCTTGAAGCTGATCAGTTCGAGAAACTGCGAGATTATGTTGATCA<br>ATTTGCCAACCCGCAACGAATTGCTCTCATGATGGTTCAAACGGCCATATACTCTGGCGC<br>TCGGCTTGGAGAAATTGGTGGCTTAACGTGGGAAGATATTGATGAGAAGAAGAGCACCAT<br>CAGTATCGACAAGACCTTCAAGTACAGGTTTGTCATTCGTAACGCGGATGGTAGCTGGCC<br>AGACGTGAAAAGTCTCGGTCCGACCAAGACTCCTTCAAGTGTTCGACTATCAAGT<br>AAGCCCAGTTCTTATCGCTAGCCTCCATAAGCTCATATTGGCTGACAGAATAAAAGCGAT<br>TAACAATCCGTACCATTTACTGTTTCTTGGGCCGACCGGCTTGCCAATATATAGCAATGG<br>TGTCAACAAGGAACTTCGCCGCGCTCTCAAACATCTTGGTATTGAGCGTCCTGGGTTCGG<br>TTTCCACGGATTGCGGCACACGCATGGCAGCTACTTGCTTTATAAAGGCCTTGACATTCA<br>GTATGTATCACATCGCCTCGGACACGAAAACGTTGGCATTACCACCAAGATCTATACACA | Fragment six1-<br>(cassette<br>mediating<br>expression of<br>secreted scFv anti-<br>SAI/II)-int-attP-<br>six2 of pEM182 |

TABLE 7-continued

Expression cassette sequences

| SEQ. ID. | Sequence | Remarks |
|---|---|---|
|  | TCTGCTGGATGCGATGACACAGAAGCAGGACGAGAAAGCAATGAATGTGTTGTGACTAAA<br>AATCGAACCAGAGAAAGCGGCTCAATGTCAACTGCCACAAGGTTTACAGCACACATTCAA<br>TTTTCGATCACGAACCATTTTCCTAAAAAATCGCAATTTCAGGCTATTTGGTTCGATGTG<br>GTTCGATGGATTATATTTTTAGGGGTTTTTCGGAGTTCAGATAAATGCAAGAATGCCGG<br>TTTAAAGCCATTTCTGAGCACTAAAAAAGACCCTCTAGGGGGCTTTGATACCGGTGATCG<br>GGGTATCACGGAATGTATACGTACTGATATGATTGCATTTATGACAAAAAGTGGTTCGAT<br>GTGGTTCGATGCTTCAAACGACAGCGACCAACAACACATCTCTATATAATAGGTAGAAAT<br>AGCTTTTAAGAGTTCAGAAATATGGGCACACAAGACCGGGGTCTAATTATTAGGGGGAGA<br>AGGAGAGAGTAGCCCGAAAACTTTTAGTTGGCTTGGACTGAACGAAGTGAGGGAAAGGCT<br>ACTAAAACGTCGAGGGGCAGTGAGAGCGAAGCGAACACTTGATCTTTTAAGTTGCTATCT<br>TTTATAGGTCAATAGAGTATACTTATTTGTCCTATTGATTAGATAGCAGTATAATAGCTT<br>TATAGAGTAGGTCATTTAAGTTGAGCATAATAGGAGGATCAAGAATGAAAAATTTATTT<br>ATCGAGTTTTAGAAAATGACGAAGTGGTGGCTATTTTTAATGAGCAAGAATATGCGCAAG<br>ATTTTATCGCTTACGAAAAGACAATTTCTGATAAGCAATTTGAAATTGAAAAGTAGCAC<br>TCGCAGATTGGTTATTGCAACCGAGAGAATTTTAGGGGTTGGTTGAAAATGGCTAAAATT<br>GGTTATGCACGACTC |  |
| 27 | AGGTCTAATTATTAGGGGGAGAAGGAGAGAGTAGCCCGAAAACTTTTAGTTGGCTTGGAC<br>TGAACGAAGTGAGGGAAAGGCTACTAAAACGTCGAGGGGCAGTGAGAGCGAAGCGAACAC<br>TTGATCTTTTAAGTTGCTATCTTTTATAGGTCAATAGAGTATACTTATTTGTCCTATTGA<br>TTAGATAGCAGTATAATAGCTTTATAGAGTAGGTCATTTAAGTTGAGCATAATAGGAGGA<br>TCAAGAATGAAAAATTTATTTATCGAGTTTTAGAAAATGACGAAGTGGTGGCTATTTTT<br>AATGAGCAAGAATATGCGCAAGATTTTATCGCTTACGAAAAGACAATTTCTGATAAGCAA<br>TTTGAAATTGAAAAGTAGCACTCGCAGATTGGTTATTGCAACCGAGAGAATTTTAGGGG<br>TTGGTTGAAAATGGCTAAAATTGGTTATGCACGACTCTAGGGGAGCTAGAGCGGCCGCCA<br>CGGCGATATCGGATCCATATGGTCGACGGATAAGGCAGAATAATGGAATAAATTAATAAA<br>AAATTTGTGAGAATTAAAAAAGAAAGAGGGAAACTCTTTCTTTTTTCGTTTTGCAAAAGTG<br>TTTCAATATATTAAATGCGAACAAGCTTTTGCACATAGCAAATAAAAATTAAAAATCGAG<br>TTAAATGGCGATCTGATGCGGTTTTGTATCATCTGAATAAATTTACATAAATATTACAAT<br>TGTTACAATTTTGACATACTTTGCAATAGTTTCTTAATCTGCAGGTGATATTCCTGTTAT<br>AGTTCTGCAATTTAAGCAAGGTAGTATATGCTGTGTCAATTGAATGGGACGGACGAATAA<br>GGTGAAAATTCGTTACTTATGACTTTTAAAATTTTAAGGAGAGAATTTTTTTGAAAATTA<br>AATCTATCTTAGTTAAGTCAATTGCAGTAACTGCTTTATCAGTTCAGGTTTAGTAGCAG<br>CTAATAACAACACTAATACTGCTCAAGCTGCTATTGTAGAAGGATCTGCGGCCCAGCCGG<br>CCATGGATCAGGTGCAGCTGCAGGACTCTGGGGGAGGATTGGTGCAGGTTGGGGACCGTC<br>TGAGTCTCTCCTGTGCAGCATCTGGACGCACCTTCAGTTCGTATGACATGGCTTGGTTCC<br>GCCAGGCTCCAGGGAAGGAGCGTGAGTTTGTCGCAGCTATTACTACATCTGAAGGCACAT<br>GGTATGGAGACGCCGGTAAGGGCCGATTCACCATCGCCAGAGTCAACGCCAAGAACACGG<br>TGTATCTGCACATGAACAGGCTGAAACCTGAGGACACGGCCGTTTATTACTGTGCAGCGT<br>CTAATCAAGGAGGCTCACTGCAAATATCTACTAATTATAACTACTGGGGCCAGGGGACCC<br>AGGTCACCGTCTCAAGCGCGGCCGCAGGTGCGCCGGTGCCGATCCGGATCCGCTGGAAC<br>CGCGTGCCGCAGCTAGCAAGAAGACTTCGCTGCTTAACCAGTTGCAATCTGTGAAGGCTG<br>CGCTGGGAACGGACTTGGGCAATCAAACTGATCCAAGCACTGGCAAAACATTTATGGCAG<br>CGTTAGACGATCTAGTGGCACAAGCTCAAGCAGGCACGCAAACGGCCGACCAGCTTCAAG<br>CGAGTCTTGCCAAGGTACTTGATGCAGTATTAGCAAAACTTGCGGAGGGTATTAAAGCGG<br>CAACACCGGCTGAGGTTGGCAATGCTAAAGATGCTGCGACTGGCAAAACTTGGTATGCCG<br>ACATTGCTGACACATTGACGTCTGGTCAAGCCAGTGCTGATGCGTCTGACAAGCTTGCAC<br>ATTTACAAGCTTTGCAAAGTCTGAAAACGAAGGTGGCAGCTGCCGTTGAAGCGGCCAAGA<br>CAGCTGGTAAAGGCGACGATACAAGCGGTACTAGCGACAAAGGCGGCGGTCAAGGTACCC<br>CGGCGCCCGCTCCAGGCGACACAGGTAAGAACAAAGGCGATGAGGGCAGCCAGCCTAGTT<br>CTGGCGGTAATATCCCAACAAAGCCAGCCACAACGACGTCAACGAGCACGGATGATACGA<br>CTGATCGTAATGGTCAACATACATCCGGTAAGGGAGCATTACCCAAGACAGCAGAGACAA<br>CTGAGCGGCCAGCGTTTGGCTTCTTGGGTGTCATTGTGGTCAGTCTGATGGGGGTATTAG<br>GATTGAAACGGAAACAACGTGAAGAATAGGAGCTCTCAACTGTAAGTGGTTCAGAAGCTA<br>GTGCTAAGGAATGGATTGCCGGTAGAGAATCTGGTGGCTCATACGGTGCTTCAAATGGTC<br>AATACGTTGGTAAATACCAACTTTCAGCTTCATACTTGAATGGTGACTATTCAGCAGCTA<br>ACCAAGAGCGAGTAGCTGATAACTATGTCAAAGGTCGTTATGGCTCATGGACTGCTGCTA<br>AGGCATTCTGGCAAGCAAACGGCTGGTACTAAAAATAAACCTCTTTTCAAAACTAAATAA<br>AATCAAACTAACTTAAAGGAGGCATGCTGTCAAAATGATAGTGTGTCTCTTTTTGATTTT<br>TTTAATTAAATAAATACGATATAATTTAAATAACAAATATTAATAATCAAAACATACAGA<br>AAGTGGAACAGCTATGAAGCAAAAATTAATTGTGACTTTGTTGACTAGTGTTTGCCTGAT<br>GGGGACGGCTAGTGTAATACACGAAACGACACCACAAACGGTTCAAGAATTCATCGATGA<br>TATCGATCCAAAATAAAAAGCGCCTACCCCACCGACCAAAGTGAATGGGTAGACGCCTA<br>ACAAATACTCGGAGCAACAAGGCTCTTTGTATACACATTTTTACACAGGAGGGCAATAAT<br>ATGGCGGTATTCAAGCGAGCTAACCGAAAAAGTAAGCCTTGGGGATTCCAGTATTCATAC<br>AAAGTGGATGGCATCTCAAGCAGAAAACATCATTTTACAAAACAAGAAAAGAAGCTAAG<br>GCTGCTGAGGCGAAGTACCTCGCTTCTACTGGCGGATCTGTAAAAATCGATCCAGTGATC<br>ACTTTCGCAGATTGGTATGACAAGTGGTTCATACCTACAAGATACGTTCGTTTCCGAA<br>CTGACGATGACCAAGTATGCAACTTCGGGTACAATCATCAGAAACTACTTCAAAGACCTT<br>AAATTAATTGACTTAACGCGCATGATTTATCAACAGTTTATTAACAACTATATTGATGAC<br>GGTTACGGCCACAAGCACGCAAGGCAATCAGTCCAGAAGCTACATTCACACGCTCATCAA<br>GCAATTATGGCCGCAGCAGACGAAGGTTTGATTAGGCGCGATTATGCCGCTCATGCAGAA<br>CTGGGTGGTACCGCAGGCAGATCAGAAGACACAAAATTTCTTGAAGCTGATCAGTTCGAG<br>AAACTGCGAGATTATGTTGATCAATTTGCCAACCCGCAACGAATTGCTCTCATGATGGTT<br>CAAACGGCCATATACTCTGGCGCTCGGCTTGGAGAAATTGGTGGCTTAACGTGGGAAGAT | fragment six1 (cassette mediating expression of anchored ARP1)-int-attP-six2 of pEM233 |

TABLE 7-continued

Expression cassette sequences

| SEQ. ID. | Sequence | Remarks |
|---|---|---|
| | ATTGATGAGAAGAAGAGCACCATCAGTATCGACAAGACCTTCAAGTACAGGTTTGTCATT<br>CGTAACGCGGATGGTAGCTGGCCAGACCGTGAAAAAGTCTTCGGTCCGACCAAGACTCCT<br>TCAAGTGTTCGTACTATCAAAGTAAGCCCAGTTCTTATCGCTAGCCTCCATAAGCTCATA<br>TTGGCTGACAGAATAAAAGCGATTAACAATCCGTACCATTTACTGTTTCTTGGGCCGACC<br>GGCTTGCCAATATATAGCAATGGTGTCAACAAGGAACTTCGCCGCGCTCTCAAACATCTT<br>GGTATTGAGCGTCCTGGGTTCGGTTTCCACGGATTGCGGCACACGCATGGCAGCTACTTG<br>CTTTATAAAGGCCTTGACATTCAGTATGTATCACATCGCCTCGGACACGAAAACGTTGGC<br>ATTACCACCAAGATCTATACACATCTGCTGGATGCGATGACACAGAAGCAGGACGAGAAA<br>GCAATGAATGTGTTGTGACTAAAAATCGAACCAGAGAAAGCGGCTCAATGTCAACTGCCA<br>CAAGGTTTACAGCACACATTCAATTTTCGATCACGAACCATTTTCCTAAAAAATCGCAAT<br>TTCAGGCTATTTGGTTCGATGTGGTTCGATGGATTATATTTTTAGGGGTTTTTCGGAGT<br>TCAGATAAATGCAAGAATGCCGGTTTAAAGCCATTTCTGAGCACTAAAAAAGACCCTCTA<br>GGGGGCTTTGATACCGGTGATCGGGGTATCACGGAATGTATACGTACTGATATGATTGCA<br>TTTATGACAAAAAGTGGTTCGATGTGGTTCGATGCTTCAAACGACAGCGACCAACAACAC<br>ATCTCTATATAATAGGTAGAAATAGCTTTTAAGAGTTCAGAAATATGGGCACACAAGACC<br>GGGGTCTAATTATTAGGGGGAGAAGGAGAGAGTAGCCCGAAAACTTTTAGTTGGCTTGGA<br>CTGAACGAAGTGAGGGAAAGGCTACTAAAACGTCGAGGGGCAGTGAGAGCGAAGCGAACA<br>CTTGATCTTTTAAGTTGCTATCTTTTATAGGTCAATAGAGTATACTTATTTGTCCTATTG<br>ATTAGATAGCAGTATAATAGCTTTATAGAGTAGGTCATTTAAGTTGAGCATAATAGGAGG<br>ATCAAGAATGAAAAAATTTATTTATCGAGTTTTAGAAAATGACGAAGTGGTGGCTATTTT<br>TAATGAGCAAGAATATGCGCAAGATTTTATCGCTTACGAAAAGACAATTTCTGATAAGCA<br>ATTTGAAATTGAAAAAGTAGCACTCGCAGATTGGTTATTGCAACCGAGAGAATTTTAGGG<br>GTTGGTTGAAAATGGCTAAAATTGGTTATGCACGACTC | |

Example 3

A recombinant bacteria (such as a *Lactobacilli*) will be used to express a functional single chain antibody or fragment thereof against ICAM-1 and/or CD18 and/or a CD11 subunit. One or more polynucleotides that encode a functional single chain antibody or fragment thereof against ICAM-1 and/or CD18 and/or a CD11 subunit will be stably integrated into a chromosome of the recombinant bacteria. The recombinant bacteria will be delivered to a human male or female at risk for infection with HIV. The recombinant bacteria will be delivered in a pharmaceutical composition to the oral mucosa, urethra, vagina or rectum. The pharmaceutical composition will be in the form of a cream or a gel. The recombinant bacteria will express a functional single chain antibody or fragment thereof against ICAM-1 and/or CD18 and/or a CD11 subunit at a level sufficient to inhibit transmission of an HIV virus across a vaginal epithelial layer.

Example 4

A population of women at risk for contraction of HIV will be recruited for participation in a protocol that decreases rates of HIV infection. The women will be administered one of two pharmaceutical compositions. One pharmaceutical composition will comprise recombinant bacteria (such as a *Lactobacilli*) that will express a functional single chain antibody or fragment thereof against ICAM-1 and/or CD18 and/or a CD11 ("Treatment composition"). One or more polynucleotides that encode a functional single chain antibody or fragment thereof against ICAM-1 and/or CD18 and/or a CD11 subunit will be stably integrated into a chromosome of the recombinant bacteria. A second pharmaceutical composition will not comprise the recombinant bacteria ("Placebo composition"). The population of women will be divided into two groups: group One will receive the Treatment composition; and group Two will receive the Placebo composition. Group One will be administered the Treatment composition at intervals sufficient to maintain colonization of their vaginal tracts and/or rectums with the recombinant bacteria. Group Two will be administered the Placebo composition at the same intervals as group one. Periodic tissue and or blood samples will be obtained from Groups One and Two to monitor their rate of infection of HIV. The protocol will continue for a length of time sufficient to determine the efficacy of the Treatment composition. At the end of protocol the rate of HIV infection in Group One will be compared to group Two. It is expected that the rate of HIV infection will be lower in Group One than Group Two.

Example 5

A population of women at risk for contraction of HIV will be recruited for participation in a protocol that decreases rates of HIV infection. The women will be administered one of two pharmaceutical compositions. One pharmaceutical composition will comprise recombinant bacteria (such as a *Lactobacilli*) that will express a functional single chain antibody or fragment thereof against ICAM-1 and/or CD18 and/or a CD11 ("Treatment composition"). One or more polynucleotides that encode a functional single chain antibody or fragment thereof against ICAM-1 and/or CD18 and/or a CD11 subunit will be stably integrated into a chromosome of the recombinant bacteria. A second pharmaceutical composition will comprise bacteria that do not express a functional a functional single chain antibody or fragment thereof against ICAM-1 and/or CD18 and/or a CD11 ("Placebo composition"). The population of women will be divided into two groups: group One will receive the Treatment composition; and group Two will receive the Placebo composition. Groups One will be administered the Treatment composition at intervals sufficient to maintain colonization of their vaginal tracts and/or rectums with the recombinant bacteria. Group Two will be administered the Placebo composition at the same intervals as group one. Periodic tissue and or blood samples will be obtained from Groups One and Two to monitor their rate of infection of HIV. The protocol will continue for a length of time sufficient to determine the efficacy of the Treatment composition. At the end of protocol the rate of HIV infection in Group One will be compared to group Two. It is expected that the rate of HIV infection will be lower in Group One than Group Two.

Example 6

A population of women at risk for contraction of HIV will be recruited for participation in a protocol that decreases rates of HIV infection. The women will be administered one of two pharmaceutical compositions. One pharmaceutical composition will comprise recombinant bacteria (such as a *Lactobacilli*) that will express a functional single chain antibody or fragment thereof against ICAM-1 and/or CD18 and/or a CD11 ("Treatment composition"). One or more polynucleotides that encode a functional single chain antibody or fragment thereof against ICAM-1 and/or CD18 and/or a CD11 subunit will be stably integrated into a chromosome of the recombinant bacteria. A second pharmaceutical composition will not comprise the recombinant bacteria ("Placebo composition"). The population of women will be divided into two groups: group One will receive the Treatment composition; and group Two will receive the Placebo composition. Group One will be administered the Treatment composition at intervals sufficient to maintain colonization of their oral mucosas with the recombinant bacteria. Group Two will be administered the Placebo composition at the same intervals as group one. Periodic tissue and or blood samples will be obtained from Groups One and Two to monitor their rate of infection of HIV. The protocol will continue for a length of time sufficient to determine the efficacy of the Treatment composition. At the end of protocol the rate of HIV infection in Group One will be compared to group Two. It is expected that the rate of HIV infection will be lower in Group One than Group Two.

Example 7

A population of women at risk for contraction of HIV will be recruited for participation in a protocol that decreases rates of HIV infection. The women will be administered one of two pharmaceutical compositions. One pharmaceutical composition will comprise recombinant bacteria (such as a *Lactobacilli*) that will express a functional single chain antibody or fragment thereof against ICAM-1 and/or CD18 and/or a CD11 ("Treatment composition"). One or more polynucleotides that encode a functional single chain antibody or fragment thereof against ICAM-1 and/or CD18 and/or a CD11 subunit will be stably integrated into a chromosome of the recombinant bacteria. A second pharmaceutical composition will comprise bacteria that do not express a functional a functional single chain antibody or fragment thereof against ICAM-1 and/or CD18 and/or a CD11 ("Placebo composition"). The population of women will be divided into two groups: group One will receive the Treatment composition; and group Two will receive the Placebo composition. Group One will be administered the Treatment composition at intervals sufficient to maintain colonization of their oral mucosas with the recombinant bacteria. Group Two will be administered the Placebo composition at the same intervals as group one. Periodic tissue and or blood samples will be obtained from Groups One and Two to monitor their rate of infection of HIV. The protocol will continue for a length of time sufficient to determine the efficacy of the Treatment composition. At the end of protocol the rate of HIV infection in Group One will be compared to group Two. It is expected that the rate of HIV infection will be lower in Group One than Group Two.

Example 8

A population of men at risk for contraction of HIV will be recruited for participation in a protocol that decreases rates of HIV infection. The men will be administered one of two pharmaceutical compositions. One pharmaceutical composition will comprise recombinant bacteria (such as a *Lactobacilli*) that will express a functional single chain antibody or fragment thereof against ICAM-1 and/or CD18 and/or a CD11 ("Treatment composition"). One or more polynucleotides that encode a functional single chain antibody or fragment thereof against ICAM-1 and/or CD18 and/or a CD11 subunit will be stably integrated into a chromosome of the recombinant bacteria. A second pharmaceutical composition will not comprise the recombinant bacteria ("Placebo composition"). The population of men will be divided into two groups: group One will receive the Treatment composition; and group Two will receive the Placebo composition. Group One will be administered the Treatment composition at intervals sufficient to maintain colonization of their urethras or rectums with the recombinant bacteria. Group Two will be administered the Placebo composition at the same intervals as group one. Periodic tissue and or blood samples will be obtained from Groups One and Two to monitor their rate of infection of HIV. The protocol will continue for a length of time sufficient to determine the efficacy of the Treatment composition. At the end of protocol the rate of HIV infection in Group One will be compared to group Two. It is expected that the rate of HIV infection will be lower in Group One than Group Two.

Example 9

A population of men at risk for contraction of HIV will be recruited for participation in a protocol that decreases rates of HIV infection. The men will be administered one of two pharmaceutical compositions. One pharmaceutical composition will comprise recombinant bacteria (such as a *Lactobacilli*) that will express a functional single chain antibody or fragment thereof against ICAM-1 and/or CD18 and/or a CD11 ("Treatment composition"). One or more polynucleotides that encode a functional single chain antibody or fragment thereof against ICAM-1 and/or CD18 and/or a CD11 subunit will be stably integrated into a chromosome of the recombinant bacteria. A second pharmaceutical composition will comprise bacteria that do not express a functional a functional single chain antibody or fragment thereof against ICAM-1 and/or CD18 and/or a CD11 ("Placebo composition"). The population of men will be divided into two groups: group One will receive the Treatment composition; and group Two will receive the Placebo composition. Group One will be administered the Treatment composition at intervals sufficient to maintain colonization of their urethras or rectums with the recombinant bacteria. Group Two will be administered the Placebo composition at the same intervals as group one. Periodic tissue and or blood samples will be obtained from Groups One and Two to monitor their rate of infection of HIV. The protocol will continue for a length of time sufficient to determine the efficacy of the Treatment composition. At the end of protocol the rate of HIV infection in Group One will be compared to group Two. It is expected that the rate of HIV infection will be lower in Group One than Group Two.

Example 10

A population of men at risk for contraction of HIV will be recruited for participation in a protocol that decreases rates of HIV infection. The men will be administered one of two pharmaceutical compositions. One pharmaceutical composition will comprise recombinant bacteria (such as a *Lactobacilli*) that will express a functional single chain antibody or fragment thereof against ICAM-1 and/or CD18 and/or a CD11 ("Treatment composition"). One or more polynucleotides that encode a functional single chain antibody or fragment thereof against ICAM-1 and/or CD18 and/or a CD11 subunit will be stably integrated into a chromosome of the recombinant bacteria. A second pharmaceutical composition will not comprise the recombinant bacteria ("Placebo composition"). The population of men will be divided into two groups: group One will receive the Treatment composition; and group Two will receive the Placebo composition. Group One will be administered the Treatment composition at intervals sufficient to maintain colonization of their oral mucosas with the recombinant bacteria. Group Two will be administered the Placebo composition at the same intervals as group one. Periodic tissue and or blood samples will be obtained from Groups One and Two to monitor their rate of infection of HIV. The protocol will continue for a length of time sufficient to determine the efficacy of the Treatment composition. At the end of protocol the rate of HIV infection in Group One will be compared to group Two. It is expected that the rate of HIV infection will be lower in Group One than Group Two.

Example 11

A population of men at risk for contraction of HIV will be recruited for participation in a protocol that decreases rates of HIV infection. The men will be administered one of two pharmaceutical compositions. One pharmaceutical composition will comprise recombinant bacteria (such as a *Lactobacilli*) that will express a functional single chain antibody or fragment thereof against ICAM-1 and/or CD18 and/or a CD11 ("Treatment composition"). One or more polynucleotides that encode a functional single chain antibody or fragment thereof against ICAM-1 and/or CD18 and/or a CD11 subunit will be stably integrated into a chromosome of the recombinant bacteria. A second pharmaceutical composition will comprise bacteria that do not express a functional a functional single chain antibody or fragment thereof against ICAM-1 and/or CD18 and/or a CD11 ("Placebo composition"). The population of men will be divided into two groups: group One will receive the Treatment composition; and group Two will receive the Placebo composition. Group One will be administered the Treatment composition at intervals sufficient to maintain colonization of their oral mucosas with the recombinant bacteria. Group Two will be administered the Placebo composition at the same intervals as group one. Periodic tissue and or blood samples will be obtained from Groups One and Two to monitor their rate of infection of HIV. The protocol will continue for a length of time sufficient to determine the efficacy of the Treatment composition. At the end of protocol the rate of HIV infection in Group One will be compared to group Two. It is expected that the rate of HIV infection will be lower in Group One than Group Two.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein can be employed in practicing the invention. It is intended that the following claims define the scope of the invention and that methods and structures within the scope of these claims and their equivalents be covered thereby.

What is claimed is:

1. An expression cassette comprising at least one polynucleotide sequence wherein said polynucleotide sequence is selected from the group consisting of SEQ ID NO:23, SEQ ID NO:24, SEQ ID NO:25, SEQ ID NO:26, and SEQ ID NO:27.

2. A host cell comprising the expression cassette of claim 1.

3. The host cell of claim 2 wherein said host cell is a microorganism.

4. The host cell of claim 3 wherein said microorganism is *Lactobacillus*.

5. The host cell of claim 4 wherein said host cell is *Lactobacillus paracasei*.

6. The expression cassette of claim 1 comprising the polynucleotide of SEQ ID NO:23.

7. The expression cassette of claim 1 comprising the polynucleotide of SEQ ID NO:24.

8. The expression cassette of claim 1 comprising the polynucleotide of SEQ ID NO:25.

9. The expression cassette of claim 1 comprising the polynucleotide of SEQ ID NO:26.

10. The expression cassette of claim 1 comprising the polynucleotide of SEQ ID NO:27.

11. The host cell of claim 5 wherein said expression cassette comprises the nucleotide of SEQ ID NO:23.

12. The host cell of claim 5 wherein said expression cassette comprises the nucleotide of SEQ ID NO:24.

13. The host cell of claim 5 wherein said expression cassette comprises the nucleotide of SEQ ID NO:25.

14. The host cell of claim 5 wherein said expression cassette comprises the nucleotide of SEQ ID NO:26.

15. The host cell of claim 5 wherein said expression cassette comprises the nucleotide of SEQ ID NO:27.

16. The expression cassette of claim 1 comprising at least two polynucleotide sequences selected from the group consisting of SEQ ID NO:24, SEQ ID NO:25, SEQ ID NO:26, and SEQ ID NO:27.

17. A host cell comprising an expression cassette of claim 16.

18. The host cell of claim 17 wherein said host cell is a microorganism.

19. The host cell of claim 18 wherein said microorganism is *Lactobacillus*.

20. The host cell of claim 19 wherein said host cell is *Lactobacillus paracasei*.

\* \* \* \* \*

SEQUENCE LISTING

```
<160> NUMBER OF SEQ ID NOS: 49

<210> SEQ ID NO 1
<211> LENGTH: 387
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
gatgtgcagc tggtggagtc tgggggaggc tcggtgcaga ctggagggtc tctgagactc      60
tcctgcttag cctctggata cacctatcgt agttactgtc gagggtggtt ccgccggcct     120
ccagggaagg agcgtgaggc ggtcgcgatt ataaatagcc ttggtcaaac gatctatgtc     180
gccgaccccg tgaagggccg attctccatc tcccaagaca acgccaagga cacggtgtat     240
ctgcaaatga acagcctgaa acttaacgac acggccatgt attactgtgc ggtagccaat     300
ggtggttgtg gtgagtcgtg gcgccctgat tacgtcggcc aggggaccca ggtcaccgtc     360
tcctcacacc accatcacca tcactaa                                         387

<210> SEQ ID NO 2
<211> LENGTH: 672
<212> TYPE: DNA
<213> ORGANISM: Lactobacillus crispatus

<400> SEQUENCE: 2
ttgaaaatta aatctatctt agttaagtca attgcagtaa ctgctttatc agttacaggt      60
ttagtagcag ctaataacaa cactaatact gctcaagctg ctattgtaga aaacgataca     120
```

```
gctgttgtaa cagttaagaa cgtttcagac aacgcaatca ctgtttacaa cagctacaag    180
aatccagagg ctactggcca aactttggca agcaacacct catggaaagt aattaagact    240
gcttacgatg ccaaaggtca caagtggtat gacttaggca agaaccaatg ggttcgtgct    300
aagtatgtaa ctcgcggcta ccacactcaa gctgctgtaa cccaagctcc agtacaacac    360
caaactcaaa ctgaaaatac taattctgca gcaactacta ctgcagcaaa taacaccaac    420
actcaaacta ctacttcaac tgtaagtggt tcagaagcta gtgctaagga atggattgcc    480
ggtagagaat ctggtggctc atacggtgct tcaaatggtc aatacgttgg taaataccaa    540 cttctcagctt catacttgaa tggtgactat tcagcagcta accaagagcg agtagctgat    600
aactatgtca aggtcgttaa tggctcatgg actgctgcta aggcattctg gcaagcaaac    660
ggctggtact aa                                                         672
```

<210> SEQ ID NO 3
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
cgcgtcgacg gataaggcag aataatggaa taa                                   33

<210> SEQ ID NO 4
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4 cgggatccett ctacaatagc agcttgagca gt                                   32

<210> SEQ ID NO 5
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cgggatccag tagtagtttg agtgttggtg tt                                    32

<210> SEQ ID NO 6
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cgggatccgt ggtagccgcg agttacatac t                                     31

<210> SEQ ID NO 7
<211> LENGTH: 31
<212> TYPE: DNA
<213> ORGANISM: Artificial Sequence
<220> FEATURE:

<223> OTHER INFORMATION: Description of Artificial Sequence: Synthetic
      primer

<400> SEQUENCE: 7
cgagctctca actgtaagtg gttcagaagc t                                       31

<210> SEQ ID NO 8
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
cggaattcct tgaaccgttt gtggtgtcgt tt                                      32

<210> SEQ ID NO 9
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
cgagctctac cacactcaag ctgctgtaac c                                       31

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gcccaggtga aactgcagga gt                                                 22

<210> SEQ ID NO 11
<211> LENGTH: 74
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tgcggcacgc ggttccagcg gatccggata cggcaccggc gcacctgcgg ccgccgcccg        60
ttttatttcc aact                                                          74

<210> SEQ ID NO 12
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
catgagatct gcggcccagc cggccatgga tgcccaggtg aaactgcag                    49

<210> SEQ ID NO 13
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ccggagctcc tcgctagcct atgcggcacg cggttccagc gga            43

<210> SEQ ID NO 14
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ccggagctcc tcgctagctg cggcacgcgg ttccagcgga                40

<210> SEQ ID NO 15
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gctctagcta gcaagaagac ttcgctgctt aaccagt                   37

<210> SEQ ID NO 16
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
taagcgagct cctattcttc acgttgtttc cgtt                      34

<210> SEQ ID NO 17
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
catgccatgg atggggtcaa ttcagaggtt cagct                     35

<210> SEQ ID NO 18
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gcatgcggcc gctttgattt ccagcttggt gcct                      34

<210> SEQ ID NO 19
<211> LENGTH: 27
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 19
agcggcccag ccggccatgg cccaggt                                            27

<210> SEQ ID NO 20
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
taagcggccg cggtgacctg ggttccctgg cccga                                   35

<210> SEQ ID NO 21
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
agcggcccag ccggccatgg cccaggt                                            27

<210> SEQ ID NO 22
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
taagcggccg cggtgacctg ggttccctgg cccga                                   35

<210> SEQ ID NO 23
<211> LENGTH: 2638
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23
aggtctaatt attaggggga gaaggagaga gtagcccgaa aacttttagt tggcttggac        60
tgaacgaagt gagggaaagg ctactaaaac gtcgaggggc agtgagagcg aagcgaacac       120
ttgatctttt aagttgctat cttttatagg tcaatagagt atacttattt gtcctattga       180
ttagatagca gtataatagc tttatagagt aggtcattta agttgagcat aataggagga       240
tcaagaatga aaaatttat ttatcgagtt ttagaaaatg acgaagtggt ggctattttt        300
aatgagcaag aatatgcgca agattttatc gcttacgaaa agacaatttc tgataagcaa       360
tttgaaattg aaaaagtagc actcgcagat tggttattgc aaccgagaga attttagggg       420
ttggttgaaa atggctaaaa ttggttatgc acgactctag gggagctcga attcgaagct       480
tctgcagacg cgtcgacgtc atatggatcc aaaataaaaa gcgcctaccc caccgaccaa       540
agtgaatggg tagacgccta acaaatactc ggagcaacaa ggctctttgt atacacattt       600
ttacacagga gggcaataat atggcggtat tcaagcgagc taaccgaaaa agtaagcctt       660
```

```
ggggattcca gtattcatac aaagtggatg gcatctccaa gcagaaaaca tcattttaca    720
aaacaagaaa agaagctaag gctgctgagg cgaagtacct cgcttctact ggcggatctg    780
taaaaatcga tccagtgatc actttcgcag attggtatga caagtggttg catacctaca    840
agatacgttc tgtttccgaa ctgacgatga ccaagtatgc aacttcgggt acaatcatca    900
gaaactactt caaagacctt aaattaattg acttaacgcg catgatttat caacagttta    960
ttaacaacta tattgatgac ggttacggcc acaagcacgc aaggcaatca gtccagaagc   1020
tacattcaca cgctcatcaa gcaattatgg ccgcagcaga cgaaggtttg attaggcgcg   1080
attatgccgc tcatgcagaa ctgggtggta ccgcaggcag atcagaagac acaaaatttc   1140
ttgaagctga tcagttcgag aaactgcgag attatgttga tcaatttgcc aacccgcaac   1200
gaattgctct catgatggtt caaacggcca tatactctgg cgctcggctt ggagaaattg   1260
gtggcttaac gtgggaagat attgatgaga agaagagcac catcagtatc gacaagacct   1320
tcaagtacag gtttgtcatt cgtaacgcgg atggtagctg gccagaccgt gaaaaagtct   1380
tcggtccgac caagactcct tcaagtgttc gtactatcaa agtaagccca gttcttatcg   1440
ctagcctcca taagctcata ttggctgaca gaataaaagc gattaacaat ccgtaccatt   1500
tactgtttct tgggccgacc ggcttgccaa tatatagcaa tggtgtcaac aaggaacttc   1560
gccgcgctct caaacatctt ggtattgagc gtcctgggtt cggtttccac ggattgcggc   1620
acacgcatgg cagctacttg ctttataaag gccttgacat tcagtatgta tcacatcgcc   1680
tcggacacga aaacgttggc attaccacca agatctatac acatctgctg gatgcgatga   1740
cacagaagca ggacgagaaa gcaatgaatg tgttgtgact aaaaatcgaa ccagagaaag   1800
cggctcaatg tcaactgcca caaggtttac agcacacatt caattttcga tcacgaacca   1860
ttttcctaaa aaatcgcaat ttcaggctat ttggttcgat gtggttcgat ggattatatt   1920
ttttaggggt ttttcggagt tcagataaat gcaagaatgc cggtttaaag ccatttctga   1980
gcactaaaaa agaccctcta gggggctttg ataccggtga tcggggtatc acggaatgta   2040
tacgtactga tatgattgca tttatgacaa aaagtggttc gatgtggttc gatgcttcaa   2100
acgacagcga ccaacaacac atctctatat aataggtaga aatagctttt aagagttcag   2160
aaatatgggc acacaagacc ggggtctaat tattaggggg agaaggagag agtagcccga   2220
aaacttttag ttggcttgga ctgaacgaag tgagggaaag gctactaaaa cgtcgagggg   2280
cagtgagagc gaagcgaaca cttgatcttt taagttgcta tcttttatag gtcaatagag   2340
tatacttatt tgtcctattg attagatagc agtataatag ctttatagag taggtcattt   2400
aagttgagca taataggagg atcaagaatg aaaaaattta tttatcgagt tttagaaaat   2460
gacgaagtgg tggctatttt taatgagcaa gaatatgcgc aagattttat cgcttacgaa   2520
aagacaattt ctgataagca atttgaaatt gaaaagtag cactcgcaga ttggttattg   2580
caaccgagag aattttaggg gttggttgaa aatggctaaa attggttatg cacgactc     2638
```

<210> SEQ ID NO 24
<211> LENGTH: 4569
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24

```
aggtctaatt attagggga gaaggagaga gtagcccgaa aacttttagt tggcttggac     60
```

```
tgaacgaagt gagggaaagg ctactaaaac gtcgagggc agtgagagcg aagcgaacac      120
ttgatctttt aagttgctat cttttatagg tcaatagagt atacttattt gtcctattga      180
ttagatagca gtaaatagc tttatagagt aggtcattta agttgagcat aataggagga       240
tcaagaatga aaaaatttat ttatcgagtt ttagaaaatg acgaagtggt ggctattttt      300
aatgagcaag aatatgcgca agattttatc gcttacgaaa agacaatttc tgataagcaa      360
tttgaaattg aaaaagtagc actcgcagat tggttattgc aaccgagaga attttagggg      420
ttggttgaaa atggctaaaa ttggttatgc acgactctag gggagctaga gcggccgcca      480
cggcgatatc ggatccatat ggtcgacgga taaggcagaa taatggaata aattaataaa      540
aaatttgtga gaattaaaaa agaaagagga aactcttctt tttcgttt tgcaaaagtg       600 tttcaatata ttaaatgcga acaagcttt gcacatagca aataaaaatt aaaaatcgag      660
ttaaatggcg atctgatgcg gttttgtatc atctgaataa atttacataa atattacaat      720
tgttacaatt ttgacatact ttgcaatagt ttcttaatct gcaggtgata ttcctgttat      780
agttctgcaa tttaagcaag gtagtatatg ctgtgtcaat tgaatgggac ggacgaataa      840
ggtgaaaatt cgttacttat gactttaaa attttaagga gagaattttt tgaaaatta      900 aatctatctt agttaagtca attgcagtaa ctgctttatc agttacaggt ttagtagcag      960
ctaataacaa cactaatact gctcaagctg ctattgtaga aggatctgcg gcccagccgg     1020
ccatggatgc ccaggtgaaa ctgcaggagt ctggacctga cctggtgaaa cctgggcct     1080 cagtgaagat atcctgcaag gcttctggat acacattcac tgactacaac atacactggg    1140
tgaagcagag ccgtggaaag agccttgagt ggattggata tatttatcct tacaatggta     1200
atacttacta caaccagaag ttcaagaaca aggccacatt gactgtagac aattcctcca    1260
cctcagccta catggagctc cgcagcctga caccctgagga ctctgcagtc tattactgtg    1320
caacctactt tgactactgg ggccaaggca ccacggtcac cgtctcctca ggtggaggcg    1380
gttcaggcgg aggtggctct ggcggtggcg gatcggacat cgagctcact cagtctccag    1440
caatcatgtc tgcatctcca ggggagaagg tcaccataac ctgcagtgcc agctcaagtg    1500
taagttacat gcactggttc cagcagaagc caggcacttc tcccaaactc tggctttata    1560
gcacatccaa cctggcttct ggagtccctg ctcgcttcag tggcagtgga tctgggacct    1620
cttactctct cacaatcagc cgaatggagg ctgaagatgc tgccacttat tactgccatc    1680
aaaggactag ttacccgtac acgttcggag gggggacaaa gttggaaata aaacgggcgg    1740
cggccgcagg tgcgccggtg ccgtatccgg atccgctgga accgcgtgcc gcagctagcg    1800
aggagctcta ccacactcaa gctgctgtaa cccaagctcc agtacaacac caaactcaaa    1860
ctgaaaatac taattctgca gcaactacta ctgcagcaaa taacaccaac actcaaacta    1920
ctacttcaac tgtaagtggt tcagaagcta gtgctaagga atggattgcc ggtagagaat    1980
ctggtggctc atacggtgct tcaaatggtc aatacgttgg taaataccaa ctttcagctt    2040
catacttgaa tggtgactat tcagcagcta accaagagcg agtagctgat aactatgtca    2100
aaggtcgtta tggctcatgg actgctgcta aggcattctg gcaagcaaac ggctggtact    2160
aaaaataaac ctcttttcaa aactaaataa aatcaaacta acttaaagga ggcatgctgt    2220
caaaatgata gtgtgtctct ttttgatttt tttaattaaa taaatacgat ataatttaaa    2280
taacaaatat taataatcaa aacatacaga aagtggaaca gctatgaagc aaaaattaat    2340
tgtgactttg ttgactagtg tttgcctgat ggggacggct agtgtaatac acgaaacgac    2400
accacaaacg gttcaaggaa ttcatcgatg atatcagatc caaaataaaa agcgcctacc    2460
```

```
ccaccgacca aagtgaatgg gtagacgcct aacaaatact cggagcaaca aggctctttg    2520
tatacacatt tttacacagg agggcaataa tatggcggta ttcaagcgag ctaaccgaaa    2580
aagtaagcct tggggattcc agtattcata caaagtggat ggcatctcca agcagaaaac    2640
atcattttac aaaacaagaa aagaagctaa ggctgctgag gcgaagtacc tcgcttctac    2700
tggcggatct gtaaaaatcg atccagtgat cactttcgca gattggtatg acaagtggtt    2760
gcatacctac aagatacgtt ctgtttccga actgacgatg accaagtatg caacttcggg    2820
tacaatcatc agaaactact tcaaagacct taaattaatt gacttaacgc gcatgattta    2880
tcaacagttt attaacaact atattgatga cggttacggc cacaagcacg caaggcaatc    2940
agtccagaag ctacattcac acgctcatca agcaattatg gccgcagcag acgaaggttt    3000
gattaggcgc gattatgccg ctcatgcaga actgggtggt accgcaggca gatcagaaga    3060
cacaaaattt cttgaagctg atcagttcga gaaactgcga gattatgttg atcaatttgc    3120
caacccgcaa cgaattgctc tcatgatggt tcaaacggcc atatactctg cgctcggct    3180 tggagaaatt ggtggcttaa cgtgggaaga tattgatgag aagaagagca ccatcagtat    3240
cgacaagacc ttcaagtaca ggtttgtcat tcgtaacgcg gatggtagct ggccagaccg    3300
tgaaaaagtc ttcggtccga ccaagactcc ttcaagtgtt cgtactatca agtaagccc    3360 agttcttatc gctagcctcc ataagctcat attggctgac agaataaaag cgattaacaa    3420
tccgtaccat ttactgtttc ttgggccgac cggcttgcca atatatagca atggtgtcaa    3480
caaggaactt cgccgcgctc tcaaacatct tggtattgag cgtcctgggt tcggtttcca    3540
cggattgcgg cacacgcatg gcagctactt gctttataaa ggccttgaca ttcagtatgt    3600
atcacatcgc ctcggacacg aaaacgttgg cattaccacc aagatctata cacatctgct    3660
ggatgcgatg acacagaagc aggacgagaa agcaatgaat gtgttgtgac taaaaatcga    3720
accagagaaa gcggctcaat gtcaactgcc acaaggttta cagcacacat tcaatttcg    3780 atcacgaacc attttcctaa aaaatcgcaa tttcaggcta tttggttcga tgtggttcga    3840
tggattatat tttttagggg ttttcggag ttcagataaa tgcaagaatg ccggtttaaa    3900
gccatttctg agcactaaaa aagaccctct aggggctttt gataccggtg atcggggtat    3960
cacggaatgt atacgtactg atatgattgc atttatgaca aaaagtggtt cgatgtggtt    4020
cgatgcttca aacgacagcg accaacaaca catctctata taataggtag aaatagcttt    4080
taagagttca gaaatatggg cacacaagac cggggtctaa ttattagggg gagaaggaga    4140
gagtagcccg aaaactttta gttggcttgg actgaacgaa gtgagggaaa ggctactaaa    4200
acgtcgaggg gcagtgagag cgaagcgaac acttgatctt ttaagttgct atcttttata    4260
ggtcaataga gtatacttat ttgtcctatt gattagatag cagtataata gctttataga    4320
gtaggtcatt taagttgagc ataataggag gatcaagaat gaaaaatttt atttatcgag    4380
ttttagaaaa tgacgaagtg gtggctattt ttaatgagca agaatatgcg caagatttta    4440
tcgcttacga aaagacaatt tctgataagc aatttgaaat tgaaaagta gcactcgcag    4500 attggttatt gcaaccgaga gaatttttagg ggttggttga aaatggctaa aattggttat    4560
gcacgactc                                                            4569
```

<210> SEQ ID NO 25
<211> LENGTH: 5181
<212> TYPE: DNA
<213> ORGANISM: Artificial Sequence
<220> FEATURE:

<223> OTHER INFORMATION: Description of Artificial Sequence: Synthetic polynucleotide

<400> SEQUENCE: 25

```
aggtctaatt attaggggga gaaggagaga gtagcccgaa aactttagt tggcttggac      60
tgaacgaagt gagggaaagg ctactaaaac gtcgaggggc agtgagagcg aagcgaacac    120
ttgatctttt aagttgctat cttttatagg tcaatagagt atacttattt gtcctattga    180
ttagatagca gtataatagc tttatagagt aggtcattta agttgagcat aataggagga    240
tcaagaatga aaaatttat ttatcgagtt ttagaaaatg acgaagtggt ggctattttt     300
aatgagcaag aatatgcgca agattttatc gcttacgaaa agacaatttc tgataagcaa    360
tttgaaattg aaaagtagc actcgcagat tggttattgc aaccgagaga attttagggg     420
ttggttgaaa atggctaaaa ttggttatgc acgactctag gggagctaga gcggccgcca    480
cggcgatatc ggatccatat ggtcgacgga taaggcagaa taatggaata aattaataaa    540
aaatttgtga gaattaaaaa agaaagagga aactcttctc tttttcgttt tgcaaaagtg    600
tttcaatata ttaaatgcga acaagctttt gcacatagca aataaaaatt aaaaatcgag    660
ttaaatggcg atctgatgcg gttttgtatc atctgaataa atttacataa atattacaat    720
tgttacaatt ttgacatact ttgcaatagt ttcttaatct gcaggtgata ttcctgttat    780
agttctgcaa tttaagcaag gtagtatatg ctgtgtcaat tgaatgggac ggacgaataa    840
ggtgaaaatt cgttacttat gacttttaaa atttaagga gagaattttt tgaaaatta     900
aatctatctt agttaagtca attgcagtaa ctgctttatc agttacaggt ttagtagcag    960
ctaataacaa cactaatact gctcaagctg ctattgtaga aggatctgcg gcccagccgg   1020
ccatggatgc ccaggtgaaa ctgcaggagt ctggacctga cctggtgaaa cctgggcct    1080
cagtgaagat atcctgcaag gcttctggat acacattcac tgactacaac atacactggg   1140
tgaagcagag ccgtgaaag agccttgagt ggattggata tatttatcct tacaatggta   1200
atacttacta caaccagaag ttcaagaaca aggccacatt gactgtagac aattcctcca   1260
cctcagccta catggagctc cgcagcctga cacctgagga ctctgcagtc tattactgtg   1320
caacctactt tgactactgg ggccaaggca ccacggtcac cgtctcctca ggtggaggcg   1380
gttcaggcgg aggtggctct ggcggtggcg gatcggacat cgagctcact cagtctccag   1440
caatcatgtc tgcatctcca ggggagaagg tcaccataac ctgcagtgcc agctcaagtg   1500
taagttacat gcactggttc cagcagaagc caggcacttc tcccaaactc tggctttata   1560
gcacatccaa cctggcttct ggagtccctg ctcgcttcag tggcagtgga tctgggacct   1620
cttactctct cacaatcagc cgaatggagg ctgaagatgc tgccacttat tactgccatc   1680
aaaggactag ttacccgtac acgttcggag ggggacaaa gttggaaata aaacgggcgg   1740
cggccgcagg tgcgccggtg ccgtatccgg atccgctgga accgcgtgcc gcagctagca   1800
agaagacttc gctgcttaac cagttgcaat ctgtgaaggc tgcgctggga acggacttgg   1860
gcaatcaaac tgatccaagc actggcaaaa catttatggc agcgttagac gatctagtgg   1920
cacaagctca agcaggcacg caaacggccg accagcttca agcgagtctt gccaaggtac   1980
ttgatgcagt attagcaaaa cttgcggagg gtattaaagc ggcaacaccg gctgaggttg   2040
gcaatgctaa agatgctgcg actggcaaaa cttggtatgc cgacattgct gacacattga   2100
cgtctggtca agccagtgct gatgcgtctg acaagcttgc acatttacaa gctttgcaaa   2160
gtctgaaaac gaaggtggca gctgccgttg aagcggccaa gacagctggt aaaggcgacg   2220
```

```
atacaagcgg tactagcgac aaaggcggcg gtcaaggtac cccggcgccc gctccaggcg   2280
acacaggtaa gaacaaaggc gatgagggca gccagcctag ttctggcggt aatatcccaa   2340
caaagccagc cacaacgacg tcaacgagca cggatgatac gactgatcgt aatggtcaac   2400
atacatccgg taaggagcat tacccaaga cagcagagac aactgagcgg ccagcgtttg    2460
gcttcttggg tgtcattgtg gtcagtctga tgggggtatt aggattgaaa cggaaacaac   2520
gtgaagaata ggagctctca actgtaagtg gttcagaagc tagtgctaag gaatggattg   2580
ccggtagaga atctggtggc tcatacggtg cttcaaatgg tcaatacgtt ggtaaatacc   2640
aactttcagc ttcatacttg aatggtgact attcagcagc taaccaagag cgagtagctg   2700
ataactatgt caaggtcgt tatggctcat ggactgctgc taaggcattc tggcaagcaa     2760
acggctggta ctaaaaataa acctcttttc aaaactaaat aaaatcaaac taacttaaag   2820
gaggcatgct gtcaaaatga tagtgtgtct cttttttgatt tttttaatta aataaatacg   2880
atataattta ataacaaat attaataatc aaaacataca gaaagtggaa cagctatgaa    2940
gcaaaaatta attgtgactt tgttgactag tgtttgcctg atggggacgg ctagtgtaat   3000
acacgaaacg acaccacaaa cggttcaagg aattcatcga tgatatcaga tccaaaataa   3060
aaagcgccta ccccaccgac caaagtgaat gggtagacgc ctaacaaata ctcggagcaa   3120
caaggctctt tgtatacaca ttttttacaca ggagggcaat aatatggcgg tattcaagcg  3180
agctaaccga aaaagtaagc cttggggatt ccagtattca tacaaagtgg atggcatctc   3240
caagcagaaa acatcattt acaaaacaag aaaagaagct aaggctgctg aggcgaagta    3300
cctcgcttct actggcggat ctgtaaaaat cgatccagtg atcactttcg cagattggta   3360
tgacaagtgg ttgcatacct acaagatacg ttctgtttcc gaactgacga tgaccaagta   3420
tgcaacttcg ggtacaatca tcagaaacta cttcaaagac cttaaattaa ttgacttaac   3480
gcgcatgatt tatcaacagt ttattaacaa ctatattgat gacggttacg ccacaagca    3540 cgcaaggcaa tcagtccaga agctacattc acacgctcat caagcaatta tggccgcagc   3600
agacgaaggt ttgattaggc gcgattatgc cgctcatgca gaactgggtg gtaccgcagg   3660
cagatcagaa gacacaaaat ttcttgaagc tgatcagttc gagaaactgc gagattatgt   3720
tgatcaattt gccaacccgc aacgaattgc tctcatgatg gttcaaacgg ccatatactc   3780
tggcgctcgg cttggagaaa ttggtggctt aacgtgggaa gatattgatg agaagaagag   3840
caccatcagt atcgacaaga ccttcaagta caggtttgtc attcgtaacg cggatggtag   3900
ctggccagac cgtgaaaaag tcttcggtcc gaccaagact ccttcaagtg ttcgtactat   3960
caaagtaagc ccagttctta tcgctagcct ccataagctc atattggctg acagaataaa   4020
agcgattaac aatccgtacc atttactgtt tcttgggccg accggcttgc caatatatag   4080
caatggtgtc aacaaggaac ttcgccgcgc tctcaaacat cttggtattg agcgtcctgg   4140
gttcggtttc cacggattgc ggcacacgca tggcagctac ttgctttata aaggccttga   4200
cattcagtat gtatcacatc gcctcggaca cgaaaacgtt ggcattacca ccaagatcta   4260
tacacatctg ctggatgcga tgacacagaa gcaggacgag aaagcaatga atgtgttgtg   4320
actaaaaatc gaaccagaga aagcggctca atgtcaactg ccacaaggtt tacagcacac   4380
attcaatttt cgatcacgaa ccatttttcct aaaaaatcgc aatttcaggc tatttggttc   4440
gatgtggttc gatggattat attttttagg ggttttttcgg agttcagata aatgcaagaa   4500
tgccggttta aagccatttc tgagcactaa aaaagaccct ctaggggct ttgataccgg     4560 tgatcggggt atcacggaat gtatacgtac tgatatgatt gcatttatga caaaaagtgg   4620
```

```
ttcgatgtgg ttcgatgctt caaacgacag cgaccaacaa cacatctcta tataataggt      4680
agaaatagct tttaagagtt cagaaatatg ggcacacaag accggggtct aattattagg      4740
gggagaagga gagagtagcc cgaaaacttt tagttggctt ggactgaacg aagtgaggga      4800
aaggctacta aaacgtcgag gggcagtgag agcgaagcga acacttgatc ttttaagttg      4860
ctatctttta taggtcaata gagtatactt atttgtccta ttgattagat agcagtataa      4920
tagctttata gagtaggtca tttaagttga gcataatagg aggatcaaga atgaaaaaat      4980
ttatttatcg agttttagaa aatgacgaag tggtggctat ttttaatgag caagaatatg      5040
cgcaagattt tatcgcttac gaaaagacaa tttctgataa gcaatttgaa attgaaaaag      5100
tagcactcgc agattggtta ttgcaaccga gagaatttta ggggttggtt gaaaatggct      5160
aaaattggtt atgcacgact c                                                 5181

<210> SEQ ID NO 26
<211> LENGTH: 4455
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26
aggtctaatt attaggggga gaaggagaga gtagcccgaa aacttttagt tggcttggac        60
tgaacgaagt gagggaaagg ctactaaaac gtcgaggggc agtgagagcg aagcgaacac       120
ttgatctttt aagttgctat cttttatagg tcaatagagt atacttattt gtcctattga       180
ttagatagca gtataatagc tttatagagt aggtcattta agttgagcat aataggagga       240
tcaagaatga aaaatttat ttatcgagtt ttagaaaatg acgaagtggt ggctattttt       300
aatgagcaag aatatgcgca agattttatc gcttacgaaa agacaatttc tgataagcaa       360
tttgaaattg aaaagtagc actcgcagat tggttattgc aaccgagaga attttagggg       420
ttggttgaaa atggctaaaa ttggttatgc acgactctag gggagctaga gcggccgcca       480
cggcgatatc ggatccatat ggtcgacgga taaggcagaa taatggaata aattaataaa       540
aaatttgtga gaattaaaaa agaaagagga aactcttttct tttttcgttt tgcaaaagtg       600
tttcaatata ttaaatgcga acaagctttt gcacatagca aataaaaatt aaaaatcgag       660
ttaaatggcg atctgatgcg gttttgtatc atctgaataa atttacataa atattacaat       720
tgttacaatt ttgacatact ttgcaatagt ttcttaatct gcaggtgata ttcctgttat       780
agttctgcaa tttaagcaag gtagtatatg ctgtgtcaat gaatgggac ggacgaataa       840 ggtgaaaatt cgttacttat gacttttaaa attttaagga gagaattttt ttgaaaatta       900
aatctatctt agttaagtca attgcagtaa ctgctttatc agttacaggt ttagtagcag       960
ctaataacaa cactaatact gctcaagctg ctattgtaga aggatctgcg gcccagccgg      1020
ccatggatgc ccaggtgaaa ctgcaggagt ctggacctga cctggtgaaa cctggggcct      1080
cagtgaagat atcctgcaag gcttctggat acacattcac tgactacaac atacactggg      1140
tgaagcagag ccgtgaaaag agccttgagt ggattggata tatttatcct tacaatggta      1200
atacttacta caaccagaag ttcaagaaca aggccacatt gactgtagac aattcctcca      1260
cctcagccta catggagctc cgcagcctga cacctgagga ctctgcagtc tattactgtg      1320
caacctactt tgactactgg ggccaaggca ccacggtcac cgtctcctca ggtggaggcg      1380
gttcaggcgg aggtggctct ggcggtggcg gatcggacat cgagctcact cagtctccag      1440
```

```
caatcatgtc tgcatctcca ggggagaagg tcaccataac ctgcagtgcc agctcaagtg    1500
taagttacat gcactggttc cagcagaagc caggcacttc tcccaaactc tggctttata    1560
gcacatccaa cctggcttct ggagtccctg ctcgcttcag tggcagtgga tctgggacct    1620
cttactctct cacaatcagc cgaatggagg ctgaagatgc tgccacttat tactgccatc    1680
aaaggactag ttacccgtac acgttcggag gggggacaaa gttggaaata aaacgggcgg    1740
cggccgcagg tgcgccggtg ccgtatccgg atccgctgga accgcgtgcc gcataggcta    1800
gcgaggagct ctcaactgta agtggttcag aagctagtgc taaggaatgg attgccggta    1860
gagaatctgg tggctcatac ggtgcttcaa atggtcaata cgttggtaaa taccaacttt    1920
cagcttcata cttgaatggt gactattcag cagctaacca agagcgagta gctgataact    1980
atgtcaaagg tcgttatggc tcatggactg ctgctaaggc attctggcaa gcaaacggct    2040
ggtactaaaa ataaacctct tttcaaaact aaataaaatc aaactaactt aaaggaggca    2100
tgctgtcaaa atgatagtgt gtctcttttt gattttttta attaaataaa tacgatataa    2160
tttaaataac aaatattaat aatcaaaaca tacagaaagt ggaacagcta tgaagcaaaa    2220
attaattgtg actttgttga ctagtgtttg cctgatgggg acggctagtg taatacacga    2280
aacgacacca caaacggttc aaggaattca tcgatgatat cagatccaaa ataaaaagcg    2340
cctaccccac cgaccaaagt gaatgggtag acgcctaaca aatactcgga gcaacaaggc    2400
tctttgtata cacattttta cacaggaggg caataatatg gcggtattca agcgagctaa    2460
ccgaaaaagt aagccttggg gattccagta ttcatacaaa gtggatggca tctccaagca    2520
gaaaacatca ttttacaaaa caagaaaaga agctaaggct gctgaggcga agtacctcgc    2580
ttctactggc ggatctgtaa aaatcgatcc agtgatcact ttcgcagatt ggtatgacaa    2640
gtggttgcat acctacaaga tacgttctgt ttccgaactg acgatgacca agtatgcaac    2700
ttcgggtaca atcatcagaa actacttcaa agaccttaaa ttaattgact taacgcgcat    2760
gatttatcaa cagtttatta caactatat tgatgacggt tacggccaca agcacgcaag    2820
gcaatcagtc cagaagctac attcacacgc tcatcaagca attatggccg cagcagacga    2880
aggtttgatt aggcgcgatt atgccgctca tgcagaactg ggtggtaccg caggcagatc    2940
agaagacaca aaatttcttg aagctgatca gttcgagaaa ctgcagagatt atgttgatca    3000 atttgccaac ccgcaacgaa ttgctctcat gatggttcaa acggccatat actctggcgc    3060
tcggcttgga gaaattggtg gcttaacgtg ggaagatatt gatgagaaga gagcaccat    3120 cagtatcgac aagaccttca agtacaggtt tgtcattcgt aacgcggatg gtagctggcc    3180
agaccgtgaa aaagtcttcg gtccgaccaa gactccttca agtgttcgta ctatcaaagt    3240
aagcccagtt cttatcgcta gcctccataa gctcatattg gctgacagaa taaaagcgat    3300
taacaatccg taccatttac tgtttcttgg gccgaccggc ttgccaatat atagcaatgg    3360
tgtcaacaag gaacttcgcc gcgctctcaa acatcttggt attgagcgtc ctgggttcgg    3420
tttccacgga ttgcggcaca cgcatggcag ctacttgctt tataaaggcc ttgacattca    3480
gtatgtatca catcgcctcg gacacgaaaa cgttggcatt accaccaaga tctatacaca    3540
tctgctggat gcgatgacac agaagcagga cgagaaagca atgaatgtgt tgtgactaaa    3600
aatcgaacca gagaaagcgg ctcaatgtca actgccacaa ggtttacagc acacattcaa    3660
ttttcgatca cgaaccattt tcctaaaaaa tcgcaatttc aggctatttg gttcgatgtg    3720
gttcgatgga ttatatttt tagggggtttt tcggagttca gataaatgca agaatgccgg    3780
```

| | |
|---|---|
| tttaaagcca tttctgagca ctaaaaaaga ccctctaggg ggctttgata ccggtgatcg | 3840 |
| gggtatcacg gaatgtatac gtactgatat gattgcattt atgacaaaaa gtggttcgat | 3900 |
| gtggttcgat gcttcaaacg acagcgacca acaacacatc tctatataat aggtagaaat | 3960 |
| agcttttaag agttcagaaa tatgggcaca caagaccggg gtctaattat taggggaga | 4020 |
| aggagagagt agcccgaaaa cttttagttg gcttggactg aacgaagtga gggaaaggct | 4080 |
| actaaaacgt cgaggggcag tgagagcgaa gcgaacactt gatcttttaa gttgctatct | 4140 |
| tttataggtc aatagagtat acttatttgt cctattgatt agatagcagt ataatagctt | 4200 |
| tatagagtag gtcatttaag ttgagcataa taggaggatc aagaatgaaa aaatttattt | 4260 |
| atcgagtttt agaaaatgac gaagtggtgg ctatttttaa tgagcaagaa tatgcgcaag | 4320 |
| attttatcgc ttacgaaaag acaatttctg ataagcaatt tgaaattgaa aaagtagcac | 4380 |
| tcgcagattg gttattgcaa ccgagagaat ttaggggtt ggttgaaaat ggctaaaatt | 4440 |
| ggttatgcac gactc | 4455 |

<210> SEQ ID NO 27
<211> LENGTH: 4838
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 27

| | |
|---|---|
| aggtctaatt attagggga gaaggagaga gtagcccgaa aacttttagt tggcttggac | 60 |
| tgaacgaagt gagggaaagg ctactaaaac gtcgaggggc agtgagagcg aagcgaacac | 120 |
| ttgatctttt aagttgctat cttttatagg tcaatagagt atacttattt gtcctattga | 180 |
| ttagatagca gtataatagc tttatagagt aggtcattta agttgagcat aataggagga | 240 |
| tcaagaatga aaaatttat ttatcgagtt ttagaaaatg acgaagtggt ggctattttt | 300 |
| aatgagcaag aatatgcgca agattttatc gcttacgaaa agacaatttc tgataagcaa | 360 |
| tttgaaattg aaaaagtagc actcgcagat tggttattgc aaccgagaga attttagggg | 420 |
| ttggttgaaa atggctaaaa ttggttatgc acgactctag gggagctaga gcggccgcca | 480 |
| cggcgatatc ggatccatat ggtcgacgga taaggcagaa taatggaata aattaataaa | 540 |
| aaatttgtga gaattaaaaa agaaagagga aactcttttct tttttcgttt tgcaaaagtg | 600 |
| tttcaatata ttaaatgcga acaagctttt gcacatagca aataaaaatt aaaaatcgag | 660 |
| ttaaatggcg atctgatgcg gttttgtatc atctgaataa atttacataa atattacaat | 720 |
| tgttacaatt ttgacatact ttgcaatagt ttcttaatct gcaggtgata ttcctgttat | 780 |
| agttctgcaa tttaagcaag gtagtatatg ctgtgtcaat tgaatgggac ggacgaataa | 840 |
| ggtgaaaatt cgttacttat gacttttaaa attttaagga gagaattttt ttgaaaatta | 900 |
| aatctatctt agtaagtca attgcagtaa ctgctttatc agttacaggt ttagtagcag | 960 |
| ctaataacaa cactaatact gctcaagctg ctattgtaga aggatctgcg gcccagccgg | 1020 |
| ccatggatca ggtgcagctg caggactctg ggggaggatt ggtgcaggtt ggggaccgtc | 1080 |
| tgagtctctc ctgtgcagca tctggacgca ccttcagttc gtatgacatg gcttggttcc | 1140 |
| gccaggctcc agggaaggag cgtgagtttg tcgcagctat tactacatct gaaggcacat | 1200 |
| ggtatggaga cgccggtaag ggccgattca ccatcgccag agtcaacgcc aagaacacgg | 1260 |
| tgtatctgca catgaacagg ctgaaacctg aggacacggc cgtttattac tgtgcagcgt | 1320 |

```
ctaatcaagg aggctcactg caaatatcta ctaattataa ctactggggc caggggaccc      1380
aggtcaccgt ctcaagcgcg gccgcaggtg cgccggtgcc gtatccggat ccgctggaac      1440
cgcgtgccgc agctagcaag aagacttcgc tgcttaacca gttgcaatct gtgaaggctg      1500
cgctgggaac ggacttgggc aatcaaactg atccaagcac tggcaaaaca tttatggcag      1560
cgttagacga tctagtggca caagctcaag caggcacgca aacggccgac cagcttcaag      1620
cgagtcttgc caaggtactt gatgcagtat tagcaaaact tgcggagggt attaaagcgg      1680
caacaccggc tgaggttggc aatgctaaag atgctgcgac tggcaaaact tggtatgccg      1740
acattgctga cacattgacg tctggtcaag ccagtgctga tgcgtctgac aagcttgcac      1800
atttacaagc tttgcaaagt ctgaaaacga aggtggcagc tgccgttgaa gcggccaaga      1860
cagctggtaa aggcgacgat acaagcggta ctagcgacaa aggcggcggt caaggtaccc      1920
cggcgcccgc tccaggcgac acaggtaaga acaaaggcga tgagggcagc cagcctagtt      1980
ctggcggtaa tatcccaaca aagccagcca caacgacgtc aacgagcacg gatgatacga      2040
ctgatcgtaa tggtcaacat acatccggta agggagcatt acccaagaca gcagagacaa      2100
ctgagcggcc agcgtttggc ttcttgggtg tcattgtggt cagtctgatg ggggtattag      2160
gattgaaacg gaaacaacgt gaagaatagg agctctcaac tgtaagtggt tcagaagcta      2220
gtgctaagga atggattgcc ggtagagaat ctggtggctc atacggtgct tcaaatggtc      2280
aatacgttgg taaataccaa cttttcagctt catacttgaa tggtgactat tcagcagcta      2340
accaagagcg agtagctgat aactatgtca aaggtcgtta tggctcatgg actgctgcta      2400
aggcattctg gcaagcaaac ggctggtact aaaaataaac ctcttttcaa aactaaataa      2460
aatcaaacta acttaaagga ggcatgctgt caaaatgata gtgtgtctct ttttgatttt      2520
tttaattaaa taaatacgat ataatttaaa taacaaatat taataatcaa acatacaga       2580
aagtggaaca gctatgaagc aaaaattaat tgtgactttg ttgactagtg tttgcctgat      2640
ggggacggct agtgtaatac acgaaacgac accacaaacg gttcaagaat tcatcgatga      2700
tatcagatcc aaaataaaaa gcgcctaccc caccgaccaa agtgaatggg tagacgccta      2760
acaaatactc ggagcaacaa ggctctttgt atacacattt ttacacagga gggcaataat      2820
atggcggtat tcaagcgagc taaccgaaaa agtaagcctt ggggattcca gtattcatac      2880
aaagtggatg gcatctccaa gcagaaaaca tcatttttaca aaacaagaaa agaagctaag      2940
gctgctgagg cgaagtacct cgcttctact ggcggatctg taaaaatcga tccagtgatc      3000
actttcgcag attggtatga caagtggttg catacctaca agatacgttc tgtttccgaa      3060
ctgacgatga ccaagtatgc aacttcgggt acaatcatca gaaactactt caaagacctt      3120
aaattaattg acttaacgcg catgatttat caacagttta ttaacaacta tattgatgac      3180
ggttacggcc acaagcacgc aaggcaatca gtccagaagc tacattcaca cgctcatcaa      3240
gcaattatgg ccgcagcaga cgaaggtttg attaggcgcg attatgccgc tcatgcagaa      3300
ctgggtggta ccgcaggcag atcagaagac acaaaatttc ttgaagctga tcagttcgag      3360
aaactgcgag attatgttga tcaatttgcc aacccgcaac gaattgctct catgatggtt      3420
caaacggcca tatactctgg cgctcggctt ggagaaattg gtgcttaac gtgggaagat      3480
attgatgaga agaagagcac catcagtatc gacaagacct tcaagtacag gtttgtcatt      3540
cgtaacgcgg atggtagctg gccagaccgt gaaaaagtct tcggtccgac caagactcct      3600
tcaagtgttc gtactatcaa agtaagccca gttcttatcg ctagcctcca taagctcata      3660
ttggctgaca gaataaaagc gattaacaat ccgtaccatt tactgtttct tgggccgacc      3720
```

```
ggcttgccaa tatatagcaa tggtgtcaac aaggaacttc gccgcgctct caaacatctt    3780
ggtattgagc gtcctgggtt cggtttccac ggattgcggc acacgcatgg cagctacttg    3840
ctttataaag gccttgacat tcagtatgta tcacatcgcc tcggacacga aaacgttggc    3900
attaccacca agatctatac acatctgctg gatgcgatga cacagaagca ggacgagaaa    3960
gcaatgaatg tgttgtgact aaaaatcgaa ccagagaaag cggctcaatg tcaactgcca    4020
caaggtttac agcacacatt caattttcga tcacgaacca ttttcctaaa aaatcgcaat    4080
ttcaggctat ttggttcgat gtggttcgat ggattatatt ttttaggggt ttttcggagt    4140
tcagataaat gcaagaatgc cggtttaaag ccatttctga gcactaaaaa agaccctcta    4200
gggggctttg ataccggtga tcgggtatc acggaatgta tacgtactga tatgattgca     4260
tttatgacaa aaagtggttc gatgtggttc gatgcttcaa acgacagcga ccaacaacac    4320
atctctatat aataggtaga aatagctttt aagagttcag aaatatgggc acacaagacc    4380
ggggtctaat tattaggggg agaaggagag agtagcccga aaactttag ttggcttgga     4440 ctgaacgaag tgagggaaag gctactaaaa cgtcgagggg cagtgagagc gaagcgaaca    4500
cttgatcttt taagttgcta tcttttatag gtcaatagag tatacttatt tgtcctattg    4560
attagatagc agtataatag ctttatagag taggtcattt aagttgagca taataggagg    4620
atcaagaatg aaaaaattta tttatcgagt tttagaaaat gacgaagtgg tggctatttt    4680
taatgagcaa gaatatgcgc aagattttat cgcttacgaa aagacaattt ctgataagca    4740
atttgaaatt gaaaaagtag cactcgcaga ttggttattg caaccgagag aattttaggg    4800
gttggttgaa aatggctaaa attggttatg cacgactc                            4838
```

<210> SEQ ID NO 28
<211> LENGTH: 2788
<212> TYPE: DNA
<213> ORGANISM: Homo sapiens

<400> SEQUENCE: 28

```
gttgggcctg agaccgtcac caagacccct tccctccaca ggacatgctg ggcctgcgcc      60
ccccacttct cgccctggtg gggctgctct ccctcgggtg cgtcctctct caggagtgca     120
cgaagttcaa ggtcagcagc tgccgggaat gcatcgagtc ggggcccggc tgcacctggt     180
gccagaagct gaacttcaca gggccggggg atcctgactc cattcgctgc gacacccggc     240
cacagctgct catgagggc tgtgcggctg acgacatcat ggaccccaca gcctcgctg      300 aaacccagga agaccacaat ggggccaga agcagctgtc cccacaaaaa gtgacgcttt      360
acctgcgacc aggccaggca gcagcgttca acgtgacctt ccggcgggcc aagggctacc    420
ccatcgacct gtactatctg atggaccrct cctactccat gcttgatgac ctcaggaatg     480
tcaagaagct aggtggcgac ctgctccggg ccctcaacga gatcaccgag tccggccgca    540
ttggcttcgg gtccttcgtg acaagaccg tgctgccgtt cgtgaacacg caccctgata     600
agctgcgaaa cccatgcccc aacaaggaga aagagtgcca gccccgttt gccttcaggc      660 acgtgctgaa gctgaccaac aactccaacc agtttcagac cgaggtcggg aagcagctga    720
tttccggaaa cctggatgca cccgagggtg ggctggacgc catgatgcag gtcgccgcct     780
gcccggagga aatcggctgg cgcaacgtca cgcggctgct ggtgtttgcc actgatgacg     840
gcttccattt cgcgggcgac gggaagctgg gcgccatcct gaccccaac gacgccgct     900 gtcacctgga ggacaacttg tacaagagga gcaacgaatt cgactaccca tcggtgggcc    960
```

-continued

```
agctggcgca caagctggct gaaaacaaca tccagcccat cttcgcggtg accagtagga      1020
tggtgaagac ctacgagaaa ctcaccgaga tcatccccaa gtcagccgtg ggggagctgt      1080
ctgaggactc cagcaatgtg gtccatctca ttaagaatgc ttacaataaa ctctcctcca      1140
gggtattcct ggatcacaac gccctccccg acaccctgaa agtcacctac gactccttct      1200
gcagcaatgg agtgacgcac aggaaccagc ccagaggtga ctgtgatggc gtgcagatca      1260
atgtcccgat caccttccag gtgaaggtca cggccacaga gtgcatccag gagcagtcgt      1320
ttgtcatccg ggcgctgggc ttcacggaca tagtgaccgt gcaggtcctt ccccagtgtg      1380
agtgccggtg ccgggaccag agcagagacc gcagcctctg ccatggcaag ggcttcttgg      1440
agtgcggcat ctgcaggtgt gacactggct acattgggaa aaactgtgag tgccagacac      1500
agggccggag cagccaggag ctggaaggaa gctgccggaa ggacaacaac tccatcatct      1560
gctcagggct gggggactgt gtctgcgggc agtgcctgtg ccacaccagc gacgtccccg      1620
gcaagctgat atacgggcag tactgcgagt gtgacaccat caactgtgag cgctacaacg      1680
gccaggtctg cggcggcccg ggggaggggc tctgcttctg cgggaagtgc cgctgccacc      1740
cgggctttga gggctcagcg tgccagtgcg agaggaccac tgagggctgc ctgaacccgc      1800
ggcgtgttga gtgtagtggt cgtggccggt gccgctgcaa cgtatgcgag tgccattcag      1860
gctaccagct gcctctgtgc caggagtgcc ccggctgccc ctcaccctgt ggcaagtaca      1920
tctcctgcgc cgagtgcctg aagttcgaaa agggccactt gggaagaac tgcagcgcgg      1980
cgtgtccggg cctgcagctg tcgaacaacc ccgtgaaggg caggacctgc aaggagaggg      2040
actcagaggg ctgctgggtg gcctacacgc tggagcagca ggacgggatg gaccgctacc      2100
tcatctatgt ggatgagagc cgagagtgtg tggcaggccc caacatcgcc gccatcgtcg      2160
ggggcaccgt ggcaggcatc gtgctgatcg gcattctcct gctggtcatc tggaaggctc      2220
tgatccacct gagcgacctc cgggagtaca gcgctttga aggagaag ctcaagtccc      2280
agtggaacaa tgataatccc cttttcaaga gcgccaccac gacggtcatg aaccccaagt      2340
ttgctgagag ttaggagcac ttggtgaaga caaggccgtc aggacccacc atgtctgccc      2400
catcacgcgg ccgagacatg gcttgccaca gctcttgagg atgtcaccaa ttaaccagaa      2460
atccagttat tttccaccct caaaatgaca gccatggccg gccgggtgct tctgggggct      2520
cgtcgggggg acagctccac tctgactggc acagtctttg catggagact tgaggaggga      2580
gggcttgagg ttggtgaggt taggtgcgtg tttcctgtgc aagtcaggac atcagtctga      2640
ttaaaggtgg tgccaattta tttacattta aacttgtcag ggtataaaat gacatcccat      2700
taattatatt gttaatcaat cacgtgtata gaaaaaaat aaaacttcaa tacaggctgt      2760
ccatggaaaa aaaaaaaaaa aaaaaaaa                                         2788
```

<210> SEQ ID NO 29
<211> LENGTH: 769
<212> TYPE: PRT
<213> ORGANISM: Homo sapiens

<400> SEQUENCE: 29

Met Leu Gly Leu Arg Pro Pro Leu Leu Ala Leu Val Gly Leu Leu Ser
1               5                   10                  15

Leu Gly Cys Val Leu Ser Gln Glu Cys Thr Lys Phe Lys Val Ser Ser
            20                  25                  30

Cys Arg Glu Cys Ile Glu Ser Gly Pro Gly Cys Thr Trp Cys Gln Lys
        35                  40                  45

```
Leu Asn Phe Thr Gly Pro Gly Asp Pro Asp Ser Ile Arg Cys Asp Thr
 50                  55                  60

Arg Pro Gln Leu Leu Met Arg Gly Cys Ala Ala Asp Asp Ile Met Asp
 65                  70                  75                  80

Pro Thr Ser Leu Ala Glu Thr Gln Glu Asp His Asn Gly Gly Gln Lys
                 85                  90                  95

Gln Leu Ser Pro Gln Lys Val Thr Leu Tyr Leu Arg Pro Gly Gln Ala
                100                 105                 110

Ala Ala Phe Asn Val Thr Phe Arg Arg Ala Lys Gly Tyr Pro Ile Asp
                115                 120                 125

Leu Tyr Tyr Leu Met Asp Leu Ser Tyr Ser Met Leu Asp Asp Leu Arg
        130                 135                 140

Asn Val Lys Lys Leu Gly Gly Asp Leu Leu Arg Ala Leu Asn Glu Ile
145                 150                 155                 160

Thr Glu Ser Gly Arg Ile Gly Phe Gly Ser Phe Val Asp Lys Thr Val
                165                 170                 175

Leu Pro Phe Val Asn Thr His Pro Asp Lys Leu Arg Asn Pro Cys Pro
                180                 185                 190

Asn Lys Glu Lys Glu Cys Gln Pro Pro Phe Ala Phe Arg His Val Leu
        195                 200                 205

Lys Leu Thr Asn Asn Ser Asn Gln Phe Gln Thr Glu Val Gly Lys Gln
210                 215                 220

Leu Ile Ser Gly Asn Leu Asp Ala Pro Glu Gly Gly Leu Asp Ala Met
225                 230                 235                 240

Met Gln Val Ala Ala Cys Pro Glu Glu Ile Gly Trp Arg Asn Val Thr
                245                 250                 255

Arg Leu Leu Val Phe Ala Thr Asp Asp Gly Phe His Phe Ala Gly Asp
                260                 265                 270

Gly Lys Leu Gly Ala Ile Leu Thr Pro Asn Asp Gly Arg Cys His Leu
        275                 280                 285

Glu Asp Asn Leu Tyr Lys Arg Ser Asn Glu Phe Asp Tyr Pro Ser Val
290                 295                 300

Gly Gln Leu Ala His Lys Leu Ala Glu Asn Asn Ile Gln Pro Ile Phe
305                 310                 315                 320

Ala Val Thr Ser Arg Met Val Lys Thr Tyr Glu Lys Leu Thr Glu Ile
                325                 330                 335

Ile Pro Lys Ser Ala Val Gly Glu Leu Ser Glu Asp Ser Ser Asn Val
                340                 345                 350

Val His Leu Ile Lys Asn Ala Tyr Asn Lys Leu Ser Ser Arg Val Phe
        355                 360                 365

Leu Asp His Asn Ala Leu Pro Asp Thr Leu Lys Val Thr Tyr Asp Ser
370                 375                 380

Phe Cys Ser Asn Gly Val Thr His Arg Asn Gln Pro Arg Gly Asp Cys
385                 390                 395                 400

Asp Gly Val Gln Ile Asn Val Pro Ile Thr Phe Gln Val Lys Val Thr
                405                 410                 415

Ala Thr Glu Cys Ile Gln Glu Gln Ser Phe Val Ile Arg Ala Leu Gly
                420                 425                 430

Phe Thr Asp Ile Val Thr Val Gln Val Leu Pro Gln Cys Glu Cys Arg
                435                 440                 445

Cys Arg Asp Gln Ser Arg Asp Arg Ser Leu Cys His Gly Lys Gly Phe
        450                 455                 460

Leu Glu Cys Gly Ile Cys Arg Cys Asp Thr Gly Tyr Ile Gly Lys Asn
```

```
                465                 470                 475                 480
Cys Glu Cys Gln Thr Gln Gly Arg Ser Ser Gln Glu Leu Gly Ser
                    485                 490                 495
Cys Arg Lys Asp Asn Asn Ser Ile Ile Cys Ser Gly Leu Gly Asp Cys
                500                 505                 510
Val Cys Gly Gln Cys Leu Cys His Thr Ser Asp Val Pro Gly Lys Leu
                515                 520                 525
Ile Tyr Gly Gln Tyr Cys Glu Cys Asp Thr Ile Asn Cys Glu Arg Tyr
            530                 535                 540
Asn Gly Gln Val Cys Gly Pro Gly Arg Gly Leu Cys Phe Cys Gly
545                 550                 555                 560
Lys Cys Arg Cys His Pro Gly Phe Glu Gly Ser Ala Cys Gln Cys Glu
                565                 570                 575
Arg Thr Thr Glu Gly Cys Leu Asn Pro Arg Arg Val Glu Cys Ser Gly
                580                 585                 590
Arg Gly Arg Cys Arg Cys Asn Val Cys Glu Cys His Ser Gly Tyr Gln
                595                 600                 605
Leu Pro Leu Cys Gln Glu Cys Pro Gly Cys Pro Ser Pro Cys Gly Lys
610                 615                 620
Tyr Ile Ser Cys Ala Glu Cys Leu Lys Phe Glu Lys Gly Pro Phe Gly
625                 630                 635                 640
Lys Asn Cys Ser Ala Ala Cys Pro Gly Leu Gln Leu Ser Asn Asn Pro
                645                 650                 655
Val Lys Gly Arg Thr Cys Lys Glu Arg Asp Ser Glu Gly Cys Trp Val
                660                 665                 670
Ala Tyr Thr Leu Glu Gln Gln Asp Gly Met Asp Arg Tyr Leu Ile Tyr
            675                 680                 685
Val Asp Glu Ser Arg Glu Cys Val Ala Gly Pro Asn Ile Ala Ala Ile
            690                 695                 700
Val Gly Gly Thr Val Ala Gly Ile Val Leu Ile Gly Ile Leu Leu Leu
705                 710                 715                 720
Val Ile Trp Lys Ala Leu Ile His Leu Ser Asp Leu Arg Glu Tyr Arg
                725                 730                 735
Arg Phe Glu Lys Glu Lys Leu Lys Ser Gln Trp Asn Asn Asp Asn Pro
                740                 745                 750
Leu Phe Lys Ser Ala Thr Thr Thr Val Met Asn Pro Lys Phe Ala Glu
                755                 760                 765
Ser

<210> SEQ ID NO 30
<211> LENGTH: 4921
<212> TYPE: DNA
<213> ORGANISM: Homo sapiens

<400> SEQUENCE: 30
cctctttcac cctgtctagg ttgccagcaa atcccacggg cctcctgacg ctgcccctgg      60
ggccacaggt ccctcgagtg ctggaaggat gaaggattcc tgcatcactg tgatggccat     120
ggcgctgctg tctgggttct ttttcttcgc gccggcctcg agctacaacc tggacgtgcg     180
gggcgcgcgg agcttctccc caccgcgcgc cgggaggcac tttggatacc gcgtcctgca     240
ggtcggaaac ggggtcatcg tgggagctca ggggaggggg aacagcacag gaagcctcta     300
tcagtgccag tcgggcacag acactgcctg ccagtcacc tgagaggtt ccaactatac      360 ctccaagtac ttgggaatga ccttggcaac agaccccaca gatggaagca ttttggcctg     420
```

```
tgaccctggg ctgtctcgaa cgtgtgacca gaacacctat ctgagtggcc tgtgttacct    480
cttccgccag aatctgcagg gtcccatgct gcagggcgc  cctggttttc aggaatgtat    540
caagggcaac gtagacctgg tatttctgtt tgatggttcg atgagcttgc agccagatga    600
atttcagaaa attctggact tcatgaagga tgtgatgaag aaactcagca acacttcgta    660
ccagtttgct gctgttcagt tttccacaag ctacaaaaca gaatttgatt tctcagatta    720
tgttaaacgg aaggaccctg atgctctgct gaagcatgta aagcacatgt tgctgttgac    780
caatatcctt ggtgccatca attatgtcgc gacagaggtg ttccgggagg agctgggggc    840
ccggccagat gccaccaaag tgcttatcat catcacggat ggggaggcca ctgacagtgg    900
caacatcgat gcggccaaag acatcatccg ctacatcatc gggattggaa agcattttca    960
gaccaaggag agtcaggaga ccctccacaa atttgcatca aaacccgcga gcagtttgt    1020
gaaaattctg acacatttg  agaagctgaa agatctattc actgagctgc agaagaagat   1080
ctatgtcatt gagggcacaa gcaaacagga cctgacttcc ttcaacatgg agctgtcctc    1140
cagcggcatc agtgctgacc tcagcagggg ccatgcagtc gtggggcag  taggagccaa   1200
ggactgggct gggggctttc ttgacctgaa ggcagacctg caggatgaca catttattgg    1260
gaatgaacca ttgacaccag aagtgagagc aggctatttg ggttacaccg tgacctggct    1320
gccctcccgg caaaagactt cgttgctggc ctcgggagcc cctcgatacc agcacatggg    1380
ccgagtgctg ctgttccaag agccacaggg cggaggacac tggagccagg tccagacaat    1440
ccatgggacc cagattggct cttatttcgg tggggagctg tgtggcgtcg acgtggacca    1500
agatggggag acagagctgc tgctgattgg tgccccactg ttctatgggg agcagagagg    1560
aggccgggtg tttatctacc agagaagaca gttgggggttt gaagaagtct cagagctgca   1620
gggggacccc ggctacccac tcgggcggtt tggagaagcc atcactgctc tgacagacat    1680
caacggcgat gggctggtag acgtggctgt ggggggcccct ctggaggagc aggggctgt    1740
gtacatcttc aatgggaggc acgggggggct tagtccccag ccaagtcagc ggatagaagg   1800
gacccaagtg ctctcaggaa ttcagtggtt tggacgctcc atccatgggg tgaaggacct    1860
tgaaggggat ggcttggcag atgtggctgt ggggggctgag agccagatga tcgtgctgag    1920
ctcccggccc gtggtggata tggtcaccct gatgtccttc tctccagctg agatcccagt    1980
gcatgaagtg gagtgctcct attcaaccag taacaagatg aaagaaggag ttaatatcac    2040
aatctgtttc cagatcaagt ctctcatccc ccagttccaa ggccgcctgg ttgccaatct    2100
cacttacact ctgcagctgg atggccaccg gaccagaaga cggggggttgt tcccaggagg   2160
gagacatgaa ctcagaagga atatagctgt caccaccagc atgtcatgca ctgacttctc    2220
atttcatttc ccggtatgtg ttcaagacct catctccccc atcaatgttt ccctgaattt    2280
ctctctttgg gaggaggaag ggacaccgag ggaccaaagg gcgcagggca aggacatacc    2340
gcccatcctg agaccctccc tgcactcgga aacctgggag atccctttttg agaagaactg   2400
tggggaggac aagaagtgtg aggcaaactt gagagtgtcc ttctctcctg caagatccag    2460
agccctgcgt ctaactgctt ttgccagcct ctctgtggag ctgagcctga gtaacttgga    2520
agaagatgct tactgggtcc agctggacct gcacttcccc ccgggactct ccttccgcaa    2580
ggtggagatg ctgaagcccc atagccagat acctgtgagc tgcgaggagc ttcctgaaga    2640
gtccaggctt ctgtccaggg cattatcttg caatgtgagc tctcccatct tcaaagcagg    2700
ccactcggtt gctctgcaga tgatgtttaa tacactggta aacagctcct ggggggactc    2760
```

```
ggttgaattg cacgccaatg tgacctgtaa caatgaggac tcagacctcc tggaggacaa    2820
ctcagccact accatcatcc ccatcctgta ccccatcaac atcctcatcc aggaccaaga    2880
agactccaca ctctatgtca gtttcacccc caaaggcccc aagatccacc aagtcaagca    2940
catgtaccag gtgaggatcc agccttccat ccacgaccac aacataccca ccctggaggc    3000
tgtggttggg gtgccacagc ctcccagcga ggggcccatc acacaccagt ggagcgtgca    3060
gatggagcct cccgtgccct gccactatga ggatctggag aggctcccgg atgcagctga    3120
gccttgtctc cccggagccc tgttccgctg ccctgttgtc ttcaggcagg agatcctcgt    3180
ccaagtgatc gggactctgg agctggtggg agagatcgag gcctcttcca tgttcagcct    3240
ctgcagctcc ctctccatct ccttcaacag cagcaagcat ttccacctct atggcagcaa    3300
cgcctccctg gcccaggttg tcatgaaggt tgacgtggtg tatgagaagc agatgctcta    3360
cctctacgtg ctgagcggca tcggggggct gctgctgctg ctgctcattt tcatagtgct    3420
gtacaaggtt ggtttcttca aacggaacct gaaggagaag atggaggctg cagaggtgt     3480
cccgaatgga atccctgcag aagactctga gcagctggca tctgggcaag aggctgggga    3540
tcccggctgc ctgaagcccc tccatgagaa ggactctgag agtggtggtg caaggactg     3600
agtccaggcc tgtgaggtgc agagtgccca gaactggact caggatgccc agggccactc    3660
tgcctctgcc tgcattctgc cgtgtgccct cgggcgagtc actgcctctc cctggccctc    3720
agtttcccta tctcgaacat ggaactcatt cctgcctgtc tcctttgcag ctcataggg     3780
aagacctgct gagggaccag ccaagagggc tgcaaaagtg agggcttgtc attaccagac    3840
ggttcaccag cctctcttgg tttccttcct tggaagagaa tgtctgatct aaatgtggag    3900
aaactgtagt ctcaggacct agggatgttc tggccctcac ccctgccctg ggatgtccac    3960
agatgcctcc accccccaga acctgtcctt gcacactccc ctgcactgga gtccagtctc    4020
ttctgctggc agaaagcaaa tgtgacctgt gtcactacgt gactgtggca cacgccttgt    4080
tcttggccaa agaccaaatt ccttggcatg ccttccagca ccctgcaaaa tgagaccctc    4140
gtggccttcc ccagcctctt ctagagccgt gatgcctccc tgttgaagct ctggtgacac    4200
cagccttttct cccaggccag gctccttcct gtcttcctgc attcacccag acagctccct    4260
ctgcctgaac cttccatctc gccacccctc cttccttgac cagcagatcc cagctcacgt    4320
cacacttggt tgggtcctca catctttcac acttccacca gcctgcacta ctccctcaaa    4380
gcacacgtca tgtttcttca tccggcagcc tggatgtttt ttccctgttt aatgattgac    4440
gtacttagca gctatctctc agtgaactgt gagggtaaag gctatacttg tcttgttcac    4500
cttgggatga tgcctcatga tatgtcaggg cgtgggacat ctagtaggtg cttgacataa    4560
tttcactgaa ttaatgacag agccagtggg aagatacaga aaagagggg ctgggctggg     4620
cgcggtggtt cacgcctgta atcccagcac tttgggaggc caaggagggt ggatcacctg    4680
aggtcaggag ttagaggcca gcctggcgaa accccatctc tactaaaaat acaaaatcca    4740
ggcgtggtgg cacacacctg tagtcccagc tactcaggag gttgaggtag gagaattgct    4800
tgaacctggg aggtggaggt tgcagtgagc caagattgcg ccattgcact ccagcctggg    4860
caacacagcg agactccgtc tcaaggaaaa aataaaaata aaaagcgggc acgggcccgt    4920
g                                                                   4921
```

<210> SEQ ID NO 31
<211> LENGTH: 1170
<212> TYPE: PRT
<213> ORGANISM: Homo sapiens

<400> SEQUENCE: 31

Met Lys Asp Ser Cys Ile Thr Val Met Ala Met Ala Leu Leu Ser Gly
1               5                   10                  15

Phe Phe Phe Phe Ala Pro Ala Ser Ser Tyr Asn Leu Asp Val Arg Gly
            20                  25                  30

Ala Arg Ser Phe Ser Pro Pro Arg Ala Gly Arg His Phe Gly Tyr Arg
        35                  40                  45

Val Leu Gln Val Gly Asn Gly Val Ile Val Gly Ala Pro Gly Glu Gly
    50                  55                  60

Asn Ser Thr Gly Ser Leu Tyr Gln Cys Gln Ser Gly Thr Gly His Cys
65                  70                  75                  80

Leu Pro Val Thr Leu Arg Gly Ser Asn Tyr Thr Ser Lys Tyr Leu Gly
                85                  90                  95

Met Thr Leu Ala Thr Asp Pro Thr Asp Gly Ser Ile Leu Ala Cys Asp
            100                 105                 110

Pro Gly Leu Ser Arg Thr Cys Asp Gln Asn Thr Tyr Leu Ser Gly Leu
        115                 120                 125

Cys Tyr Leu Phe Arg Gln Asn Leu Gln Gly Pro Met Leu Gln Gly Arg
130                 135                 140

Pro Gly Phe Gln Glu Cys Ile Lys Gly Asn Val Asp Leu Val Phe Leu
145                 150                 155                 160

Phe Asp Gly Ser Met Ser Leu Gln Pro Asp Glu Phe Gln Lys Ile Leu
                165                 170                 175

Asp Phe Met Lys Asp Val Met Lys Lys Leu Ser Asn Thr Ser Tyr Gln
            180                 185                 190

Phe Ala Ala Val Gln Phe Ser Thr Ser Tyr Lys Thr Glu Phe Asp Phe
        195                 200                 205

Ser Asp Tyr Val Lys Arg Lys Asp Pro Asp Ala Leu Leu Lys His Val
210                 215                 220

Lys His Met Leu Leu Leu Thr Asn Thr Phe Gly Ala Ile Asn Tyr Val
225                 230                 235                 240

Ala Thr Glu Val Phe Arg Glu Glu Leu Gly Ala Arg Pro Asp Ala Thr
                245                 250                 255

Lys Val Leu Ile Ile Ile Thr Asp Gly Glu Ala Thr Asp Ser Gly Asn
            260                 265                 270

Ile Asp Ala Ala Lys Asp Ile Ile Arg Tyr Ile Ile Gly Ile Gly Lys
        275                 280                 285

His Phe Gln Thr Lys Glu Ser Gln Glu Thr Leu His Lys Phe Ala Ser
290                 295                 300

Lys Pro Ala Ser Glu Phe Val Lys Ile Leu Asp Thr Phe Glu Lys Leu
305                 310                 315                 320

Lys Asp Leu Phe Thr Glu Leu Gln Lys Lys Ile Tyr Val Ile Glu Gly
                325                 330                 335

Thr Ser Lys Gln Asp Leu Thr Ser Phe Asn Met Glu Leu Ser Ser Ser
            340                 345                 350

Gly Ile Ser Ala Asp Leu Ser Arg Gly His Ala Val Val Gly Ala Val
        355                 360                 365

Gly Ala Lys Asp Trp Ala Gly Gly Phe Leu Asp Leu Lys Ala Asp Leu
370                 375                 380

Gln Asp Asp Thr Phe Ile Gly Asn Glu Pro Leu Thr Pro Glu Val Arg
385                 390                 395                 400

Ala Gly Tyr Leu Gly Tyr Thr Val Thr Trp Leu Pro Ser Arg Gln Lys

-continued

```
                405                 410                 415
Thr Ser Leu Leu Ala Ser Gly Ala Pro Arg Tyr Gln His Met Gly Arg
            420                 425                 430

Val Leu Leu Phe Gln Glu Pro Gln Gly Gly His Trp Ser Gln Val
            435                 440                 445

Gln Thr Ile His Gly Thr Gln Ile Gly Ser Tyr Phe Gly Gly Glu Leu
            450                 455                 460

Cys Gly Val Asp Val Asp Gln Asp Gly Glu Thr Glu Leu Leu Leu Ile
465                 470                 475                 480

Gly Ala Pro Leu Phe Tyr Gly Glu Gln Arg Gly Gly Arg Val Phe Ile
                485                 490                 495

Tyr Gln Arg Arg Gln Leu Gly Phe Glu Glu Val Ser Glu Leu Gln Gly
            500                 505                 510

Asp Pro Gly Tyr Pro Leu Gly Arg Phe Gly Glu Ala Ile Thr Ala Leu
            515                 520                 525

Thr Asp Ile Asn Gly Asp Gly Leu Val Asp Val Ala Val Gly Ala Pro
            530                 535                 540

Leu Glu Glu Gln Gly Ala Val Tyr Ile Phe Asn Gly Arg His Gly Gly
545                 550                 555                 560

Leu Ser Pro Gln Pro Ser Gln Arg Ile Glu Gly Thr Gln Val Leu Ser
                565                 570                 575

Gly Ile Gln Trp Phe Gly Arg Ser Ile His Gly Val Lys Asp Leu Glu
            580                 585                 590

Gly Asp Gly Leu Ala Asp Val Ala Val Gly Ala Glu Ser Gln Met Ile
            595                 600                 605

Val Leu Ser Ser Arg Pro Val Val Asp Met Val Thr Leu Met Ser Phe
            610                 615                 620

Ser Pro Ala Glu Ile Pro Val His Glu Val Glu Cys Ser Tyr Ser Thr
625                 630                 635                 640

Ser Asn Lys Met Lys Glu Gly Val Asn Ile Thr Ile Cys Phe Gln Ile
                645                 650                 655

Lys Ser Leu Ile Pro Gln Phe Gln Gly Arg Leu Val Ala Asn Leu Thr
            660                 665                 670

Tyr Thr Leu Gln Leu Asp Gly His Arg Thr Arg Arg Arg Gly Leu Phe
            675                 680                 685

Pro Gly Gly Arg His Glu Leu Arg Arg Asn Ile Ala Val Thr Thr Ser
            690                 695                 700

Met Ser Cys Thr Asp Phe Ser Phe His Phe Pro Val Cys Val Gln Asp
705                 710                 715                 720

Leu Ile Ser Pro Ile Asn Val Ser Leu Asn Phe Ser Leu Trp Glu Glu
                725                 730                 735

Glu Gly Thr Pro Arg Asp Gln Arg Ala Gln Gly Lys Asp Ile Pro Pro
            740                 745                 750

Ile Leu Arg Pro Ser Leu His Ser Glu Thr Trp Glu Ile Pro Phe Glu
            755                 760                 765

Lys Asn Cys Gly Glu Asp Lys Lys Cys Glu Ala Asn Leu Arg Val Ser
            770                 775                 780

Phe Ser Pro Ala Arg Ser Arg Ala Leu Arg Leu Thr Ala Phe Ala Ser
785                 790                 795                 800

Leu Ser Val Glu Leu Ser Leu Ser Asn Leu Glu Glu Asp Ala Tyr Trp
                805                 810                 815

Val Gln Leu Asp Leu His Phe Pro Pro Gly Leu Ser Phe Arg Lys Val
            820                 825                 830
```

Glu Met Leu Lys Pro His Ser Gln Ile Pro Val Ser Cys Glu Glu Leu
    835                 840                 845

Pro Glu Glu Ser Arg Leu Leu Ser Arg Ala Leu Ser Cys Asn Val Ser
850                 855                 860

Ser Pro Ile Phe Lys Ala Gly His Ser Val Ala Leu Gln Met Met Phe
865                 870                 875                 880

Asn Thr Leu Val Asn Ser Ser Trp Gly Asp Ser Val Glu Leu His Ala
                885                 890                 895

Asn Val Thr Cys Asn Asn Glu Asp Ser Asp Leu Leu Glu Asp Asn Ser
                900                 905                 910

Ala Thr Thr Ile Ile Pro Ile Leu Tyr Pro Ile Asn Ile Leu Ile Gln
                915                 920                 925

Asp Gln Glu Asp Ser Thr Leu Tyr Val Ser Phe Thr Pro Lys Gly Pro
        930                 935                 940

Lys Ile His Gln Val Lys His Met Tyr Gln Val Arg Ile Gln Pro Ser
945                 950                 955                 960

Ile His Asp His Asn Ile Pro Thr Leu Glu Ala Val Val Gly Val Pro
                965                 970                 975

Gln Pro Pro Ser Glu Gly Pro Ile Thr His Gln Trp Ser Val Gln Met
            980                 985                 990

Glu Pro Pro Val Pro Cys His Tyr Glu Asp Leu Glu Arg Leu Pro Asp
        995                 1000                1005

Ala Ala Glu Pro Cys Leu Pro Gly Ala Leu Phe Arg Cys Pro Val
    1010                1015                1020

Val Phe Arg Gln Glu Ile Leu Val Gln Val Ile Gly Thr Leu Glu
    1025                1030                1035

Leu Val Gly Glu Ile Glu Ala Ser Ser Met Phe Ser Leu Cys Ser
    1040                1045                1050

Ser Leu Ser Ile Ser Phe Asn Ser Ser Lys His Phe His Leu Tyr
    1055                1060                1065

Gly Ser Asn Ala Ser Leu Ala Gln Val Val Met Lys Val Asp Val
    1070                1075                1080

Val Tyr Glu Lys Gln Met Leu Tyr Leu Tyr Val Leu Ser Gly Ile
    1085                1090                1095

Gly Gly Leu Leu Leu Leu Leu Leu Ile Phe Ile Val Leu Tyr Lys
    1100                1105                1110

Val Gly Phe Phe Lys Arg Asn Leu Lys Glu Lys Met Glu Ala Gly
    1115                1120                1125

Arg Gly Val Pro Asn Gly Ile Pro Ala Glu Asp Ser Glu Gln Leu
    1130                1135                1140

Ala Ser Gly Gln Glu Ala Gly Asp Pro Gly Cys Leu Lys Pro Leu
    1145                1150                1155

His Glu Lys Asp Ser Glu Ser Gly Gly Gly Lys Asp
    1160                1165                1170

<210> SEQ ID NO 32
<211> LENGTH: 4740
<212> TYPE: DNA
<213> ORGANISM: Homo sapiens

<400> SEQUENCE: 32
gaattccgtg gttcctcagt ggtgcctgca acccctggtt cacctccttc caggttctgg     60
ctccttccag ccatggctct cagagtcctt ctgttaacag ccttgacctt atgtcatggg    120

```
ttcaacttgg acactgaaaa cgcaatgacc ttccaagaga acgcaagggg cttcgggcag      180
agcgtggtcc agcttcaggg atccaggtgt gtggttggag ccccccagga gatagtggct      240
gccaaccaaa ggggcagcct ctaccagtgc gactacagca caggctcatg cgagcccatc      300
cgcctgcagg tccccgtgga ggccgtgaac atgtccctgg cctgtccct ggcagccacc       360 accagccccc ctcagctgct ggcctgtggt cccaccgtgc accagacttg cagtgagaac      420
acgtatgtga aagggctctg cttcctgttt ggatccaacc tacggcagca gccccagaag      480
ttcccagagg ccctccgagg gtgtcctcaa gaggatagtg acattgcctt cttgattgat      540
ggctctggta gcatcatccc acatgacttt cggcggatga aggagtttgt ctcaactgtg      600
atggagcaat taaaaaagtc caaaaccttg ttctctttga tgcagtactc tgaagaattc      660
cggattcact ttaccttcaa agagttccag aacaacccta acccaagatc actggtgaag      720
ccaataacgc agctgcttgg gcggacacac acggccacgg gcatccgcaa agtggtacga      780
gagctgttta acatcaccaa cggagcccga aagaatgcct ttaagatcct agttgtcatc      840
acggatggag aaaagtttgg cgatcccttg ggatatgagg atgtcatccc tgaggcagac      900
agagagggag tcattcgcta cgtcattggg gtgggagatg ccttccgcag tgagaaatcc      960
cgccaagagc ttaataccat cgcatccaag ccgcctcgtg atcacgtgtt ccaggtgaat      1020
aactttgagg ctctgaagac cattcagaac cagcttcggg agaagatctt tgcgatcgag      1080
ggtactcaga caggaagtag cagctccttt gagcatgaga tgtctcagga aggcttcagc      1140
gctgccatca cctctaatgg cccccttgctg agcactgtgg ggagctatga ctgggctggt      1200
ggagtctttc tatatacatc aaaggagaaa agcaccttca tcaacatgac cagagtggat      1260
tcagacatga atgatgctta cttgggttat gctgccgcca tcatcttacg gaaccgggtg      1320
caaagcctgt tctgggggc acctcgatat cagcacatcg gcctggtagc gatgttcagg      1380
cagaacactg gcatgtggga gtccaacgct aatgtcaagg gcacccagat cggcgcctac      1440 ttcgggcct ccctctgctc cgtggacgtg acagcaacg gcagcaccga cctggtcctc       1500
atcggggccc cccattacta cgagcagacc cgaggggggcc aggtgtccgt gtgccccttg     1560 cccaggggge agagggctcg gtggcagtgt gatgctgttc tctacgggga gcagggccaa     1620
ccctggggcc gctttggggc agccctaaca gtgctggggg acgtaaatgg ggacaagctg     1680
acggacgtgg ccattggggc cccaggagag gaggacaacc ggggtgctgt ttacctgttt     1740
cacggaacct caggatctgg catcagcccc tcccatagcc agcggatagc aggctccaag     1800
ctctctccca ggctccagta ttttggtcag tcactgagtg ggggccagga cctcacaatg     1860
gatggactgg tagacctgac tgtaggagcc caggggcacg tgctgctgct caggtcccag     1920
ccagtactga gagtcaaggc aatcatggag ttcaatccca gggaagtggc aaggaatgta     1980
tttgagtgta atgatcaggt ggtgaaaggc aaggaagccg gagaggtcag agtctgcctc     2040
catgtccaga gagcacacg ggatcggcta agagaaggac agatccagag tgttgtgact      2100
tatgacctgg ctctggactc cggccgccca cattcccgcg ccgtcttcaa tgagacaaag     2160
aacagcacac gcagacagac acaggtcttg gggctgaccc agacttgtga gaccctgaaa     2220
ctacagttgc cgaattgcat cgaggaccca gtgagcccca ttgtgctgcg cctgaacttc     2280
tctctggtgg gaacgccatt gtctgctttc gggaacctcc ggccagtgct ggcggaggat     2340
gctcagagac tcttcacagc cttgtttccc tttgagaaga attgtggcaa tgacaacatc     2400
tgccaggatg acctcagcat caccttcagt ttcatgagcc tggactgcct cgtggtgggt     2460
gggccccggg agttcaacgt gacagtgact gtgagaaatg atggtgagga ctcctacagg     2520
```

```
acacaggtca ccttcttctt cccgcttgac ctgtcctacc ggaaggtgtc cacactccag    2580
aaccagcgct cacagcgatc ctggcgcctg gcctgtgagt ctgcctcctc caccgaagtg    2640
tctggggcct tgaagagcac cagctgcagc ataaaccacc ccatcttccc ggaaaactca    2700
gaggtcacct ttaatatcac gtttgatgta gactctaagg cttcccttgg aaacaaactg    2760
ctcctcaagg ccaatgtgac cagtgagaac aacatgccca gaaccaacaa aaccgaattc    2820
caactggagc tgccggtgaa atatgctgtc tacatggtgg tcaccagcca tggggtctcc    2880
actaaatatc tcaacttcac ggcctcagag aataccagtc gggtcatgca gcatcaatat    2940
caggtcagca acctggggca gaggagcctc cccatcagcc tggtgttctt ggtgcccgtc    3000
cggctgaacc agactgtcat atgggaccgc ccccaggtca ccttctccga aacctctcg     3060 agtacgtgcc acaccaagga gcgcttgccc tctcactccg actttctggc tgagcttcgg    3120 aaggccccg tggtgaactg ctccatcgct gtctgccaga aatccagtg tgacatcccg      3180 ttctttggca tccaggaaga attcaatgct accctcaaag caacctctc gtttgactgg     3240 tacatcaaga cctcgcataa ccacctcctg atcgtgagca cagctgagat cttgtttaac    3300
gattccgtgt tcaccctgct gccgggacag ggggcgtttg tgaggtccca gacggagacc    3360
aaagtggagc cgttcgaggt ccccaacccc ctgccgctca tcgtgggcag ctctgtcggg    3420
ggactgctgc tcctggccct catcaccgcc gcgctgtaca agctcggctt cttcaagcgg    3480
caatacaagg acatgatgag tgaagggggt ccccgggg ccgaacccca gtagcggctc     3540
cttcccgaca gagctgcctc tcggtggcca gcaggactct gcccagacca cacgtagccc    3600
ccaggctgct ggacacgtcg gacagcgaag tatccccgac aggacgggct tgggcttcca    3660
tttgtgtgtg tgcaagtgtg tatgtgcgtg tgtgcgagtg tgtgcaagtg tctgtgtgca    3720
agtgtgtgca cgtgtgcgtg tgcgtgcatg tgcactcgca cgcccatgtg tgagtgtgtg    3780
caagtatgtg agtgtgtcca gtgtgtgtgc gtgtgtccat gtgtgtgcag tgtgtgcatg    3840
tgtgcgagtg tgtgcatgtg tgtgctcagg ggctgtggct cacgtgtgtg actcagagtg    3900
tctctggcgt gtgggtaggt gacggcagcg tagcctctcc ggcagaaggg aactgcctgg    3960
gctcccttgt gcgtgggtaa gccgctgctg ggttttcctc cgggagaggg gacggtcaat    4020
cctgtgggtg aagagagagg gaaacacagc agcatctctc cactgaaaga agtgggactt    4080
cccgtcgcct gcgagcctgc ggcctgctgg agcctgcgca gcttggatgg atactccatg    4140
agaaaagccg tgggtggaac caggagcctc ctccacacca gcgctgatgc ccaataaaga    4200
tgcccactga ggaatcatga agcttccttt ctggattcat ttattatttc aatgtgactt    4260
taattttttg gatggataag cctgtctatg gtacaaaaat cacaaggcat tcaagtgtac    4320
agtgaaaagt ctcccttttcc agatattcaa gtcacctcct taaaggtagt caagattgtg    4380
ttttgaggtt tccttcagac agattccagg cgatgtgcaa gtgtatgcac gtgtgcacac    4440
accacacaca tacacacaca caagcttttt tacacaaatg gtagcatact ttatattggt    4500
ctgtatcttg cttttttttca ccaatatttc tcagacatcg gttcatatta agacataaat    4560
tactttttca ttcttttata ccgctgcata gtattccatt gtgtgagtgt accataatgt    4620
atttaaccag tcttcttttg atatactatt ttcatctctt gttattgcat ctgctgagtt    4680
aataaatcaa atatatgtca aaaaaaaaaa aaaaaaaaa aaaaaaaaaa aaaaaaaaaa     4740
```

<210> SEQ ID NO 33
<211> LENGTH: 1153
<212> TYPE: PRT

<213> ORGANISM: Homo sapiens

<400> SEQUENCE: 33

```
Met Ala Leu Arg Val Leu Leu Leu Thr Ala Leu Thr Leu Cys His Gly
1               5                   10                  15

Phe Asn Leu Asp Thr Glu Asn Ala Met Thr Phe Gln Glu Asn Ala Arg
            20                  25                  30

Gly Phe Gly Gln Ser Val Val Gln Leu Gln Gly Ser Arg Val Val Val
        35                  40                  45

Gly Ala Pro Gln Glu Ile Val Ala Ala Asn Gln Arg Gly Ser Leu Tyr
    50                  55                  60

Gln Cys Asp Tyr Ser Thr Gly Ser Cys Glu Pro Ile Arg Leu Gln Val
65                  70                  75                  80

Pro Val Glu Ala Val Asn Met Ser Leu Gly Leu Ser Leu Ala Ala Thr
                85                  90                  95

Thr Ser Pro Pro Gln Leu Leu Ala Cys Gly Pro Thr Val His Gln Thr
            100                 105                 110

Cys Ser Glu Asn Thr Tyr Val Lys Gly Leu Cys Phe Leu Phe Gly Ser
        115                 120                 125

Asn Leu Arg Gln Gln Pro Gln Lys Phe Pro Glu Ala Leu Arg Gly Cys
    130                 135                 140

Pro Gln Glu Asp Ser Asp Ile Ala Phe Leu Ile Asp Gly Ser Gly Ser
145                 150                 155                 160

Ile Ile Pro His Asp Phe Arg Arg Met Lys Glu Phe Val Ser Thr Val
                165                 170                 175

Met Glu Gln Leu Lys Lys Ser Lys Thr Leu Phe Ser Leu Met Gln Tyr
            180                 185                 190

Ser Glu Glu Phe Arg Ile His Phe Thr Phe Lys Glu Phe Gln Asn Asn
        195                 200                 205

Pro Asn Pro Arg Ser Leu Val Lys Pro Ile Thr Gln Leu Leu Gly Arg
    210                 215                 220

Thr His Thr Ala Thr Gly Ile Arg Lys Val Val Arg Glu Leu Phe Asn
225                 230                 235                 240

Ile Thr Asn Gly Ala Arg Lys Asn Ala Phe Lys Ile Leu Val Val Ile
                245                 250                 255

Thr Asp Gly Glu Lys Phe Gly Asp Pro Leu Gly Tyr Glu Asp Val Ile
            260                 265                 270

Pro Glu Ala Asp Arg Glu Gly Val Ile Arg Tyr Val Ile Gly Val Gly
        275                 280                 285

Asp Ala Phe Arg Ser Glu Lys Ser Arg Gln Glu Leu Asn Thr Ile Ala
    290                 295                 300

Ser Lys Pro Pro Arg Asp His Val Phe Gln Val Asn Asn Phe Glu Ala
305                 310                 315                 320

Leu Lys Thr Ile Gln Asn Gln Leu Arg Glu Lys Ile Phe Ala Ile Glu
                325                 330                 335

Gly Thr Gln Thr Gly Ser Ser Ser Phe Glu His Glu Met Ser Gln
            340                 345                 350

Glu Gly Phe Ser Ala Ala Ile Thr Ser Asn Gly Pro Leu Leu Ser Thr
        355                 360                 365

Val Gly Ser Tyr Asp Trp Ala Gly Gly Val Phe Leu Tyr Thr Ser Lys
    370                 375                 380

Glu Lys Ser Thr Phe Ile Asn Met Thr Arg Val Asp Ser Asp Met Asn
385                 390                 395                 400
```

-continued

```
Asp Ala Tyr Leu Gly Tyr Ala Ala Ala Ile Leu Arg Asn Arg Val
                405                 410                 415
Gln Ser Leu Val Leu Gly Ala Pro Arg Tyr Gln His Ile Gly Leu Val
            420                 425                 430
Ala Met Phe Arg Gln Asn Thr Gly Met Trp Glu Ser Asn Ala Asn Val
        435                 440                 445
Lys Gly Thr Gln Ile Gly Ala Tyr Phe Gly Ala Ser Leu Cys Ser Val
    450                 455                 460
Asp Val Asp Ser Asn Gly Ser Thr Asp Leu Val Leu Ile Gly Ala Pro
465                 470                 475                 480
His Tyr Tyr Glu Gln Thr Arg Gly Gly Gln Val Ser Val Cys Pro Leu
                485                 490                 495
Pro Arg Gly Gln Arg Ala Arg Trp Gln Cys Asp Ala Val Leu Tyr Gly
            500                 505                 510
Glu Gln Gly Gln Pro Trp Gly Arg Phe Gly Ala Ala Leu Thr Val Leu
        515                 520                 525
Gly Asp Val Asn Gly Asp Lys Leu Thr Asp Val Ala Ile Gly Ala Pro
    530                 535                 540
Gly Glu Glu Asp Asn Arg Gly Ala Val Tyr Leu Phe His Gly Thr Ser
545                 550                 555                 560
Gly Ser Gly Ile Ser Pro Ser His Ser Gln Arg Ile Ala Gly Ser Lys
                565                 570                 575
Leu Ser Pro Arg Leu Gln Tyr Phe Gly Gln Ser Leu Ser Gly Gly Gln
            580                 585                 590
Asp Leu Thr Met Asp Gly Leu Val Asp Leu Thr Val Gly Ala Gln Gly
        595                 600                 605
His Val Leu Leu Leu Arg Ser Gln Pro Val Leu Arg Val Lys Ala Ile
    610                 615                 620
Met Glu Phe Asn Pro Arg Glu Val Ala Arg Asn Val Phe Glu Cys Asn
625                 630                 635                 640
Asp Gln Val Val Lys Gly Lys Glu Ala Gly Glu Val Arg Val Cys Leu
                645                 650                 655
His Val Gln Lys Ser Thr Arg Asp Arg Leu Arg Glu Gly Gln Ile Gln
            660                 665                 670
Ser Val Val Thr Tyr Asp Leu Ala Leu Asp Ser Gly Arg Pro His Ser
        675                 680                 685
Arg Ala Val Phe Asn Glu Thr Lys Asn Ser Thr Arg Arg Gln Thr Gln
    690                 695                 700
Val Leu Gly Leu Thr Gln Thr Cys Glu Thr Leu Lys Leu Gln Leu Pro
705                 710                 715                 720
Asn Cys Ile Glu Asp Pro Val Ser Pro Ile Val Leu Arg Leu Asn Phe
                725                 730                 735
Ser Leu Val Gly Thr Pro Leu Ser Ala Phe Gly Asn Leu Arg Pro Val
            740                 745                 750
Leu Ala Glu Asp Ala Gln Arg Leu Phe Thr Ala Leu Phe Pro Phe Glu
        755                 760                 765
Lys Asn Cys Gly Asn Asp Asn Ile Cys Gln Asp Asp Leu Ser Ile Thr
    770                 775                 780
Phe Ser Phe Met Ser Leu Asp Cys Leu Val Val Gly Gly Pro Arg Glu
785                 790                 795                 800
Phe Asn Val Thr Val Thr Val Arg Asn Asp Gly Glu Asp Ser Tyr Arg
                805                 810                 815
Thr Gln Val Thr Phe Phe Phe Pro Leu Asp Leu Ser Tyr Arg Lys Val
```

```
                    820                 825                 830
      Ser Thr Leu Gln Asn Gln Arg Ser Gln Arg Ser Trp Arg Leu Ala Cys
                    835                 840                 845

Glu Ser Ala Ser Ser Thr Glu Val Ser Gly Ala Leu Lys Ser Thr Ser
      850                 855                 860

Cys Ser Ile Asn His Pro Ile Phe Pro Glu Asn Ser Glu Val Thr Phe
      865                 870                 875                 880

Asn Ile Thr Phe Asp Val Asp Ser Lys Ala Ser Leu Gly Asn Lys Leu
                        885                 890                 895

Leu Leu Lys Ala Asn Val Thr Ser Glu Asn Asn Met Pro Arg Thr Asn
                    900                 905                 910

Lys Thr Glu Phe Gln Leu Glu Leu Pro Val Lys Tyr Ala Val Tyr Met
                    915                 920                 925

Val Val Thr Ser His Gly Val Ser Thr Lys Tyr Leu Asn Phe Thr Ala
                    930                 935                 940

Ser Glu Asn Thr Ser Arg Val Met Gln His Gln Tyr Gln Val Ser Asn
      945                 950                 955                 960

Leu Gly Gln Arg Ser Leu Pro Ile Ser Leu Val Phe Leu Val Pro Val
                        965                 970                 975

Arg Leu Asn Gln Thr Val Ile Trp Asp Arg Pro Gln Val Thr Phe Ser
                    980                 985                 990

Glu Asn Leu Ser Ser Thr Cys His  Thr Lys Glu Arg Leu  Pro Ser His
                    995                1000                1005

Ser Asp  Phe Leu Ala Glu Leu  Arg Lys Ala Pro Val  Val Asn Cys
          1010                1015                1020

Ser Ile  Ala Val Cys Gln Arg  Ile Gln Cys Asp Ile  Pro Phe Phe
          1025                1030                1035

Gly Ile  Gln Glu Glu Phe Asn  Ala Thr Leu Lys Gly  Asn Leu Ser
          1040                1045                1050

Phe Asp  Trp Tyr Ile Lys Thr  Ser His Asn His Leu  Leu Ile Val
          1055                1060                1065

Ser Thr  Ala Glu Ile Leu Phe  Asn Asp Ser Val Phe  Thr Leu Leu
          1070                1075                1080

Pro Gly  Gln Gly Ala Phe Val  Arg Ser Gln Thr Glu  Thr Lys Val
          1085                1090                1095

Glu Pro  Phe Glu Val Pro Asn  Pro Leu Pro Leu Ile  Val Gly Ser
          1100                1105                1110

Ser Val  Gly Gly Leu Leu Leu  Leu Ala Leu Ile Thr  Ala Ala Leu
          1115                1120                1125

Tyr Lys  Leu Gly Phe Phe Lys  Arg Gln Tyr Lys Asp  Met Met Ser
          1130                1135                1140

Glu Gly  Gly Pro Pro Gly Ala  Glu Pro Gln
          1145                1150

<210> SEQ ID NO 34
<211> LENGTH: 4654
<212> TYPE: DNA
<213> ORGANISM: Homo sapiens

<400> SEQUENCE: 34
gaattcctgc cactcttcct gcaacggccc aggagctcag agctccacat ctgaccttct      60
agtcatgacc aggaccaggg cagcactcct cctgttcaca gccttagcaa cttctctagg     120
tttcaacttg gacacagagg agctgacagc cttccgtgtg gacagcgctg ggtttggaga     180
```

-continued

| | |
|---|---|
| cagcgtggtc cagtatgcca actcctgggt ggtggttgga gccccccaaa agataacagc | 240 |
| tgccaaccaa acgggtggcc tctaccagtg tggctacagc actggtgcct gtgagcccat | 300 |
| cggcctgcag gtgcccccgg aggccgtgaa catgtccctg ggcctgtccc tggcgtctac | 360 |
| caccagccct tcccagctgc tggcctgcgg ccccaccgtg caccacgagt gcggaggaa | 420 |
| catgtacctc accggactct gcttcctcct gggccccacc cagctcaccc agaggctccc | 480 |
| ggtgtccagg caggagtgcc caagacagga gcaggacatt gtgttcctga tcgatggctc | 540 |
| aggcagcatc tcctcccgca actttgccac gatgatgaac ttcgtgagag ctgtgataag | 600 |
| ccagttccag agaccagca cccagttttc cctgatgcag ttctccaaca aattccaaac | 660 |
| acacttcact ttcgaggaat tcaggcgcac gtcaaacccc ctcagcctgt ggcttctgt | 720 |
| tcaccagctg caagggttta catacacggc caccgccatc caaaatgtcg tgcaccgatt | 780 |
| gttccatgcc tcatatgggg cccgtaggga tgccaccaaa attctcattg tcatcactga | 840 |
| tgggaagaaa gaaggcgaca gcctggatta aaggatgtc atcccatgg ctgatgcagc | 900 |
| aggcatcatc cgctatgcaa ttggggttgg attagctttt caaaacagaa attcttggaa | 960 |
| agaattaaat gacattgcat cgaagccctc ccaggaacac atatttaaag tggaggactt | 1020 |
| tgatgctctg aaagatattc aaaaccaact gaaggagaag atctttgcca ttgagggtac | 1080 |
| ggagaccaca agcagtagct ccttcgaatt ggagatggca caggagggct cagcgctgt | 1140 |
| gttcacacct gatggcccg ttctgggggc tgtggggagc ttcacctggt ctggaggtgc | 1200 |
| cttcctgtac ccccaaata tgagccctac cttcatcaac atgtctcagg agaatgtgga | 1260 |
| catgagggac tcttacctgg gttactccac cgagctggcc ctctggaaag gggtgcagag | 1320 |
| cctggtcctg ggggccccc gctaccagca caccgggaag gctgtcatct tcacccaggt | 1380 |
| gtccaggcaa tggaggatga aggccgaagt cacgggact cagatcggct cctacttcgg | 1440 |
| ggcctccctc tgctccgtgg acgtagacac cgacggcagc accgacctgg tcctcatcgg | 1500 |
| ggcccccat tactacgagc agacccgagg gggccaggtg tctgtgtgtc ccttgcccag | 1560 |
| ggggtggaga aggtggtggt gtgatgctgt tctctacggg gagcagggcc acccctgggg | 1620 |
| tcgctttggg gcggctctga cagtgctggg ggatgtgaat ggggacaagc tgacagacgt | 1680 |
| ggtcatcggg gccccaggag aggaggagaa ccggggtgct gtctacctgt ttcacggagt | 1740 |
| cttgggaccc agcatcagcc cctcccacag ccagcgatc gcgggctccc agctctcctc | 1800 |
| caggctgcag tattttgggc aggcactgag cggggtcaa gacctcaccc aggatggact | 1860 |
| ggtgacctg gctgtggggg cccggggcca ggtgctcctg ctcaggacca gacctgtgct | 1920 |
| ctgggtgggg gtgagcatgc agttcatacc tgccgagatc cccaggtctg cgtttgagtg | 1980 |
| tcggagcag gtggtctctg agcagaccct ggtacagtcc aacatctgcc tttacattga | 2040 |
| caaacgttct aagaacctgc ttgggagccg tgacctccaa agctctgtga ccttggacct | 2100 |
| ggccctcgac cctggccgcc tgagtccccg tgccaccttc caggaaacaa agaaccggag | 2160 |
| tctgagccga gtccgagtcc tcgggctgaa ggcacactgt gaaaacttca acctgctgct | 2220 |
| cccgagctgc gtggaggact ctgtgacccc cattaccttg cgtctgaact tcacgctggt | 2280 |
| gggcaagccc ctccttgcct tcagaaacct gcggccatg ctggccgcac tggctcagag | 2340 |
| atacttcacg gcctccctac cctttgagaa gaactgtgga gccgaccata tctgccagga | 2400 |
| caatctcggc atctccttca gcttcccagg cttgaagtcc ctgctggtgg ggagtaacct | 2460 |
| ggagctgaac gcagaagtga tggtgtgaa tgacggggaa gactcctacg gaaccaccat | 2520 |
| caccttctcc caccccgcag gactgtccta ccgctacgtg gcagagggcc agaaacaagg | 2580 |

```
gcagctgcgt tccctgcacc tgacatgtga cagcgcccca gttgggagcc agggcacctg      2640
gagcaccagc tgcagaatca accacctcat cttccgtggc ggcgcccaga tcaccttctt      2700
ggctaccttt gacgtctccc ccaaggctgt cctgggagac cggctgcttc tgacagccaa      2760
tgtgagcagt gagaacaaca ctcccaggac cagcaagacc accttccagc tggagctccc      2820
ggtgaagtat gctgtctaca ctgtggttag cagccacgaa caattcacca aatacctcaa      2880
cttctcagag tctgaggaga aggaaagcca tgtggccatg cacagatacc aggtcaataa      2940
cctgggacag agggacctgc ctgtcagcat caacttctgg gtgcctgtgg agctgaacca      3000
ggaggctgtg tggatggatg tggaggtctc ccaccccag aacccatccc ttcggtgctc      3060
ctcagagaaa atcgcacccc cagcatctga cttcctggcg cacattcaga agaatcccgt      3120
gctggactgc tccattgctg gctgcctgcg gttccgctgt gacgtcccct ccttcagcgt      3180
ccaggaggag ctggatttca ccctgaaggg caacctcagc tttggctggg tccgccagat      3240
attgcagaag aaggtgtcgg tcgtgagtgt ggctgaaatt acgttcgaca catccgtgta      3300
ctcccagctt ccaggacagg aggcatttat gagagctcag acgacaacgg tgctggagaa      3360
gtacaaggtc cacaaccca cccccctcat cgtaggcagc tccattgggg gtctgttgct      3420
gctggcactc atcacagcgg tactgtacaa agttggcttc ttcaagcgtc agtacaagga      3480
aatgatggag gaggcaaatg gacaaattgc cccagaaaac gggacacaga ccccagccc      3540 gcccagtgag aaatgatccc tctttgcctt ggacttcttc tcccgcgatt ttccccactt      3600
acttaccctc acctgtcagg ctgacgggga ggaaccactg caccaccgag agaggctggg      3660
atgggcctgc ttcctgtctt tgggagaaaa cgtcttgctt gggaaggggc ctttgtcttg      3720
tcaaggttcc aactggaaac ccttaggaca gggtccctgc tgtgttcccc aaaaggactt      3780
gacttgcaat ttctacctag aaatacatgg acaataccc caggcctcag tctcccttct      3840
cccatgaggc acgaatgatc tttctttcct ttccttttt tttttttct tttcttttt      3900 tttttttg agacggagtc tcgctctgtc acccaggctg gagtgcaatg gcgtgatctc      3960
ggctcgctgc aacctccgcc tcccgggttc aagtaattct gctgtctcag cctcctgcgt      4020
agctgggact acaggcacac gccacctcgc ccggcccgat ctttctaaaa tacagttctg      4080
aatatgctgc tcatccccac ctgtcttcaa cagctcccca ttaccctcag gacaatgtct      4140
gaactctcca gcttcgcgtg agaagtcccc ttccatccca gagggtgggc ttcagggcgc      4200
acagcatgag agcctctgtg cccccatcac cctcgtttcc agtgaattag tgtcatgtca      4260
gcatcagctc agggcttcat cgtggggctc tcagttccga ttccccaggc tgaattggga      4320
gtgagatgcc tgcatgctgg gttctgcaca gctggcctcc cgcggttggg tcaacattgc      4380
tggcctggaa gggaggagcg ccctctaggg agggacatgg ccccggtgcg gctgcagctc      4440
accagcccca ggggcagaag agacccaacc acttcctatt ttttgaggct atgaatatag      4500
tacctgaaaa aatgccaagc actagattat tttttaaaa agcgtacttt aaatgtttgt      4560
gttaatacac attaaaacat cgcacaaaaa cgatgcatct accgctcctt gggaaataat      4620
ctgaaaggtc taaaataaa aaagccttct gtgg                                   4654
```

<210> SEQ ID NO 35
<211> LENGTH: 1163
<212> TYPE: PRT
<213> ORGANISM: Homo sapiens

<400> SEQUENCE: 35

```
Met Thr Arg Thr Arg Ala Ala Leu Leu Leu Phe Thr Ala Leu Ala Thr
1               5                   10                  15

Ser Leu Gly Phe Asn Leu Asp Thr Glu Glu Leu Thr Ala Phe Arg Val
            20                  25                  30

Asp Ser Ala Gly Phe Gly Asp Ser Val Val Gln Tyr Ala Asn Ser Trp
        35                  40                  45

Val Val Val Gly Ala Pro Gln Lys Ile Thr Ala Ala Asn Gln Thr Gly
50                  55                  60

Gly Leu Tyr Gln Cys Gly Tyr Ser Thr Gly Ala Cys Glu Pro Ile Gly
65              70                  75                  80

Leu Gln Val Pro Pro Glu Ala Val Asn Met Ser Leu Gly Leu Ser Leu
                85                  90                  95

Ala Ser Thr Thr Ser Pro Ser Gln Leu Leu Ala Cys Gly Pro Thr Val
            100                 105                 110

His His Glu Cys Gly Arg Asn Met Tyr Leu Thr Gly Leu Cys Phe Leu
        115                 120                 125

Leu Gly Pro Thr Gln Leu Thr Gln Arg Leu Pro Val Ser Arg Gln Glu
    130                 135                 140

Cys Pro Arg Gln Glu Gln Asp Ile Val Phe Leu Ile Asp Gly Ser Gly
145                 150                 155                 160

Ser Ile Ser Ser Arg Asn Phe Ala Thr Met Met Asn Phe Val Arg Ala
            165                 170                 175

Val Ile Ser Gln Phe Gln Arg Pro Ser Thr Gln Phe Ser Leu Met Gln
            180                 185                 190

Phe Ser Asn Lys Phe Gln Thr His Phe Thr Phe Glu Glu Phe Arg Arg
        195                 200                 205

Thr Ser Asn Pro Leu Ser Leu Leu Ala Ser Val His Gln Leu Gln Gly
    210                 215                 220

Phe Thr Tyr Thr Ala Thr Ala Ile Gln Asn Val Val His Arg Leu Phe
225                 230                 235                 240

His Ala Ser Tyr Gly Ala Arg Arg Asp Ala Thr Lys Ile Leu Ile Val
            245                 250                 255

Ile Thr Asp Gly Lys Lys Glu Gly Asp Ser Leu Asp Tyr Lys Asp Val
            260                 265                 270

Ile Pro Met Ala Asp Ala Ala Gly Ile Ile Arg Tyr Ala Ile Gly Val
        275                 280                 285

Gly Leu Ala Phe Gln Asn Arg Asn Ser Trp Lys Glu Leu Asn Asp Ile
    290                 295                 300

Ala Ser Lys Pro Ser Gln Glu His Ile Phe Lys Val Glu Asp Phe Asp
305                 310                 315                 320

Ala Leu Lys Asp Ile Gln Asn Gln Leu Lys Glu Lys Ile Phe Ala Ile
            325                 330                 335

Glu Gly Thr Glu Thr Thr Ser Ser Ser Phe Glu Leu Glu Met Ala
            340                 345                 350

Gln Glu Gly Phe Ser Ala Val Phe Thr Pro Asp Gly Pro Val Leu Gly
        355                 360                 365

Ala Val Gly Ser Phe Thr Trp Ser Gly Gly Ala Phe Leu Tyr Pro Pro
    370                 375                 380

Asn Met Ser Pro Thr Phe Ile Asn Met Ser Gln Glu Asn Val Asp Met
385                 390                 395                 400

Arg Asp Ser Tyr Leu Gly Tyr Ser Thr Glu Leu Ala Leu Trp Lys Gly
            405                 410                 415

Val Gln Ser Leu Val Leu Gly Ala Pro Arg Tyr Gln His Thr Gly Lys
```

```
              420                 425                 430
Ala Val Ile Phe Thr Gln Val Ser Arg Gln Trp Arg Met Lys Ala Glu
                435                 440                 445
Val Thr Gly Thr Gln Ile Gly Ser Tyr Phe Gly Ala Ser Leu Cys Ser
                450                 455                 460
Val Asp Val Asp Thr Asp Gly Ser Thr Asp Leu Val Leu Ile Gly Ala
465                 470                 475                 480
Pro His Tyr Tyr Glu Gln Thr Arg Gly Gly Gln Val Ser Val Cys Pro
                485                 490                 495
Leu Pro Arg Gly Trp Arg Arg Trp Cys Asp Ala Val Leu Tyr Gly
                500                 505                 510
Glu Gln Gly His Pro Trp Gly Arg Phe Gly Ala Ala Leu Thr Val Leu
                515                 520                 525
Gly Asp Val Asn Gly Asp Lys Leu Thr Asp Val Val Ile Gly Ala Pro
                530                 535                 540
Gly Glu Glu Glu Asn Arg Gly Ala Val Tyr Leu Phe His Gly Val Leu
545                 550                 555                 560
Gly Pro Ser Ile Ser Pro Ser His Ser Gln Arg Ile Ala Gly Ser Gln
                565                 570                 575
Leu Ser Ser Arg Leu Gln Tyr Phe Gly Gln Ala Leu Ser Gly Gly Gln
                580                 585                 590
Asp Leu Thr Gln Asp Gly Leu Val Asp Leu Ala Val Gly Ala Arg Gly
                595                 600                 605
Gln Val Leu Leu Leu Arg Thr Arg Pro Val Leu Trp Val Gly Val Ser
                610                 615                 620
Met Gln Phe Ile Pro Ala Glu Ile Pro Arg Ser Ala Phe Glu Cys Arg
625                 630                 635                 640
Glu Gln Val Val Ser Glu Gln Thr Leu Val Gln Ser Asn Ile Cys Leu
                645                 650                 655
Tyr Ile Asp Lys Arg Ser Lys Asn Leu Leu Gly Ser Arg Asp Leu Gln
                660                 665                 670
Ser Ser Val Thr Leu Asp Leu Ala Leu Asp Pro Gly Arg Leu Ser Pro
                675                 680                 685
Arg Ala Thr Phe Gln Glu Thr Lys Asn Arg Ser Leu Ser Arg Val Arg
                690                 695                 700
Val Leu Gly Leu Lys Ala His Cys Glu Asn Phe Asn Leu Leu Leu Pro
705                 710                 715                 720
Ser Cys Val Glu Asp Ser Val Thr Pro Ile Thr Leu Arg Leu Asn Phe
                725                 730                 735
Thr Leu Val Gly Lys Pro Leu Leu Ala Phe Arg Asn Leu Arg Pro Met
                740                 745                 750
Leu Ala Ala Leu Ala Gln Arg Tyr Phe Thr Ala Ser Leu Pro Phe Glu
                755                 760                 765
Lys Asn Cys Gly Ala Asp His Ile Cys Gln Asp Asn Leu Gly Ile Ser
                770                 775                 780
Phe Ser Phe Pro Gly Leu Lys Ser Leu Leu Val Gly Ser Asn Leu Glu
785                 790                 795                 800
Leu Asn Ala Glu Val Met Val Trp Asn Asp Gly Glu Asp Ser Tyr Gly
                805                 810                 815
Thr Thr Ile Thr Phe Ser His Pro Ala Gly Leu Ser Tyr Arg Tyr Val
                820                 825                 830
Ala Glu Gly Gln Lys Gln Gly Gln Leu Arg Ser Leu His Leu Thr Cys
                835                 840                 845
```

Asp Ser Ala Pro Val Gly Ser Gln Gly Thr Trp Ser Thr Ser Cys Arg
    850                 855                 860

Ile Asn His Leu Ile Phe Arg Gly Gly Ala Gln Ile Thr Phe Leu Ala
865                 870                 875                 880

Thr Phe Asp Val Ser Pro Lys Ala Val Leu Gly Asp Arg Leu Leu Leu
                885                 890                 895

Thr Ala Asn Val Ser Ser Glu Asn Asn Thr Pro Arg Thr Ser Lys Thr
            900                 905                 910

Thr Phe Gln Leu Glu Leu Pro Val Lys Tyr Ala Val Tyr Thr Val Val
        915                 920                 925

Ser Ser His Glu Gln Phe Thr Lys Tyr Leu Asn Phe Ser Glu Ser Glu
    930                 935                 940

Glu Lys Glu Ser His Val Ala Met His Arg Tyr Gln Val Asn Asn Leu
945                 950                 955                 960

Gly Gln Arg Asp Leu Pro Val Ser Ile Asn Phe Trp Val Pro Val Glu
                965                 970                 975

Leu Asn Gln Glu Ala Val Trp Met Asp Val Glu Val Ser His Pro Gln
            980                 985                 990

Asn Pro Ser Leu Arg Cys Ser Ser  Glu Lys Ile Ala Pro  Pro Ala Ser
        995                 1000                 1005

Asp Phe Leu Ala His Ile Gln  Lys Asn Pro Val Leu  Asp Cys Ser
    1010                1015                 1020

Ile Ala Gly Cys Leu Arg Phe  Arg Cys Asp Val Pro  Ser Phe Ser
    1025                1030                 1035

Val Gln Glu Glu Leu Asp Phe  Thr Leu Lys Gly Asn  Leu Ser Phe
    1040                1045                 1050

Gly Trp Val Arg Gln Ile Leu  Gln Lys Lys Val Ser  Val Val Ser
    1055                1060                 1065

Val Ala Glu Ile Thr Phe Asp  Thr Ser Val Tyr Ser  Gln Leu Pro
    1070                1075                 1080

Gly Gln Glu Ala Phe Met Arg  Ala Gln Thr Thr Thr  Val Leu Glu
    1085                1090                 1095

Lys Tyr Lys Val His Asn Pro  Thr Pro Leu Ile Val  Gly Ser Ser
    1100                1105                 1110

Ile Gly Gly Leu Leu Leu Leu  Ala Leu Ile Thr Ala  Val Leu Tyr
    1115                1120                 1125

Lys Val Gly Phe Phe Lys Arg  Gln Tyr Lys Glu Met  Met Glu Glu
    1130                1135                 1140

Ala Asn Gly Gln Ile Ala Pro  Glu Asn Gly Thr Gln  Thr Pro Ser
    1145                1150                 1155

Pro Pro Ser Glu Lys
    1160

<210> SEQ ID NO 36
<211> LENGTH: 3912
<212> TYPE: DNA
<213> ORGANISM: Homo sapiens

<400> SEQUENCE: 36
ctgtgctctg tccccaacct tccacttccc ctcaacgcgc tgctcaggga tgaccttcgg      60
cactgtgctt cttctgagtg tcctggcttc ttatcatgga ttcaacctgg atgtggagga    120
gcctacgatc ttccaggagg atgcaggcgg ctttgggcag agcgtggtgc agttcggtgg    180
atctcgactc gtggtgggag cacccctgga ggtggtggcg gccaaccaga cgggacggct    240

```
gtatgactgc gcagctgcca ccggcatgtg ccagcccatc ccgctgcaca tccgccctga    300
ggccgtgaac atgtccttgg gcctgaccct ggcagcctcc accaacggct cccggctcct    360
ggcctgtggc ccgaccctgc acagagtctg tggggagaac tcatactcaa agggttcctg    420
cctcctgctg ggctcgcgct gggagatcat ccagacagtc cccgacgcca cgccagagtg    480
tccacatcaa gagatggaca tcgtcttcct gattgacggc tctggaagca ttgaccaaaa    540
tgactttaac cagatgaagg gctttgtcca agctgtcatg ggccagtttg agggcactga    600
caccctgttt gcactgatgc agtactcaaa cctcctgaag atccacttca ccttcaccca    660
attccggacc agcccgagcc agcagagcct ggtggatccc atcgtccaac tgaaaggcct    720
gacgttcacg gccacgggca tcctgacagt ggtgacacag ctatttcatc ataagaatgg    780
ggcccgaaaa agtgccaaga agatcctcat tgtcatcaca gatgggcaga agtacaaaga    840 cccctggaa tacagtgatg tcatccccca ggcagagaag gctggcatca tccgctacgc    900
tatcggggtg ggacacgctt tccagggacc cactgccagg caggagctga ataccatcag    960
ctcagcgcct ccgcaggacc acgtgttcaa ggtggacaac tttgcagccc ttggcagcat    1020
ccagaagcag ctgcaggaga agatctatgc agttgaggga acccagtcca gggcaagcag    1080
ctccttccag cacgagatgt cccaagaagg cttcagcaca gccctcacaa tggatggcct    1140
cttcctgggg gctgtgggga ctttagctg tctggaggt gccttcctgt atcccccaaa    1200
tatgagcccc accttcatca acatgtctca ggagaatgtg gacatgaggg actcttacct    1260
gggttactcc accgagctag ccctgtggaa ggggtacag aacctggtcc tgggggcccc    1320
ccgctaccag ataccgggga aggctgtcat cttcacccag gtgtccaggc aatggaggaa    1380
gaaggccgaa gtcacaggga cgcagatcgg ctcctacttc ggggcctccc tctgctccgt    1440
ggatgtggac agcgatggca gcaccgacct gatcctcatt ggggccccc attactatga    1500 gcagacccga gggggccagg tgtccgtgtg tcccttgcct aggggagggg tgcagtggca    1560
gtgtgacgct gttctccgtg gtgagcaggg ccaccctgg ggccgctttg gggcagccct    1620
gacagtgttg ggggatgtga atgaggacaa gctgatagac gtggccattg ggcccggg    1680 agagcaggag aaccggggtg ctgtctacct gtttcacgga gcctcagaat ccggcatcag    1740
cccctcccac agccagcgga ttgccagctc ccagctctcc cccaggctgc agtattttgg    1800
gcaggcgctg agtggggtc aggacctcac ccaggatgga ctgatggacc tggccgtggg    1860
ggcccggggc caggtgctcc tgctcaggag tctgccggtg ctgaaagtgg gggtggccat    1920
gagattcagc cctgtggagg tggccaaggc tgtgtaccgg tgctgggaag agaagcccag    1980
tgccctggaa gctggggacg ccaccgtctg tctcaccatc cagaaaagct cactggacca    2040
gctaggtgac atccaaagct ctgtcaggtt tgatctggca ctggacccag tcgtctgac    2100 ttctcgtgcc attttcaatg aaaccaagaa ccccactttg actcgaagaa aaaccctggg    2160 actgggatt cactgtgaaa ccctgaagct gcttttgcca gattgtgtgg aggatgtggt    2220
gagccccatc attctgcacc tcaacttctc actggtgaga gagcccatcc cctcccccca    2280
gaacctgcgt cctgtgctgg ccgtgggctc acaagacctc ttcactgctt ctctcccctt    2340
cgagaagaac tgtgggcaag atggcctctg tgaagggac ctgggtgtca ccctcagctt    2400
ctcaggcctg cagaccctga ccgtggggag ctccctggag ctcaacgtga ttgtgactgt    2460
gtggaacgca ggtgaggatt cctacggaac cgtggtcagc ctctactatc agcagggct    2520 gtcgcaccga cgggtgtcag gagcccagaa gcagcccat cagagtgccc tgcgcctggc    2580
```

| | |
|---|---|
| atgtgagaca gtgcccactg aggatgaggg cctaagaagc agccgctgca gtgtcaacca | 2640 |
| ccccatcttc catgagggct ctaacggcac cttcatagtc acattcgatg tctcctacaa | 2700 |
| ggccaccctg ggagacagga tgcttatgag ggccagtgca agcagtgaga acaataaggc | 2760 |
| ttcaagcagc aaggccacct tccagctgga gctcccggtg aagtatgcag tctacaccat | 2820 |
| gatcagcagg caggaagaat ccaccaagta cttcaacttt gcaacctccg atgagaagaa | 2880 |
| aatgaaagag gctgagcatc gataccgtgt gaataacctc agccagcgag atctggccat | 2940 |
| cagcattaac ttctgggttc ctgtcctgct gaacggggtg gctgtgtggg atgtggtcat | 3000 |
| ggaggcccca tctcagagtc tccctgtgt tcagagaga aaacctcccc agcattctga | 3060 |
| cttcctgacc cagatttcaa gaagtcccat gctggactgc tccattgctg actgcctgca | 3120 |
| gttccgctgt gacgtcccct ccttcagcgt ccaggaggag ctggatttca ccctgaaggg | 3180 |
| caatctcagt ttcggctggg tccgcgagac attgcagaag aaggtgttgg tcgtgagtgt | 3240 |
| ggctgaaatt acgttcgaca catccgtgta ctcccagctt ccaggacagg aggcatttat | 3300 |
| gagagctcag atggagatgg tgctagaaga agacgaggtc tacaatgcca ttcccatcat | 3360 |
| catgggcagc tctgtggggg ctctgctact gctggcgctc atcacagcca cactgtacaa | 3420 |
| gcttggcttc ttcaaacgcc actacaagga atgctggag acaagcctg aagacactgc | 3480 |
| cacattcagt ggggacgatt tcagctgtgt ggccccaaat gtgcctttgt cctaataatc | 3540 |
| cactttcctg tttatctcta ccactgtggg ctggacttgc ttgcaaccat aaatcaactt | 3600 |
| acatggaaac aacttctgca tagatctgca ctggcctaag caacctacca ggtgctaagc | 3660 |
| accttctcgg agagatagag attgtaatgt ttttacatat ctgtccatct tttcagcaa | 3720 |
| tgacccactt tttacagaag caggcatggt gccagcataa attttcatat gcttaagaat | 3780 |
| tgtcacatga aatgaggatg tttatagcac actttccttg cgtggaagag ctataaccca | 3840 |
| gggacctgag tgcctctctg ggaatagtcg ggggaaccta tttgtgggca ttgaaaaagt | 3900 |
| tttttcactt tc | 3912 |

<210> SEQ ID NO 37
<211> LENGTH: 1161
<212> TYPE: PRT
<213> ORGANISM: Homo sapiens

<400> SEQUENCE: 37

Met Thr Phe Gly Thr Val Leu Leu Leu Ser Val Leu Ala Ser Tyr His
1               5                   10                  15

Gly Phe Asn Leu Asp Val Glu Glu Pro Thr Ile Phe Gln Glu Asp Ala
            20                  25                  30

Gly Gly Phe Gly Gln Ser Val Val Gln Phe Gly Gly Ser Arg Leu Val
        35                  40                  45

Val Gly Ala Pro Leu Glu Val Val Ala Ala Asn Gln Thr Gly Arg Leu
    50                  55                  60

Tyr Asp Cys Ala Ala Ala Thr Gly Met Cys Gln Pro Ile Pro Leu His
65                  70                  75                  80

Ile Arg Pro Glu Ala Val Asn Met Ser Leu Gly Leu Thr Leu Ala Ala
                85                  90                  95

Ser Thr Asn Gly Ser Arg Leu Leu Ala Cys Gly Pro Thr Leu His Arg
            100                 105                 110

Val Cys Gly Glu Asn Ser Tyr Ser Lys Gly Ser Cys Leu Leu Leu Gly
        115                 120                 125

Ser Arg Trp Glu Ile Ile Gln Thr Val Pro Asp Ala Thr Pro Glu Cys

```
            130                 135                 140
Pro His Gln Glu Met Asp Ile Val Phe Leu Ile Asp Gly Ser Gly Ser
145                 150                 155                 160

Ile Asp Gln Asn Asp Phe Asn Gln Met Lys Gly Phe Val Gln Ala Val
                    165                 170                 175

Met Gly Gln Phe Glu Gly Thr Asp Thr Leu Phe Ala Leu Met Gln Tyr
                180                 185                 190

Ser Asn Leu Leu Lys Ile His Phe Thr Phe Thr Gln Phe Arg Thr Ser
            195                 200                 205

Pro Ser Gln Gln Ser Leu Val Asp Pro Ile Val Gln Leu Lys Gly Leu
        210                 215                 220

Thr Phe Thr Ala Thr Gly Ile Leu Thr Val Val Thr Gln Leu Phe His
225                 230                 235                 240

His Lys Asn Gly Ala Arg Lys Ser Ala Lys Lys Ile Leu Ile Val Ile
                    245                 250                 255

Thr Asp Gly Gln Lys Tyr Lys Asp Pro Leu Glu Tyr Ser Asp Val Ile
                260                 265                 270

Pro Gln Ala Glu Lys Ala Gly Ile Ile Arg Tyr Ala Ile Gly Val Gly
            275                 280                 285

His Ala Phe Gln Gly Pro Thr Ala Arg Gln Glu Leu Asn Thr Ile Ser
        290                 295                 300

Ser Ala Pro Pro Gln Asp His Val Phe Lys Val Asp Asn Phe Ala Ala
305                 310                 315                 320

Leu Gly Ser Ile Gln Lys Gln Leu Gln Glu Lys Ile Tyr Ala Val Glu
                    325                 330                 335

Gly Thr Gln Ser Arg Ala Ser Ser Phe Gln His Glu Met Ser Gln
                340                 345                 350

Glu Gly Phe Ser Thr Ala Leu Thr Met Asp Gly Leu Phe Leu Gly Ala
            355                 360                 365

Val Gly Ser Phe Ser Trp Ser Gly Gly Ala Phe Leu Tyr Pro Pro Asn
        370                 375                 380

Met Ser Pro Thr Phe Ile Asn Met Ser Gln Glu Asn Val Asp Met Arg
385                 390                 395                 400

Asp Ser Tyr Leu Gly Tyr Ser Thr Glu Leu Ala Leu Trp Lys Gly Val
                    405                 410                 415

Gln Asn Leu Val Leu Gly Ala Pro Arg Tyr Gln His Thr Gly Lys Ala
                420                 425                 430

Val Ile Phe Thr Gln Val Ser Arg Gln Trp Arg Lys Lys Ala Glu Val
            435                 440                 445

Thr Gly Thr Gln Ile Gly Ser Tyr Phe Gly Ala Ser Leu Cys Ser Val
        450                 455                 460

Asp Val Asp Ser Asp Gly Ser Thr Asp Leu Ile Leu Ile Gly Ala Pro
465                 470                 475                 480

His Tyr Tyr Glu Gln Thr Arg Gly Gly Gln Val Ser Val Cys Pro Leu
                    485                 490                 495

Pro Arg Gly Arg Val Gln Trp Gln Cys Asp Ala Val Leu Arg Gly Glu
                500                 505                 510

Gln Gly His Pro Trp Gly Arg Phe Gly Ala Ala Leu Thr Val Leu Gly
            515                 520                 525

Asp Val Asn Glu Asp Lys Leu Ile Asp Val Ala Ile Gly Ala Pro Gly
        530                 535                 540

Glu Gln Glu Asn Arg Gly Ala Val Tyr Leu Phe His Gly Ala Ser Glu
545                 550                 555                 560
```

-continued

```
Ser Gly Ile Ser Pro Ser His Ser Gln Arg Ile Ala Ser Ser Gln Leu
            565                 570                 575

Ser Pro Arg Leu Gln Tyr Phe Gly Gln Ala Leu Ser Gly Gly Gln Asp
            580                 585                 590

Leu Thr Gln Asp Gly Leu Met Asp Leu Ala Val Gly Ala Arg Gly Gln
            595                 600                 605

Val Leu Leu Leu Arg Ser Leu Pro Val Leu Lys Val Gly Val Ala Met
            610                 615                 620

Arg Phe Ser Pro Val Glu Val Ala Lys Ala Val Tyr Arg Cys Trp Glu
625                 630                 635                 640

Glu Lys Pro Ser Ala Leu Glu Ala Gly Asp Ala Thr Val Cys Leu Thr
            645                 650                 655

Ile Gln Lys Ser Ser Leu Asp Gln Leu Gly Asp Ile Gln Ser Ser Val
            660                 665                 670

Arg Phe Asp Leu Ala Leu Asp Pro Gly Arg Leu Thr Ser Arg Ala Ile
            675                 680                 685

Phe Asn Glu Thr Lys Asn Pro Thr Leu Thr Arg Arg Lys Thr Leu Gly
            690                 695                 700

Leu Gly Ile His Cys Glu Thr Leu Lys Leu Leu Leu Pro Asp Cys Val
705                 710                 715                 720

Glu Asp Val Val Ser Pro Ile Ile Leu His Leu Asn Phe Ser Leu Val
                    725                 730                 735

Arg Glu Pro Ile Pro Ser Pro Gln Asn Leu Arg Pro Val Leu Ala Val
                    740                 745                 750

Gly Ser Gln Asp Leu Phe Thr Ala Ser Leu Pro Phe Glu Lys Asn Cys
            755                 760                 765

Gly Gln Asp Gly Leu Cys Glu Gly Asp Leu Gly Val Thr Leu Ser Phe
            770                 775                 780

Ser Gly Leu Gln Thr Leu Thr Val Gly Ser Ser Leu Glu Leu Asn Val
785                 790                 795                 800

Ile Val Thr Val Trp Asn Ala Gly Glu Asp Ser Tyr Gly Thr Val Val
                    805                 810                 815

Ser Leu Tyr Tyr Pro Ala Gly Leu Ser His Arg Arg Val Ser Gly Ala
            820                 825                 830

Gln Lys Gln Pro His Gln Ser Ala Leu Arg Leu Ala Cys Glu Thr Val
            835                 840                 845

Pro Thr Glu Asp Glu Gly Leu Arg Ser Ser Arg Cys Ser Val Asn His
850                 855                 860

Pro Ile Phe His Glu Gly Ser Asn Gly Thr Phe Ile Val Thr Phe Asp
865                 870                 875                 880

Val Ser Tyr Lys Ala Thr Leu Gly Asp Arg Met Leu Met Arg Ala Ser
            885                 890                 895

Ala Ser Ser Glu Asn Asn Lys Ala Ser Ser Lys Ala Thr Phe Gln
            900                 905                 910

Leu Glu Leu Pro Val Lys Tyr Ala Val Tyr Thr Met Ile Ser Arg Gln
            915                 920                 925

Glu Glu Ser Thr Lys Tyr Phe Asn Phe Ala Thr Ser Asp Glu Lys Lys
            930                 935                 940

Met Lys Glu Ala Glu His Arg Tyr Arg Val Asn Asn Leu Ser Gln Arg
945                 950                 955                 960

Asp Leu Ala Ile Ser Ile Asn Phe Trp Val Pro Val Leu Leu Asn Gly
                    965                 970                 975
```

Val Ala Val Trp Asp Val Met Glu Ala Pro Ser Gln Ser Leu Pro
          980                 985                 990

Cys Val Ser Glu Arg Lys Pro Pro Gln His Ser Asp Phe Leu Thr Gln
        995                 1000                1005

Ile Ser Arg Ser Pro Met Leu Asp Cys Ser Ile Ala Asp Cys Leu
    1010                1015                1020

Gln Phe Arg Cys Asp Val Pro Ser Phe Ser Val Gln Glu Glu Leu
    1025                1030                1035

Asp Phe Thr Leu Lys Gly Asn Leu Ser Phe Gly Trp Val Arg Glu
    1040                1045                1050

Thr Leu Gln Lys Lys Val Leu Val Val Ser Val Ala Glu Ile Thr
    1055                1060                1065

Phe Asp Thr Ser Val Tyr Ser Gln Leu Pro Gly Gln Glu Ala Phe
    1070                1075                1080

Met Arg Ala Gln Met Glu Met Val Leu Glu Glu Asp Glu Val Tyr
    1085                1090                1095

Asn Ala Ile Pro Ile Ile Met Gly Ser Ser Val Gly Ala Leu Leu
    1100                1105                1110

Leu Leu Ala Leu Ile Thr Ala Thr Leu Tyr Lys Leu Gly Phe Phe
    1115                1120                1125

Lys Arg His Tyr Lys Glu Met Leu Glu Asp Lys Pro Glu Asp Thr
    1130                1135                1140

Ala Thr Phe Ser Gly Asp Asp Phe Ser Cys Val Ala Pro Asn Val
    1145                1150                1155

Pro Leu Ser
    1160

<210> SEQ ID NO 38
<211> LENGTH: 2418
<212> TYPE: DNA
<213> ORGANISM: Mus musculus

<400> SEQUENCE: 38
tcagcctgga gtcacctgct ccttctctcc acaggacatg ctgggcccac actcactgct      60
gcttgcccta gctggactgt tcttcctggg atctgctgtg tcccaggaat gcaccaagta     120
caaagtcagc agttgccggg actgtatcca gtcggggcct ggctgttcct ggtgccagaa     180
gctgaacttc actggaccag agaacctga ctccttgcgc tgtgacacac gggcacagct     240
gctgctgaag ggttgtccag ccgatgatat catggacccc aggagcatcg ctaatcctga     300
gttcgaccaa cgggggcaac ggaaacagct atctccacaa aaagtgacac tttacttgcg     360
accaggacag gctgccgcat tcaatgtgac tttccggcgg gccaagggat accccattga     420
tctgtactac ctcatggatc tctcctactc catgcttgat gacctcaaca acgtcaagaa     480
gctgggcggg gacttgctgc aggccctcaa cgagatcacc gagtctggcc gcatcggctt     540
tgggtcgttt gtggacaaga cggtgctgcc ttttgttaac acccatcctg agaagctgag     600
gaacccatgt cccaacaagg agaaggcctg ccagccccca tttgcctttc ggcacgtgct     660
caagttaacc gacaactcca accagtttca gacagaggtc ggcaagcaac tgatttccgg     720
aaacctggac gcccctgagg gtgggctgga tgccataatg caagttgctg catgtccgga     780
ggaaattggc tggcgcaatg tcacgaggct gctggtgttt gccacagacg atggcttcca     840
ctttgctggt gatggcaaac tgggtgccat cctgacccc aatgatggcc gctgccacct     900
ggaggataac atgtacaaga ggagcaatga gttcgactac ccatccgtgg gtcagctggc     960

```
acacaaactt tccgagagca acatccagcc catctttgcg gtgacaaaga agatggtgaa    1020
aacgtatgag aaactcacgg agatcatccc caagtcagca gtgggggaac tgtctgacga    1080
ctccagcaac gtggtgcagc tcatcaagaa tgcctactat aaactctcct ctagagtctt    1140
cctggaccac agcacccctcc cggacaccct gaaagtcacc tatgactcct tctgcagtaa    1200
tggagcatcg agtataggca atcccgtgg ggactgtgat ggcgtacaga tcaacaaccc    1260
ggtcaccttc caggtaaagg tcatggcttc cgagtgtatc caggagcagt cctttgtcat    1320
ccgggcactg ggtttcacgg atacagtgac cgtgcaggtc cgtccccagt gtgagtgtca    1380
gtgccgggac cagagtcggg agcagagtct ctgtggaggc aagggagtca tggagtgtgg    1440
tatctgcagg tgtgagtctg gctacattgg gaaaaactgt gagtgccaga ctcagggtcg    1500
gagcagccag gagctggaga gaaactgtcg gaaggacaat agttccatcg tgtgctcagg    1560
gcttggggac tgcatctgtg gcagtgtgt atgccatacc agtgacgtcc ccaacaaaga    1620
gatctttggg caatactgcg agtgtgacaa tgtcaactgt gagagatata acagccaagt    1680
ctgcggtggc tcagatcggg gttcctgcaa ctgtggcaaa tgtagttgca agcccggtta    1740
cgagggctcg gcctgccagt gtcagaggtc caccacgggc tgtctgaatg cacggctggt    1800
agagtgcagt ggccgtggcc actgccaatg caacaggtgc atatgtgacg aaggctacca    1860
gccaccgatg tgtgaggatt gtcccagctg tggctcgcac tgcagggaca accacacctc    1920
ttgtgccgag tgcctgaagt ttgataaggg cccttttgag aagaactgta gtgttcagtg    1980
tgctggtatg acgctgcaga ctatcccttt gaagaaaaag ccctgcaagg agagggactc    2040
ggaaggctgt tggataactt acactttgca gcagaaggac ggaaggaaca tttacaacat    2100
ccatgtggag gacagtctag agtgtgtgaa gggccccaat gtggctgcca tcgtaggggg    2160
caccgtggta ggtgtcgtac tgattggtgt cctcctcctg gtcatctgga aggccctgac    2220
ccacctgact gacctcaggg agtacaggcg ctttgagaag gagaaactca gtcccaatg    2280 gaacaatgac aaccccctct tcaagagtgc tacgacaacg tcatgaacc ccaagtttgc    2340 tgaaagctag agcatgagtt atcataatca agcagatgtg accccctcag accacgcctc    2400
ctcccctctg caaacaca                                                  2418
```

<210> SEQ ID NO 39
<211> LENGTH: 770
<212> TYPE: PRT
<213> ORGANISM: Mus musculus

<400> SEQUENCE: 39

Met Leu Gly Pro His Ser Leu Leu Leu Ala Leu Ala Gly Leu Phe Phe
1               5                   10                  15

Leu Gly Ser Ala Val Ser Gln Glu Cys Thr Lys Tyr Lys Val Ser Ser
            20                  25                  30

Cys Arg Asp Cys Ile Gln Ser Gly Pro Gly Cys Ser Trp Cys Gln Lys
        35                  40                  45

Leu Asn Phe Thr Gly Pro Gly Glu Pro Asp Ser Leu Arg Cys Asp Thr
    50                  55                  60

Arg Ala Gln Leu Leu Leu Lys Gly Cys Pro Ala Asp Asp Ile Met Asp
65                  70                  75                  80

Pro Arg Ser Ile Ala Asn Pro Glu Phe Asp Gln Arg Gly Gln Arg Lys
                85                  90                  95

Gln Leu Ser Pro Gln Lys Val Thr Leu Tyr Leu Arg Pro Gly Gln Ala
            100                 105                 110

```
Ala Ala Phe Asn Val Thr Phe Arg Arg Ala Lys Gly Tyr Pro Ile Asp
            115                 120                 125
Leu Tyr Tyr Leu Met Asp Leu Ser Tyr Ser Met Leu Asp Asp Leu Asn
130                 135                 140
Asn Val Lys Lys Leu Gly Gly Asp Leu Leu Gln Ala Leu Asn Glu Ile
145                 150                 155                 160
Thr Glu Ser Gly Arg Ile Gly Phe Gly Ser Phe Val Asp Lys Thr Val
                165                 170                 175
Leu Pro Phe Val Asn Thr His Pro Glu Lys Leu Arg Asn Pro Cys Pro
                180                 185                 190
Asn Lys Glu Lys Ala Cys Gln Pro Pro Phe Ala Phe Arg His Val Leu
            195                 200                 205
Lys Leu Thr Asp Asn Ser Asn Gln Phe Gln Thr Glu Val Gly Lys Gln
            210                 215                 220
Leu Ile Ser Gly Asn Leu Asp Ala Pro Glu Gly Gly Leu Asp Ala Ile
225                 230                 235                 240
Met Gln Val Ala Ala Cys Pro Glu Glu Ile Gly Trp Arg Asn Val Thr
                245                 250                 255
Arg Leu Leu Val Phe Ala Thr Asp Asp Gly Phe His Phe Ala Gly Asp
                260                 265                 270
Gly Lys Leu Gly Ala Ile Leu Thr Pro Asn Asp Gly Arg Cys His Leu
            275                 280                 285
Glu Asp Asn Met Tyr Lys Arg Ser Asn Glu Phe Asp Tyr Pro Ser Val
            290                 295                 300
Gly Gln Leu Ala His Lys Leu Ser Glu Ser Asn Ile Gln Pro Ile Phe
305                 310                 315                 320
Ala Val Thr Lys Lys Met Val Lys Thr Tyr Glu Lys Leu Thr Glu Ile
                325                 330                 335
Ile Pro Lys Ser Ala Val Gly Glu Leu Ser Asp Asp Ser Ser Asn Val
                340                 345                 350
Val Gln Leu Ile Lys Asn Ala Tyr Tyr Lys Leu Ser Ser Arg Val Phe
            355                 360                 365
Leu Asp His Ser Thr Leu Pro Asp Thr Leu Lys Val Thr Tyr Asp Ser
370                 375                 380
Phe Cys Ser Asn Gly Ala Ser Ser Ile Gly Lys Ser Arg Gly Asp Cys
385                 390                 395                 400
Asp Gly Val Gln Ile Asn Asn Pro Val Thr Phe Gln Val Lys Val Met
                405                 410                 415
Ala Ser Glu Cys Ile Gln Glu Gln Ser Phe Val Ile Arg Ala Leu Gly
            420                 425                 430
Phe Thr Asp Thr Val Thr Val Gln Val Arg Pro Gln Cys Glu Cys Gln
            435                 440                 445
Cys Arg Asp Gln Ser Arg Glu Gln Ser Leu Cys Gly Gly Lys Gly Val
        450                 455                 460
Met Glu Cys Gly Ile Cys Arg Cys Glu Ser Gly Tyr Ile Gly Lys Asn
465                 470                 475                 480
Cys Glu Cys Gln Thr Gln Gly Arg Ser Ser Gln Glu Leu Glu Arg Asn
                485                 490                 495
Cys Arg Lys Asp Asn Ser Ser Ile Val Cys Ser Gly Leu Gly Asp Cys
            500                 505                 510
Ile Cys Gly Gln Cys Val Cys His Thr Ser Asp Val Pro Asn Lys Glu
        515                 520                 525
Ile Phe Gly Gln Tyr Cys Glu Cys Asp Asn Val Asn Cys Glu Arg Tyr
```

```
                    530              535              540
Asn Ser Gln Val Cys Gly Gly Ser Asp Arg Gly Ser Cys Asn Cys Gly
545                 550              555              560

Lys Cys Ser Cys Lys Pro Gly Tyr Glu Gly Ser Ala Cys Gln Cys Gln
                565              570              575

Arg Ser Thr Thr Gly Cys Leu Asn Ala Arg Leu Val Glu Cys Ser Gly
            580              585              590

Arg Gly His Cys Gln Cys Asn Arg Cys Ile Cys Asp Glu Gly Tyr Gln
        595              600              605

Pro Pro Met Cys Glu Asp Cys Pro Ser Cys Gly Ser His Cys Arg Asp
    610              615              620

Asn His Thr Ser Cys Ala Glu Cys Leu Lys Phe Asp Lys Gly Pro Phe
625              630              635              640

Glu Lys Asn Cys Ser Val Gln Cys Ala Gly Met Thr Leu Gln Thr Ile
                645              650              655

Pro Leu Lys Lys Lys Pro Cys Lys Glu Arg Asp Ser Glu Gly Cys Trp
                660              665              670

Ile Thr Tyr Thr Leu Gln Gln Lys Asp Gly Arg Asn Ile Tyr Asn Ile
            675              680              685

His Val Glu Asp Ser Leu Glu Cys Val Lys Gly Pro Asn Val Ala Ala
        690              695              700

Ile Val Gly Gly Thr Val Val Gly Val Val Leu Ile Gly Val Leu Leu
705              710              715              720

Leu Val Ile Trp Lys Ala Leu Thr His Leu Thr Asp Leu Arg Glu Tyr
                725              730              735

Arg Arg Phe Glu Lys Glu Lys Leu Lys Ser Gln Trp Asn Asn Asp Asn
            740              745              750

Pro Leu Phe Lys Ser Ala Thr Thr Thr Val Met Asn Pro Lys Phe Ala
        755              760              765

Glu Ser
    770

<210> SEQ ID NO 40
<211> LENGTH: 3571
<212> TYPE: DNA
<213> ORGANISM: Mus musculus

<400> SEQUENCE: 40
cctaagcgca gatgagtttc cggattgcgg gccccagact tttgctactg ggactccagc     60
tgtttgccaa ggcctggagc tacaacctgg acacacggcc tacgcagagc ttcttggcac    120
aagctggaag acattttggg taccaggtct tgcagattga agatggggtt gtcgtgggag    180
ccccaggtga gggggacaac acgggaggcc tctatcactg ccgaacaagc agcgagttct    240
gccagccagt cagcctacat ggttctaacc atacctccaa gtacttggga atgacgctgg    300
caacagatgc cgccaaggga agccttttgg cctgtgaccc tggactgtct cggacatgcg    360
atcagaacac ttacctcagt ggcctctgct acctcttccc ccagagtctg gagggaccta    420
tgttacaaaa tcgtcccgcc tatcaggaat gtatgaaggg caaagtcgac ctggtgtttc    480
tgttcgatgg ctcacagagc ttggatagaa aggactttga aaaatcctg gaattcatga    540 aggatgtgat gaggaagctc agcaatactt cctaccagtt tgctgccgtc agttctcca    600 cagactgcag aacagaattt actttcttgg actacgttaa gcagaacaag aaccccgatg    660
ttctgctagg cagcgtgcag cccatgttct tgctgaccaa taccttcgt gccatcaact    720
```

```
atgtggtggc acacgtgttc aaagaagagt ctggtgccag gcctgatgct accaaggtgc    780
ttgtcatcat tacagacggg gaggcaagtg ataaaggcaa catcagtgcg gcccacgaca    840
taacccgcta catcatcggg attggcaagc attttgtgag cgtacaaaag caaaagacgc    900
tccacatatt tgcctcagaa cctgtagagg aatttgtgaa gattctggac acctttgaga    960
agctgaagga tctttttact gacctgcaga ggaggattta tgctattgag ggcacaaaca   1020
gacaggacct gacatccttt aacatggaac tctcctccag cgggatcagc gcagacctca   1080
gcaagggcca tgcagttgtg ggagctgttg gggctaagga ttgggccggg ggctttctgg   1140
acctgcgtga agacctgcag ggtgccacat ttgttgggca ggaaccgctg acctcagatg   1200 tgagagggg ctacctgggt tacactgtgg cctggatgac ctcccggagc tccagacccc   1260
tgctggcagc aggagcccca cggtaccagc atgtgggaca agtactgctt ttccaagccc   1320
cagaggctgg aggacgttgg aaccaaaccc agaagataga agggactcag atcggatctt   1380
actttggtgg ggaactatgt agtgttgacc tggaccaaga tggcgaggca gagctgctgc   1440
tgattggagc accctgttc tttggggagc agagaggagg ccgagtgttc acttaccaga   1500
gaagacagtc gctgttgaa atggtctcag agctacaggg tgaccctggc tacccgcttg   1560
gtcggtttgg agccgccata actgccctga cggacatcaa tggggatagg ctgactgatg   1620
tggctgtggg agcccctttg gaggagcagg gtgctgtgta catcttcaat gggaagcctg   1680
gtgggctcag tccccagcca agccagcgta taccaggagc ccaggtgttc ccaggaatcc   1740
ggtggtttgg ccgctccatc catggggtga aggaccttgg aggggacagg ctggcaaatg   1800
tggttgtagg acctgagggt cggtggttg tgctgagctc caggccggtg gtggatgtgg   1860
tcactgagct gtcgttctcc ccagaggaaa tcccagtgca cgaggtggag tgctcctact   1920
cagccaggga ggagcagaaa cacggagtca agctcaaggc atgcttccgg atcaagcccc   1980
tcacgccaca gtttcaaggt cgcctgcttg ccaacctcag ctacaccctg cagctggatg   2040
gccatcggat gaggagccga gggttgttcc cagatggaag ccacgagctc agtggaaaca   2100
cctccatcac cccagataaa tcctgcttgg acttccactt ccacttcccg atctgcattc   2160
aagacctcat ctcccctatc aatgtctccc tgaatttctc tcttttggag gaagaaggaa   2220
caccaaggga ccaaaagggc agggccatgc agcctatcct gagaccttca atccacacag   2280
tgactaagga gatccctttt gagaagaact gtggtgaaga taagaagtgt gaggcaaacc   2340 tgacctgtc atcccctgcc agatctggac ccctgcgtct gatgtcctct gccagccttg   2400
ctgtggagtg gacactgagc aactcagggg aagatgccta ctgggtgcga ttagacctgg   2460
acttccctcg gggactctcc ttccggaaag tggagatgct tcagccacac agccgaatgc   2520
ctgtgagctg cgaggagctc accgaggggt caagtctcct gactaagaca ctgaaatgca   2580
atgtaagctc tcccatcttc aaagcaggcc aggaggtgag cctccaggtg atgtttaaca   2640
cgctactcaa cagctcctgg gaagacttcg tcgagctgaa tggcactgtg cactgtgaga   2700
atgagaactc aagcctccag gaggacaact cagccgccac ccacattcct gtcctgtacc   2760
ctgtcaacat ccttactaag gagcaggaga actccaccct ctatatcagt ttcacccta   2820 aaggtcccaa gacccaacaa gtccagcatg tctaccaggt gaggattcag ccatctgcct   2880
atgaccacaa catgcccaca ctagaggcct tggttgggt gccccggcct cacagtgagg   2940
acctcatcac atacacatgg agtgtacaga cggatcccct tgtcacttgc cacagcgagg   3000
acctgaagag gccgtccagc gaagctgagc cttgtctgcc tggagtccag ttccgctgtc   3060
caattgtctt caggtgggag atcctcatcc aagtgacggg gaccgtggaa ctctccaagg   3120
```

```
aaatcaaggc ctcctccaca ctcagcctct gcagctcact ctccgtctcc ttcaacagca   3180
gcaagcattt ccatttgtat ggcagcaaag cctctgaggc ccaggtcctc gtgaaggttg   3240
acctgatcca cgagaaggag atgcttcacg tgtacgtgct cagcggcatt gggggcctcg   3300
tgcttctgtt cctgattttc ctggcgctct acaaggttgg cttcttcaaa cggaacctga   3360
aggagaagat ggaggctgat ggaggtgttc caaatggaag ccctccagaa gacactgacc   3420
ctctggcagt acctggggaa gagaccaaag atatgggctg tctagagccc ctccgggaga   3480
gtgacaagga ctaaggccta ggtctgatac actgacagcc caggaataga cttgagagcc   3540
ctggctctga ccagcttcag tcacatgcca c                                 3571
```

<210> SEQ ID NO 41
<211> LENGTH: 1160
<212> TYPE: PRT
<213> ORGANISM: Mus musculus

<400> SEQUENCE: 41

```
Met Ser Phe Arg Ile Ala Gly Pro Arg Leu Leu Leu Gly Leu Gln
1               5                   10                  15

Leu Phe Ala Lys Ala Trp Ser Tyr Asn Leu Asp Thr Arg Pro Thr Gln
            20                  25                  30

Ser Phe Leu Ala Gln Ala Gly Arg His Phe Gly Tyr Gln Val Leu Gln
        35                  40                  45

Ile Glu Asp Gly Val Val Gly Ala Pro Gly Glu Gly Asp Asn Thr
    50                  55                  60

Gly Gly Leu Tyr His Cys Arg Thr Ser Ser Glu Phe Cys Gln Pro Val
65                  70                  75                  80

Ser Leu His Gly Ser Asn His Thr Ser Lys Tyr Leu Gly Met Thr Leu
                85                  90                  95

Ala Thr Asp Ala Ala Lys Gly Ser Leu Leu Ala Cys Asp Pro Gly Leu
            100                 105                 110

Ser Arg Thr Cys Asp Gln Asn Thr Tyr Leu Ser Gly Leu Cys Tyr Leu
        115                 120                 125

Phe Pro Gln Ser Leu Glu Gly Pro Met Leu Gln Asn Arg Pro Ala Tyr
    130                 135                 140

Gln Glu Cys Met Lys Gly Lys Val Asp Leu Val Phe Leu Phe Asp Gly
145                 150                 155                 160

Ser Gln Ser Leu Asp Arg Lys Asp Phe Glu Lys Ile Leu Glu Phe Met
                165                 170                 175

Lys Asp Val Met Arg Lys Leu Ser Asn Thr Ser Tyr Gln Phe Ala Ala
            180                 185                 190

Val Gln Phe Ser Thr Asp Cys Arg Thr Glu Phe Thr Phe Leu Asp Tyr
        195                 200                 205

Val Lys Gln Asn Lys Asn Pro Asp Val Leu Leu Gly Ser Val Gln Pro
    210                 215                 220

Met Phe Leu Leu Thr Asn Thr Phe Arg Ala Ile Asn Tyr Val Val Ala
225                 230                 235                 240

His Val Phe Lys Glu Glu Ser Gly Ala Arg Pro Asp Ala Thr Lys Val
                245                 250                 255

Leu Val Ile Ile Thr Asp Gly Glu Ala Ser Asp Lys Gly Asn Ile Ser
            260                 265                 270

Ala Ala His Asp Ile Thr Arg Tyr Ile Ile Gly Ile Gly Lys His Phe
        275                 280                 285
```

```
Val Ser Val Gln Lys Gln Lys Thr Leu His Ile Phe Ala Ser Glu Pro
    290                 295                 300

Val Glu Glu Phe Val Lys Ile Leu Asp Thr Phe Glu Lys Leu Lys Asp
305                 310                 315                 320

Leu Phe Thr Asp Leu Gln Arg Arg Ile Tyr Ala Ile Glu Gly Thr Asn
                    325                 330                 335

Arg Gln Asp Leu Thr Ser Phe Asn Met Glu Leu Ser Ser Ser Gly Ile
                340                 345                 350

Ser Ala Asp Leu Ser Lys Gly His Ala Val Val Gly Ala Val Gly Ala
            355                 360                 365

Lys Asp Trp Ala Gly Gly Phe Leu Asp Leu Arg Glu Asp Leu Gln Gly
370                 375                 380

Ala Thr Phe Val Gly Gln Glu Pro Leu Thr Ser Asp Val Arg Gly Gly
385                 390                 395                 400

Tyr Leu Gly Tyr Thr Val Ala Trp Met Thr Ser Arg Ser Ser Arg Pro
                405                 410                 415

Leu Leu Ala Ala Gly Ala Pro Arg Tyr Gln His Val Gly Gln Val Leu
                420                 425                 430

Leu Phe Gln Ala Pro Glu Ala Gly Gly Arg Trp Asn Gln Thr Gln Lys
            435                 440                 445

Ile Glu Gly Thr Gln Ile Gly Ser Tyr Phe Gly Glu Leu Cys Ser
            450                 455                 460

Val Asp Leu Asp Gln Asp Gly Glu Ala Glu Leu Leu Leu Ile Gly Ala
465                 470                 475                 480

Pro Leu Phe Phe Gly Glu Gln Arg Gly Gly Arg Val Phe Thr Tyr Gln
                485                 490                 495

Arg Arg Gln Ser Leu Phe Glu Met Val Ser Glu Leu Gln Gly Asp Pro
                500                 505                 510

Gly Tyr Pro Leu Gly Arg Phe Gly Ala Ala Ile Thr Ala Leu Thr Asp
            515                 520                 525

Ile Asn Gly Asp Arg Leu Thr Asp Val Ala Val Gly Ala Pro Leu Glu
            530                 535                 540

Glu Gln Gly Ala Val Tyr Ile Phe Asn Gly Lys Pro Gly Gly Leu Ser
545                 550                 555                 560

Pro Gln Pro Ser Gln Arg Ile Gln Gly Ala Gln Val Phe Pro Gly Ile
                565                 570                 575

Arg Trp Phe Gly Arg Ser Ile His Gly Val Lys Asp Leu Gly Gly Asp
                580                 585                 590

Arg Leu Ala Asn Val Val Gly Pro Glu Gly Arg Val Val Val Leu
            595                 600                 605

Ser Ser Arg Pro Val Val Asp Val Val Thr Glu Leu Ser Phe Ser Pro
            610                 615                 620

Glu Glu Ile Pro Val His Glu Val Glu Cys Ser Tyr Ser Ala Arg Glu
625                 630                 635                 640

Glu Gln Lys His Gly Val Lys Leu Lys Ala Cys Phe Arg Ile Lys Pro
                645                 650                 655

Leu Thr Pro Gln Phe Gln Gly Arg Leu Leu Ala Asn Leu Ser Tyr Thr
                660                 665                 670

Leu Gln Leu Asp Gly His Arg Met Arg Ser Arg Gly Leu Phe Pro Asp
            675                 680                 685

Gly Ser His Glu Leu Ser Gly Asn Thr Ser Ile Thr Pro Asp Lys Ser
            690                 695                 700

Cys Leu Asp Phe His Phe His Phe Pro Ile Cys Ile Gln Asp Leu Ile
```

```
            705                 710                 715                 720
Ser Pro Ile Asn Val Ser Leu Asn Phe Ser Leu Leu Glu Glu Glu Gly
                    725                 730                 735

Thr Pro Arg Asp Gln Lys Gly Arg Ala Met Gln Pro Ile Leu Arg Pro
                    740                 745                 750

Ser Ile His Thr Val Thr Lys Glu Ile Pro Phe Glu Lys Asn Cys Gly
                    755                 760                 765

Glu Asp Lys Lys Cys Glu Ala Asn Leu Thr Leu Ser Ser Pro Ala Arg
                    770                 775                 780

Ser Gly Pro Leu Arg Leu Met Ser Ser Ala Ser Leu Ala Val Glu Trp
785                 790                 795                 800

Thr Leu Ser Asn Ser Gly Glu Asp Ala Tyr Trp Val Arg Leu Asp Leu
                    805                 810                 815

Asp Phe Pro Arg Gly Leu Ser Phe Arg Lys Val Glu Met Leu Gln Pro
                    820                 825                 830

His Ser Arg Met Pro Val Ser Cys Glu Glu Leu Thr Glu Gly Ser Ser
                    835                 840                 845

Leu Leu Thr Lys Thr Leu Lys Cys Asn Val Ser Ser Pro Ile Phe Lys
850                 855                 860

Ala Gly Gln Glu Val Ser Leu Gln Val Met Phe Asn Thr Leu Leu Asn
865                 870                 875                 880

Ser Ser Trp Glu Asp Phe Val Glu Leu Asn Gly Thr Val His Cys Glu
                    885                 890                 895

Asn Glu Asn Ser Ser Leu Gln Glu Asp Asn Ser Ala Ala Thr His Ile
                    900                 905                 910

Pro Val Leu Tyr Pro Val Asn Ile Leu Thr Lys Glu Gln Glu Asn Ser
                    915                 920                 925

Thr Leu Tyr Ile Ser Phe Thr Pro Lys Gly Pro Lys Thr Gln Gln Val
                    930                 935                 940

Gln His Val Tyr Gln Val Arg Ile Gln Pro Ser Ala Tyr Asp His Asn
945                 950                 955                 960

Met Pro Thr Leu Glu Ala Leu Val Gly Val Pro Arg Pro His Ser Glu
                    965                 970                 975

Asp Leu Ile Thr Tyr Thr Trp Ser Val Gln Thr Asp Pro Leu Val Thr
                    980                 985                 990

Cys His Ser Glu Asp Leu Lys Arg Pro Ser Ser Glu Ala Glu Pro Cys
                    995                 1000                1005

Leu Pro Gly Val Gln Phe Arg Cys Pro Ile Val Phe Arg Trp Glu
        1010                1015                1020

Ile Leu Ile Gln Val Thr Gly Thr Val Glu Leu Ser Lys Glu Ile
        1025                1030                1035

Lys Ala Ser Ser Thr Leu Ser Leu Cys Ser Ser Leu Ser Val Ser
        1040                1045                1050

Phe Asn Ser Ser Lys His Phe His Leu Tyr Gly Ser Lys Ala Ser
        1055                1060                1065

Glu Ala Gln Val Leu Val Lys Val Asp Leu Ile His Glu Lys Glu
        1070                1075                1080

Met Leu His Val Tyr Val Leu Ser Gly Ile Gly Gly Leu Val Leu
        1085                1090                1095

Leu Phe Leu Ile Phe Leu Ala Leu Tyr Lys Val Gly Phe Phe Lys
        1100                1105                1110

Arg Asn Leu Lys Glu Lys Met Glu Ala Asp Gly Gly Val Pro Asn
        1115                1120                1125
```

```
Gly Ser Pro Pro Glu Asp Thr Asp Pro Leu Ala Val Pro Gly Glu
    1130                1135                1140

Glu Thr Lys Asp Met Gly Cys Leu Glu Pro Leu Arg Glu Ser Asp
    1145                1150                1155

Lys Asp
    1160
```

<210> SEQ ID NO 42
<211> LENGTH: 2459
<212> TYPE: DNA
<213> ORGANISM: Mus musculus
<220> FEATURE:
<221> NAME/KEY: modified_base
<222> LOCATION: (2443)..(2443)
<223> OTHER INFORMATION: a, c, t, g, unknown or other

<400> SEQUENCE: 42

```
atgctgggcc tgcgcccctc actgctgctt gccctagctg gactgttctt cctgggatct    60
gctgtgtccc aggaatgcac caagtacaaa gtcagcagtt gccgggactg tatccagtcg   120
gggcctggct gttcctggtg ccagaagctg aacttcactg gaccaggaga acctgactcc   180
ttgcgctgtg acacacgggc acagctgctg ctgaagggtg gtccagccga tgatatcatg   240
gaccccagga gcatcgctaa tcctgagttc gaccaacggg ggcaacggaa acagctatct   300
ccacaaaaag tgcacacttta cttgcgacca ggacaggctc cgcattcaa tgtgactttc   360
cggcgggcca agggataccc cattgatctg tactacctca tggatctctc ctactccatg   420
cttgatgacc tcaacaacgt caagaagctg gcggggact gctgcaggc cctcaacgag   480
atcaccgagt ctggccgcat cggctttggg tcgtttgtgg acaagacggt gctgcctttt   540
gttaacaccc atcctgagaa gctgaggaac ccatgtccca caaggagaa ggcctgccag   600
cccccatttg cctttcggca cgtgctcaag ttaaccgaca actccaacca gtttcagaca   660
gaggtcggca gcaactgat ttccggaaac ctggacgccc ctgagggtgg gctggatgcc   720
ataatgcaag ttgctgcatg tccggaggaa attggctggc gcaatgtcac gaggctgctg   780
gtgtttgcca cagacgatgg cttccacttt gctggtgatg caaactggg tgccatcctg   840
acccccaatg atggccgctg ccacctggag ataacatgt acaagaggag caatgagttc   900
gactacccat ccgtgggtca gctggcacac aaactttccg agagcaacat ccagcccatc   960
tttgcggtga caaagaagat ggtgaaaacg tatgagaaac tcacggagat catccccaag  1020
tcagcagtgg gggaactgtc tgacgactcc agcaacgtgg tgcagctcat caagaatgcc  1080
tactataaac tctcctctag agtcttcctg gaccacagca ccctcccgga caccctgaaa  1140
gtcacctatg actccttctg cagtaatgga gcatcgagta taggcaaatc ccgtggggac  1200
tgtgatggcg tacagatcaa caacccggtc accttccagg taaaggtcat ggcttccgag  1260
tgtatccagg agcagtcctt tgtcatccgg gcactgggtt tcacggatac agtgaccgtg  1320
caggtccgtc cccagtgtga gtgtcactgc cgggaccaga gtcgggagca gagtctctgt  1380
ggaggcaagg gagtcatgga gtgtggtatc tgcaggtgtg agtctggcta cattgggaaa  1440
aactgtgagt gccagactca gggtcggagc agccaggagc tggagagaaa ctgtcggaag  1500
gacaatagtt ccatcgtgtg ctcagggctt ggggactgca tctgtgggca gtgtgtatgc  1560
cataccagtg acgtccccaa caaagagatc tttgggcaat actgcgagtg tgacaatgtc  1620
aactgtgaga gatataacag ccaagtctgc ggtggctcag atcggggttc ctgcaactgt  1680
ggcaaatgta gttgcaagcc cggttacgag ggctcggcct gccagtgtca gaggtccacc  1740
```

```
acgggctgtc tgaatgcacg gctggtagag tgcagtggcc gtggccactg ccaatgcaac   1800
aggtgcatat gtgacgaagg ctaccagcca ccgatgtgtg aggattgtcc cagctgtggc   1860
tcgcactgca gggacaacca cacctcttgt gccgagtgcc tgaagtttga taagggccct   1920
tttgagaaga actgtagtgt tcagtgtgct ggtatgacgc tgcagactat ccctttgaag   1980
aaaaagccct gcaaggagaa ggactcggaa ggctgttgga taacttacac tttgcagcag   2040
aaggacggaa ggaacattta caacatccat gtggaggaca gtctagagtg tgtgaagggc   2100
cccaatgtgg ctgccatcgt agggggcacc gtggtaggtg tcgtactgat tggtgtcctc   2160
ctcctggtca tctggaaggc cctgacccac tgactgacc tcagggagta caggcgcttt   2220
gagaaggaga aactcaagtc ccaatggaac aatgacaacc ccctcttcaa gagtgctacg   2280
acaacggtca tgaaccccaa gtttgctgaa agctagagca tgagttatca taatcaagca   2340
gatgtgaccc cctcagacca cgcctcctcc cctctgcaaa cacaacgtgg cttacagctc   2400
accccagtgc tgccaaggat ccaaaagcct gctcggtttc ttnccgccat tatatcaag    2459
```

<210> SEQ ID NO 43
<211> LENGTH: 771
<212> TYPE: PRT
<213> ORGANISM: Mus musculus

<400> SEQUENCE: 43

```
Met Leu Gly Leu Arg Pro Ser Leu Leu Leu Ala Leu Ala Gly Leu Phe
1               5                   10                  15

Phe Leu Gly Ser Ala Val Ser Gln Glu Cys Thr Lys Tyr Lys Val Ser
                20                  25                  30

Ser Cys Arg Asp Cys Ile Gln Ser Gly Pro Gly Cys Ser Trp Cys Gln
            35                  40                  45

Lys Leu Asn Phe Thr Gly Pro Gly Glu Pro Asp Ser Leu Arg Cys Asp
        50                  55                  60

Thr Arg Ala Gln Leu Leu Leu Lys Gly Cys Pro Ala Asp Asp Ile Met
65                  70                  75                  80

Asp Pro Arg Ser Ile Ala Asn Pro Glu Phe Asp Gln Arg Gly Gln Arg
                85                  90                  95

Lys Gln Leu Ser Pro Gln Lys Val Thr Leu Tyr Leu Arg Pro Gly Gln
            100                 105                 110

Ala Ala Ala Phe Asn Val Thr Phe Arg Arg Ala Lys Gly Tyr Pro Ile
        115                 120                 125

Asp Leu Tyr Tyr Leu Met Asp Leu Ser Tyr Ser Met Leu Asp Asp Leu
    130                 135                 140

Asn Asn Val Lys Lys Leu Gly Gly Asp Leu Leu Gln Ala Leu Asn Glu
145                 150                 155                 160

Ile Thr Glu Ser Gly Arg Ile Gly Phe Gly Ser Phe Val Asp Lys Thr
                165                 170                 175

Val Leu Pro Phe Val Asn Thr His Pro Glu Lys Leu Arg Asn Pro Cys
            180                 185                 190

Pro Asn Lys Glu Lys Ala Cys Gln Pro Pro Phe Ala Phe Arg His Val
        195                 200                 205

Leu Lys Leu Thr Asp Asn Ser Asn Gln Phe Gln Thr Glu Val Gly Lys
    210                 215                 220

Gln Leu Ile Ser Gly Asn Leu Asp Ala Pro Glu Gly Gly Leu Asp Ala
225                 230                 235                 240

Ile Met Gln Val Ala Ala Cys Pro Glu Glu Ile Gly Trp Arg Asn Val
```

```
                    245                 250                 255
Thr Arg Leu Leu Val Phe Ala Thr Asp Asp Gly Phe His Phe Ala Gly
            260                 265                 270

Asp Gly Lys Leu Gly Ala Ile Leu Thr Pro Asn Asp Gly Arg Cys His
            275                 280                 285

Leu Glu Asp Asn Met Tyr Lys Arg Ser Asn Glu Phe Asp Tyr Pro Ser
        290                 295                 300

Val Gly Gln Leu Ala His Lys Leu Ser Glu Ser Asn Ile Gln Pro Ile
305                 310                 315                 320

Phe Ala Val Thr Lys Lys Met Val Lys Thr Tyr Glu Lys Leu Thr Glu
                325                 330                 335

Ile Ile Pro Lys Ser Ala Val Gly Glu Leu Ser Asp Asp Ser Ser Asn
            340                 345                 350

Val Val Gln Leu Ile Lys Asn Ala Tyr Tyr Lys Leu Ser Ser Arg Val
        355                 360                 365

Phe Leu Asp His Ser Thr Leu Pro Asp Thr Leu Lys Val Thr Tyr Asp
    370                 375                 380

Ser Phe Cys Ser Asn Gly Ala Ser Ser Ile Gly Lys Ser Arg Gly Asp
385                 390                 395                 400

Cys Asp Gly Val Gln Ile Asn Asn Pro Val Thr Phe Gln Val Lys Val
                405                 410                 415

Met Ala Ser Glu Cys Ile Gln Glu Gln Ser Phe Val Ile Arg Ala Leu
            420                 425                 430

Gly Phe Thr Asp Thr Val Thr Val Gln Val Arg Pro Gln Cys Glu Cys
        435                 440                 445

His Cys Arg Asp Gln Ser Arg Glu Gln Ser Leu Cys Gly Lys Gly
    450                 455                 460

Val Met Glu Cys Gly Ile Cys Arg Cys Glu Ser Gly Tyr Ile Gly Lys
465                 470                 475                 480

Asn Cys Glu Cys Gln Thr Gln Gly Arg Ser Ser Gln Glu Leu Glu Arg
                485                 490                 495

Asn Cys Arg Lys Asp Asn Ser Ser Ile Val Cys Ser Gly Leu Gly Asp
            500                 505                 510

Cys Ile Cys Gly Gln Cys Val Cys His Thr Ser Asp Val Pro Asn Lys
        515                 520                 525

Glu Ile Phe Gly Gln Tyr Cys Glu Cys Asp Asn Val Asn Cys Glu Arg
    530                 535                 540

Tyr Asn Ser Gln Val Cys Gly Gly Ser Asp Arg Gly Ser Cys Asn Cys
545                 550                 555                 560

Gly Lys Cys Ser Cys Lys Pro Gly Tyr Glu Gly Ser Ala Cys Gln Cys
                565                 570                 575

Gln Arg Ser Thr Thr Gly Cys Leu Asn Ala Arg Leu Val Glu Cys Ser
            580                 585                 590

Gly Arg Gly His Cys Gln Cys Asn Arg Cys Ile Cys Asp Glu Gly Tyr
        595                 600                 605

Gln Pro Pro Met Cys Glu Asp Cys Pro Ser Cys Gly Ser His Cys Arg
    610                 615                 620

Asp Asn His Thr Ser Cys Ala Glu Cys Leu Lys Phe Asp Lys Gly Pro
625                 630                 635                 640

Phe Glu Lys Asn Cys Ser Val Gln Cys Ala Gly Met Thr Leu Gln Thr
                645                 650                 655

Ile Pro Leu Lys Lys Pro Cys Lys Glu Lys Asp Ser Glu Gly Cys
            660                 665                 670
```

```
Trp Ile Thr Tyr Thr Leu Gln Gln Lys Asp Gly Arg Asn Ile Tyr Asn
            675                 680                 685

Ile His Val Glu Asp Ser Leu Glu Cys Val Lys Gly Pro Asn Val Ala
    690                 695                 700

Ala Ile Val Gly Gly Thr Val Gly Val Val Leu Ile Gly Val Leu
705                 710                 715                 720

Leu Leu Val Ile Trp Lys Ala Leu Thr His Leu Thr Asp Leu Arg Glu
                725                 730                 735

Tyr Arg Arg Phe Glu Lys Glu Lys Leu Lys Ser Gln Trp Asn Asn Asp
                740                 745                 750

Asn Pro Leu Phe Lys Ser Ala Thr Thr Thr Val Met Asn Pro Lys Phe
            755                 760                 765

Ala Glu Ser
    770
```

```
<210> SEQ ID NO 44
<211> LENGTH: 1207
<212> TYPE: DNA
<213> ORGANISM: Mus musculus

<400> SEQUENCE: 44
gcagctgtct ccaagttgct cagagcctgc ttctgttctc cagtcatgag ctgtacctgg     60
atagccttc ttctgctgtt gggggtttgtt tcttgtcttg gcttcaactt ggatgcagag    120
aagccgacac attttcacat ggacggtgct gagttcggac acagtgtgct ccagtatgat    180
agttcctggg tggtggttgg agcaccaaag gaaataaaag ccactaacca aataggtggc    240
ctctacaaat gtggctatca cacaggcaac tgtgagccca tcttcctcca ggtgccccca    300
gaggctgtga acatgtccct gggcctgtcc cttgctgctg ccaccaaccc ttcctggctg    360
ttggcttgtg gtcctactgt gcaccacaca tgcagagaga atatatactt gacagggctc    420
tgctttctac tgagttcatc attcaagcag agccagaact cccaactgc acagcaggag    480
tgtccaaagc aagaccaaga catcgtgttc ctgattgatg gctcgggtag catcagttcc    540
acagattttg aaaaaatgct ggactttgtt aaagctgtga tgagccagct tcagagacct    600
agcacacggt tctccctgat gcagttctct gattacttcc gagtacattt tactttcaac    660
aacttcatct ccacgtcaag cccttttaagt ctgttggatt ctgtaaggca gctaagaggg    720
tacacataca cagcctcggc tatcaagcat gtcataacag aactgttcac cacccaaagt    780
ggagctcggc aagatgccac caaggtcctc attgtcatca ctgatgggag aaaacaaggg    840
gacaacttga gttatgatag tgtcatcccc atggcagagg ctgcaagcat cattcgttat    900
gcaattgggg taggacacaa agatggtttc ccaccacttc ctcctgtaac ttcctcttga    960
agcaacttcc tctaaaggta gaaagcactt ttctcatctc ctgctgcctt agatatatgg   1020
aaccagggga ggctccttca gcctgggaac ctgtgaccca attgcttcaa ctccctaatg   1080
ttatttgagc ctcatttaga aagaatctcc aaggctgatt gaagagtttt gggtgacagt   1140
gtaggtgata ccttagccat gtttgcctca ttgtagtaaa agcatccaac ataaaaaaaa   1200
aaaaaaa                                                              1207

<210> SEQ ID NO 45
<211> LENGTH: 304
<212> TYPE: PRT
<213> ORGANISM: Mus musculus

<400> SEQUENCE: 45
```

```
Met Ser Cys Thr Trp Ile Ala Phe Leu Leu Leu Gly Phe Val Ser
1               5                   10                  15

Cys Leu Gly Phe Asn Leu Asp Ala Glu Lys Pro Thr His Phe His Met
            20                  25                  30

Asp Gly Ala Glu Phe Gly His Ser Val Leu Gln Tyr Asp Ser Ser Trp
                35                  40                  45

Val Val Val Gly Ala Pro Lys Glu Ile Lys Ala Thr Asn Gln Ile Gly
    50                  55                  60

Gly Leu Tyr Lys Cys Gly Tyr His Thr Gly Asn Cys Glu Pro Ile Phe
65                  70                  75                  80

Leu Gln Val Pro Pro Glu Ala Val Asn Met Ser Leu Gly Leu Ser Leu
                85                  90                  95

Ala Ala Ala Thr Asn Pro Ser Trp Leu Leu Ala Cys Gly Pro Thr Val
                100                 105                 110

His His Thr Cys Arg Glu Asn Ile Tyr Leu Thr Gly Leu Cys Phe Leu
            115                 120                 125

Leu Ser Ser Ser Phe Lys Gln Ser Gln Asn Phe Pro Thr Ala Gln Gln
    130                 135                 140

Glu Cys Pro Lys Gln Asp Gln Asp Ile Val Phe Leu Ile Asp Gly Ser
145                 150                 155                 160

Gly Ser Ile Ser Ser Thr Asp Phe Glu Lys Met Leu Asp Phe Val Lys
                165                 170                 175

Ala Val Met Ser Gln Leu Gln Arg Pro Ser Thr Arg Phe Ser Leu Met
                180                 185                 190

Gln Phe Ser Asp Tyr Phe Arg Val His Phe Thr Phe Asn Asn Phe Ile
        195                 200                 205

Ser Thr Ser Ser Pro Leu Ser Leu Leu Asp Ser Val Arg Gln Leu Arg
    210                 215                 220

Gly Tyr Thr Tyr Thr Ala Ser Ala Ile Lys His Val Ile Thr Glu Leu
225                 230                 235                 240

Phe Thr Thr Gln Ser Gly Ala Arg Gln Asp Ala Thr Lys Val Leu Ile
                245                 250                 255

Val Ile Thr Asp Gly Arg Lys Gln Gly Asp Asn Leu Ser Tyr Asp Ser
                260                 265                 270

Val Ile Pro Met Ala Glu Ala Ala Ser Ile Ile Arg Tyr Ala Ile Gly
            275                 280                 285

Val Gly His Lys Asp Gly Phe Pro Pro Leu Pro Val Thr Ser Ser
290                 295                 300
```

<210> SEQ ID NO 46
<211> LENGTH: 3975
<212> TYPE: DNA
<213> ORGANISM: Mus musculus

<400> SEQUENCE: 46

```
gcaggctcta cagctctcta cttcctaatg cactgctcag ctatggtccg tggagttgtg    60
atcctcctgt gtggctgggc cctggcttcc tgtcatgggt ctaacctgga tgtggagaag   120
cccgtcgtgt tcaaagagga tgcagccagc ttcggacaga ctgtggtgca gtttggtgga   180
tctcgactcg tggtgggagc ccctctggag gcggtggcag tcaaccaaac aggacagttg   240
tatgactgtg cgcctgccac tggcgtgtgc agcccatcct actgcacat  tccctagag   300 gcagtgaaca tgtccctggg cctgtctctg gtggctgaca ccaataactc ccagttgctg   360
gcttgtggtc caactgcaca gagagcttgt gcaaagaaca tgtatgcaaa aggttcctgc   420
```

```
ctccttctgg gctccagctt gcagttcatc caggcaatcc ctgctaccat gccagagtgt      480
ccaggacaag agatggacat tgctttcctg attgatggct ccggcagcat tgatcaaagt      540
gactttaccc agatgaagga cttcgtcaaa gctttgatgg ccagttggc gagcaccagc       600 acctcgttct ccctgatgca atactcaaac atcctgaaga ctcattttac cttcacggaa      660
ttcaagagca gcctgagccc tcagagcctg gtggatgcca tcgtccagct ccaaggcctg      720
acgtacacag cctcgggcat ccagaaagtg gtagacagca caggctcct tcttctacgt       780 gtctggtcag cactgaagcc aggttgccac tacaacactc acatgccatg gtgggtctgg      840
cagagggtac ggttctcctg gaaagagcta tttcatagca agaatggggc ccgaaaaagt      900
gccaagaaga tactaattgt catcacagat gggcagaaat tcagagaccc cctggagtat      960
agacatgtca tccctgaagc agagaaagct gggatcattc gctatgctat aggggtggga     1020
gatgccttcc gggaacccac tgccctacag gagctgaaca ccattggctc agctccctcg     1080
caggaccacg tgttcaaggt gggcaatttt gtagcacttc gcagcatcca gcggcaaatt     1140
caggagaaaa tctttgccat tgaaggaacc gaatcaaggt caagtagttc ctttcagcac     1200
gagatgtcac aagaaggttt cagctcagct ctctcaatgg atggaccagt tctgggggct     1260
gtgggaagct tcagctggtc tggaggtgcc ttcttgtacc cctcaaatat gagatccacc     1320
ttcatcaaca tgtctcagga gaacgaggat atgagggacg cttacctggg ttactccacc     1380
gcactggcct tttggaaggg ggtccacagc ctgatcctgg ggcccctcg ccaccagcac      1440 acggggaagg ttgtcatctt tacccaggaa tccaggcact ggaggcccaa gtctgaagtc     1500
agagggacac agatcggctc ctactttggg gcatctctct gttctgtgga catggataga    1560
gatggcagca ctgacctggt cctgattgga gtcccccatt actatgagca cacccgaggg    1620
gggcaggtgt cggtgtgccc catgcctggt gtgaggagca ggtggcattg tgggaccacc    1680
ctccatgggg agcagggcca tccttggggc cgctttgggg cggctctgac agtgctaggg   1740
gacgtgaatg gggacagtct ggcggatgtg gctattggtg cacccggaga ggaggagaac   1800
agaggtgctg tctacatatt tcatggagcc tcgagacagg acatcgctcc ctcgcctagc    1860
cagcgggtca ctggctccca gctcttcctg aggctccaat attttgggca gtcattaagt    1920
gggggtcagg accttacaca ggatggcctg gtggacctgg ccgtgggagc ccaggggcac    1980
gtgctgctgc ttaggagtct gcctttgctg aaagtgggga tctccattag atttgccccc    2040
tcagaggtgg caaagactgt gtaccagtgc tggggaagga ctcccactgt cctcgaagct    2100
ggagaggcca ccgtctgtct cactgtccgc aaaggttcac ctgacctgtt aggtgatgtc    2160
caaagctctg tcaggtatga tctggcgttg gatccgggcc gtctgatttc tcgtgccatt    2220
tttgatgaga cgaagaactg cactttgacc cgaaggaaga ctctggggct tggtgatcac    2280
tgcgaaacaa tgaagctgct tttgccagac tgtgtggagg atgcagtgac ccctatcatc    2340
ctgcgcctta acttatccct ggcagggac tctgctccat ccaggaacct tcgtcctgtg     2400
ctggctgtgg gctcacaaga ccatgtaaca gcttctttcc cgtttgagaa gaactgtaag    2460
caggagctcc tgtgtgaggg gaacctgggc gtcagcttca acttctcagg cctgcaggtc    2520
ttggaggtag gaagctcccc agagctcact gtgacagtaa cagttggaa tgagggtgag     2580 gacagctatg gaaccttaat caagttctac tacccagcag agctatctta ccgacgggtg    2640
acaagagccc agcaacctca tccgtaccca ctacgcctgg catgtgaggc tgagcccacg    2700
ggccaggaga gcctgaggag cagcagctgt agcatcaatc accccatctt ccgagaaggt    2760
```

-continued

```
gccaaggcca ccttcatgat cacatttgat gtctcctaca aggccttcct gggagacagg   2820
ttgcttctga gggccagcgc aagcagtgag aataataagc ctgaaaccag caagactgcc   2880
ttccagctgg agcttccggt gaagtacacg gtctataccg tgatcagtag gcaggaagat   2940
tctaccaagc atttcaactt ctcatcttcc cacggggaga gacagaaaga ggccgaacat   3000
cgatatcgtg tgaataacct gagtccattg acgctggcca tcagcgttaa cttctgggtc   3060
cccatccttc tgaatggtgt ggccgtgtgg gatgtgactc tgaggagccc agcacagggt   3120
gtctcctgtg tgtcacagag ggaacctcct caacattccg accttctgac ccagatccaa   3180
ggacgctctg tgctggactg cgccatcgcc gactgcctgc acctccgctg tgacatcccc   3240
tccttgggca ccctggatga gcttgacttc attctgaagg gcaacctcag cttcggctgg   3300
atcagtcaga cattgcagaa aaaggtgttg ctcctgagtg aggctgaaat cacattcaac   3360
acatctgtgt attcccagct gccgggacag gaggcatttc tgagagccca ggtgtcaacg   3420
atgctagaag aatacgtggt ctatgagccc gtcttcctca tggtgttcag ctcagtggga   3480
ggtctgctgt tactggctct catcactgtg gcgctgtaca agcttggctt cttcaaacgt   3540
cagtataaag agatgctgga tctaccatct gcagatcctg acccagccgg ccaggcagat   3600
tccaaccatg agactcctcc acatctcacg tcctaggaat ctactttcct gtatatctcc   3660
acaattacga gattggtttt gcttttgcct atgaatctac tggcatggga acaagttctc   3720
ttcagctctg ggctagcctg ggaaacttcc cagaaatgat gccctacctc ctgagctggg   3780 agattttttat ggtttgccca tgtgtcagat ttcagtgctg atccactttt tttgcaagag   3840
caggaatggg gtcagcataa atttacatat ggataagaac taacacaaga ctgagtaata   3900
tgctcaatat tcaatgtatt gcttgtataa atttttaaaa aataaaatga aaatgcaggt   3960
ggaaaaaaaa aaaaa                                                    3975
```

<210> SEQ ID NO 47
<211> LENGTH: 1202
<212> TYPE: PRT
<213> ORGANISM: Mus musculus

<400> SEQUENCE: 47

```
Met His Cys Ser Ala Met Val Arg Gly Val Ile Leu Leu Cys Gly
1               5                   10                  15

Trp Ala Leu Ala Ser Cys His Gly Ser Asn Leu Asp Val Glu Lys Pro
            20                  25                  30

Val Val Phe Lys Glu Asp Ala Ala Ser Phe Gly Gln Thr Val Val Gln
        35                  40                  45

Phe Gly Gly Ser Arg Leu Val Val Gly Ala Pro Leu Glu Ala Val Ala
    50                  55                  60

Val Asn Gln Thr Gly Gln Leu Tyr Asp Cys Pro Ala Thr Gly Val
65                  70                  75                  80

Cys Gln Pro Ile Leu Leu His Ile Pro Leu Glu Ala Val Asn Met Ser
                85                  90                  95

Leu Gly Leu Ser Leu Val Ala Asp Thr Asn Asn Ser Gln Leu Leu Ala
            100                 105                 110

Cys Gly Pro Thr Ala Gln Arg Ala Cys Ala Lys Asn Met Tyr Ala Lys
        115                 120                 125

Gly Ser Cys Leu Leu Leu Gly Ser Ser Leu Gln Phe Ile Gln Ala Ile
    130                 135                 140

Pro Ala Thr Met Pro Glu Cys Pro Gly Gln Glu Met Asp Ile Ala Phe
145                 150                 155                 160
```

```
Leu Ile Asp Gly Ser Gly Ser Ile Asp Gln Ser Asp Phe Thr Gln Met
            165                 170                 175

Lys Asp Phe Val Lys Ala Leu Met Gly Gln Leu Ala Ser Thr Ser Thr
        180                 185                 190

Ser Phe Ser Leu Met Gln Tyr Ser Asn Ile Leu Lys Thr His Phe Thr
    195                 200                 205

Phe Thr Glu Phe Lys Ser Ser Leu Ser Pro Gln Ser Leu Val Asp Ala
210                 215                 220

Ile Val Gln Leu Gln Gly Leu Thr Tyr Thr Ala Ser Gly Ile Gln Lys
225                 230                 235                 240

Val Val Asp Ser Asn Arg Leu Leu Leu Arg Val Trp Ser Ala Leu
                245                 250                 255

Lys Pro Gly Cys His Tyr Asn Thr His Met Pro Trp Trp Val Trp Gln
            260                 265                 270

Arg Val Arg Phe Ser Trp Lys Glu Leu Phe His Ser Lys Asn Gly Ala
        275                 280                 285

Arg Lys Ser Ala Lys Lys Ile Leu Ile Val Ile Thr Asp Gly Gln Lys
    290                 295                 300

Phe Arg Asp Pro Leu Glu Tyr Arg His Val Ile Pro Glu Ala Glu Lys
305                 310                 315                 320

Ala Gly Ile Ile Arg Tyr Ala Ile Gly Val Gly Asp Ala Phe Arg Glu
                325                 330                 335

Pro Thr Ala Leu Gln Glu Leu Asn Thr Ile Gly Ser Ala Pro Ser Gln
            340                 345                 350

Asp His Val Phe Lys Val Gly Asn Phe Val Ala Leu Arg Ser Ile Gln
        355                 360                 365

Arg Gln Ile Gln Glu Lys Ile Phe Ala Ile Glu Gly Thr Glu Ser Arg
    370                 375                 380

Ser Ser Ser Ser Phe Gln His Glu Met Ser Gln Glu Gly Phe Ser Ser
385                 390                 395                 400

Ala Leu Ser Met Asp Gly Pro Val Leu Gly Ala Val Gly Ser Phe Ser
                405                 410                 415

Trp Ser Gly Gly Ala Phe Leu Tyr Pro Ser Asn Met Arg Ser Thr Phe
            420                 425                 430

Ile Asn Met Ser Gln Glu Asn Glu Asp Met Arg Asp Ala Tyr Leu Gly
        435                 440                 445

Tyr Ser Thr Ala Leu Ala Phe Trp Lys Gly Val His Ser Leu Ile Leu
    450                 455                 460

Gly Ala Pro Arg His Gln His Thr Gly Lys Val Val Ile Phe Thr Gln
465                 470                 475                 480

Glu Ser Arg His Trp Arg Pro Lys Ser Glu Val Arg Gly Thr Gln Ile
                485                 490                 495

Gly Ser Tyr Phe Gly Ala Ser Leu Cys Ser Val Asp Met Asp Arg Asp
            500                 505                 510

Gly Ser Thr Asp Leu Val Leu Ile Gly Val Pro His Tyr Tyr Glu His
        515                 520                 525

Thr Arg Gly Gly Gln Val Ser Val Cys Pro Met Pro Gly Val Arg Ser
    530                 535                 540

Arg Trp His Cys Gly Thr Thr Leu His Gly Glu Gln Gly His Pro Trp
545                 550                 555                 560

Gly Arg Phe Gly Ala Ala Leu Thr Val Leu Gly Asp Val Asn Gly Asp
                565                 570                 575
```

```
Ser Leu Ala Asp Val Ala Ile Gly Ala Pro Gly Glu Glu Asn Arg
            580                 585                 590
Gly Ala Val Tyr Ile Phe His Gly Ala Ser Arg Gln Asp Ile Ala Pro
        595                 600                 605
Ser Pro Ser Gln Arg Val Thr Gly Ser Gln Leu Phe Leu Arg Leu Gln
610                 615                 620
Tyr Phe Gly Gln Ser Leu Ser Gly Gly Gln Asp Leu Thr Gln Asp Gly
625                 630                 635                 640
Leu Val Asp Leu Ala Val Gly Ala Gln Gly His Val Leu Leu Leu Arg
                645                 650                 655
Ser Leu Pro Leu Leu Lys Val Gly Ile Ser Ile Arg Phe Ala Pro Ser
            660                 665                 670
Glu Val Ala Lys Thr Val Tyr Gln Cys Trp Gly Arg Thr Pro Thr Val
            675                 680                 685
Leu Glu Ala Gly Glu Ala Thr Val Cys Leu Thr Val Arg Lys Gly Ser
        690                 695                 700
Pro Asp Leu Leu Gly Asp Val Gln Ser Ser Val Arg Tyr Asp Leu Ala
705                 710                 715                 720
Leu Asp Pro Gly Arg Leu Ile Ser Arg Ala Ile Phe Asp Glu Thr Lys
                725                 730                 735
Asn Cys Thr Leu Thr Arg Arg Lys Thr Leu Gly Leu Gly Asp His Cys
            740                 745                 750
Glu Thr Met Lys Leu Leu Leu Pro Asp Cys Val Glu Asp Ala Val Thr
            755                 760                 765
Pro Ile Ile Leu Arg Leu Asn Leu Ser Leu Ala Gly Asp Ser Ala Pro
        770                 775                 780
Ser Arg Asn Leu Arg Pro Val Leu Ala Val Gly Ser Gln Asp His Val
785                 790                 795                 800
Thr Ala Ser Phe Pro Phe Glu Lys Asn Cys Lys Gln Glu Leu Leu Cys
                805                 810                 815
Glu Gly Asn Leu Gly Val Ser Phe Asn Phe Ser Gly Leu Gln Val Leu
            820                 825                 830
Glu Val Gly Ser Ser Pro Glu Leu Thr Val Thr Val Thr Val Trp Asn
            835                 840                 845
Glu Gly Glu Asp Ser Tyr Gly Thr Leu Ile Lys Phe Tyr Tyr Pro Ala
        850                 855                 860
Glu Leu Ser Tyr Arg Arg Val Thr Arg Ala Gln Gln Pro His Pro Tyr
865                 870                 875                 880
Pro Leu Arg Leu Ala Cys Glu Ala Glu Pro Thr Gly Gln Glu Ser Leu
                885                 890                 895
Arg Ser Ser Ser Cys Ser Ile Asn His Pro Ile Phe Arg Glu Gly Ala
            900                 905                 910
Lys Ala Thr Phe Met Ile Thr Phe Asp Val Ser Tyr Lys Ala Phe Leu
            915                 920                 925
Gly Asp Arg Leu Leu Leu Arg Ala Ser Ala Ser Ser Glu Asn Asn Lys
        930                 935                 940
Pro Glu Thr Ser Lys Thr Ala Phe Gln Leu Glu Leu Pro Val Lys Tyr
945                 950                 955                 960
Thr Val Tyr Thr Val Ile Ser Arg Gln Glu Asp Ser Thr Lys His Phe
                965                 970                 975
Asn Phe Ser Ser Ser His Gly Glu Arg Gln Lys Glu Ala Glu His Arg
            980                 985                 990
Tyr Arg Val Asn Asn Leu Ser Pro  Leu Thr Leu Ala Ile  Ser Val Asn
```

-continued

```
                995                 1000                1005

Phe Trp Val Pro Ile Leu Leu Asn Gly Val Ala Val Trp Asp Val
    1010            1015                1020

Thr Leu Arg Ser Pro Ala Gln Gly Val Ser Cys Val Ser Gln Arg
    1025            1030                1035

Glu Pro Pro Gln His Ser Asp Leu Leu Thr Gln Ile Gln Gly Arg
    1040            1045                1050

Ser Val Leu Asp Cys Ala Ile Ala Asp Cys Leu His Leu Arg Cys
    1055            1060                1065

Asp Ile Pro Ser Leu Gly Thr Leu Asp Glu Leu Asp Phe Ile Leu
    1070            1075                1080

Lys Gly Asn Leu Ser Phe Gly Trp Ile Ser Gln Thr Leu Gln Lys
    1085            1090                1095

Lys Val Leu Leu Leu Ser Glu Ala Glu Ile Thr Phe Asn Thr Ser
    1100            1105                1110

Val Tyr Ser Gln Leu Pro Gly Gln Glu Ala Phe Leu Arg Ala Gln
    1115            1120                1125

Val Ser Thr Met Leu Glu Glu Tyr Val Val Tyr Glu Pro Val Phe
    1130            1135                1140

Leu Met Val Phe Ser Ser Val Gly Gly Leu Leu Leu Leu Ala Leu
    1145            1150                1155

Ile Thr Val Ala Leu Tyr Lys Leu Gly Phe Phe Lys Arg Gln Tyr
    1160            1165                1170

Lys Glu Met Leu Asp Leu Pro Ser Ala Asp Pro Asp Pro Ala Gly
    1175            1180                1185

Gln Ala Asp Ser Asn His Glu Thr Pro Pro His Leu Thr Ser
    1190            1195                1200

<210> SEQ ID NO 48
<211> LENGTH: 5
<212> TYPE: PRT
<213> ORGANISM: Artificial Sequence
<220> FEATURE:
<223> OTHER INFORMATION: Description of Artificial Sequence: Synthetic
      motif peptide
<220> FEATURE:
<221> NAME/KEY: MOD_RES
<222> LOCATION: (3)..(3)
<223> OTHER INFORMATION: Any amino acid

<400> SEQUENCE: 48

Leu Pro Xaa Thr Gly
1               5

<210> SEQ ID NO 49
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Gly Gly Gly Gly Ser Gly Gly Gly Gly Ser Gly Gly Gly Gly Ser
1               5                   10                  15
```